(12) United States Patent
Seidel, III et al.

(10) Patent No.: US 12,180,258 B2
(45) Date of Patent: *Dec. 31, 2024

(54) T-CELL MODULATORY MULTIMERIC POLYPEPTIDES AND METHODS OF USE THEREOF

(71) Applicant: Cue Biopharma, Inc., Boston, MA (US)

(72) Inventors: Ronald D. Seidel, III, Boston, MA (US); Rodolfo J. Chaparro, Cambridge, MA (US)

(73) Assignee: Cue Biopharma, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/391,486

(22) Filed: Dec. 20, 2023

(65) Prior Publication Data

US 2024/0199715 A1  Jun. 20, 2024

Related U.S. Application Data

(63) Continuation of application No. 18/202,596, filed on May 26, 2023, now Pat. No. 11,905,320, which is a continuation of application No. 17/845,583, filed on Jun. 21, 2022, now Pat. No. 11,708,400, which is a continuation of application No. 17/578,094, filed on Jan. 18, 2022, now Pat. No. 11,377,478, which is a continuation of application No. 17/507,113, filed on Oct. 21, 2021, now Pat. No. 11,370,821, which is a continuation of application No. 17/386,109, filed on Jul. 27, 2021, now abandoned, which is a continuation of application No. 17/176,777, filed on Feb. 16, 2021, now Pat. No. 11,117,945, which is a continuation of application No. 16/812,926, filed on Mar. 9, 2020, now Pat. No. 10,927,158, which is a continuation of application No. 16/741,202, filed on Jan. 13, 2020, now abandoned, which is a continuation of application No. 16/462,443, filed as application No. PCT/US2017/067663 on Dec. 20, 2017, now abandoned.

(60) Provisional application No. 62/582,132, filed on Nov. 6, 2017, provisional application No. 62/555,435, filed on Sep. 7, 2017, provisional application No. 62/470,774, filed on Mar. 13, 2017, provisional application No. 62/438,272, filed on Dec. 22, 2016.

(51) Int. Cl.
| | | |
|---|---|---|
| *C07K 14/55* | (2006.01) | |
| *A61K 9/00* | (2006.01) | |
| *A61K 35/17* | (2015.01) | |
| *C07K 14/005* | (2006.01) | |
| *C07K 14/47* | (2006.01) | |
| *C07K 14/74* | (2006.01) | |
| *G01N 33/50* | (2006.01) | |
| *A61K 38/00* | (2006.01) | |
| *A61K 39/00* | (2006.01) | |

(52) U.S. Cl.
CPC ............ *C07K 14/55* (2013.01); *A61K 9/0019* (2013.01); *A61K 35/17* (2013.01); *C07K 14/005* (2013.01); *C07K 14/4748* (2013.01); *C07K 14/70539* (2013.01); *G01N 33/5008* (2013.01); *A61K 38/00* (2013.01); *A61K 2039/505* (2013.01); *C07K 2317/34* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,635,363 A | 6/1997 | Altman et al. | |
| 6,197,302 B1 | 3/2001 | Hirsch et al. | |
| 6,211,342 B1 | 4/2001 | Hirsch et al. | |
| 6,268,411 B1 | 7/2001 | Schneck et al. | |
| 6,322,789 B1 | 11/2001 | Vitiello et al. | |

(Continued)

FOREIGN PATENT DOCUMENTS

| | | |
|---|---|---|
| CN | 1791675 | 6/2006 |
| CN | 101384621 | 3/2009 |

(Continued)

OTHER PUBLICATIONS

Anonymous; "Rationally engineered biologics to harness nature's cues for selective and specific immune modulation", Powerpoint presentation; 24 pages (Feb. 1, 2021).

(Continued)

*Primary Examiner* — Agnieszka Boesen
(74) *Attorney, Agent, or Firm* — James J. Diehl; Bozicevic, Field & Francis LLP

(57) ABSTRACT

The present disclosure provides variant immunomodulatory polypeptides, and fusion polypeptides comprising the variant immunomodulatory peptides. The present disclosure provides T-cell modulatory multimeric polypeptides, and compositions comprising same, where the T-cell modulatory multimeric polypeptides comprise a variant immunomodulatory polypeptide of the present disclosure. The present disclosure provides nucleic acids comprising nucleotide sequences encoding the T-cell modulatory multimeric polypeptides, and host cells comprising the nucleic acids. The present disclosure provides methods of modulating the activity of a T cell; the methods comprise contacting the T cell with a T-cell modulatory multimeric polypeptide of the present disclosure.

30 Claims, 60 Drawing Sheets

Specification includes a Sequence Listing.

(56) References Cited

U.S. PATENT DOCUMENTS

| | | | |
|---|---|---|---|
| 6,600,012 B1 | 7/2003 | Agrawal et al. | |
| 6,696,304 B1 | 2/2004 | Parker | |
| 7,098,306 B2 | 8/2006 | Economou et al. | |
| 7,186,804 B2* | 3/2007 | Gillies | A61P 35/00 |
| | | | 435/69.7 |
| 7,432,351 B1 | 10/2008 | Chen | |
| 7,670,595 B2 | 3/2010 | Gillies et al. | |
| 8,435,494 B2 | 5/2013 | Gelfand | |
| 8,992,937 B2 | 3/2015 | Hansen et al. | |
| 9,284,349 B2 | 3/2016 | Tsunoda et al. | |
| 9,359,424 B2 | 6/2016 | Maoult et al. | |
| 9,494,588 B2 | 11/2016 | Springer et al. | |
| 10,059,750 B2 | 8/2018 | Davis et al. | |
| 10,272,042 B2* | 4/2019 | Daftarian | A61K 31/4745 |
| 10,501,521 B2* | 12/2019 | Georges | A61P 31/12 |
| 10,927,158 B2 | 2/2021 | Seidel et al. | |
| 10,927,161 B2 | 2/2021 | Seidel et al. | |
| 11,104,712 B2 | 8/2021 | Seidel, III et al. | |
| 11,117,945 B2 | 9/2021 | Seidel et al. | |
| 11,370,821 B2 | 6/2022 | Seidel, III et al. | |
| 11,377,478 B2* | 7/2022 | Seidel, III | G01N 33/5008 |
| 11,380,821 B2 | 7/2022 | Jia et al. | |
| 11,401,314 B2 | 8/2022 | Seidel, III et al. | |
| 11,479,595 B2 | 10/2022 | Seidel et al. | |
| 11,505,588 B2 | 11/2022 | Seidel, III et al. | |
| 11,505,591 B2 | 11/2022 | Seidel, III et al. | |
| 11,530,248 B2 | 12/2022 | Seidel, III et al. | |
| 11,702,461 B2 | 7/2023 | Seidel, III et al. | |
| 11,708,400 B2* | 7/2023 | Seidel, III | G01N 33/5008 |
| | | | 530/351 |
| 11,739,133 B2 | 8/2023 | Seidel, III et al. | |
| 11,767,355 B2 | 9/2023 | Seidel, III et al. | |
| 11,851,467 B2 | 12/2023 | Seidel, III et al. | |
| 11,878,062 B2 | 1/2024 | Cemerski et al. | |
| 11,905,320 B2* | 2/2024 | Seidel, III | C07K 14/005 |
| 2002/0006664 A1 | 1/2002 | Sabatini | |
| 2002/0031520 A1 | 3/2002 | Economou et al. | |
| 2002/0165136 A1 | 11/2002 | Baserga et al. | |
| 2003/0235536 A1 | 12/2003 | Blumberg et al. | |
| 2004/0038349 A1 | 2/2004 | Hilbert et al. | |
| 2004/0132977 A1 | 7/2004 | Gantier et al. | |
| 2004/0161817 A1 | 8/2004 | Benton et al. | |
| 2004/0209363 A1 | 10/2004 | Watts et al. | |
| 2005/0003431 A1 | 1/2005 | Wucherpfennig et al. | |
| 2005/0009012 A1 | 1/2005 | Holzberg et al. | |
| 2005/0100926 A1 | 5/2005 | Hedley et al. | |
| 2005/0142142 A1 | 6/2005 | Burrows et al. | |
| 2006/0034865 A1 | 2/2006 | Hildebrand et al. | |
| 2006/0269515 A1 | 11/2006 | Deniz-Mize et al. | |
| 2007/0036752 A1 | 2/2007 | Gillies et al. | |
| 2007/0148162 A1 | 6/2007 | Bhardwaj et al. | |
| 2007/0286843 A1 | 12/2007 | Pfizenmaier et al. | |
| 2008/0199485 A1 | 8/2008 | Kundig et al. | |
| 2008/0219947 A1 | 9/2008 | Linette et al. | |
| 2008/0269070 A1 | 10/2008 | Ramseier et al. | |
| 2010/0159594 A1 | 6/2010 | Hansen et al. | |
| 2010/0190720 A1 | 7/2010 | Hollingsworth et al. | |
| 2010/0226854 A1 | 9/2010 | Schøller et al. | |
| 2011/0002956 A1 | 1/2011 | Weiner et al. | |
| 2011/0268737 A1 | 11/2011 | Favier et al. | |
| 2011/0318380 A1 | 12/2011 | Brix et al. | |
| 2012/0003220 A1 | 1/2012 | Chen | |
| 2012/0121577 A1 | 5/2012 | Weidanz et al. | |
| 2012/0177595 A1 | 7/2012 | Wong et al. | |
| 2012/0264161 A1 | 10/2012 | Scholler et al. | |
| 2013/0017199 A1 | 1/2013 | Langermann | |
| 2013/0149305 A1 | 6/2013 | Ostrand-Rosenberg | |
| 2014/0046026 A1 | 2/2014 | Garcia et al. | |
| 2014/0162293 A1 | 6/2014 | Springer et al. | |
| 2014/0242077 A1 | 8/2014 | Choi et al. | |
| 2015/0071987 A1 | 3/2015 | Selvaraj | |
| 2015/0224186 A1 | 8/2015 | Nakagawa | |
| 2015/0232532 A1 | 8/2015 | Ostrand-Rosenberg | |
| 2015/0352201 A1 | 12/2015 | David et al. | |
| 2015/0374788 A1 | 12/2015 | Paulsen et al. | |
| 2016/0011204 A1 | 1/2016 | Almo et al. | |
| 2016/0083477 A1 | 3/2016 | Klein et al. | |
| 2016/0090407 A1 | 3/2016 | Hosse et al. | |
| 2016/0114019 A1 | 4/2016 | Li et al. | |
| 2016/0152725 A1 | 6/2016 | Cheung et al. | |
| 2016/0175397 A1 | 6/2016 | Umana et al. | |
| 2016/0304580 A1 | 10/2016 | Ellmark et al. | |
| 2016/0362465 A1 | 12/2016 | Nishimura et al. | |
| 2017/0044229 A1 | 2/2017 | Garcia et al. | |
| 2017/0058015 A1 | 3/2017 | Seidel, III et al. | |
| 2017/0334951 A1 | 11/2017 | O'Reilly et al. | |
| 2018/0044404 A1 | 2/2018 | Oda et al. | |
| 2018/0064795 A1 | 3/2018 | Sugiyama | |
| 2018/0086832 A1 | 3/2018 | Vogelstein et al. | |
| 2018/0127481 A1 | 5/2018 | Santamaria | |
| 2018/0208626 A1 | 7/2018 | Scheinberg et al. | |
| 2018/0282392 A1 | 10/2018 | Seidel, III et al. | |
| 2018/0339030 A1 | 11/2018 | Scheinberg | |
| 2019/0046648 A1 | 2/2019 | Seidel, III et al. | |
| 2019/0119377 A1 | 4/2019 | Spirig et al. | |
| 2020/0140519 A1 | 5/2020 | Seidel, III et al. | |
| 2020/0317747 A1 | 10/2020 | Seidel, III et al. | |
| 2020/0369745 A1 | 11/2020 | Seidel, III et al. | |
| 2021/0284709 A1 | 9/2021 | Brandt et al. | |
| 2021/0284712 A1 | 9/2021 | Seidel, III et al. | |
| 2021/0393693 A1 | 12/2021 | Seidel, III et al. | |
| 2022/0008467 A1 | 1/2022 | Seidel, III et al. | |
| 2022/0017596 A1 | 1/2022 | Cemerski et al. | |
| 2022/0017597 A1 | 1/2022 | Seidel, III et al. | |
| 2022/0079985 A1 | 3/2022 | Seidel, III et al. | |
| 2022/0089680 A1 | 3/2022 | Seidel, III et al. | |
| 2022/0089681 A1 | 3/2022 | Seidel, III et al. | |
| 2022/0105162 A1 | 4/2022 | Seidel, III et al. | |
| 2022/0106378 A1 | 4/2022 | Seidel, III et al. | |
| 2022/0112252 A1 | 4/2022 | Seidel, III et al. | |
| 2022/0143063 A1 | 5/2022 | Seidel, III et al. | |
| 2022/0162314 A1 | 5/2022 | Yeung et al. | |
| 2022/0251202 A1 | 8/2022 | Djuretic et al. | |
| 2022/0389079 A1 | 12/2022 | Seidel, III et al. | |
| 2022/0409732 A1 | 12/2022 | MacDonald et al. | |
| 2023/0000914 A1 | 1/2023 | Suri | |
| 2023/0055644 A1 | 2/2023 | Suri | |
| 2023/0117521 A1 | 4/2023 | Seidel, III et al. | |
| 2023/0126199 A1 | 4/2023 | Hanayama et al. | |
| 2023/0139456 A1 | 5/2023 | Cemerski et al. | |
| 2023/0227530 A1 | 7/2023 | Seidel, III et al. | |
| 2023/0257439 A1 | 8/2023 | Seidel, III et al. | |
| 2023/0390407 A1 | 12/2023 | Cemerski et al. | |
| 2023/0399372 A1 | 12/2023 | Seidel, III et al. | |
| 2024/0025964 A1 | 1/2024 | Seidel, III et al. | |
| 2024/0067700 A1 | 2/2024 | Seidel, III et al. | |

FOREIGN PATENT DOCUMENTS

| | | |
|---|---|---|
| CN | 101418309 | 4/2009 |
| CN | 101448951 | 6/2009 |
| CN | 101688213 | 3/2010 |
| CN | 105121715 | 12/2015 |
| CN | 106456733 | 2/2017 |
| CN | 108431022 | 8/2018 |
| EP | 2998740 | 3/2016 |
| EP | 3596118 | 1/2020 |
| JP | 2000515363 | 11/2000 |
| JP | 2004580 | 1/2004 |
| JP | 2005506058 | 3/2005 |
| JP | 2007530021 | 11/2007 |
| JP | 2009537175 | 10/2009 |
| JP | 2010524506 | 7/2010 |
| JP | 2012516854 | 7/2012 |
| JP | 2015537043 | 12/2015 |
| WO | WO 1997/028191 | 8/1997 |
| WO | WO 2001/090747 | 11/2001 |
| WO | WO 2002/072631 | 9/2002 |
| WO | WO 2002/087613 | 11/2002 |
| WO | WO 2002/093129 | 11/2002 |
| WO | WO 2002/102299 | 12/2002 |
| WO | WO 2003/048334 | 6/2003 |
| WO | WO 2004/029197 | 4/2004 |
| WO | WO2004040262 A2 | 5/2004 |

(56) References Cited

FOREIGN PATENT DOCUMENTS

| WO | WO 2004/111190 | 12/2004 |
|---|---|---|
| WO | WO2005017148 A1 | 2/2005 |
| WO | WO2006073941 A2 | 7/2006 |
| WO | WO 2007/136778 | 11/2007 |
| WO | WO 2008/019888 | 2/2008 |
| WO | WO 2008/113970 | 9/2008 |
| WO | WO 2008/116468 | 10/2008 |
| WO | WO 2008/134461 | 11/2008 |
| WO | WO 2009/023270 | 2/2009 |
| WO | WO 2010/037395 | 4/2010 |
| WO | WO2010037514 A2 | 4/2010 |
| WO | WO 2010/085495 | 7/2010 |
| WO | WO 2010/091122 | 8/2010 |
| WO | WO 2011/066342 | 6/2011 |
| WO | WO 2011/066389 | 6/2011 |
| WO | WO 2012/007951 | 1/2012 |
| WO | WO 2012/107417 | 2/2012 |
| WO | WO 2012/146628 | 4/2012 |
| WO | WO 2012/127464 | 9/2012 |
| WO | WO 2012/175508 | 12/2012 |
| WO | WO 2013/003761 | 1/2013 |
| WO | WO 2013/079174 | 6/2013 |
| WO | WO 2014/083004 | 6/2014 |
| WO | WO 2014/093118 | 6/2014 |
| WO | WO 2014/145806 | 9/2014 |
| WO | WO 2015/007903 | 1/2015 |
| WO | WO 2015/112541 | 7/2015 |
| WO | WO 2015/164815 | 10/2015 |
| WO | WO 2015/195531 | 12/2015 |
| WO | WO 2016/000619 | 1/2016 |
| WO | WO 2016/014428 | 1/2016 |
| WO | WO 2016/025642 | 2/2016 |
| WO | WO 2016/029043 | 2/2016 |
| WO | WO 2016/030350 | 3/2016 |
| WO | WO 2016/141357 | 9/2016 |
| WO | WO 2016/164937 | 10/2016 |
| WO | WO 2016/168771 | 10/2016 |
| WO | WO 2016/198932 | 12/2016 |
| WO | WO 2017/008844 | 1/2017 |
| WO | WO 2017/023779 | 2/2017 |
| WO | WO 2017/059819 | 4/2017 |
| WO | WO 2017/120222 | 7/2017 |
| WO | WO 2017/151818 | 9/2017 |
| WO | WO 2017/151940 | 9/2017 |
| WO | WO 2017/201131 | 11/2017 |
| WO | WO 2017/201210 | 11/2017 |
| WO | WO 2018/119114 | 6/2018 |
| WO | WO 2018/165631 | 9/2018 |
| WO | WO 2018/170168 | 9/2018 |
| WO | WO 2018/170475 | 9/2018 |
| WO | WO 2019/038230 | 2/2019 |
| WO | WO 2019/051091 | 3/2019 |
| WO | WO 2019/051094 | 3/2019 |
| WO | WO 2019/051126 | 3/2019 |
| WO | WO 2019/051127 | 3/2019 |
| WO | WO 2019/139896 | 7/2019 |
| WO | WO 2019/162937 | 8/2019 |
| WO | WO 2020/243315 | 12/2020 |
| WO | WO 2020/247843 | 12/2020 |
| WO | WO 2020/257191 | 12/2020 |
| WO | WO 2021/055594 | 3/2021 |
| WO | WO 2021/081232 | 4/2021 |
| WO | WO 2021/081239 | 4/2021 |
| WO | WO 2021/127495 | 6/2021 |
| WO | WO 2021/172596 | 9/2021 |
| WO | WO 2021/209759 | 10/2021 |
| WO | WO 2022/015880 | 1/2022 |
| WO | WO 2022/087458 | 4/2022 |
| WO | WO 2022/099156 | 5/2022 |
| WO | WO 2022/125694 | 6/2022 |
| WO | WO 2022/125711 | 6/2022 |

OTHER PUBLICATIONS

Genbank:ALM96677.1; "MHC class I antigen, partial [*Homo sapiens*]"; 3 pages (Nov. 11, 2015).
Johannsen, et al.; "Definition of Key Variables for the Induction of Optimal NY-ESO-1-Specific T Cells in HLA Transgene Mice"; The Journal of Immunology; vol. 185, pp. 3445-3455 (2010).
Linard, et al.; "A ras-Mutated Peptide Targeted by CTL Infiltrating a Human Melanoma Lesion"; The Journal of Immunology; vol. 168, pp. 4802-4808 (2002).
Terashima, et al.; "P53, hTERT, WT-1, and VEGFR2 are the most suitable targets for cancer vaccine therapy in HLA-A24 positive pancreatic adenocarcinoma"; Cancer Immunol Immunother; vol. 63, pp. 479-489 (2014).
Accession No. 1 IRL_A chain A Interleukin-2; 1 page (Aug. 25, 1995).
Ackerman, et al.; "Highly Avid Magnetic Bead Capture: An Efficient Selection Method for de novo Protein Engineering Utilizing yeast Surface Display"; Biotechnol. Prog.; vol. 25, No. 3, pp. 774-783 (2009).
Aina, et al.; "Identification of novel targeting peptides for human ovarian cancer cells using 'one-bead one-compount' combinatorial libraries"; Mol. Cancer Ther.; vol. 4, No. 5, 8 pages (May 2005).
Arduin, et al.; "Highly reduced binding to high and low affinity mouse Fc gamma receptors by L234A/L235A and N297A Fc mutations engineered into mouse IgG2a"; Molecular Immunology; vol. 63, pp. 456-463 (Feb. 2015).
Azuma, et al.; "B7-H1 is a ubiquitous antiapoptotic receptor on cancer cells"; Immunobiology; vol. 111, No. 7, pp. 3635-3643 (Apr. 1, 2008).
Baldi, et al.; "Recombinant protein production by large-scale transient gene expression in mammalian cells: state of the art and future perspectives"; Biotechnol. Lett.; vol. 29, pp. 677-684 (2007).
Bowers, et al.; "Coupling mammalian cell surface display with somatic hypermutation for the discovery and maturation of human antibodies"; PNAS; vol. 108, No. 51, pp. 20455-20460 (Dec. 20, 2011).
Bresson, et al; "Anti-CD3 and nasal proinsulin combination therapy enhances remission from recent-onset autoimmune diabetes by inducing Tregs"; The Journal of Clinical Investigation; vol. 116, No. 5, pp. 1371-1381 (May 2006).
Brophy, et al.; "A yeast display system for engineering functional peptide-MHC complexes"; Journal of Immunological Methods; vol. 272, pp. 235-246 (2003).
Buonaguro, et al.; "Translating Tumor Antigens into Cancer Vaccines"; Clinical and Vaccine Immunology; vol. 18, No. 1, pp. 23-24 (Jan. 2011).
Büttner; "Cell-based assays for high-throughput screening"; Expert Opin. Drug Discov..; vol. 1, No. 4, pp. 301-306 (Sep. 2006).
Cafri, et al.; "Development of novel genetic cancer vaccines based on membrane-attached β2 microglobulin"; Ann. N.Y. Acad. Sci.; vol. 1283, pp. 87-90 (2013).
Card, et al.; "A soluble single-chain T-cell receptor IL-2 fusion protein retains MHC-restricted peptide specificity and IL-2 bioactivity"; Cancer Immunol Immunother; vol. 53, pp. 345-357 (Nov. 11, 2003).
Carey, et al.; "A soluble divalent class I MHC/IgG1 fusion protein activates CD8+ T cells in vivo"; Clinical Immunology; vol. 116, pp. 65-76 (2005).
Carmenate, et al.; "Human IL-2 Mutein with Higher Antitumor Efficacy Than Wild Type IL-2"; The Journal of Immunology; vol. 190, No. 12, pp. 6230-6238 (Jun. 15, 2013).
Casares, et al.; "A Peptide-Major Histocompatibility Complex II Chimera Favors Survival of Pancreatic β-Islets Grafted in Type 1 Diabetic Mice"; Transplantation; vol. 85, No. 12, pp. 1717-1725 (Jun. 27, 2008).
Cebecauer, et al.; "Soluble MHC-Peptide Complexes Induce Rapid Death of CD8+ CTL"; The Journal of Immunology; vol. 174, pp. 6809-6819 (2005).
Celis, et al.; "Identification of Potential CTL Epitopes of Tumor-Associated Antigen Mage-1 for Five Common HLA-A Alleles"; Molecular Immunology; vol. 31, No. 18, pp. 1423-1430 (1994).

(56) References Cited

OTHER PUBLICATIONS

Center for Disease Control and Prevention; "How Many Cancers Are Linked with HPV Each Year?"; 4 pages (2016).
Chames, et al.; "Bispecific antibodies for cancer therapy; The light at the end of the tunnel?" mAbs; vol. 1, No. 6, pp. 539-547 (Nov.-Dec. 2009).
Cheever, et al.; "The Prioritization of Cancer Antigens: A National Cancer Institute Pilot Project for the Acceleration of Translational Research"; Clinical Cancer Research; vol. 15, No. 17, pp. 5324-5337 (Sep. 1, 2009).
Chung, et al.; "A phase 1 dose-escalation and expansion study of CUE-101, a novel HPV16 E7-pHLA-IL2-Fc fusion protein, given alone and in combination with pembrolizumab in patients with recurrent/metastatic HPV16+ head and neck cancer."; poster, ASCO 2022 (1 page).
Chung, et al.; "#674 A phase 1 dose-escalation and expansion study of CUE-101, given as monotherapy and in combination with pembrolizumab in recurrent/metastatic HPV16+ head and neck cancer patients"; Poster; Presented at the Society for Immunotherapy of Cancer (SITC) Annual Meeting; 1 page (Nov. 3-5, 2023).
Chung, et al.; "# 681 A phase 1 study of CUE-101, a novel HPV16 E7-pHLA-IL2-Fc fusion protein, as monotherapy and in combination with pembrolizumab in patients with recurrent/metastatic HPV16+ head and neck cancer"; poster, Presented at the Society for Immunotherapy of Cancer (SITC) Annual Meeting, 1 page (Nov. 8-12, 2022).
Chung, et al.; "A phase 1 dose-escalation and expansion study of CUE-101, a novel HPV16 E7-pHLA-IL2-Fc fusion protein, given as monotherapy and in combination with pembrolizumab in patients with recurrent/metastatic HPV16+ head and neck cancer."; poster, ASCO 2023 (1 page).
Crawford, et al.; "Use of baculovirus MHC/ peptide display libraries to characterize T-cell receptor ligands"; Immunological Reviews; vol. 210, pp. 156-170 (2006).
Crisci, et al.; "Virus-like particles: The new frontier of vaccines for animal viral infections"; Veterinary Immunology and Immunopathology; vol. 148, pp. 211-225 (2012).
Czajkowsky, et al.; "Fc-fusion proteins: new developments and future perspectives"; EMBO Mol. Med.; vol. 4, pp. 1015-1028 (2012).
Das, et al.; "Generation of murine tumor cell lines deficient in MHC molecule surface expression using the CRISPR/Cas9 system"; PLoS One; vol. 12, No. 3, 19 pages (Mar. 16, 2017).
De Charette, et al.; "Turning tumour cells into antigen presenting cells: The next step to improve cancer immunotherapy?"; European Journal of Cancer; vol. 68, pp. 134-147 (Oct. 2016).
Desmond, et al.; "A systematic review of T-cell epitopes in hepatitis B virus: identification, genotypic variation and relevance to antiviral therapeutics"; Antiviral Therapy; vol. 13, pp. 161-175 (2008).
Dimasi, et al.; "The design and characterization of oligospecific antibodies for simultaneous targeting of multiple disease mediators"; Journal of Molecular Biology; 393(3): p. 672-692 (2009).
Doussal, et al.; "Phage display of peptide /major histocompatibility complex"; Journal of Immunological Methods; vol. 241, pp. 147-158 (2000).
Dulberger, et al.; "Human leukocyte antigen F (HLA-F) presents peptides and regulates immunity through interactions with NK-cell receptors"; Immunity; vol. 46, No. 6, pp. 1018-1027 (Jun. 20, 2017).
Durinovic-Bello, et al.; "DRB1*0401-restricted human T cell clone specific for the major proinsulin73-90 epitope expresses a down-regulatory T helper 2 phenotype"; PNAS; vol. 103, No. 31, pp. 11683-11688 (Aug. 1, 2006).
Emboss Needle; 2 pages (Feb. 10, 2022).
Edwards, et al.; "The Remarkable Flexibility of the Human Antibody Repertoire; Isolation of Over One Thousand Different Antibodies to a Single Protein, BLyS"; J. Mol. Biol.; vol. 334, pp. 103-118 (2003).
Engelhard; "Structure of peptides associated with MHC class I molecules"; Current Opinion in Immunology; vol. 6, pp. 13-23 (1994).

Engler, et al.; "Peptide vaccines against hepatitis B virus: from animal model to human studies"; Molecular Immunology; vol. 38, pp. 457-465 (Dec. 2001).
Favier, et al.; "Tolerogenic Function of Dimeric Forms of HLA-G Recombinant Proteins: A Comparative Study In Vivo"; PLoS One; vol. 6, No. 7, 26 pages (Jul. 2011).
Fellner; "Ipilimumab (Yervoy) Prolongs Survival in Advanced Melanoma"; Drug Forecast; vol. 37, No. 9, pp. 503-530 (Sep. 2012).
Genbank:AEV43323.1; "Fc IgG1 heavy chain constant region, partial [Homo sapiens]"; 2 pages (Jul. 25, 2016).
Genbank:NP_068693.1; "programmed cell death 1 ligand 1 precursor [Mus musculus]"; 3 pages (Jun. 9, 2021).
Genbank:NP_001009066.1; 2 pages (2003).
Genbank:NP_001300958.1; "programmed cell death 1 ligand 1 isoform c precursor [Homo sapiens]"; 3 pages (Jun. 9, 2021).
GenCore AEE04235; 4 pages (2005).
Goel, et al.; "Plasticity within the Antigen-Combining Site May Manifest as Molecufar Mimicry in the Humoral Immune Response"; The Journal of Immunology; vol. 173, pp. 7358-7367 (2004).
Gojanovich, et al.; "The Use of Peptide-Major-Histocompatibility-Complex Multimers in Type 1 Diabetes Mellitus"; Journal of Diabetes Science and Technology; vol. 6, No. 3, pp. 515-524 (May 2012).
Gough, et al.; "The HLA Region and Autoimmune Disease: Associations and Mechanisms of Action"; Current Genomics; vol. 8, pp. 453-465 (2007).
Greten, et al.; "Peptide-β2-microglobulin-MHC fusion molecules bind antigen-specific T cells and can be used for multivalent MHC-Ig complexes"; Journal of Immunological Methods; vol. 271, pp. 125-135 (2002).
Grupp, et al.; "Adoptive Cellular Therapy"; Curr Top Microbiol Immunol.; 344: p. 149-172 (2011).
Guo, et al.; "Different length peptides bind to HLA-Aw68 similarly at their ends but bulge out in the middle"; Nature; vol. 360, pp. 364-366 (Nov. 26, 1992).
Hansen, et al.; "Phage display of peptide/major histocompatibility class I complexes"; Eur. J. Immunol.; vol. 31, pp. 32-38 (2001).
HLA Nomenclature; "HLA Alleles Numbers"; 2 pages (Mar. 17, 2015).
Huang, et al.; "Bone regeneration in a rat cranial defect with delivery of PEI-condensed plasmid DNA encoding for bone morphogenetic protein-4 (BMP-4)"; Gene Therapy; vol. 12, No. 5, p. 418 (2005).
Huang, et al.; "Cancer immunotherapy using a DNA vaccine encoding a single-chain trimer of MHC class I linked to an HPV-16 E6 immunodominant CTL epitope"; Gene Ther.; vol. 12, No. 15, pp. 1180-1186 (Aug. 2005).
Hug, et al.; "T-cadherin is a receptor for hexameric and high-molecular-weight forms of Acrp30/adiponectin"; PNAS; vol. 101, No. 28, pp. 10308-10313 (Jul. 13, 2004).
Hugues, et al.; "Generation and use of alternative multimers of peptide/MHC complexes"; Journal of Immunological Methods; vol. 268, pp. 83-92 (2002).
Judkowski, et al.; "Identification of MHC Class II-Restricted Peptide Ligands, Including a Glutamic Acid Decarboxylase 65 Sequence, that Stimulate Diabetogenic T Cells from Transgenic BDC2.5 Nonobese Diabetic Mice"; The Journal of Immunology; vol. 166, pp. 908-917 (2001).
Karaki, et al.; "Is There Still Room for Cancer Vaccines at the Era of Checkpoint Inhibitors"; Vaccines; vol. 4, No. 37, 24 pages (2016).
Karin, et al.; "Reversal of Experimental Autoimmune Encephalomyelitis by a Soluble Peptide Variant of a Myelin Basic Protein Epitope: T Cell Receptor Antagonism and Reduction of Interferon γ and Tumor Necrosis Factor α Production"; J. Exp. Med.; vol. 180, pp. 2227-2237 (Dec. 1994).
Khan, et al.; "Adjustable Locks and Flexible Keys: Plasticity of Epitope-Paratope Interactions in Germline Antibodies"; The Journal of Immunology; vol. 192, pp. 5398-5405 (2014).
Kim, et al.; "Single chain MHC I trimer-based DNA vaccines for protection against Listeria monocytogenes infection"; Vaccine; vol. 30, pp. 2178-2186 (2012).

(56) References Cited

OTHER PUBLICATIONS

Kowalski, et al.; "Delivering the Messenger: Advances in Technologies for Therapeutic mRNA Delivery"; Molecular Therapy; vol. 27, No. 4, pp. 710-728 (Feb. 18, 2019).
Krautwurst, et al.; "Identification of Ligands for Olfactory Receptors by Functional Expression of a Receptor Library"; Cell; vol. 95, pp. 917-926 (Dec. 23, 1998).
Kreiter, et al.; "Increased Antigen Presentation Efficiency by Coupling Antigens to MHC Class I Trafficking Signals"; The Journal of Immunology; vol. 180, No. 1, pp. 309-318 (Jan. 1, 2008).
Kushnir, et al.; "Virus-like particles as a highly efficient vaccine platform: Diversity of targets and production systems and advances in clinical development"; Vaccine; vol. 31, pp. 58-83 (2012).
Lazar-Molnar, et al.; "Crystal structure of the complex between programmed death-1 (PD-1) and its ligand PD-L2"; PNAS; vol. 105, No. 30, pp. 10483-10488 (Jul. 29, 2008).
Lazar-Molnar, et al.; "The PD-1/PD-L costimulatory pathway critically affects host resistance to the pathogenic fungus *Histoplasma capsulatum*"; PNAS; vol. 105, No. 7, pp. 2658-2663 (Feb. 19, 2008).
Lenormand, et al.; "HLA-DQA2 and HLA-DQB2 Genes Are Specifically Expressed in Human Langerhans Cells and Encode a New HLA Class II Molecule"; The Journal of Immunology; vol. 199, No. 8, pp. 3903-3911 (Apr. 15, 2012).
Li, et al.; "Chain A, anti-connexin26 scFv,Ig heavy chain,Linker, anti-connexin26 scFv,Ig light chain"; Accession 5WYM_A, Front Mol Neurosci 10, 298, 3 pages (Jan. 13, 2017).
Li, et al.; "Suppression of Ongoing T Cell-Mediated Autoimmunity by Peptide-MHC Class II Dimer Vaccination"; The Journal of Immunology; vol. 183, pp. 4809-4816 (Sep. 14, 2009).
Liao, et al.; "Interleukin-2 at the Crossroads of Effector Responses, Tolerance, and Immunotherapy"; Immunity; vol. 38, No. 1, pp. 13-25 (Jan. 1, 2013).
Lin, et al.; "Reversal of type 1 diabetes by a new MHC II-peptide chimera: "Single-epitope-mediated suppression" to stabilize a polyclonal autoimmune T-cell process"; Eur. J. Immunol.; vol. 40, pp. 2277-2288 (2010).
Lin, et al.; "The PD-1/PD-L1 complex resembles the antigen-binding Fv domains of antibodies and T cell receptors"; PNAS; vol. 105, No. 8, pp. 3011-3016 (Feb. 26, 2008).
Liu, et al.; "Attaining High Transient Titers in CHO Cells"; Genetic Engineering & Biotechnology News; vol. 35, No. 17, 3 pages (Oct. 1, 2015).
Liu, et al.; "Major Histocompatibility Complex: Interaction with Peptides"; eLS; 12 pages (Aug. 15, 2011).
Lloyd, et al.; "Modelling the human immune response: performance of a 1011 human antibody repertoire against a broad panel of therapeutically relevant antigens"; Protein Engineering, Design & Selection; vol. 22, No. 3, pp. 159-168 (2009).
Mallone, et al.; "T Cell Recognition of Autoantigens in Human Type 1 Diabetes: Clinical Perspectives"; Clinical and Developmental Immunology; vol. 2011, 16 pages (2011).
Margalit, et al.; "Induction of Antitumor Immunity by CTL Epitopes Genetically Linked to Membrane-Anchored β2-Microglobulin"; The Journal of Immunology; vol. 176, pp. 217-224 (2006).
Martin-Orozco, et al.; "Melanoma Cells Express ICOS Ligand to Promote the Activation and Expansion of T-Regulatory Cells"; Cancer Research; vol. 70, No. 23, pp. 9581-9590 (2010).
McAllister, et al.; "Adaptation of Recombinant HEK-293 Cells to Growth in Serum Free Suspension"; Animal Cell Technology: Products from Cells, Cells as Products; 3 pages (1999).
McNally, et al.; "CD4+CD25+ regulatory T cells control CD8+ T-cell effector differentiation by modulating IL-2 homeostasis"; PNAS; vol. 108, No. 18, pp. 7529-7534 (May 3, 2011).
Medina, et al.; "PD-1 Pathway Inhibitors: Immuno-Onology Agents for Restoring Anititumor Immune Responses"; Pharmacotherapy; vol. 36, No. 3, pp. 317-334 (Mar. 2016).
Miao, et al.; "Transient expression of fluorescent fusion proteins in protoplasts of suspension cultured cells"; Nature Protocols; vol. 2, No. 10, pp. 2348-2353 (2007).

Michels, et al.; "Islet-Derived CD4 T Cells Targeting Proinsulin in Human Autoimmune Diabetes"; Diabetes; vol. 66, pp. 722-734 (Mar. 2017).
Mizukoshi, et al.; "Identification of α-fetoprotein-derived peptides recognized by cytotoxic T lymphocytes in HLA-A24+ patients with hepatocellular carcinoma"; Int. J. Cancer; vol. 118, pp. 1194-1204 (2006).
Mott, et al.; "The Solution Structure of the F42A Mutant of Human Interleukin 2"; J. Mol. Biol.; vol. 247, pp. 979-994 (1995).
Mottez, et al.; "Cells Expressing a Major Histocompatibility Complex Class I Molecule with a Single Covalently Bound Peptide Are Highly Immunogenic"; J. Exp. Med.; vol. 181, pp. 493-502 (Feb. 1995).
Motz, et al.; "Tumor Endothelium FasL Establishes a Selective Immune Barrier Promoting Tolerance in Tumors"; Nat. Med.; vol. 20, No. 6, pp. 607-615 (Jun. 2014).
Muller, et al.; "Random peptide libraries displayed on adeno-associated virus to select for targeted gene therapy vectors"; Nature Biotechnology; vol. 21, No. 9, pp. 1040-1046 (Sep. 2003).
Naidoo, et al.; "Toxicities of the anti-PD-1 and anti-PD-L1 immune checkpoint antibodies"; Annals of Oncology; vol. 26, pp. 2375-2391 (Sep. 2015).
Nielsen, et al.; "MHC Class II epitope predictive algorithms"; Immunology; vol. 130, pp. 319-328 (2010).
Oates, et al.; "ImmTACs: Novel bi-specific agents for targeted cancer therapy"; OncoImmunology; vol. 2, No. 2, 3 pages (Feb. 2013).
Obermann, et al.; "Peptide-β2-microglobulin-major histocompatibility complex expressing cells are potent antigen-presenting cells that can generate specific T cells"; Immunology; vol. 122, pp. 90-97 (2007).
Ochoa-Garay, et al.; "The Ability of Peptides to Induce Cytotoxic T Cells In Vitro Does Not Strongly Correlate with Their Affinity for the $H-2L^d$ Molecule: Implications for Vaccine Design and Immunotherapy"; Molecular Immunology; vol. 34, No. 3, pp. 273-281 (1997).
Oka, et al.; "Induction of WT1 (Wilms' tumor gene)-specific cytotoxic T lymphocytes by WT1 peptide vaccine and the resultant cancer regression"; PNAS; vol. 101, No. 38, pp. 13885-13890 (Sep. 21, 2004).
Oliveira, et al.; "Design, Immune Responses and Anti-Tumor Potential of an HPV16 E6E7 Multi-Epitope Vaccine"; PLoS One; vol. 10, No. 9, 13 pages (Sep. 21, 2015).
PDB:1I8L_A; "Chain A, T Lymphocyte Activation Antigen Cd80" 2 pages (Dec. 27, 2012).
Peach, et al.; "Both Extracellular Immunoglobin-like Domains of CD80 Contain Residues Critical for Binding T Cell Surface Receptors CTLA-4 and CD28*"; The Journal of Biological Chemistry; vol. 270, No. 36, pp. 21181-21187 (1995).
Ponstingl, et al.; "The Rule of Antibody Structure: The Primary Structure of a Monoclonal IgG1 Immunoglobulin (Myeloma Protein Nie)"; Hoppe Seylers Z Physiol Chem.; vol. 357, No. 11, pp. 1571-1604 (Nov. 1976). [English translation of Abstract Only].
Poosarla, et al.; "Computational De Novo Design of Antibodies Binding to a Peptide With High Affinity"; Biotechnology & Bioengineering; vol. 114, No. 6, pp. 1331-1342 (Jun. 2017).
Preda, et al.; "Soluble, dimeric HLA DR4-peptide chimeras: An approach for detection and immunoregulation of human type-1 diabetes"; Eur. J. Immunol.; vol. 35, pp. 2763-2776 (Aug. 16, 2005).
Quayle, et al.; "CUE-101, a Novel HPV16 E7-pHLA-IL-2-Fc Fusion Protein, Enhances Tumor Antigen Specific T Cell Activation for the Treatment of HPV16-Driven Malignancies"; Clinical Cancer Research; vol. 26, No. 8, pp. 1953-1964 (Jan. 21, 2020).
Quayle, et al.; "Immuno-STAT(TM) (Selective Targeting and Alteration of T cells) Platform: Targeting Tumor Heterogeneity and Tumor Escape Mechanisms"; DOI:10.1158/1078-0432.CCR-19-3354; URL:https://www.cuebiopharma.com/our-appro ch/scien ific-presentations-publications/; 1 page (Jan. 21, 2020).
Rabu, et al.; "Production of recombinant human trimeric CD137L (4-1BBL). Cross-linking is essential to its T cell co-stimulation activity"; The Journal of Biological Chemistry; vol. 280, No. 50, pp. 41472-41481 (Dec. 16, 2005).

(56) References Cited

OTHER PUBLICATIONS

Ramani, et al.; "A secreted protein microarray platform for extracellular protein interaction discovery"; Analytical Biochemistry; vol. 420, pp. 127-138 (2012).

Reche, et al.; "Sequence Variability Analysis of Human Class I and Class II MHC Molecules: Functional and Structural Correlates of Amino Acid Polymorphisms"; Journal of Molecular Biology; vol. 331, No. 3, pp. 623-641 (Aug. 15, 2003).

Repana, et al.; "The Network of Cancer Genes (NCG): a comprehensive catalogue of known and candidate cancer genes from cancer sequencing screens"; Genome Biology; vol. 20, No. 1, 12 pages (2019).

Ressing, et al.; "Human CTL epitopes encoded by human papillomavirus type 16 E6 and E7 identified through in vivo and in vitro immunogenicity studies of HLA-A*0201-binding peptides"; The Journal of Immunology; vol. 154, pp. 5934-5943 (1995).

Rocha-Zavaleta, et al.; "Interleukin-2 (IL-2) receptor-βγ signalling is activated by c-Kit in the absence of IL-2, or by exogenous IL-2 via JAK3/STAT5 in human papillomavirus-associated cervical cancer"; Cellular Signalling; vol. 16, pp. 1239-1247 (2004).

Sang, et al.; "Long-term silencing of autoimmune diabetes and improved life expectancy by a soluble pHLA-DR4 chimera in a newly-humanized NOD-DR4/B7 mouse"; Human Vaccines & Immunotherapeutics; vol. 10, No. 3, pp. 693-699 (Mar. 2014).

Schmittnaegel, et al.; "A New Class of Bifunctional Major Histocompatibility Class I Antibody Fusion Molecules to Redirect CD8 T Cells"; Molecular Cancer Therapeutics; vol. 15, No. 9, pp. 2130-2142 (Sep. 2016).

Schumacher, et al.; "Neoantigens in cancer immunotherapy"; Science; vol. 348, No. 6230, pp. 69-74 (Apr. 2, 2015).

Seidel, et al.; "Peptide-HLA-based immunotherapeutics platforms for direct modulation of antigen-specific T cells"; Scientific Reports; vol. 11, No. 19220, 8 pages (Sep. 2021).

Shah, et al.; "Bio-layer Interferometry for Measuring Kinetics of Protein-protein Interactions and Allosteric Ligand Effects"; Journal of Visualized Experiments; vol. 84, 11 pages (2014).

Sharma, et al.; "A synthetic chimeric peptide harboring human papillomavirus 16 cytotoxic T lymphocyte epitopes shows therapeutic potential in a murine model of cervical cancer"; Immunologic Research; 58(1): p. 132-138 (2014).

Solinas, et al.; "The rationale behind targeting the ICOS-ICOS ligand costimulatory pathway in cancer immunotherapy"; ESMO Open; vol. 5, 7 pages (Jan. 2020).

Spang, et al.; "Heterodimeric Barnase-Barstar Vaccine Molecules: Influence of One versus Two Targeting Units Specific for Antigen Presenting Cells"; PLoS One; vol. 7, No. 9, 11 pages (Sep. 2012).

Stadinski, et al.; "Diabetogenic T cells recognize insulin bound to IAg7 in an unexpected, weakly binding register"; PNAS; vol. 107, No. 24, pp. 10978-10983 (Jun. 15, 2010).

Stamper, et al.; "Crystal structure of the B7-1/CTLA-4 complex that inhibits human immune responses"; Nature; vol. 410, pp. 608-611 (Mar. 29, 2001).

Stauber et al.; "Crystal structure of the IL-2 signaling complex: Paradigm for a heterotrimeric cytokine receptor"; Proc. Natl. Acad. Sci.; vol. 103, No. 8, pp. 2788-2793 (Feb. 21, 2006).

Strohl; "Optimization of Fc-mediated effector functions of monoclonal antibodies"; Current Opinion in Biotechnology; vol. 20, pp. 685-691 (2009).

Tafuro, et al.; "Reconstitution of antigen presentation in HLA class I-negative cancer cells with peptide-β2m fusion molecules"; Eur. J. Immunol.; vol. 31, pp. 440-449 (2001).

Tan, et al.; "Type 1 diabetes induction in humanized mice"; PNAS; vol. 114, No. 41, pp. 10954-10959 (Oct. 10, 2017).

Taube, et al.; "Lentivirus Display: Stable Expression of Human Antibodies on the Surface of Human Cells and Virus Particles"; PLoS One; vol. 3, No. 9, 12 pages (Sep. 2008).

Tham, et al.; "Activation of antigen-specific T cells by artificial cell constructs having immobilized multimeric peptide-class I complexes and recombinant B7-Fc proteins"; Journal of Immunological Methods; vol. 249, pp. 111-119 (2001).

Torres, et al.; "The immunoglobulin constant region contributes to affinity and specificity"; Trends in Immunology; vol. 29, No. 2, pp. 91-97 (Jan. 10, 2008).

Toukam, et al.; "Targeting Antibody Responses to the Membrane Proximal External Region of the Envelope Glycoprotein of Human Immunodeficiency Virus"; PLoS One; vol. 7, No. 5, 10 pages (May 2012).

Trolle, et al.; "The length distribution of class I restricted T cell epitopes is determined by both peptide supply and MHC allele specific binding preference"; J Immunol; vol. 196, No. 4, pp. 1480-1487 (Feb. 15, 2016).

Unverdorben, et al.; "Pharmacokinetic properties of IgG and various Fc fusion proteins in mice"; MABS; vol. 8, No. 1, pp. 120-128 (Oct. 29, 2015).

Van Der Burg, et al.; "An HLA Class I Peptide-Binding Assay Based on Competition for Binding to Class I Molecules on Intact Human B Cells Identification of Conserved HIV-1 Polymerase Peptides Binding to HLA-A*0301"; Hum. Immunol.; vol. 44, No. 4, pp. 189-198 (Dec. 1995).

Venkatakrishnan, et al.; "The Structural Biology of Hepatitis B Virus: Form and Function"; Annu. Rev. Virol.; vol. 3, No. 1, pp. 429-451 (Sep. 29, 2016).

Vitello, et al.; "Neoantigen prediction and the need for validation"; Nature Biotechnology; vol. 35, No. 9, pp. 815-817 (Sep. 2017).

Wang, et al.; "Molecular Modeling and Functional Mapping of B7-H1 and B7-DC Uncouple Costimulatory Function from PD-1 Interaction"; J. Exp. Med.; vol. 197, No. 9, pp. 1083-1091 (May 5, 2003).

Wang, et al.; "Using a baculovirus display library to identify MHC class I mimotopes"; PNAS; vol. 102, No. 7, pp. 2476-2481 (Feb. 15, 2005).

Wen, et al.; "Construction and screening of an antigen-derived peptide library displayed on yeast cell surface for CD4+ T cell egitoge identification"; Methods Mol. Biol.; vol. 1061, pp. 245-264 (2013).

White, et al.; "Soluble Class I MHC with β$_2$-MicroglobulinCovalently Linked Peptides: Specific Binding to a T Cell Hybridoma"; J Immunol; vol. 162, pp. 2671-2676 (1999).

Whitehead, et al.; "Optimization of affinity, specificity and function of designed influenza inhibitors using deep seguencing"; Nat. Biotechnol.; vol. 30, No. 6, pp. 543-548 (Apr. 29, 2013).

Wieczorek, et al.; "Major Histocompatibility Complex (MHC) Class I and MHC Class II Proteins: Conformational Plasticity in Antigen Presentation"; Frontiers in Immunology; vol. 8, No. 292, pp. 1-16 (Mar. 2017).

Won, et al.; "The structure of the trimer of human 4-1BB ligand is unique among members of the tumor necrosis factor superfamily"; J Biol Chem; vol. 285, No. 12, pp. 9202-9210 (Mar. 19, 2010).

Woodham, et al.; "In vivo detection of antigen-specific CD8T cells by immune-positron emission tomography"; Nat Methods.; vol. 17, No. 10, pp. 1025-1032 (Oct. 2020).

Wu, et al.; "Remote control of therapeutic T cells through a small molecule-gated chimeric receptor"; Science; vol. 350, No. 6258, 12 pages (Oct. 16, 2015).

Wu, et al.; "Simultaneous targeting of multiple disease mediators by a dual-variable-domain immunoglobulin"; Nature Biotechnology; 25: p. 1290-1297 (2007).

Xu, et al.; "Cytokine release syndrome in cancer immunotherapy with chimeric antigen receptor engineered T cells"; Cancer Letters; 343(2): p. 172-178 (2014).

Zhang, et al.; "Monoclonal antibody blocking the recognition of an insulin peptide-MHC complex modulates type 1 diabetes"; PNAS; vol. 111, No. 7, pp. 2656-2661 (Feb. 18, 2014).

Zheng, et al.; "B7-CTLA4 interaction enhances both production of antitumor cytotoxic T lymphocytes and resistance to tumor challenge"; PNAS; vol. 95, pp. 6284-6289 (May 1998).

Zhou, et al.; "Epitopes of MUC1 Tandem Repeats in Cancer as Revealed by Antibody Crystallography: Toward Glycogegtide Signature-Guided Therapy"; Molecules; vol. 23, No. 1326, 27 pages (2018).

Ziauddin, et al.; "Microarrays of cells expressing defined cDNAs"; Nature; vol. 411, pp. 107-110 (May 3, 2011).

\* cited by examiner

FIG. 2A

IL2 – *Homo sapiens*

APTSSSTKKT QLQLEHLLLD LQMILNGINN YKNPKLTRML TFKYMPKKA TELKHLQCLE
EELKPLEEVL NLAQSKNFHL RPRDLISNIN VIVLELKGSE TTFMCEYADE TATIVEFLNR
WITFCQSIIS TLT (SEQ ID NO:1)

FIG. 2B

IL2(F42X) (SEQ ID NO:38)

APTSSSTKKT QLQLEHLLLD LQMILNGINN YKNPKLTRML TXKFYMPKKA TELKHLQCLE
EELKPLEEVL NLAQSKNFHL RPRDLISNIN VIVLELKGSE TTFMCEYADE TATIVEFLNR
WITFCQSIIS TLT

FIG. 2C

IL2(D20X) (SEQ ID NO:39)

APTSSSTKKT QLQLEHLLLX LQMILNGINN YKNPKLTRML TFKFYMPKKA TELKHLQCLE
EELKPLEEVL NLAQSKNFHL RPRDLISNIN VIVLELKGSE TTFMCEYADE TATIVEFLNR
WITFCQSIIS TLT

FIG. 2D

IL2(E15X) (SEQ ID NO:40)

APTSSSTKKT QLQLXHLLLD LQMILNGINN YKNPKLTRML TFKFYMPKKA TELKHLQCLE
EELKPLEEVL NLAQSKNFHL RPRDLISNIN VIVLELKGSE TTFMCEYADE TATIVEFLNR
WITFCQSIIS TLT

FIG. 2E

IL2(H16X)(SEQ ID NO:41)

APTSSSTKKT QLQLEXLLLD LQMILNGINN YKNPKLTRML TFKFYMPKKA TELKHLQCLE
EELKPLEEVL NLAQSKNFHL RPRDLISNIN VIVLELKGSE TTFMCEYADE TATIVEFLNR
WITFCQSIIS TLT

FIG. 2F

IL2(Y45X)(SEQ ID NO:42)

APTSSSTKKT QLQLEHLLLD LQMILNGINN YKNPKLTRML TFKFXMPKKA TELKHLQCLE
EELKPLEEVL NLAQSKNFHL RPRDLISNIN VIVLELKGSE TTFMCEYADE TATIVEFLNR
WITFCQSIIS TLT

FIG. 2G

IL2(Q126X)(SEQ ID NO:43)

APTSSSTKKT QLQLEHLLLD LQMILNGINN YKNPKLTRML TFKFYMPKKA TELKHLQCLE
EELKPLEEVL NLAQSKNFHL RPRDLISNIN VIVLELKGSE TTFMCEYADE TATIVEFLNR
WITFCXSIIS TLT

FIG. 2H

IL2(F42X;H16X)(SEQ ID NO:44)

APTSSSTKKT QLQLEXLLLD LQMILNGINN YKNPKLTRML TXKFYMPKKA TELKHLQCLE
EELKPLEEVL NLAQSKNFHL RPRDLISNIN VIVLELKGSE TTFMCEYADE TATIVEFLNR
WITFCQSIIS TLT

FIG. 2I

IL2 (F42X; D20X) (SEQ ID NO:45)

APTSSSTKKT QLQLEHLLLX LQMILNGINN YKNPKLTRML TXKFYMPKKA TELKHLQCLE
EELKPLEEVL NLAQSKNFHL RPRDLISNIN VIVLELKGSE TTFMCEYADE TATIVEFLNR
WITFCQSIIS TLT

FIG. 2J

IL2 (F42X; D20X; E15X) (SEQ ID NO:46)

APTSSSTKKT QLQLXHLLLX LQMILNGINN YKNPKLTRML TXKFYMPKKA TELKHLQCLE
EELKPLEEVL NLAQSKNFHL RPRDLISNIN VIVLELKGSE TTFMCEYADE TATIVEFLNR
WITFCQSIIS TLT

FIG. 2K

IL2 (F42X; D20X; H16X) (SEQ ID NO:47)

APTSSSTKKT QLQLEXLLLX LQMILNGINN YKNPKLTRML TXKFYMPKKA TELKHLQCLE
EELKPLEEVL NLAQSKNFHL RPRDLISNIN VIVLELKGSE TTFMCEYADE TATIVEFLNR
WITFCQSIIS TLT

FIG. 2L

IL2 (F42X; D20X; Q126X) (SEQ ID NO:48)

APTSSSTKKT QLQLEHLLLX LQMILNGINN YKNPKLTRML TXKFYMPKKA TELKHLQCLE
EELKPLEEVL NLAQSKNFHL RPRDLISNIN VIVLELKGSE TTFMCEYADE TATIVEFLNR
WITFCXSIIS TLT

FIG. 2M

IL2 (F42X; D20X; Y45X) (SEQ ID NO:49)

APTSSSTKKT QLQLEHLLLX LQMILNGINN YKNPKLTRML TXKFXMPKKA TELKHLQCLE
EELKPLEEVL NLAQSKNFHL RPRDLISNIN VIVLELKGSE TTFMCEYADE TATIVEFLNR
WITFCQSIIS TLT

FIG. 2N

IL2 (F42X; D20X; Y45X; H16X) (SEQ ID NO:50)

APTSSSTKKT QLQLEXLLLX LQMILNGINN YKNPKLTRML TXKFXMPKKA TELKHLQCLE
EELKPLEEVL NLAQSKNFHL RPRDLISNIN VIVLELKGSE TTFMCEYADE TATIVEFLNR
WITFCQSIIS TLT

FIG. 2O

IL2 (F42X; D20X; Y45X; Q126X) (SEQ ID NO:51)

APTSSSTKKT QLQLEHLLLX LQMILNGINN YKNPKLTRML TXKFXMPKKA TELKHLQCLE
EELKPLEEVL NLAQSKNFHL RPRDLISNIN VIVLELKGSE TTFMCEYADE TATIVEFLNR
WITFCXSIIS TLT

FIG. 2P

IL2 (F42X; D20X; Y45X; H16X; Q126X) (SEQ ID NO:52)

APTSSSTKKT QLQLEXLLLX LQMILNGINN YKNPKLTRML TXKFXMPKKA TELKHLQCLE
EELKPLEEVL NLAQSKNFHL RPRDLISNIN VIVLELKGSE TTFMCEYADE TATIVEFLNR
WITFCXSIIS TLT

FIG. 2Q

IL2 – (F42X, H16X, Q126X) (SEQ ID NO:53)

APTS

FIG. 3A
IL2R-alpha chain (SEQ ID NO:54)
*Homo sapiens*

```
  1 MDSYLLMWGL LTFIMVPGCQ AELCDDDPPE IPHATFKAMA YKEGTMLNCE CKRGFRRIKS
 61 GSLYMLCTGN SSHSSWDNQC QCTSSATRNT TKQVTPQPEE QKERKTTEMQ SPMQPVDQAS
121 LPGHCREPPP WENEATERIY HFVVGQMVIY QCVQGYRALH RGPAESVCKM THGKTRWTQP
181 QLICTGEMET SQFPGEEKPQ ASPEGRPESE TSCLVTTTDF QIQTEMAATM ETSIFTTEYQ
241 VAVAGCVFLL ISVLLLSGLT WQRRQRKSRR TI
```

Mature = amino acids 22-272

FIG. 3B
IL2R-beta chain (SEQ ID NO:55)
*Homo sapiens*

```
  1 MAAPALSWRL PLLILLLPLA TSWASAAVNG TSQFTCFYNS RANISCVWSQ DGALQDTSCQ
 61 VHAWPDRRRW NQTCELLPVS QASWACNLIL GAPDSQKLTT GAPDSQKLTT VDIVTLRVLC REGVRWRVMA
121 IQDFKPFENL RLMAPISLQV VHVETHRCNI SWEISQASHY FERHLEFEAR TLSPGHTWEE
181 APLLTLKQKQ EWICLETLTP DTQYEFQVRV KPLQGEFTTW SPWSQPLAFR TKPAALGKDT
241 IPWLGHLLVG LSGAFGFIIL VYLLINCRNT GPWLKKVLKC NTPDPSKFFS QLSSEHGGDV
301 QKWLSSPFPS SSFSPGGLAP EISPLEVLER DKVTQLLLQQ DKVPEPASLS SNHSLTSCFT
361 NQGYFFFHLP DALEIEACQV YFTYDPYSEE DPDEGVAGAP TGSSPQPLQP LSGEDDAYCT
421 FPSRDDLLLF SPSLLGGPSP PSTAPGGSGA GEERMPPSLQ ERVPRDWDPQ PLGPPTPGVP
481 DLVDFQPPPE LVLREAGEEV PDAGPREGVS FPWSRPPGQG EFRALNARLP LNTDAYLSLQ
541 ELQGQDPTHL V
```

Mature = amino acids 27-551

FIG. 3C
IL2R-gamma chain (SEQ ID NO:56)
*Homo sapiens*

```
  1 MLKPSLPFTS LLFLQLPLLG VGLNTTILTP NGNEDTTADF FLTTMPTDSL SVSTLPLPEV
 61 QCFVFNVEYM NCTWNSSSEP QPTNLTLHYW YKNSDNDKVQ KCSHYLFSEE ITSGCQLQKK
121 EIHLYQTFVV QLQDPREPRR QATQMLKLQN LVIPWAPENL TLHKLSESQL ELNWNNRFLN
181 HCLEHLVQYR TDWDHSWTEQ SVDYRHKFSL PSVDGQKRYT FRVRSRFNPL CGSAQHWSEW
241 SHPIHWGSNT SKENPFLFAL EAVVISVGSM GLIISLLCVY FWLERTMPRI PTLKNLEDLV
301 TEYHGNFSAW SGVSKGLAES LQPDYSERLC LVSEIPPKGG ALGEGPGASP CNQHSPYWAP
361 PCYTLKPET
```

Mature = amino acids 23-369

Figure 4A
GenBank 3S7G_A (SEQ ID NO: 57)
*Homo sapiens* IgG1 Fc
227 aa

```
  1 dkthtcppcp apellggpsv flfppkpkdt lmisrtpevt cvvvdvshed pevkfnwyvd
 61 gvevhnaktk preeqynsty rvvsvltvlh qdwlngkeyk ckvsnkalpa piektiskak
121 gqprepqvyt lppsrdeltk nqvsltclvk gfypsdiave wesngqpenn ykttppvlds
181 dgsfflyskl tvdksrwqqg nvfscsvmhe alhnhytqks lslspgk
```

GenBank AAN76044 (SEQ ID NO: 58)
*Homo sapiens* IgG2 Fc (amino acids 99-325)
227 aa

```
  1 stkgpsvfpl apcsrstses taalgclvkd yfpepvtvsw nsgaltsgvh tfpavlqssg
 61 lyslssvvtv pssnfgtqty tcnvdhkpsn tkvdktverk ccvecppcpa ppvagpsvfl
121 fppkpkdtlm isrtpevtcv vvdvshedpe vqfnwyvdgv evhnaktkpr eeqfnstfrv
181 vsvltvvhqd wlngkeyk ck istkt qkg prepqvytlp psreemtkn q
241 vsltclvkgf ypsdiavewe sngqpennyk ttppmldsdg sfflyskltv dksrwqqgnv
301 fscsvmheal hnhytqksls lspgk
```

GenBank AAW65947 (SEQ ID NO: 59)
*Homo sapiens* IgG3 Fc (amino acids 19-246)
238 aa

```
  1 hkpsntkvdk rveiktplgd ttht cppcpa peliggpsvf lfppkpkdtl misrtpevtc
 61 vvvdvshedp evkfnwyvdg vevhnaktkp reeqynstyr vvsvltvlhq dwlngkeykc
121 kvsnkalpap iektiskakg qprepqvytl ppsrdeltkn qvsltclvkg fypsdiavew
181 esngqpenny kttppvldsd gsfflyskit vdksrwqqgn vfscsvmhea lhnhytqksl
241 slspgk
```

Figure 4B

GenBank AAA52770 (SEQ ID NO:60)
*Homo sapiens* IgD Fc (amino acids 162-383)
222 aa

```
  1 ptkapdvfpi isgcrhpkdn spvvlaciit gyhptsvtvt wymgtqsqpg rtfpeiqrrd
 61 syymtssqls tplqwrgge ykcvvqhtas kskkeifrwp espkaqassv ptaqpqaegs
121 lakattapat trntgrggee kkkekekeeq eeretktpec pshtqplgvy litpavqdiw
181 lrdkatftcf vvgsdlkdah itwevagkvp tggveeglle rhsngsqsqh srtlprsiw
241 nagtsvtctl nhpslppqri malrepaaqa pvkisinlla ssdppeaasw ilcevsgfsp
301 pnilimwled qrevntsgfa parpppqprs ttfwawsvlr vpappspqpa tytcvvshed
361 srtlinasrs levsyvtdhg pmk
```

GenBank O308221A (SEQ ID NO:61)
*Homo sapiens* IgM Fc
276 aa

```
  1 vtstltitkzs dwlgesmftc rvdhrgltfq qnassmcvpd qdtairvfai ppsfasiflt
 61 kstkltclvt dittybsvti swtreengav kthtniseash pnatfsavge asicedbdws
121 gerftctvth tdlpsplkqt isrpkgvaih rpbvyilppa rzzinlresa titclvtgfs
181 padvfvewmq rgeplspqky vtsapmpepq apgryfahsi ltvseeewnt ggtytcvvah
241 ealpnrvter tvdkstgkpt lynvslvmsd tagtcy
```

Figure 4C

GenBank P01876 (SEQ ID NO:62)
*Homo sapiens* IgA Fc (amino acids 120-353)
234 aa

```
  1 asptspkvfp lslcstqpdg nvviaclvqg ffpqeplsvt wsesgqgvta rnfppsqdas
 61 gdlyttsspl tipatqclag ksvtchvkhy tnpsqdvtvp cpvpstpptp spstpptpsp
121 scchprislh rpaledllg seanltctlt glrdasgvtf twtpssgksa vqgpperdic
181 gcysvssvlp gcaepwnhgk tftctaaype sktpitatls ksgntfrpev hllpppseel
241 alnelvtltc largfspkdv ivrwlqgsqe lprekyltwa srqepsqgtt tfavtsilrv
301 aaedwkkgdt fscmvghealp fscmvghal plaftqktid rlagkpthvn vsvvmaevdg tcy
```

GenBank 1F6A_B (SEQ ID NO:63)
*Homo sapiens* IgE Fc (amino acids 6-222)
212 aa

```
  1 adpcdsnprg vsaylsrpsp fdlfirkspt itclvvdlap skgtvnltws rasgkpvnhs
 61 trkeekqrng gtlrdwieget yqcrvthphl pralmrsttk tsgpraapev
121 yafatpewpg srdkrtlaci lqnfmpedis vqwlhnevgl pdarhsttqp rktkgsgffv
181 fsrlevtrae weqkdeficr avheaaspsq tvqravsvnp gk
```

GenBank P01861 (SEQ ID NO:64)
*Homo sapiens* IgG4 Fc (amino acids 100-327)
228 aa

```
  1 astkgpsvfp lapcsrstse staalgclvk dyfpepvtvs wnsgaltsgv htfpavlqss
 61 glyslssvvt vpssslgtkt ytcnvdhkps ntkvdkrves kygppcpscp apeflggpsv
121 flfppkpkdt lmisrtpevt cvvvdvsqed pevqfnwyvd gvevhnaktk preeqfnsty
181 rvvsvltvlh qdwlngkeyk ckvsnkgips siektiskak gqprepqvyt lppsqeemtk
241 nqvsltclvk gfypsdiave wesngqpenn ykttppvlds dgsfflysrl tvdksrwqeg
301 nvfscsvmhe alhnhytqks lslslgk
```

Figure 5A
*Homo sapiens* (SEQ ID NO:65)
GenBank NP_001229687
HLA-A
Amino acids 25-365

```
  1 mavmaprtll lilsgalalt qtwagshsmr yfftsvsrpg rgeprfiavg yvddtqfvrf
 61 dsdaasqkme prapwieqeg peywdqetrn mkahsqtdra nigtlrgyyn qsedgshtiq
121 imygcdvgpd grfirgyrqd aydgkdyial nedirswtaa dmaaqitkrk weavhaaeqr
181 rvylegrcvd girrylengk etlqrtdppk thmthhpisd heatlrcwai gfypaeitlt
241 wqrdgedqtq dteivetrpa gdgtfqkwaa vvvpsgeeqr ytchvqhegl pkpltirwel
301 ssqptipivg iiaglvllga vitgavvaav mwrrkssdrk ggsytqaass dsaggsdvsl
361 tackv
```

Figure 5B
*Homo sapiens* (SEQ ID NO:66)
GenBank NP_005505
HLA-B
Amino acids 25-362

```
  1 mlvmaprtvl lilsaalalt etwagshsmr yfytsvsrpg rgeprfisvg yvddtqfvrf
 61 dsdaaspree prapwieqeg peywdrntqi ykaqaqtdre sirnlrgyyn qseagshtiq
121 smygcdvgpd grlirghdqy aydgkdyial nedirswtaa dtaaqitqrk weaareaeqr
181 raylegecve wirrylengk dkleradppk thvthhpisd heatlrcwai gfypaeitlt
241 wqrdgedqtq dteivetrpa gdrtfqkwaa vvvpsgeeqr ytchvqhegl pkpltirwep
301 ssqstvpivg ivaglavlav vviqavvaav mcrrkssggk ggsysqaacs dsaqgsdvsl
361 ta
```

Figure 5C
*Homo sapiens*
GenBank NP_001229971 (SEQ ID NO:67)
HLA-C
Amino acids 25-366

```
  1 mrvmaprall llisgglalt etwacshsmr yfdtavsrpg rgeprfisvg yvddtqfvrf
 61 dsdaasprge prapwvegeg peywdretqn ykrqaqadrv sirnlrgyyn qsedgshtliq
121 rmygcdigpd grilrgydqs aydgkdyial nedirswtaa dtaaqitqrk leaaraaeql
181 raylegtcve wirrylengk etlqraeppk thvthhplsd heatlrcwai gfypaeitlt
241 wqrdgedgtq dteivetrpa gdgtfqkwaa vvvpsgqeqr ytchmqhegl qepltiswep
301 ssqptipimg ivaglavlvv lavlgavvta mmcrrkssgg kggscsqaac snsaggsdes
361 litcka
```

FIG. 6

```
NP_004039.1      MSRSVALAVLALLSLSGLEAIQRTPKIQVYSRHPAENGKSNFLNCYVSGFHPSDIEVDLL   60
NP_001009066.1   MSRSVALAVLALLSLSGLEAIQRTPKIQVYSRHPAENGKSNFLNCYVSGFHPSDIEVDLL   60
NP_001040602.1   MSRSVALAVLALLSLSGLEAIQRTPKIQVYSRHPPENGKPNFLNCYVSGFHPSDIEVDLL   60
NP_776318.1      MARFVALVLLGLLSLSGLDAIQRPEKIQVYSRHPPEDGKPNYLNCYVYGFHPPQIEIDLL   60
NP_033865.2      MARSVTLVFLVLVSLTGLYAIQKTPQIQVYSRHPPENGKRPNILNCYVTQFHPHIEIQML   60
                 *:*.* *:*:: *.* *  **:..:*:****** *:** *.:****.  **  *:: ::

NP_004039.1      KNGERIEKVEHSDLSFSKDWSFYLLYYTEFTPTEKDEYACRVNHVTLSQPKIVKWDRDM   119
NP_001009066.1   KNGERIEKVEHSDLSFSKDWSFYLLYYTEFTPTEKDEYACRVNHVTLSQPKIVKWDRDM   119
NP_001040602.1   KNGERKMGKVEHSDLSFSKDWSFYLLYYTEFTPNERDEYACRVNHVTLSGPRTVNWDRDM   119
NP_776318.1      KNGEKI-KSEQSDLSFSKDWSFYLLSHAEFTPMSKDQYSCRVKHVTLEQPRIVTWTRDLL  118
NP_033865.2      KNGKKIPKVEMSTMSFSKDWSFYILAHTEFTPTETDTYACRVRHASMAEPKTVYWDRDM   119
                 ***::* : . * :********:*  : ***. .*  *:***.*.:   *: * * **:
```

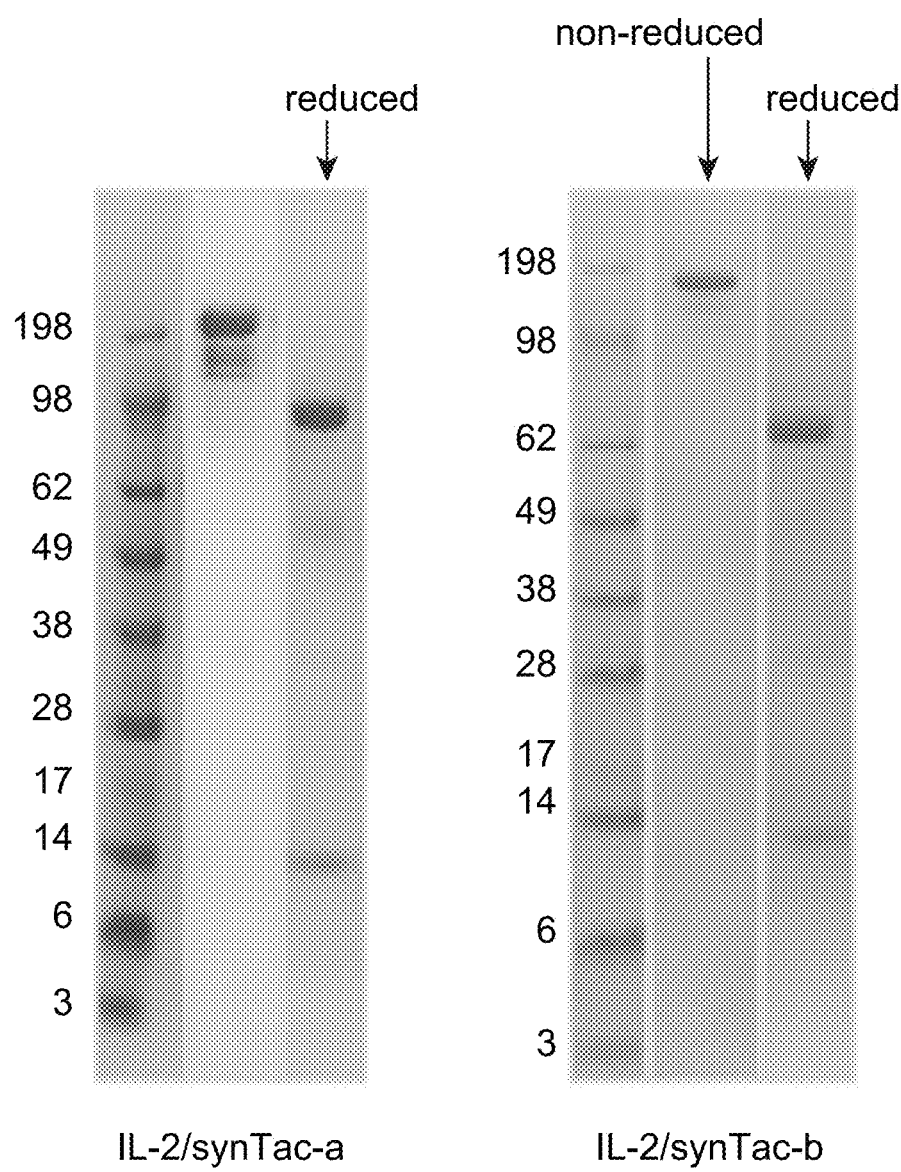

FIG. 12
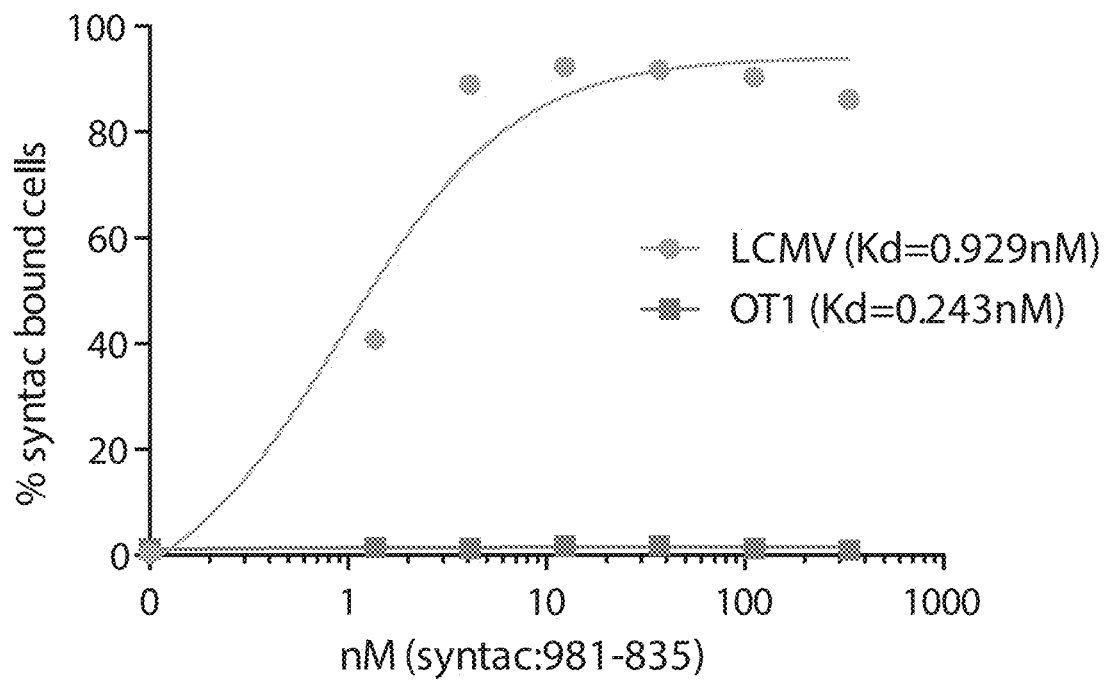
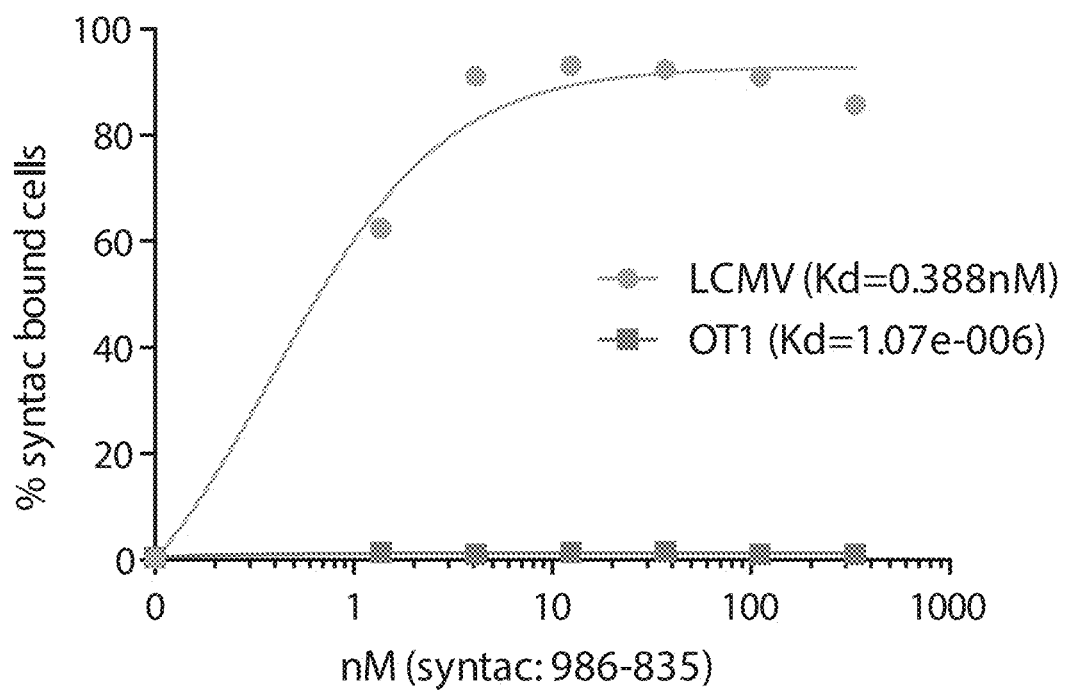

FIG. 13

Number of IL-2 Repeats versus Mutations

F42A 971-835 (1X-hIL2, F42A)

LCMV-1X-hIL2

- LCMV (EC50=11)
- BL6 (EC50=334)

X-axis: nM, Y-axis: % pSTAT5+

F42A, H16A 975-835 (1X-hIL2, F42A, H16A)

LCMV-1X-hIL2

- LCMV (EC50=78)
- BL6 (EC50=1129)

X-axis: nM, Y-axis: % pSTAT5+

FIG. 13 (Cont.)

Number of IL-2 Repeats versus Mutations

F42A

982-835 (2X-hIL2, F42A)

LCMV-2X-hIL2

- LCMV (EC50=3)
- BL6 (EC50=168)

y-axis: % pSTAT5+
x-axis: nM

F42A, H16A

986-835 (2X-hIL2, F42A, H16A)

LCMV-2X-hIL2

- LCMV (EC50=9)
- BL6 (EC50=356)

y-axis: % pSTAT5+
x-axis: nM

FIG. 13 (Cont.)

Number of IL-2 Repeats versus Mutations

F42A

993-835 (3X-hIL2, F42A)

LCMV-3X-hIL2

- LCMV (EC50=1)
- BL6 (EC50=50)

F42A, H16A

997-835 (3X-hIL2, F42A, H16A)

LCMV-3X-hIL2

- LCMV (EC50=10)
- BL6 (EC50=412)

FIG. 14A
One copy of IL-2
Mutation: F42A, D20K
Mutation: F42A, D20K, Q126A
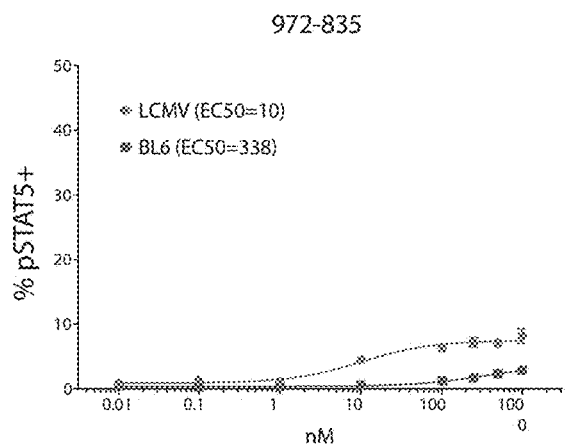
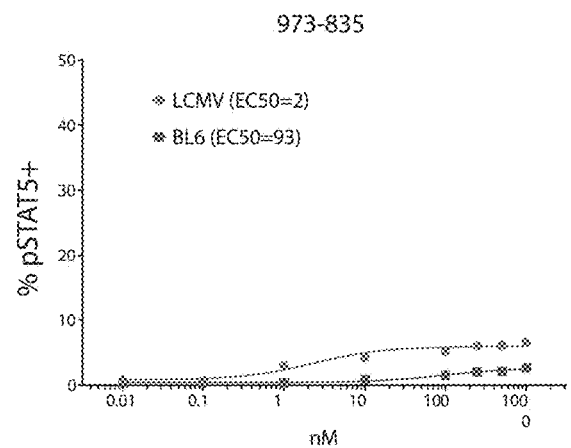
Mutation: F42A, D20K, E15A
Mutation: F42A, D20K, H16A
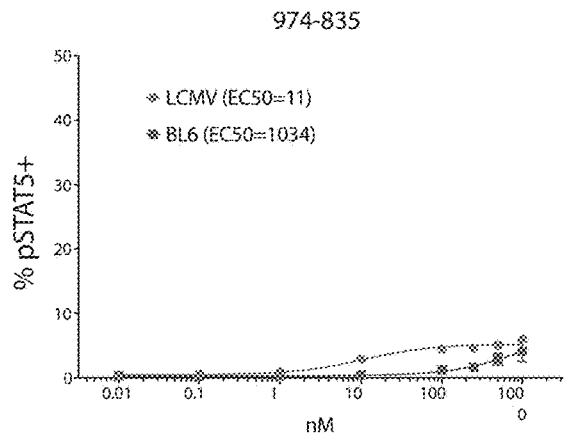
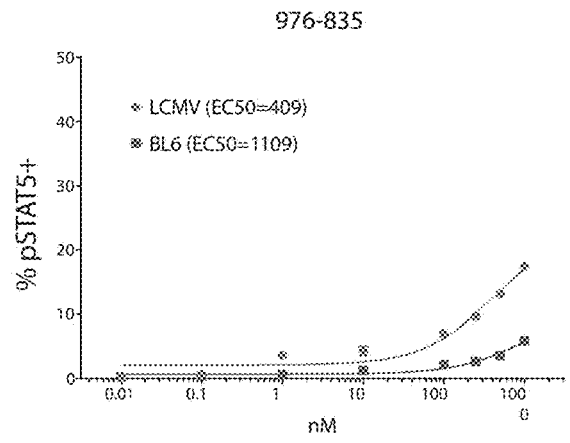

FIG. 14B
One copy of IL-2
Mutation: F42A, Y45A, D20K, H16A
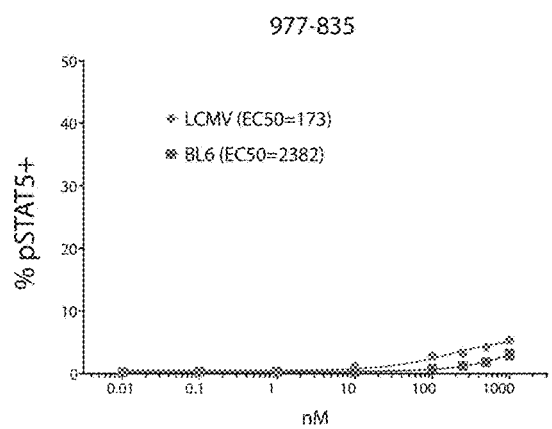
Mutation: F42A, Y45A, D20K
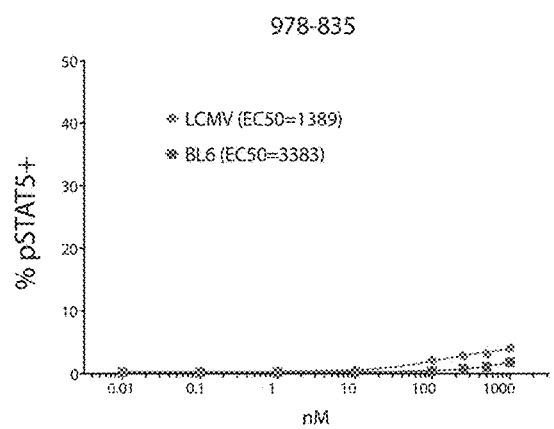
Mutation: F42A, Y45A, D20K, H16A, Q126A
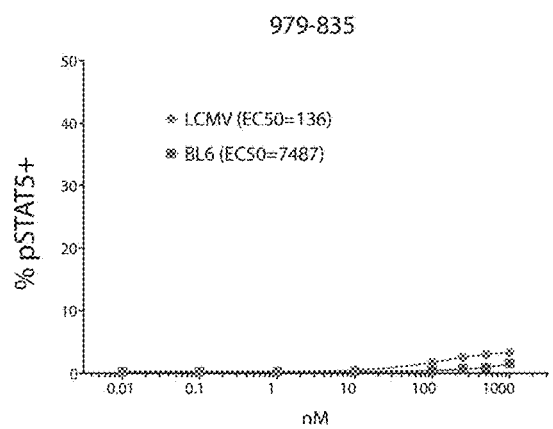
Mutation: F42A, Y45A, D20K, Q126A
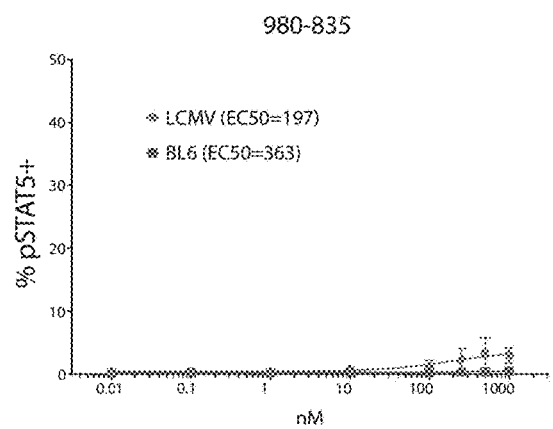

FIG. 14C
Two copies of IL-2
Mutation: F42A, D20K
Mutation: F42A, D20K, Q126A
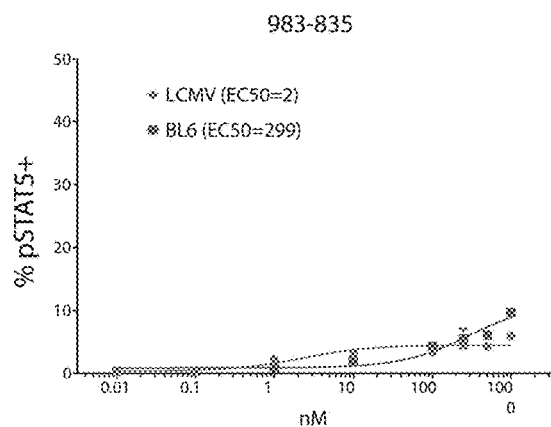
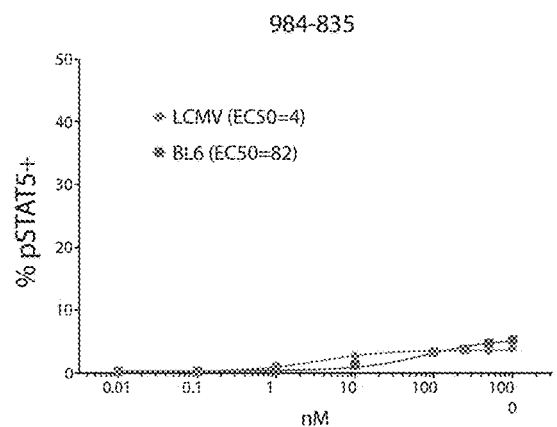
Mutation: F42A, D20K, H16A
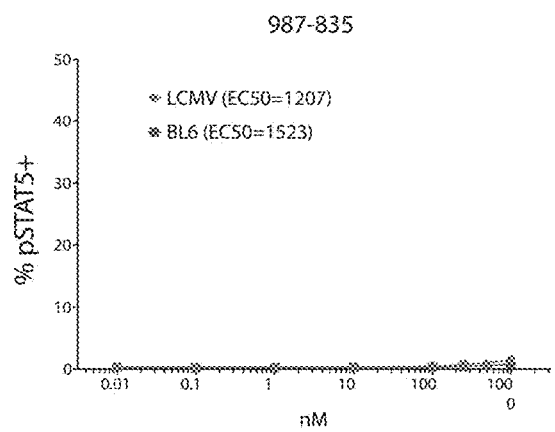

FIG. 14D
Two copies of IL-2
Mutation: F42A, Y45A, D20K, H16A
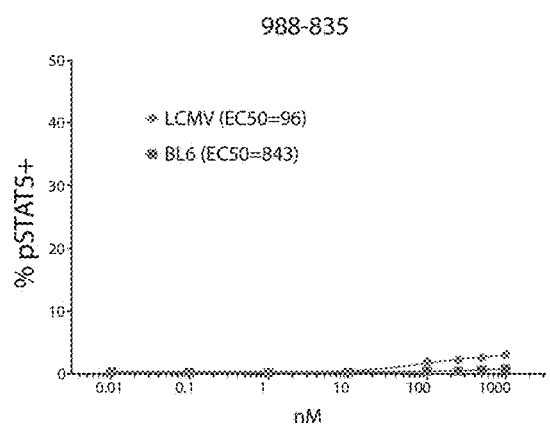
Mutation: F42A, Y45A, D20K
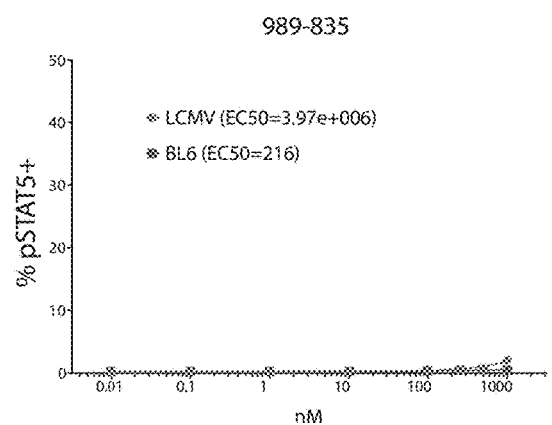
Mutation: F42A, Y45A, D20K, H16A, Q126A
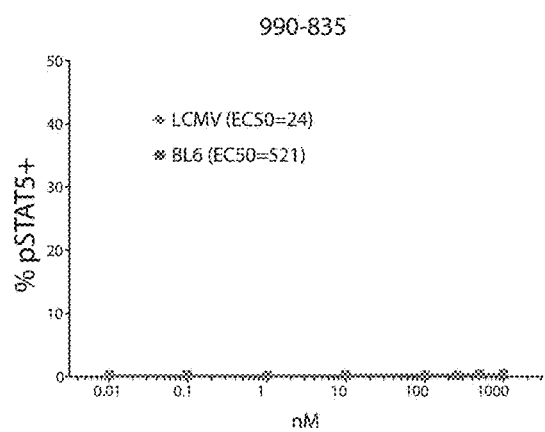
Mutation: F42A, Y45A, D20K, Q126A
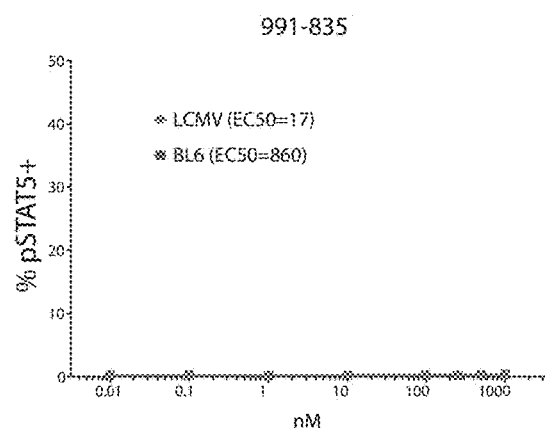

FIG. 14E
Three copies of IL-2
Mutation: F42A, D20K
Mutation: F42A, D20K, E15A
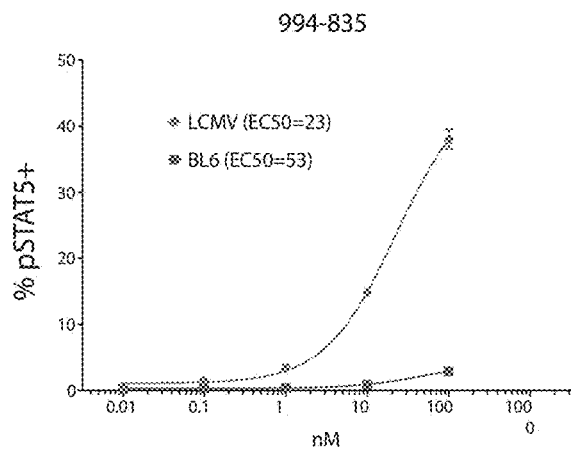
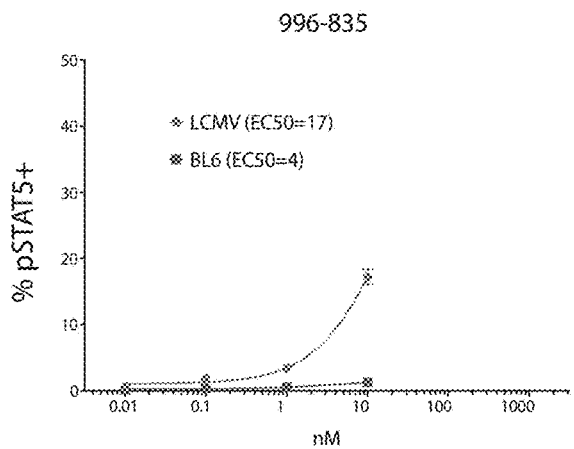
Mutation: F42A, D20K, H16A
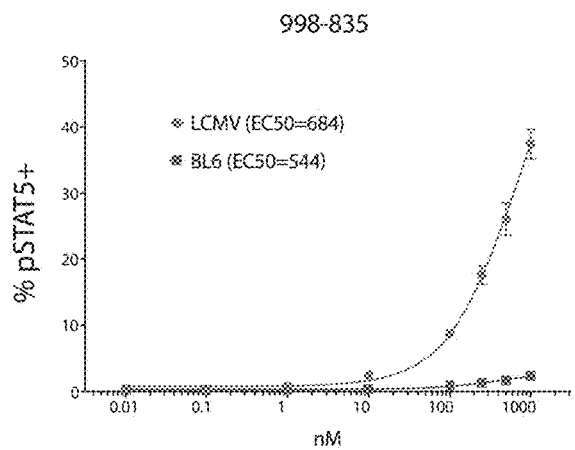

FIG. 14F
Three copies of IL-2
Mutation: F42A, Y45A, D20K, H16A
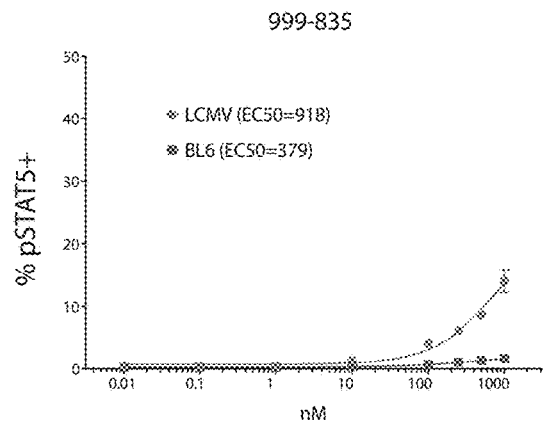
Mutation: F42A, Y45A, D20K
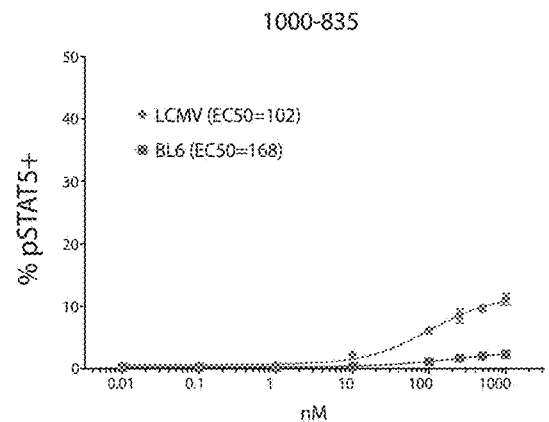
Mutation: F42A, Y45A, D20K, H16A, Q126A
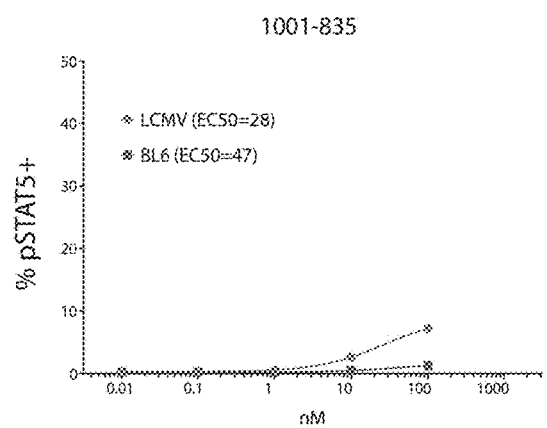
Mutation: F42A, Y45A, D20K, Q126A
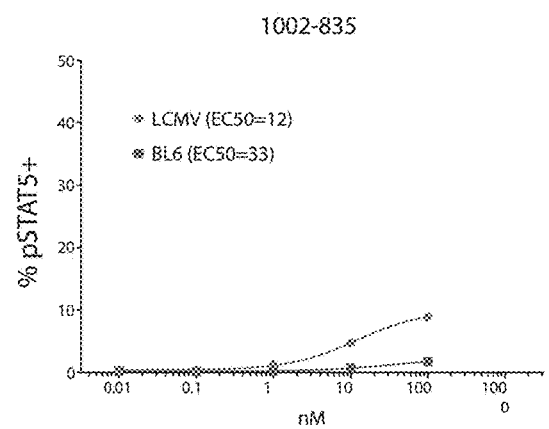

FIG. 15
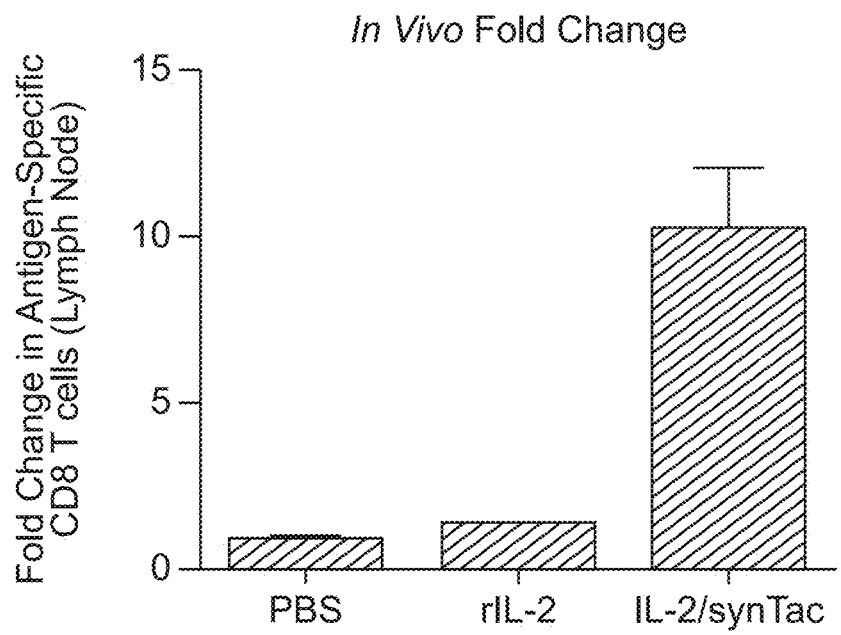
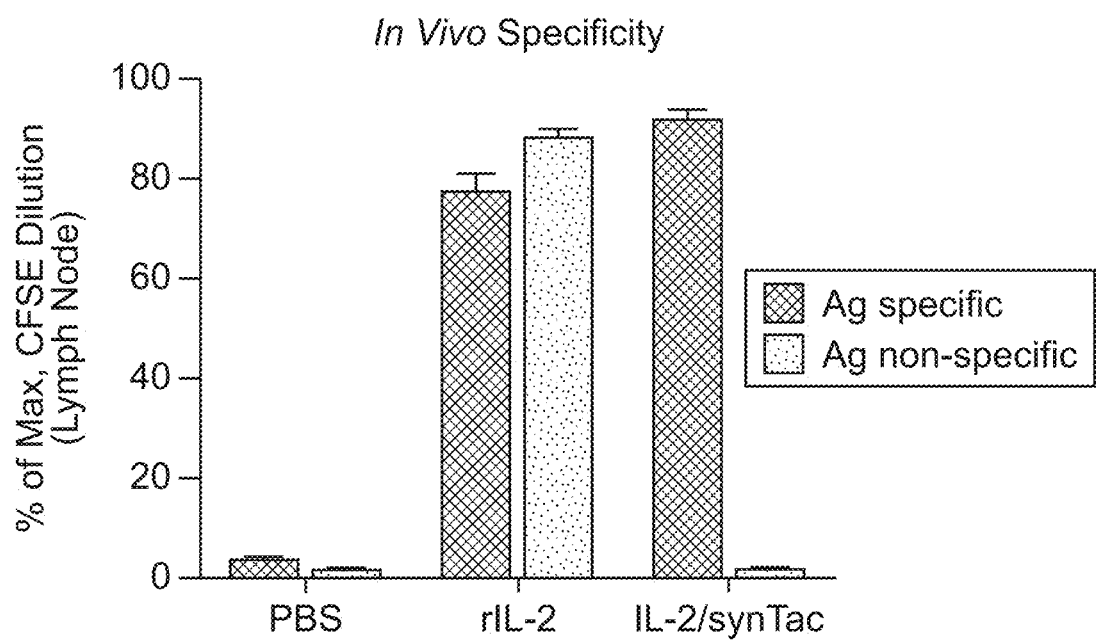

1X IL-2 (F42A, H16A)-Fc synTac

Western blot analysis

FIG. 21
CUE101-N297A with leader peptide (SEQ ID NO:68)

*MYRMQLLSCIALSLALVTNS*APTSSSTKKTQLQLEALLLDLQMILNGINNYKNPKLTRML
TAKFYMPKKATELKHLQCLEEELKPLEEVLNLAQSKNFHLRPRDLISNINVIVLELKGSE
TTFMCEYADETATIVEFLNRWITFCQSIISTLTGGGGSGGGGSGGGGSGGGGSAPTSSST
KKTQLQLEALLLDLQMILNGINNYKNPKLTRMLTAKFYMPKKATELKHLQCLEEELKPLE
EVLNLAQSKNFHLRPRDLISNINVIVLELKGSETTFMCEYADETATIVEFLNRWITFCQS
IISTLTGGGGSGGGGSGGGGSGGGGSGSHSMRYFFTSVSRPGRGEPRFIAVGYVDDTQFV
RFDSDAASQRMEPRAPWIEQEGPEYWDGETRKVKAHSQTHRVDLGTLRGAYNQSEAGSHT
VQRMYGCDVGSDWRFLRGYHQYAYDGKDYIALKEDLRSWTAADMAAQTTKHKWEAAHVAE
QLRAYLEGTCVEWLRRYLENGKETLQRTDAPKTHMTHHAVSDHEATLRCWALSFYPAEIT
LTWQRDGEDQTQDTELVETRPCGDGTFQKWAAVVVPSGQEQRYTCHVQHEGLPKPLTLRW
EAAAGGDKTHTCPPCPAPELLGGPSVFLFPPKPKDTLMISRTPEVTCVVVDVSHEDPEVK
FNWYVDGVEVHNAKTKPREEQYASTYRVVSVLTVLHQDWLNGKEYKCKVSNKALPAPIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

Human IL2 Leader sequence – italics
IL-2 (H16A/F42A) – bold (with H16 and F42 underlined)
(G4S)4 Linkers – single underlined
MHC H chain Y84A; A236C– double underlined (with Y84A and A236C in bold)
AAAGG linker – single underlined
Human IgG1 Fc; N297A – (bold and underlined, with N297A unbolded)

FIG. 22
CUE101-N297A without leader peptide (SEQ ID NO:69)

APTSSSTKKTQLQLEALLLDLQMILNGINNYKNPKLTRML
TAKFYMPKKATELKHLQCLEEELKPLEEVLNLAQSKNFHLRPRDLISNINVIVLELKGSE
TTFMCEYADETATIVEFLNRWITFCQSIISTLTGGGGSGGGGSGGGGSGGGGSAPTSSST
KKTQLQLEALLLDLQMILNGINNYKNPKLTRMLTAKFYMPKKATELKHLQCLEEELKPLE
EVLNLAQSKNFHLRPRDLISNINVIVLELKGSETTFMCEYADETATIVEFLNRWITFCQS
IISTLTGGGGSGGGGSGGGGSGGGGSGSHSMRYFFTSVSRPGRGEPRFIAVGYVDDTQFV
RFDSDAASQRMEPRAPWIEQEGPEYWDGETRKVKAHSQTHRVDLGTLRGAYNQSEAGSHT
VQRMYGCDVGSDWRFLRGYHQYAYDGKDYIALKEDLRSWTAADMAAQTTKHKWEAAHVAE
QLRAYLEGTCVEWLRRYLENGKETLQRTDAPKTHMTHHAVSDHEATLRCWALSFYPAEIT
LTWQRDGEDQTQDTELVETRPCGDGTFQKWAAVVVPSGQEQRYTCHVQHEGLPKPLTLRW
EAAAGG DKTHTCPPCPAPELLGGPSVFLFPPKPKDTLMISRTPEVTCVVVDVSHEDPEVK
FNWYVDGVEVHNAKTKPREEQYASTYRVVSVLTVLHQDWLNGKEYKCKVSNKALPAPIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

IL-2 (H16A/F42A) – bold (with H16 and F42 underlined)
(G4S)4 Linkers – single underlined
MHC H chain Y84A; A236C– double underlined (with Y84A and A236C in bold)
AAAGG linker – single underlined
Human IgG1 Fc; N297A – (bold and underlined, with N297A unbolded)

FIG. 23A
CUE101-N297A (SEQ ID NO:70)
1360:
ATGTACAGGATGCAACTCCTGTCTTGCATTGCACTAAGTCTTGCACTTGTCACAAACAGTGCACCTACTTC
AAGTTCTACAAAGAAAACAGCTACAACTGGAGGCATTACTGCTGGATTTACAGATGATTTTGAATG
GAATTAATAATTACAAGAATCCCAAACTCACCAGGATGCTCACAGCAAAGTTTTACATGCCCAAGAAG
GCCACAGAACTGAAACATCTTCAGTGTCTAGAAGAAGAACTCAAACCTCTGGAGGAAGTGCTAAATTT
AGCTCAAAGCAAAAACTTTCACTTAAGACCCAGGGACTTAATCAGCAATATCAACGTAATAGTTCTGGA
ACTAAAGGGATCTGAAACAACATTCATGTGTGAATATGCTGATGAGACAGCAACCATTGTAGAATTTC
TGAACAGATGGATTACCTTTTGTCAAAGCATCATCTCAACACTGACTGGAGGCGGAGGATCTGGTGGTG
GAGGTTCTGGTGGTGGGGGATCTGGAGGCGGAGGATCTGCACCTACTTCAAGTTCTACAAAGAAAACA
CAGCTACAACTGGAGGCATTACTGCTGGATTTACAGATGATTTTGAATGGAATTAATAATTACAAGAAT
CCCAAACTCACCAGGATGCTCACAGCAAAGTTTTACATGCCCAAGAAGGCCACAGAACTGAAACATCTT
CAGTGTCTAGAAGAAGAACTCAAACCTCTGGAGGAAGTGCTAAATTTAGCTCAAAGCAAAAACTTTCA
CTTAAGACCCAGGGACTTAATCAGCAATATCAACGTAATAGTTCTGGAACTAAAGGGATCTGAAACAA
CATTCATGTGTGAATATGCTGATGAGACAGCAACCATTGTAGAATTTCTGAACAGATGGATTACCTTTT
GTCAAAGCATCATCTCAACACTGACTGGAGGCGGAGGATCTGGTGGTGGAGGTTCTGGTGGTGGGGGA
TCTGGAGGCGGAGGATCTGGCTCTCACTCCATGAGGTATTTCTTCACATCCGTGTCCCGGCCCGGCCGCG
GGGAGCCCCGCTTCATCGCAGTGGGCTACGTGGACGACACGCAGTTCGTGCGGTTCGACAGCGACGCCG
CGAGCCAGAGGATGGAGCCGCGGGCGCCGTGGATAGAGCAGGAGGGTCCGGAGTATTGGGACGGGGA
GACACGGAAAGTGAAGGCCCACTCACAGACTCACCGAGTGGACCTGGGGACCCTGCGCGGCGCCTACA
ACCAGAGCGAGGCCGGTTCTCACACCGTCCAGAGGATGTATGGCTGCGACGTGGGGTCGGACTGGCGC
TTCCTCCGCGGGTACCACCAGTACGCCTACGACGGCAAGGATTACATCGCCCTGAAAGAGGACCTGCGCT
CTTGGACCGCGGCGGACATGGCAGCTCAGACCACCAAGCACAAGTGGGAGGCGGCCCATGTGGCGGAG
CAGTTGAGAGCCTACCTGGAGGGCACGTGCGTGGAGTGGCTCCGCAGATACCTGGAGAACGGGAAGGA
GACGCTGCAGCGCACGGACGCCCCCAAAACGCATATGACTCACCACGCTGTCTCTGACCATGAAGCCACC
CTGAGGTGCTGGGCCCTGAGCTTCTACCCTGCGGAGATCACACTGACCTGGCAGCGGGATGGGGAGGA
CCAGACCCAGGACACGGAGCTCGTGGAGACCAGGCCTTGCGGGGATGGAACCTTCCAGAAGTGGGCGG
CTGTGGTGGTGCCTTCTGGACAGGAGCAGAGATACACCTGCCATGTGCAGCATGAGGGTTTGCCCAAGC
CCCTCACCCTGAGATGGGAGGCAGCTGCGGGTGGCGACAAAACTCACACATGCCCACCGTGCCCAGCA
CCTGAACTCCTGGGGGGACCGTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTTCAACTG
GTACGTGGACGGCGTGGAGGTGCATAATGCCAAGACAAAGCCGCGGGAGGAGCAGTACGCAAGCAC
GTACCGTGTGGTCAGCGTCCTCACCGTCCTGCACCAGGACTGGCTGAATGGCAAGGAGTACAAGTGCA
AGGTCTCCAACAAAGCCCTCCCAGCCCCCATCGAGAAAACCATCTCCAAAGCCAAAGGGCAGCCCCGA
GAACCACAGGTGTACACCCTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCAATGGGCAGCCGGAGAAC
AACTACAAGACCACGCCTCCCGTGCTGGACTCCGACGGCTCCTTCTTCCTCTACAGCAAGCTCACCGTGG
ACAAGAGCAGATGGCAGCAGGGGAACGTCTTCTCATGCTCCGTGATGCACGAGGCTCTGCACAACCAC
TACACGCAGAAGTCCCTCTCCCTGTCTCCGGGTAAATAGTGA

FIG. 23B
Human IL2 Leader sequence – italics
Human IL2; H16A=GCA; F42A=GCA – bold (with GCA underlined)
(G4S)4 linker – single underlined
Human A0201; Y84A=GCC; A236C=TGC
AAAGG linker – single underlined
Human IgG1 Fc; N297A= GCA; AGG to AGA (still R) and AGC to TCC (still S) – (bold and underlined, with GCA italicized)
Stop codons (TAGTGA)

FIG. 24
CUE101-LALA with leader peptide (SEQ ID NO:71)

*MYRMQLLSCIALSLALVTNS*APTSSSTKKTQLQLEALLLDLQMILNGINNYKNPKLTRML
TAKFYMPKKATELKHLQCLEEELKPLEEVLNLAQSKNFHLRPRDLISNINVIVLELKGSE
TTFMCEYADETATIVEFLNRWITFCQSIISTLTGGGGSGGGGSGGGGSGGGGSAPTSSST
KKTQLQLEALLLDLQMILNGINNYKNPKLTRMLTAKFYMPKKATELKHLQCLEEELKPLE
EVLNLAQSKNFHLRPRDLISNINVIVLELKGSETTFMCEYADETATIVEFLNRWITFCQS
IISTLTGGGGSGGGGSGGGGSGGGGSGSHSMRYFFTSVSRPGRGEPRFIAVGYVDDTQFV
RFDSDAASQRMEPRAPWIEQEGPEYWDGETRKVKAHSQTHRVDLGTLRGAYNQSEAGSHT
VQRMYGCDVGSDWRFLRGYHQYAYDGKDYIALKEDLRSWTAADMAAQTTKHKWEAAHVAE
QLRAYLEGTCVEWLRRYLENGKETLQRTDAPKTHMTHHAVSDHEATLRCWALSFYPAEIT
LTWQRDGEDQTQDTELVETTRPCGDGTFQKWAAVVVPSGQEQRYTCHVQHEGLPKPLTLRW
EAAAGGDKTHTCPPCPAPEAAGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

Leader peptide – italics
IL-2 (H16A/F42A) – bold (with H16 and F42 underlined)
(G4S)4 Linkers – single underlined
MHC H chain Y84A; A236C– double underlined (with Y84A and A236C in bold)
AAAGG linker – single underlined
Human IgG1 Fc; L234A; L235A – (bold and underlined, with L234A and L235A unbolded)

FIG. 25
CUE101-LALA without leader peptide (SEQ ID NO:72)

APTSSSTKKTQLQLEALLLDLQMILNGINNYKNPKLTRML
TAKFYMPKKATELKHLQCLEEELKPLEEVLNLAQSKNFHLRPRDLISNINVIVLELKGSE
TTFMCEYADETATIVEFLNRWITFCQSIISTLTGGGGSGGGGSGGGGSGGGGSAPTSSST
KKTQLQLEALLLDLQMILNGINNYKNPKLTRMLTAKFYMPKKATELKHLQCLEEELKPLE
EVLNLAQSKNFHLRPRDLISNINVIVLELKGSETTFMCEYADETATIVEFLNRWITFCQS
IISTLTGGGGSGGGGSGGGGSGGGGSGSHSMRYFFTSVSRPGRGEPRFIAVGYVDDTQFV
RFDSDAASQRMEPRAPWIEQEGPEYWDGETRKVKAHSQTHRVDLGTLRGAYNQSEAGSHT
VQRMYGCDVGSDWRFLRGYHQYAYDGKDYIALKEDLRSWTAADMAAQTTKHKWEAAHVAE
QLRAYLEGTCVEWLRRYLENGKETLQRTDAPKTHMTHHAVSDHEATLRCWALSFYPAEIT
LTWQRDGEDQTQDTELVETRPCGDGTFQKWAAVVVPSGQEQRYTCHVQHEGLPKPLTLRW
EAAAGGDKTHTCPPCPAPEAAGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

IL-2 (H16A/F42A) – bold (with H16 and F42 underlined)
(G4S)4 Linkers – single underlined
MHC H chain Y84A; A236C– double underlined (with Y84A and A236C in bold)
AAAGG linker – single underlined
Human IgG1 Fc; L234A; L235A – (bold and underlined, with L234A and L235A unbolded)

FIG. 26A (SEQ ID NO:73)
CUE101-LALA: nucleotide sequence encoding CUE101-LALA with leader peptide

*ATGTACAGGATGCAACTCCTGTCTTGCATTGCACTAAGTCTTGCACTTGTCACAAACAGT*GCACCTACTTC
AAGTTCTACAAAGAAAACACAGCTACAACTGGAGGCATTACTGCTGGATTTACAGATGATTTTGAATG
GAATTAATAATTACAAGAATCCCAAACTCACCAGGATGCTCACAGCAAAGTTTTACATGCCCAAGAAG
GCCACAGAACTGAAACATCTTCAGTGTCTAGAAGAAGAACTCAAACCTCTGGAGGAAGTGCTAAATTT
AGCTCAAAGCAAAAACTTTCACTTAAGACCCAGGGACTTAATCAGCAATATCAACGTAATAGTTCTGGA
ACTAAAGGGATCTGAAACAACATTCATGTGTGAATATGCTGATGAGACAGCAACCATTGTAGAATTTC
TGAACAGATGGATTACCTTTGTCAAAGCATCATCTCAACACTGACTGGAGGCGGAGGATCTGGTGGTG
GAGGTTCTGGTGGTGGGGGATCTGGAGGCGGAGGATCTGCACCTACTTCAAGTTCTACAAAGAAAACA
CAGCTACAACTGGAGGCATTACTGCTGGATTTACAGATGATTTTGAATGGAATTAATAATTACAAGAAT
CCCAAACTCACCAGGATGCTCACAGCAAAGTTTTACATGCCCAAGAAGGCCACAGAACTGAAACATCTT
CAGTGTCTAGAAGAAGAACTCAAACCTCTGGAGGAAGTGCTAAATTTAGCTCAAAGCAAAAACTTTCA
CTTAAGACCCAGGGACTTAATCAGCAATATCAACGTAATAGTTCTGGAACTAAAGGGATCTGAAACAA
CATTCATGTGTGAATATGCTGATGAGACAGCAACCATTGTAGAATTTCTGAACAGATGGATTACCTTTT
GTCAAAGCATCATCTCAACACTGACTGGAGGCGGAGGATCTGGTGGTGGAGGTTCTGGTGGTGGGGGA
TCTGGAGGCGGAGGATCTGGCTCTCACTCCATGAGGTATTTCTTCACATCCGTGTCCCGGCCCGGCCGCG
GGGAGCCCCGCTTCATCGCAGTGGGCTACGTGGACGACACGCAGTTCGTGCGGTTCGACAGCGACGCCG
CGAGCCAGAGGATGGAGCCGCGGGCGCCGTGGATAGAGCAGGAGGGTCCGGAGTATTGGGACGGGGA
GACACGGAAAGTGAAGGCCCACTCACAGACTCACCGAGTGGACCTGGGGACCCTGCGCGGCGCCTACA
ACCAGAGCGAGGCCGGTTCTCACACCGTCCAGAGGATGTATGGCTGCGACGTGGGGTCGGACTGGCGC
TTCCTCCGCGGGTACCACCAGTACGCCTACGACGGCAAGGATTACATCGCCCTGAAAGAGGACCTGCGCT
CTTGGACCGCGGCGGACATGGCAGCTCAGACCACCAAGCACAAGTGGGAGGCGGCCCATGTGGCGGAG
CAGTTGAGAGCCTACCTGGAGGGCACGTGCGTGGAGTGGCTCCGCAGATACCTGGAGAACGGGAAGGA
GACGCTGCAGCGCACGGACGCCCCCAAAACGCATATGACTCACCACGCTGTCTCTGACCATGAAGCCACC
CTGAGGTGCTGGGCCCTGAGCTTCTACCCTGCGGAGATCACACTGACCTGGCAGCGGGATGGGGAGGA
CCAGACCCAGGACACGGAGCTCGTGGAGACCAGGCCTGCGGGGATGGAACCTTCCAGAAGTGGGCGG
CTGTGGTGGTGCCTTCTGGACAGGAGCAGAGATACACCTGCCATGTGCAGCATGAGGGTTTGCCCAAGC
CCCTCACCCTGAGATGGGAGGCAGCTGCGGGTGGCGACAAAACTCACACATGCCCACCGTGCCCAGCA
CCTGAAGCCGCCGGGGGACCGTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTTCAACTG
GTACGTGGACGGCGTGGAGGTGCATAATGCCAAGACAAAGCCGCGGGAGGAGCAGTACAACAGCAC
GTACCGTGTGGTCAGCGTCCTCACCGTCCTGCACCAGGACTGGCTGAATGGCAAGGAGTACAAGTGCA
AGGTCTCCAACAAAGCCCTCCCAGCCCCCATCGAGAAAACCATCTCCAAAGCCAAAGGGCAGCCCCGA
GAACCACAGGTGTACACCCTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCAATGGGCAGCCGGAGAAC
AACTACAAGACCACGCCTCCCGTGCTGGACTCCGACGGCTCCTTCTTCCTCTACAGCAAGCTCACCGTGG
ACAAGAGCAGATGGCAGCAGGGGAACGTCTTCTCATGCTCCGTGATGCACGAGGCTCTGCACAACCAC
TACACGCAGAAGTCCCTCTCCCTGTCTCCGGGTAAATAGTGA*

FIG. 26B

Human IL2 Leader sequence – italics
Human IL2; H16A=GCA; F42A=GCA – bold (with GCA underlined)
(G4S)4 linker – single underlined
Human A0201; Y84A=GCC; A236C=TGC – double underlined (with GCC and TGC in bold)
AAAGG linker – single underlined
Human IgG1 Fc; L234A, L235A = GCCGCC
    N297= AAC; AGG to AGA (still R) and AGC to TCC (still S) – (bold and underlined, with GCCGCC italicized)
Stop codons (TAGTGA)

FIG. 27 (SEQ ID NO: 74)
CUE101-TM with leader peptide

*MYRMQLLSCIALSLALVTNS*APTSSSTKKTQLQLEALLLDLQMILNGINNYKNPKLTRML
TAKFYMPKKATELKHLQCLEEELKPLEEVLNLAQSKNFHLRPRDLISNINVIVLELKGSE
TTFMCEYADETATIVEFLNRWITFCQSIISTLTGGGGSGGGGSGGGGSGGGGSAPTSSST
KKTQLQLEALLLDLQMILNGINNYKNPKLTRMLTAKFYMPKKATELKHLQCLEEELKPLE
EVLNLAQSKNFHLRPRDLISNINVIVLELKGSETTFMCEYADETATIVEFLNRWITFCQS
IISTLTGGGGSGGGGSGGGGSGGGGSGSHSMRYFFTSVSRPGRGEPRFIAVGYVDDTQFV
RFDSDAASQRMEPRAPWIEQEGPEYWDGETRKVKAHSQTHRVDLGTLRGAYNQSEAGSHT
VQRMYGCDVGSDWRFLRGYHQYAYDGKDYIALKEDLRSWTAADMAAQTTKHKWEAAHVAE
QLRAYLEGTCVEWLRRYLENGKETLQRTDAPKTHMTHHAVSDHEATLRCWALSFYPAEIT
LTWQRDGEDQTQDTELVETRPCGDGTFQKWAAVVVPSGQEQRYTCHVQHEGLPKPLTLRW
EAAAGGDKTHTCPPCPAPEFEGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPASIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

Leader peptide – italics
IL-2 (H16A/F42A) – bold (with H16 and F42 underlined)
(G4S)4 Linkers – single underlined
MHC H chain Y84A; A236C– double underlined (with Y84A and A236C in bold)
AAAGG linker – single underlined
Human IgG1 Fc; L234F; L235E; P331S – (bold and underlined, with L234F, L235E, and P331S unbolded)

FIG. 28
CUE101-TM without leader peptide (SEQ ID NO:75)

APTSSSTKKTQLQLEALLLDLQMILNGINNYKNPKLTRML
TAKFYMPKKATELKHLQCLEEELKPLEEVLNLAQSKNFHLRPRDLISNINVIVLELKGSE
TTFMCEYADETATIVEFLNRWITFCQSIISTLTGGGGSGGGGSGGGGSGGGGSAPTSSST
KKTQLQLEALLLDLQMILNGINNYKNPKLTRMLTAKFYMPKKATELKHLQCLEEELKPLE
EVLNLAQSKNFHLRPRDLISNINVIVLELKGSETTFMCEYADETATIVEFLNRWITFCQS
IISTLTGGGGSGGGGSGGGGSGGGGSGSHSMRYFFTSVSRPGRGEPRFIAVGYVDDTQFV
RFDSDAASQRMEPRAPWIEQEGPEYWDGETRKVKAHSQTHRVDLGTLRGAYNQSEAGSHT
VQRMYGCDVGSDWRFLRGYHQYAYDGKDYIALKEDLRSWTAADMAAQTTKHKWEAAHVAE
QLRAYLEGTCVEWLRRYLENGKETLQRTDAPKTHMTHHAVSDHEATLRCWALSFYPAEIT
LTWQRDGEDQTQDTELVETRPCGDGTFQKWAAVVVPSGQEQRYTCHVQHEGLPKPLTLRW
EAAAGG DKTHTCPPCPAPEFEGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPASIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

IL-2 (H16A/F42A) – bold (with H16 and F42 underlined)
(G4S)4 Linkers – single underlined
MHC H chain Y84A; A236C– double underlined (with Y84A and A236C in bold)
AAAGG linker – single underlined
Human IgG1 Fc; L234F; L235E; P331S – (bold and underlined, with L234F, L235E, and P331S unbolded)

FIG. 29A (SEQ ID NO:76)
CUE101-TM: nucleotide sequence encoding CUE101-TM with leader sequence

*ATGTACAGGATGCAACTCCTGTCTTGCATTGCACTAAGTCTTGCACTTGTCACAAACAGT*GCACCTACTTC
AAGTTCTACAAAGAAAACACAGCTACAACTGGAGGCATTACTGCTGGATTTACAGATGATTTTGAATG
GAATTAATAATTACAAGAATCCCAAACTCACCAGGATGCTCACAGCAAAGTTTTACATGCCCAAGAAG
GCCACAGAACTGAAACATCTTCAGTGTCTAGAAGAAGAACTCAAACCTCTGGAGGAAGTGCTAAATTT
AGCTCAAAGCAAAAACTTTCACTTAAGACCCAGGGACTTAATCAGCAATATCAACGTAATAGTTCTGGA
ACTAAAGGGATCTGAAACAACATTCATGTGTGAATATGCTGATGAGACAGCAACCATTGTAGAATTTC
TGAACAGATGGATTACCTTTTGTCAAAGCATCATCTCAACACTGACTGGAGGCGGAGGATCTGGTGGTG
GAGGTTCTGGTGGTGGGGGATCTGGAGGCGGAGGATCTGCACCTACTTCAAGTTCTACAAAGAAAACA
CAGCTACAACTGGAGGCATTACTGCTGGATTTACAGATGATTTTGAATGGAATTAATAATTACAAGAAT
CCCAAACTCACCAGGATGCTCACAGCAAAGTTTTACATGCCCAAGAAGGCCACAGAACTGAAACATCTT
CAGTGTCTAGAAGAAGAACTCAAACCTCTGGAGGAAGTGCTAAATTTAGCTCAAAGCAAAAACTTTCA
CTTAAGACCCAGGGACTTAATCAGCAATATCAACGTAATAGTTCTGGAACTAAAGGGATCTGAAACAA
CATTCATGTGTGAATATGCTGATGAGACAGCAACCATTGTAGAATTTCTGAACAGATGGATTACCTTTT
GTCAAAGCATCATCTCAACACTGACTGGAGGCGGAGGATCTGGTGGTGGAGGTTCTGGTGGTGGGGGA
TCTGGAGGCGGAGGATCTGGCTCTCACTCCATGAGGTATTTCTTCACATCCGTGTCCCGGCCCGGCCGCG
GGGAGCCCCGCTTCATCGCAGTGGGCTACGTGGACGACACGCAGTTCGTGCGGTTCGACAGCGACGCCG
CGAGCCAGAGGATGGAGCCGCGGGCGCCGTGGATAGAGCAGGAGGGTCCGGAGTATTGGGACGGGGA
GACACGGAAAGTGAAGGCCCACTCACAGACTCACCGAGTGGACCTGGGGACCCTGCGCGGCGCCTACA
ACCAGAGCGAGGCCGGTTCTCACACCGTCCAGAGGATGTATGGCTGCGACGTGGGGTCGGACTGGCGC
TTCCTCCGCGGGTACCACCAGTACGCCTACGACGGCAAGGATTACATCGCCCTGAAAGAGGACCTGCGCT
CTTGGACCGCGGCGGACATGGCAGCTCAGACCACCAAGCACAAGTGGGAGGCGGCCCATGTGGCGGAG
CAGTTGAGAGCCTACCTGGAGGGCACGTGCGTGGAGTGGCTCCGCAGATACCTGGAGAACGGGAAGGA
GACGCTGCAGCGCACGGACGCCCCCAAAACGCATATGACTCACCACGCTGTCTCTGACCATGAAGCCACC
CTGAGGTGCTGGGCCCTGAGCTTCTACCCTGCGGAGATCACACTGACCTGGCAGCGGGATGGGGAGGA
CCAGACCCAGGACACGGAGCTCGTGGAGACCAGGCCTGCGGGGATGGAACCTTCCAGAAGTGGGCGG
CTGTGGTGGTGCCTTCTGGACAGGAGCAGAGATACACCTGCCATGTGCAGCATGAGGGTTTGCCCAAGC
CCCTCACCCTGAGATGGGAGGCAGCTGCGGGTGGC**GACAAAACTCACACATGCCCACCGTGCCCAGCA
CCTGAATTCGAGGGGGGACCGTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTTCAACTG
GTACGTGGACGGCGTGGAGGTGCATAATGCCAAGACAAAGCCGCGGGAGGAGCAGTACAACAGCAC
GTACCGTGTGGTCAGCGTCCTCACCGTCCTGCACCAGGACTGGCTGAATGGCAAGGAGTACAAGTGCA
AGGTCTCCAACAAAGCCCTCCCAGCCAGCATCGAGAAAACCATCTCCAAAGCCAAAGGGCAGCCCCGA
GAACCACAGGTGTACACCCTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCAATGGGCAGCCGGAGAAC
AACTACAAGACCACGCCTCCCGTGCTGGACTCCGACGGCTCCTTCTTCCTCTACAGCAAGCTCACCGTGG
ACAAGAGCAGATGGCAGCAGGGGAACGTCTTCTCATGCTCCGTGATGCACGAGGCTCTGCACAACCAC
TACACGCAGAAGTCCCTCTCCCTGTCTCCGGGTAAA*TAGTGA*

FIG. 29B

Human IL2 Leader sequence – italics
Human IL2; H16A=GCA; F42A=GCA – bold (with GCA underlined)
(G4S)4 linker – single underlined
Human A0201; Y84A=GCC; A236C=TGC – double underlined (with GCC and TGC in bold)
AAAGG linker – single underlined
Human IgG1 Fc; L234F=TTC; L235E=GAG; P331S=AGC
     N297= AAC; AGG to AGA (still R) and AGC to TCC (still S) – (bold and underlined, with TTC, GAG, AAC, and AGC italicized)
Stop codons (TAGTGA)

FIG. 30
1274: (SEQ ID NO:77)
*MSRSVALAVLALLSLSGLEA*YMLDLQPETT<u>GGGGSGGGGSGGGGS</u><u><u>IQRTPKIQVYSCHPA
ENGKSNFLNCYVSGFHPSDIEVDLLKNGERIEKVEHSDLSFSKDWSFYLLYYTEFTPTEK
DEYACRVNHVTLSQPKIVKWDRDM</u></u>

Human β2M leader sequence -- italics
E7(11-20) – bold and underlined
(G4S)3 linker – single underlined
Human β2M; R12C– double underlined (R12C bolded)

FIG. 31

1274 without leader peptide (SEQ ID NO:78)

YMLDLQPETT<u>GGGGSGGGGSGGGGS</u>IQYMLDLQPETT<u>GGGGSGGGGSGGGGS</u><u><u>IQRTPKIQVYSCH
PAENGKSNFLNCYVSGFHPSDIEVDLLKNGERIEKVEHSDLSFSKDWSFYLLYYTEFTPTEKDEY
ACRVNHVTLSQPKIVKWDRDMRTPKIQVYSCHPAENGKSNFLNCYVSGFHPSDIEVDLLKNGERI
EKVEHSDLSFSKDWSFYLLYYTEFTPTEKDEYACRVNHVTLSQPKIVKWDRDM</u></u>

E7(11-20) – bold and underlined (YMLDLQPETT; SEQ ID NO:13)
(G4S)3 linker – single underlined (<u>GGGGSGGGGSGGGGS</u>; SEQ ID NO:89)
Human β2M; R12C – double underlined

FIG. 32 (SEQ ID NO:79)
1274 nucleotide sequence encoding 1274 with leader peptide

*ATGTCTCGCTCCGTGGCCTTAGCTGTGCTCGCGCTACTCTCTCTTTCTGGCCTGGAGGCC*<u>**TACATGCTCGA
TTTGCAGCCCGAAACGACG**</u><u>GGTGGAGGTGGTTCTGGAGGAGGCGGTTCGGGCGGAGGTGGTAGT</u><u><u>ATC
CAGCGTACTCCAAAGATTCAGGTTTACT</u></u>CAT<u><u>GC</u></u>CATCCAGCAGAGAATGGAAAGTCAAATTTCCTGAATT
GCTATGTGTCTGGGTTTCATCCATCCGACATTGAAGTTGACTTACTGAAGAATGGAGAGAGAATTGAAAA
AGTGGAGCATTCAGACTTGTCTTTCAGCAAGGACTGGTCTTTCTATCTCTTGTATTATACTGAATTCACCCC
CACTGAAAAAGATGAGTATGCCTGCCGTGTGAACCACGTGACTTTGTCACAGCCCAAGATAGTTAAGTG
GGATCGAGACATG*TAGTGA

Human β2M leader sequence -- italics
E7(11-20) – bold and underlined
(G4S)3 linker – single underlined
Human β2M; R12C=TGC – double underlined (TGC in bold)
Stop codons TAGTGA

FIG. 33A

WT Human IgG1 Fc Sequence: (SEQ ID NO:80)

DKTHTCPPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

FIG. 33B

Human IgG1 Fc Mutant: L234F/L235E/P331S (Triple Mutant "TM") (SEQ ID NO:81)

DKTHTCPPCPAPEFEGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPASIEKTISKAKGQPREP
QVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

FIG. 33C

Human IgG1 Fc Mutant: N297A (SEQ ID NO:82)

DKTHTCPPCPAPELLGGPSVFLFPPKPKDTLMISRTPEVTCVVVDVSHEDPEVKFNWYVDGVE
VHNAKTKPREEQYASTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

FIG. 33D

Human IgG1 Fc Mutant: L234A/L235A ("LALA") (SEQ ID NO:83)

DKTHTCPPCPAPEAAGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

Residue numbered according to EU index (Kabat Numbering)

FIG. 34A
B2M R12C (SEQ ID NO:17)

IQRTPKIQVYSCHPAENGKSNFLNCYVSGFHPSDIEVDLLKNGERIEKVEHSDLSFSKDWSFYLL
YYTEFTPTEKDEYACRVNHVTLSQPKIVKWDRDM

FIG. 34B
IL-2 (H16A; F42A) (SEQ ID NO:84)

APTSSSTKKTQLQLEALLLDLQMILNGINNYKNPKLTRMLTAKFYMPKKATELKHLQCLEEELKP
LEEVLNLAQSKNFHLRPRDLISNINVIVLELKGSETTFMCEYADETATIVEFLNRWITFCQSIIS
TLT

FIG. 34C
Class I MHC-H chain A0201 (Y84A; A236C) (SEQ ID NO:19)

GSHSMRYFFTSVSRPGRGEPRFIAVGYVDDTQFVRFDSDAASQRMEPRAPWIEQEGPEYWDGETR
KVKAHSQTHRVDLGTLRGAYNQSEAGSHTVQRMYGCDVGSDWRFLRGYHQYAYDGKDYIALKEDL
RSWTAADMAAQTTKHKWEAAHVAEQLRAYLEGTCVEWLRRYLENGKETLQRTDAPKTHMTHHAVS
DHEATLRCWALSFYPAEITLTWQRDGEDQTQDTELVETRPCGDGTFQKWAAVVVPSGQEQRYTCH
VQHEGLPKPLTLRWE

FIG. 36

| Amino Acid | Syntac Number | Expression level (mg/L) | Receptor binding by Octet (KD in nM) | | | EC50 for cell binding, nM | | EC50 for pSTAT5, nM | | |
|---|---|---|---|---|---|---|---|---|---|---|
| | | | αβγ | βγ | β | LCMV | Black6 | LCMV | Black6 | B6/LCMV |
| H | 982 | 77 | 14.9 | | | 0.25 | >100 | 5.019 | 57.05 | 11 |
| A | 986 | 89 | 16.5 | | | 0.22 | >100 | 20.09 | 543.8 | 27 |
| R | 1284 | 81 | ND | | | 0.29 | >100 | >1000 | >1000 | ND |
| N | 1285 | 50 | 9.0 | | | 0.48 | >100 | 35.19 | 1041 | 30 |
| D | 1286 | 31 | 12.3 | | | 0.28 | >100 | 0.6365 | 15.71 | 25 |
| C | 1287 | 37 | 7.6 | | | 0.50 | >100 | 59.98 | 1152 | 19 |
| Q | 1288 | 66 | 13.8 | | | 0.23 | >100 | 21.64 | 530.1 | 24 |
| E | 1289 | 66 | 12.7 | | | 0.31 | >100 | 3.899 | 117.2 | 30 |
| G | 1290 | | | | | | | | | ND |
| I | 1291 | 61 | 8.4 | | | 0.31 | >100 | >1000 | >1000 | ND |
| L | 1292 | 50 | 12.5 | | | 0.36 | >100 | >1000 | >1000 | ND |
| K | 1293 | 74 | ND | | | 0.27 | >100 | >1000 | >1000 | ND |
| M | 1294 | 81 | 19.2 | | | 0.41 | >100 | 34.88 | 674.5 | 19 |
| F | 1295 | 32 | 19.6 | | | 0.46 | >100 | 4.864 | 69.1 | 14 |
| P | 1296 | 2 | | | | | | | | |
| S | 1297 | 77 | 21.2 | | | 0.28 | >100 | 14.42 | 113.4 | 8 |
| T | 1298 | 123 | 29.5 | | | 0.31 | >100 | 29.66 | >1000 | >34 |
| W | 1299 | 24 | 18.6 | | | 0.59 | >100 | 70.95 | >1000 | >14 |
| Y | 1300 | 31 | 29.4 | | | 0.49 | >100 | 16.82 | 188 | 11 |
| V | 1301 | 87 | 7.8 | | | 0.28 | >100 | 230.4 | >1000 | >4 |

T-CELL MODULATORY MULTIMERIC POLYPEPTIDES AND METHODS OF USE THEREOF

CROSS-REFERENCE

This application claims the benefit of U.S. Provisional Patent Application No. 62/438,272, filed Dec. 22, 2016, U.S. Provisional Patent Application No. 62/470,774, filed Mar. 13, 2017, U.S. Provisional Patent Application No. 62/555,435, filed Sep. 7, 2017, and U.S. Provisional Patent Application No. 62/582,132, filed Nov. 6, 2017, each of which applications is incorporated herein by reference in its entirety.

INCORPORATION BY REFERENCE OF SEQUENCE LISTING PROVIDED AS A TEXT FILE

A Sequence Listing is provided herewith as a text file, "CUEB-107WO_SEQ_LISTING_171133_ST25.txt" created on Nov. 14, 2017 and having a size of 153 KB. The contents of the text file are incorporated by reference herein in their entirety.

INTRODUCTION

An adaptive immune response involves the engagement of the T cell receptor (TCR), present on the surface of a T cell, with a small peptide antigen non-covalently presented on the surface of an antigen presenting cell (APC) by a major histocompatibility complex (MHC; also referred to in humans as a human leukocyte antigen (HLA) complex). This engagement represents the immune system's targeting mechanism and is a requisite molecular interaction for T cell modulation (activation or inhibition) and effector function. Following epitope-specific cell targeting, the targeted T cells are activated through engagement of costimulatory proteins found on the APC with counterpart costimulatory proteins the T cells. Both signals—epitope/TCR binding and engagement of APC costimulatory proteins with T cell costimulatory proteins—are required to drive T cell specificity and activation or inhibition. The TCR is specific for a given epitope; however, the costimulatory protein is not epitope specific and instead is generally expressed on all T cells or on large T cell subsets.

SUMMARY

The present disclosure provides variant immunomodulatory polypeptides, and fusion polypeptides comprising the variant immunomodulatory peptides. The present disclosure provides T-cell modulatory multimeric polypeptides, and compositions comprising same, where the T-cell modulatory multimeric polypeptides comprise a variant immunomodulatory polypeptide of the present disclosure. The present disclosure provides nucleic acids comprising nucleotide sequences encoding the T-cell modulatory multimeric polypeptides, and host cells comprising the nucleic acids. The present disclosure provides methods of modulating the activity of a T cell; the methods comprise contacting the T cell with a T-cell modulatory multimeric polypeptide of the present disclosure.

BRIEF DESCRIPTION OF THE DRAWINGS

FIG. 2A-2Q provide an amino acid sequence of wild-type human IL-2 (FIG. 2A); and amino acid sequences of variant IL-2 polypeptides (FIG. 2B-2Q).

FIG. 3A-3C provide amino acid sequences of IL-2 receptor alpha chain (FIG. 3A), beta chain (FIG. 3B), and gamma chain (FIG. 3C).

FIG. 4A-4C provide amino acid sequences of immunoglobulin Fc polypeptides.

FIG. 5A-5C provide amino acid sequences of human leukocyte antigen (HLA) Class I heavy chain polypeptides. Signal sequences are underlined.

FIG. 6 provides a multiple amino acid sequence alignment of beta-2 microglobulin (β2M) precursors (i.e., including the leader sequence) from *Homo sapiens* (NP_004039.1; SEQ ID NO:95), Pan troglodytes (NP_001009066.1; SEQ ID NO:96), *Macaca mulatta* (NP_001040602.1; SEQ ID NO:97), *Bos Taurus* (NP_776318.1; SEQ ID NO:98) and *Mus musculus* (NP_033865.2; SEQ ID NO:99). Amino acids 1-20 are a signal peptide.

FIG. 7A-7B depict production of IL-2/synTacs ("Cue-IL-2-a" and Cue-IL-2-b") of the present disclosure following transient transfection. FIG. 7A depicts unpurified yields; FIG. 7B depicts purified product.

FIG. 12 depicts IL-2/synTac binding to specific (lymphocytic choriomeningitis virus; LCMV) or non-specific (OT1; recognizing ovalbumin) CD8$^+$ T cells.

FIG. 13 depicts IL-2/synTac-mediated signaling in antigen-specific (LCMV) or non-specific (BL6) CD8$^+$ T cells.

FIG. 14A-14F depict the percent phospho-signal transducer and activator of transcription 5 (pSTAT5)-positive cells following stimulation of CD8$^+$ antigen-specific (LCMV) or non-specific (BL6) cells with IL-2/synTacs of the present disclosure at various IL-2/synTac concentrations.

FIG. 15 depicts in vivo activity of an IL-2/synTac of the present disclosure. The left panel depicts the fold change in the number of antigen-specific CD8$^+$ T cells following administration of phosphate buffered saline (PBS), recombinant IL-2 (rIL-2), or an IL-2/synTac of the present disclosure. The right panel depicts antigen-specific and non-antigen-specific responses following administration of PBS, rIL-2, or an IL-2/synTac of the present disclosure.

FIG. 21 provides an amino acid sequence of a heavy chain of an IL-2/synTac of the present disclosure, with a leader peptide, where the IL-2/synTac heavy chain comprises an IgG1 Fc with an N297A substitution.

FIG. 22 provides an amino acid sequence of a heavy chain of an IL-2/synTac of the present disclosure, without a leader peptide, where the IL-2/synTac heavy chain comprises an IgG1 Fc with an N297A substitution.

FIG. 23A-23B provide a nucleotide sequence (FIG. 23A) encoding the IL-2/synTac heavy chain depicted in FIG. 21; and a key (FIG. 23B) to the sequence.

FIG. 24 provides an amino acid sequence of a heavy chain of an IL-2/synTac of the present disclosure, with a leader peptide, where the IL-2/synTac heavy chain comprises an IgG1 Fc with L234A and L235A substitutions.

FIG. 25 provides an amino acid sequence of a heavy chain of an IL-2/synTac of the present disclosure, without a leader peptide, where the IL-2/synTac heavy chain comprises an IgG1 Fc with L234A and L235A substitutions.

FIG. 26A-26B provide a nucleotide sequence (FIG. 26A) encoding the IL-2/synTac heavy chain depicted in FIG. 24; and a key (FIG. 26B) to the sequence.

FIG. 27 provides an amino acid sequence of a heavy chain of an IL-2/synTac of the present disclosure, with a leader peptide, where the IL-2/synTac heavy chain comprises an IgG1 Fc with L234F, L235E, and P331S substitutions.

FIG. 28 provides an amino acid sequence of a heavy chain of an IL-2/synTac of the present disclosure, without a leader peptide, where the IL-2/synTac heavy chain comprises an IgG1 Fc with L234F, L235E, and P331S substitutions.

FIG. 29A-29B provide a nucleotide sequence (FIG. 29A) encoding the IL-2/synTac heavy chain depicted in FIG. 27; and a key (FIG. 29B) to the sequence.

FIG. 30 provides an amino acid sequence of a light chain of an IL-2/synTac of the present disclosure, with a leader peptide, where the IL-2/synTac light chain comprises a human papilloma virus (HPV) E7 epitope.

FIG. 31 provides an amino acid sequence of a light chain of an IL-2/synTac of the present disclosure, without a leader peptide, where the IL-2/synTac light chain comprises an HPV E7 epitope.

FIG. 32 provides a nucleotide sequence encoding the IL-2/synTac light chain depicted in FIG. 30.

FIG. 33A-33D provide amino acid sequences of a wild-type human IgG1 Fc (FIG. 33A), an IgG1 Fc with L234F, L235E, and P331S substitutions (FIG. 33B), an IgG1 Fc with an N297A substitution (FIG. 33C), and an IgG1 Fc with L234A and L235A substitutions (FIG. 33D).

FIG. 34A-34C provide amino acid sequence of a β2-microglobulin (R12C) polypeptide (FIG. 34A), a variant IL-2 (H16A; F42A) polypeptide (FIG. 34B), and a Class I MHC-H chain A0201 (Y84A; A236C) (FIG. 34C).

FIG. 36 provides expression data and receptor binding data for synTacs with variant IL-2 polypeptides.

DEFINITIONS

Figure 1C:
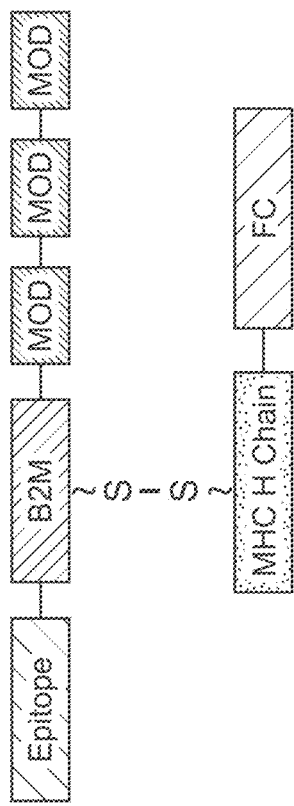
FIG. 1A-1D schematically depict various embodiments of a T-cell modulatory multimeric polypeptide of the present disclosure. In these embodiments, disulfide bonds are formed between MHC (e.g., HLA) polypeptides present in separate polypeptides.
Figure 1D:
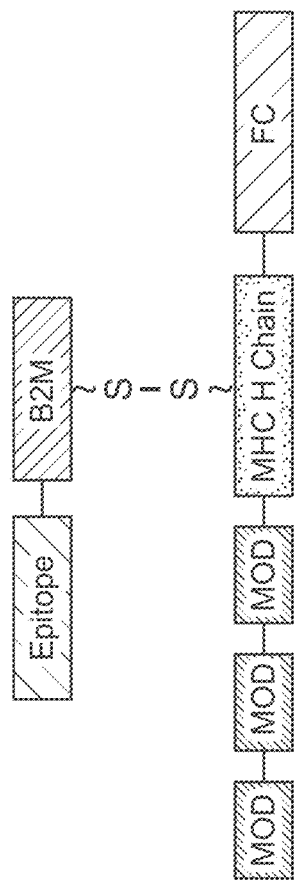

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various convenient methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

"Binding" as used herein (e.g. with reference to binding of a T-cell modulatory multimeric polypeptide of the present disclosure to a polypeptide (e.g., a T-cell receptor) on a T cell) refers to a non-covalent interaction between. Binding interactions are generally characterized by a dissociation constant ($K_D$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-5}$ M. "Affinity" refers to the strength of binding, increased binding affinity being correlated with a lower $K_D$.

The term "immunological synapse" or "immune synapse" as used herein generally refers to the natural interface between two interacting immune cells of an adaptive immune response including, e.g., the interface between an antigen-presenting cell (APC) or target cell and an effector cell, e.g., a lymphocyte, an effector T cell, a natural killer cell, and the like. An immunological synapse between an APC and a T cell is generally initiated by the interaction of a T cell antigen receptor and major histocompatibility complex molecules, e.g., as described in Bromley et al., Annu Rev Immunol. 2001; 19:375-96; the disclosure of which is incorporated herein by reference in its entirety.

"T cell" includes all types of immune cells expressing CD3, including T-helper cells (CD4$^+$ cells), cytotoxic T-cells (CD8$^+$ cells), T-regulatory cells (Treg), and NK-T cells.

"Co-stimulatory polypeptide," as the term is used herein, includes a polypeptide on an antigen presenting cell (APC) (e.g., a dendritic cell, a B cell, and the like) that specifically binds a cognate co-stimulatory polypeptide on a T cell, thereby providing a signal which, in addition to the primary signal provided by, for instance, binding of a TCR/CD3 complex with a major histocompatibility complex (MHC) polypeptide loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, Fas ligand (FasL), inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, LIGHT, NKG2C, B7-H3, and a ligand that specifically binds to CD83.

A "modulatory domain" ("MOD") of a T-cell modulatory multimeric polypeptide of the present disclosure comprises a co-stimulatory polypeptide, e.g., an IL-2 polypeptide, such as a variant IL-2 polypeptide of the present disclosure.

"Heterologous," as used herein, means a nucleotide or polypeptide that is not found in the native nucleic acid or protein, respectively.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells, for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication.

A "host cell," as used herein, denotes an in vivo or in vitro eukaryotic cell or a cell from a multicellular organism (e.g., a cell line) cultured as a unicellular entity, which eukaryotic cells can be, or have been, used as recipients for a nucleic acid (e.g., an expression vector that comprises a nucleotide sequence encoding a multimeric polypeptide of the present disclosure), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a genetically modified eukaryotic host cell is genetically modified by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired. Mammals include, e.g., humans, non-human primates, rodents (e.g., rats; mice), lagomorphs (e.g., rabbits), ungulates (e.g., cows, sheep, pigs, horses, goats, and the like), etc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a variant IL-2 polypeptide" includes a plurality of such polypeptides and reference to "the Class I HLA heavy chain polypeptide" includes reference to one or more Class I HLA heavy chain polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides variant immunomodulatory polypeptides, and fusion polypeptides comprising the variant immunomodulatory peptides. The present disclosure provides T-cell modulatory multimeric polypeptides, and compositions comprising same, where the T-cell modulatory multimeric polypeptides comprise a variant immunomodulatory polypeptide of the present disclosure. The present disclosure provides nucleic acids comprising nucleotide sequences encoding the T-cell modulatory multimeric polypeptides, and host cells comprising the nucleic acids. The present disclosure provides methods of modulating the activity of a T cell; the methods comprise contacting the T cell with a T-cell modulatory multimeric polypeptide of the present disclosure.

In embodiments described herein, a multimeric polypeptide functions as a surrogate APC, and mimics the adaptive immune response. The multimeric polypeptide does so by engaging a TCR present on the surface of a T cell with an epitope-presenting peptide complexed with an MHC present in the multimeric polypeptide. This engagement provides the multimeric polypeptide with the ability to achieve epitope-specific cell targeting. In embodiments described herein, the multimeric polypeptide also possesses at least one immunomodulatory protein (also referred to herein as a "modulatory domain" or "MOD") that engages a counterpart costimulatory protein (also referred to herein as an "immunomodulatory polypeptide," a "cognate immunomodulatory polypeptide," or a "cognate costimulatory protein," and the like) on the T cell. Both signals—epitope/MHC binding to a TCR and immunomodulatory polypeptide binding to a cognate costimulatory polypeptide—then drive both the desired T cell specificity and either inhibition or activation/proliferation. As further described herein, the at least one immunomodulatory protein may be a variant of a naturally occurring immunomodulatory protein (e.g., naturally occurring IL-2), which variant exhibits a reduced affinity for its counterpart costimulatory protein on the T cell (e.g., IL-2R) as compared to the affinity of the naturally occurring immunomodulatory protein for the counterpart costimulatory protein.

A T-cell modulatory multimeric polypeptide of the present disclosure is also referred to as a "synTac polypeptide." A synTac polypeptide of the present disclosure comprises a variant modulatory domain, where the variant modulatory domain exhibits reduced binding affinity to an immunomodulatory polypeptide (a cognate costimulatory polypeptide, e.g., a cognate costimulatory polypeptide on the surface of a T cell), compared to the affinity of a wild-type modulatory domain for the immunomodulatory polypeptide. A synTac polypeptide of the present disclosure can modulate the activity of a target T-cell. A synTac polypeptide of the present disclosure provides for enhanced target cell specificity.

Variant Immunomodulatory Polypeptides

The present disclosure provides variant IL-2 modulatory polypeptides. A wild-type amino acid sequence of human IL-2 is provided in FIG. 2A. A wild-type amino acid sequence of a human IL-2 polypeptide can be as follows: APTSSSTKKT QLQLEHLLLD LQMILNGINN YKNPKLTRML TFKFYMPKKA TELKHLQCLEEELKPLEEVL NLAQSKNFHL

RPRDLISNIN VIVLELKGSE TTFMCEYADE TATIVE-
FLNRWITFCQSIIS TLT (SEQ ID NO:1).

Wild-type IL-2 binds to an IL-2 receptor (IL-2R) on the surface of a cell. An IL-2 receptor is in some cases a heterotrimeric polypeptide comprising an alpha chain (IL-2Rα; also referred to as CD25), a beta chain (IL-2Rβ; also referred to as CD122: and a gamma chain (IL-2Rγ; also referred to as CD132). Amino acid sequences of human IL-2Rα, IL-2Rβ, and IL-2Rγ are provided in FIG. 3A-3C.

In some cases, a variant IL-2 polypeptide of the present disclosure exhibits reduced binding affinity to IL-2R, compared to the binding affinity of an IL-2 polypeptide comprising the amino acid sequence depicted in FIG. 2A for IL-2R. For example, in some cases, a variant IL-2 polypeptide of the present disclosure binds IL-2R with a binding affinity that is less than the binding affinity of an IL-2 polypeptide comprising the amino acid sequence depicted in FIG. 2A for an IL-2R polypeptide comprising alpha, beta, and gamma chains comprising the amino acid sequences depicted in FIG. 3A-3C. For example, in some cases, a variant IL-2 polypeptide of the present disclosure binds IL-2R with a binding affinity that is at least 5%, at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence depicted in FIG. 2A for an IL-2R (e.g., an IL-2R comprising alpha, beta, and gamma chains comprising the amino acid sequences (mature forms) depicted in FIG. 3A-3C). In such cases, binding affinity is determined using the procedure described below.

In some cases, a variant IL-2 polypeptide of the present disclosure has a binding affinity for IL-2R that is from 100 nM to 100 μM. As another example, in some cases, a variant IL-2 polypeptide of the present disclosure has a binding affinity for IL-2R (e.g., an IL-2R comprising alpha, beta, and gamma chains comprising the amino acid sequences depicted in FIG. 3A-3C) that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In such cases, binding affinity is determined using the procedure described below.

A variant IL-2 polypeptide of the present disclosure can have a single amino acid substitution relative to a wild-type IL-2 polypeptide (e.g., an IL-2 polypeptide comprising the amino acid sequence depicted in FIG. 2A or as set forth in SEQ ID NO:1). In some cases, a variant IL-2 polypeptide of the present disclosure has from 2 to 10 amino acid substitutions relative to a wild-type IL-2 polypeptide (e.g., an IL-2 polypeptide comprising the amino acid sequence depicted in FIG. 2A or as set forth in SEQ ID NO:1). In some cases, a variant IL-2 polypeptide of the present disclosure has 2 amino acid substitutions relative to a wild-type IL-2 polypeptide (e.g., an IL-2 polypeptide comprising the amino acid sequence depicted in SEQ ID NO:1). In some cases, a variant IL-2 polypeptide of the present disclosure has 3 amino acid substitutions relative to a wild-type IL-2 polypeptide (e.g., an IL-2 polypeptide comprising the amino acid sequence depicted in FIG. 2A or as set forth in SEQ ID NO:1). In some cases, a variant IL-2 polypeptide of the present disclosure has 4 amino acid substitutions relative to a wild-type IL-2 polypeptide (e.g., an IL-2 polypeptide comprising the amino acid sequence depicted in FIG. 2A or as set forth in SEQ ID NO:1). In some cases, a variant IL-2 polypeptide of the present disclosure has 5 amino acid substitutions relative to a wild-type IL-2 polypeptide (e.g., an IL-2 polypeptide comprising the amino acid sequence depicted in FIG. 2A or as set forth in SEQ ID NO:1). In some cases, a variant IL-2 polypeptide of the present disclosure has 6 amino acid substitutions relative to a wild-type IL-2 polypeptide (e.g., an IL-2 polypeptide comprising the amino acid sequence depicted in FIG. 2A or as set forth in SEQ ID NO:1). In some cases, a variant IL-2 polypeptide of the present disclosure has 7 amino acid substitutions relative to a wild-type IL-2 polypeptide (e.g., an IL-2 polypeptide comprising the amino acid sequence depicted in FIG. 2A or as set forth in SEQ ID NO:1). In some cases, a variant IL-2 polypeptide of the present disclosure has 8 amino acid substitutions relative to a wild-type IL-2 polypeptide (e.g., an IL-2 polypeptide comprising the amino acid sequence depicted in FIG. 2A or as set forth in SEQ ID NO:1). In some cases, a variant IL-2 polypeptide of the present disclosure has 9 amino acid substitutions relative to a wild-type IL-2 polypeptide (e.g., an IL-2 polypeptide comprising the amino acid sequence depicted in FIG. 2A or as set forth in SEQ ID NO:1). In some cases, a variant IL-2 polypeptide of the present disclosure has 10 amino acid substitutions relative to a wild-type IL-2 polypeptide (e.g., an IL-2 polypeptide comprising the amino acid sequence depicted in FIG. 2A or as set forth in SEQ ID NO:1).

A variant IL-2 polypeptide of the present disclosure can have a length of from 120 amino acids to 140 amino acids, e.g., from 120 amino acids to 125 amino acids, from 125 amino acids to 130 amino acids, from 130 amino acids to 135 amino acids, or from 135 amino acids to 140 amino acids. In some cases, a variant IL-2 polypeptide of the present disclosure has a length of 133 amino acids.

E15 Substitution

In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2D, where amino acid 15 is an amino acid other than a glutamic acid, e.g., where amino acid 15 is Gly, Ala, Val, Leu, Ile, Pro, Phe, Tyr, Trp, Ser, Thr, Cys, Met, Asn, Gln, Lys, Arg, His, or Asp. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2D, where amino acid 15 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2D, where amino acid 15 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2D, where amino acid 15 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2D, where amino acid 15 is Val. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2D, where amino acid 15 is Leu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2D, where amino acid 15 is Ile. In some cases, the E15 substitution variant IL-2 polypeptides described above have a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, such variant IL-2 polypeptides bind IL-2R with a binding affinity that is at least 5%, 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence depicted in FIG. 2A for an IL-2R (e.g., an IL-2R comprising alpha, beta, and gamma chains comprising the amino acid sequences (mature forms) depicted in FIG. 3A-3C). In some cases, such variant IL-2 polypeptide has a length of 133 amino acids.

H16 Substitution

In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2E, where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2E, where amino acid 16 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2E, where amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2E, where amino acid 16 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2E, where amino acid 16 is Val. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2E, where amino acid 16 is Leu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2E, where amino acid 16 is Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2E, where amino acid 16 is Asn. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2E, where amino acid 16 is Asp. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2E, where amino acid 16 is Cys. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2E, where amino acid 16 is Gln. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2E, where amino acid 16 is Glu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2E, where amino acid 16 is Met. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2E, where amino acid 16 is Phe. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2E, where amino acid 16 is Ser. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2E, where amino acid 16 is Thr. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2E, where amino acid 16 is Trp. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2E, where amino acid 16 is Tyr. In some cases, the H16 substitution variant IL-2 polypeptides described above have a binding affinity for IL-2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, such variant IL-2 polypeptides bind IL-2R with a binding affinity that is at least 5%, 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence depicted in FIG. 2A for an IL-2R (e.g., an IL-2R comprising alpha, beta, and gamma chains comprising the amino acid sequences (mature forms) depicted in FIG. 3A-3C). In some cases, such variant IL-2 polypeptide has a length of 133 amino acids.

D20 Substitution

In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2C, where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2C, where amino acid 20 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2C, where amino acid 20 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2C, where amino acid 20 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2C, where amino acid 20 is Val. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2C, where amino acid 20 is Leu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2C, where amino acid 20 is Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2C, where amino acid 20 is Asn, Gln, Lys, Arg, or His. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2C, where amino acid 20 is Lys. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2C, where amino acid 20 is Asn. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2C, where amino acid 20 is Gln. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2C, where amino acid 20 is His. In some cases, the D20 substitution variant IL-2 polypeptides described above have a binding affinity for IL-2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, such variant IL-2 polypeptides bind IL-2R with a binding affinity that is at least 5%, 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence depicted in FIG. 2A for an IL-2R (e.g., an IL-2R comprising alpha, beta, and gamma chains comprising the amino acid sequences (mature forms) depicted in FIG. 3A-3C). In some cases, such variant IL-2 polypeptide has a length of 133 amino acids.

F42 Substitution

In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2B, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2B, where amino acid 42 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2B, where amino acid 42 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2B, where amino acid 42 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2B, where amino acid 42 is Val. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2B, where amino acid 42 is Leu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2B, where amino acid 42 is Ile. In some cases, the F42 substitution variant IL-2 polypeptides described above have a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, such variant IL-2 polypeptides bind IL2R with a binding affinity that is at least 5%, 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence depicted in FIG. 2A for an IL2R (e.g., an IL2R comprising alpha, beta, and gamma chains comprising the amino acid sequences (mature forms) depicted in FIG. 3A-3C). In some cases, such variant IL-2 polypeptide has a length of 133 amino acids.

Y45 Substitution

In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2F, where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2F, where amino acid 45 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2F, where amino acid 45 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2F, where amino acid 45 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2F, where amino acid 45 is Val. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2F, where amino acid 45 is Leu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2F, where amino acid 45 is Ile. In some cases, the Y45 substitution variant IL-2 polypeptides described above have a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, such variant IL-2 polypeptides bind IL2R with a binding affinity that is at least 5%, 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence depicted in FIG. 2A for an IL2R (e.g., an IL2R comprising alpha, beta, and gamma chains comprising the amino acid sequences (mature forms) depicted in FIG. 3A-3C). In some cases, such variant IL-2 polypeptide has a length of 133 amino acids.

Q126 Substitution

In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2G, where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2G, where amino acid 126 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2G, where amino acid 126 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2G, where amino acid 126 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2G, where amino acid 126 is Val. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2G, where amino acid 126 is Leu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2G, where amino acid 126 is Ile. In some cases, the Q126 substitution variant IL-2 polypeptides described above have a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, such variant IL-2 polypeptides bind IL2R with a binding affinity that is at least 5%, 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence depicted in FIG. 2A for an IL2R (e.g., an IL2R comprising alpha, beta, and gamma chains comprising the amino acid sequences (mature forms) depicted in FIG. 3A-3C). In some cases, such variant IL-2 polypeptide has a length of 133 amino acids.

F42 and H16 Substitutions

In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2H, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2H, where amino acid 42 is Ala, Gly, Val, Leu, or Ile; and where amino acid 16 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2H, where amino acid 42 is Ala and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2H, where amino acid 42 is Ala and amino acid 16 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2H, where amino acid 42 is Val and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2H, where amino acid 42 is Leu, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2H, where amino acid 42 is Ile and amino acid 16 is Ala. In some cases, the F42/H16 substitution variant IL-2 polypeptides described above have a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, such variant IL-2 polypeptides bind IL2R with a binding affinity that is at least 5%, 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence depicted in FIG. 2A for an IL2R (e.g., an IL2R comprising alpha, beta, and gamma chains comprising the amino acid sequences (mature forms) depicted in FIG. 3A-3C). In some cases, such variant IL-2 polypeptide has a length of 133 amino acids.

F42 and D20 Substitutions

In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2I, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; and where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala, Gly, Val, Leu, or Ile; and where amino acid 20 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala, Gly, Val, Leu, or Ile; and where amino acid 20 is Asn, Gln, Lys, Arg, or His. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2I, where amino acid 42 is Val and amino acid 20 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2I, where amino acid 42 is Leu, and amino acid 20 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ile and amino acid 20 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Asn. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Gln. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Lys. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Arg. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is His. In some cases, the F42/D20 substitution variant IL-2 polypeptides described above have a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, such variant IL-2 polypeptides bind IL2R with a binding affinity that is at least 5%, 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence depicted in FIG. 2A for an IL2R (e.g., an IL2R comprising alpha, beta, and gamma chains comprising the amino acid sequences (mature forms) depicted in FIG. 3A-3C). In some cases, such variant IL-2 polypeptide has a length of 133 amino acids.

F42, D20, and E15 Substitutions

In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2J, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; and where amino acid 15 is an amino acid other than a glutamic acid, e.g., where amino acid 15 is Gly, Ala, Val, Leu, Ile, Pro, Phe, Tyr, Trp, Ser, Thr, Cys, Met, Asn, Gln, Lys, Arg, His, or Asp. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, Gly, Val, Leu, or Ile; where amino acid 20 is Ala, Gly, Val, Leu, or Ile; and where amino acid 15 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, Gly, Val, Leu, or Ile; where amino acid 20 is Asn, Gln, Lys, Arg, or His; and where amino acid 15 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Ala, and amino acid 15 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Gly, and amino acid 15 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2J, where amino acid 42 is Val, amino acid 20 is Ala, and amino acid 15 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2J, where amino acid 42 is Leu, amino acid 20 is Ala, and amino acid 15 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ile, amino acid 20 is Ala, and amino acid 15 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Asn, and amino acid 15 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala, amino acid 20 is Gln, and amino acid 15 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Lys, and amino acid 15 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Arg, and amino acid 15 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala, amino acid 20 is His, and amino acid 15 is Ala. In some cases, the F42/D20/E15 substitution variant IL-2 polypeptides described above have a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, such variant IL-2 polypeptides bind IL2R with a binding affinity that is at least 5%, 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence depicted in FIG. 2A for an IL2R (e.g., an IL2R comprising alpha, beta, and gamma chains comprising the amino acid sequences (mature forms) depicted in FIG. 3A-3C). In some cases, such variant IL-2 polypeptide has a length of 133 amino acids.

F42, D20, and H16 Substitutions

In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2K, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, Gly, Val, Leu, or Ile; where amino acid 20 is Ala, Gly, Val, Leu, or Ile; and where amino acid 16 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, Gly, Val, Leu, or Ile; where amino acid 20 is Asn, Gln, Lys, Arg, or His; and where amino acid 16 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Ala, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Gly, and amino acid 16 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2K, where amino acid 42 is Val, amino acid 20 is Ala, and amino acid 16 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2K, where amino acid 42 is Leu, amino acid 20 is Ala, and amino acid 16 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ile, amino acid 20 is Ala, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Asn, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Gln, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Lys, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Arg, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is His, and amino acid 16 is Ala. In some cases, the F42/D20/H16 substitution variant IL-2 polypeptides described above have a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, such variant IL-2 polypeptides bind IL2R with a binding affinity that is at least 5%, 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence depicted in FIG. 2A for an IL2R (e.g., an IL2R comprising alpha, beta, and gamma chains comprising the amino acid sequences (mature forms) depicted in FIG. 3A-3C). In some cases, such variant IL-2 polypeptide has a length of 133 amino acids.

F42, D20, and Q126 Substitutions

In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2L, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; and where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, Gly, Val, Leu, or Ile; where amino acid 20 is Ala, Gly, Val, Leu, or Ile; and where amino acid 126 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, Gly, Val, Leu, or Ile; where amino acid 20 is Asn, Gln, Lys, Arg, or His; and where amino acid 126 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Ala, and amino acid 126 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Gly, and amino acid 126 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2L, where amino acid 42 is Val, amino acid 20 is Ala, and amino acid 126 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2L, where amino acid 42 is Leu, amino acid 20 is Ala, and amino acid 126 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ile, amino acid 20 is Ala, and amino acid 126 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Asn, and amino acid 126 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Gln, and amino acid 126 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Lys, and amino acid 126 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Arg, and amino acid 126 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is His, and amino acid 126 is Ala. In some cases, the F42/D20/Q126 substitution variant IL-2 polypeptides described above have a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, such variant IL-2 polypeptides bind IL2R with a binding affinity that is at least 5%, 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence depicted in FIG. 2A for an IL2R (e.g., an IL2R comprising alpha, beta, and gamma chains comprising the amino acid sequences (mature forms) depicted in FIG. 3A-3C). In some cases, such variant IL-2 polypeptide has a length of 133 amino acids.

F42, D20, and Y45 Substitutions

In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2M, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; and where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, Gly, Val, Leu, or Ile; where amino acid 20 is Ala, Gly, Val, Leu, or Ile; and where amino acid 45 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, Gly, Val, Leu, or Ile; where amino acid 20 is Asn, Gln, Lys, Arg, or His; and where amino acid 45 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Ala, and amino acid 45 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Gly, and amino acid 45 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2M, where amino acid 42 is Val, amino acid 20 is Ala, and amino acid 45 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2M, where amino acid 42 is Leu, amino acid 20 is Ala, and amino acid 45 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ile, amino acid 20 is Ala, and amino acid 45 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Asn, and amino acid 45 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Gln, and amino acid 45 is Ala.

In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Lys, and amino acid 45 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Arg, and amino acid 45 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is His, and amino acid 45 is Ala. In some cases, the F42/D20/Y45 substitution variant IL-2 polypeptides described above have a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, such variant IL-2 polypeptides bind IL2R with a binding affinity that is at least 5%, 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence depicted in FIG. 2A for an IL2R (e.g., an IL2R comprising alpha, beta, and gamma chains comprising the amino acid sequences (mature forms) depicted in FIG. 3A-3C). In some cases, such variant IL-2 polypeptide has a length of 133 amino acids.

F42, D20, Y45, and H16 Substitutions

In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2N, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, Gly, Val, Leu, or Ile; where amino acid 20 is Ala, Gly, Val, Leu, or Ile; where amino acid 45 is Ala, Gly, Val, Leu, or Ile; and where amino acid 16 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, Gly, Val, Leu, or Ile; where amino acid 20 is Asn, Gln, Lys, Arg, or His; where amino acid 45 is Ala, Gly, Val, Leu, or Ile; and where amino acid 16 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Ala, amino acid 45 is Ala, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Gly, amino acid 45 is Gly, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2N, where amino acid 42 is Val, amino acid 20 is Ala, amino acid 45 is Gly, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2N, where amino acid 42 is Leu, amino acid 20 is Ala, amino acid 45 is Gly, and amino acid 16 is Val. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ile, amino acid 20 is Ala, amino acid 45 is Ala, and amino acid 16 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Asn, amino acid 45 is Ala, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Gln, amino acid 45 is Ala, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Lys, amino acid 45 is Ala, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Arg, amino acid 45 is Ala, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is His, amino acid 45 is Ala, and amino acid 16 is Ala. In some cases, the F42/D20/Y45/H16 substitution variant IL-2 polypeptides described above have a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, such variant IL-2 polypeptides bind IL2R with a binding affinity that is at least 5%, 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence depicted in FIG. 2A for an IL2R (e.g., an IL2R comprising alpha, beta, and gamma chains comprising the amino acid sequences (mature forms) depicted in FIG. 3A-3C). In some cases, such variant IL-2 polypeptide has a length of 133 amino acids.

F42, D20, Y45, and Q126 Substitutions

In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2O, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu; and where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, Gly, Val, Leu, or Ile; where amino acid 20 is Ala, Gly, Val, Leu, or Ile; where amino acid 45 is Ala, Gly, Val, Leu, or Ile; and where amino acid 126 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, Gly, Val, Leu, or Ile; where amino acid 20 is Asn, Gln, Lys, Arg, or His; where amino acid 45 is Ala, Gly, Val, Leu, or Ile; and where amino acid 126 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Ala, amino acid 45 is Ala, and amino acid 126 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Gly, amino acid 45 is Gly, and amino acid 126 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2O, where amino acid 42 is Val, amino acid 20 is Ala, amino acid 45 is Gly, and amino acid 126 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2O, where amino acid 42 is Leu, amino acid 20 is Ala, amino acid 45 is Gly, and amino acid 126 is Val. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ile, amino acid 20 is Ala, amino acid 45 is Ala, and amino acid 126 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Asn, amino acid 45 is Ala, and amino acid 126 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Gln, amino acid 45 is Ala, and amino acid 126 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Lys, amino acid 45 is Ala, and amino acid 126 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Arg, amino acid 45 is Ala, and amino acid 126 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is His, amino acid 45 is Ala, and amino acid 126 is Ala. In some cases, the F42/D20/Y45/Q126 substitution variant IL-2 polypeptides described above have a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, such variant IL-2 polypeptides bind IL2R with a binding affinity that is at least 5%, 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence depicted in FIG. 2A for an IL2R (e.g., an IL2R comprising alpha, beta, and gamma chains comprising the amino acid sequences (mature forms) depicted in FIG. 3A-3C). In some cases, such variant IL-2 polypeptide has a length of 133 amino acids.

F42, D20, Y45, H16, and Q126 Substitutions

In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2P, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu; where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, Gly, Val, Leu, or Ile; where amino acid 20 is Ala, Gly, Val, Leu, or Ile; where amino acid 45 is Ala, Gly, Val, Leu, or Ile; where amino acid 126 is Ala, Gly, Val, Leu, or Ile; and where amino acid 16 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, Gly, Val, Leu, or Ile; where amino acid 20 is Asn, Gln, Lys, Arg, or His; where amino acid 45 is Ala, Gly, Val, Leu, or Ile; where amino acid 126 is Ala, Gly, Val, Leu, or Ile; and where amino acid 16 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Ala, amino acid 45 is Ala, amino acid 126 is Ala, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Gly, amino acid 45 is Gly, amino acid 126 is Ala, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2P, where amino acid 42 is Val, amino acid 20 is Ala, amino acid 45 is Gly, amino acid 126 is Ala, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2P, where amino acid 42 is Leu, amino acid 20 is Ala, amino acid 45 is Gly, amino acid 126 is Val, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ile, amino acid 20 is Ala, amino acid 45 is Ala, amino acid 126 is Gly, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Asn, amino acid 45 is Ala, amino acid 126 is Ala, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Gln, amino acid 45 is Ala, amino acid 126 is Ala, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Lys, amino acid 45 is Ala, amino acid 126 is Ala, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Arg, amino acid 45 is Ala, amino acid 126 is Ala, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is His, amino acid 45 is Ala, amino acid 126 is Ala, and amino acid 16 is Ala. In some cases, the F42/D20/Y45/H16/Q126 substitution variant IL-2 polypeptides described above have a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, such variant IL-2 polypeptides bind IL2R with a binding affinity that is at least 5%, 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence depicted in FIG. 2A for an IL2R (e.g., an IL2R comprising alpha, beta, and gamma chains comprising the amino acid sequences (mature forms) depicted in FIG. 3A-3C). In some cases, such variant IL-2 polypeptide has a length of 133 amino acids.

F42, Q126, and H16 Substitutions

Figure 2Q:
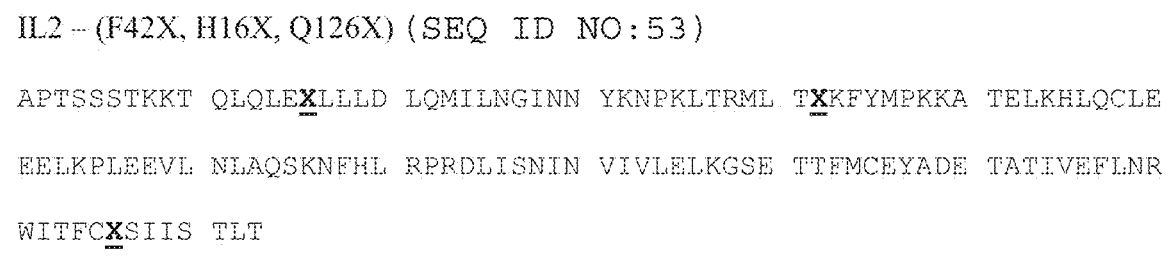

In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2Q, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, Gly, Val, Leu, or Ile; where amino acid 126 is Ala, Gly, Val, Leu, or Ile; and where amino acid 16 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, Gly, Val, Leu, or Ile; where amino acid 126 is Asn, Gln, Lys, Arg, or His; and where amino acid 16 is Ala, Gly, Val, Leu, or Ile. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Ala, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Gly, and amino acid 16 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Val, amino acid 126 is Ala, and amino acid 16 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Leu, amino acid 126 is Ala, and amino acid 16 is Gly. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ile, amino acid 126 is Ala, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Asn, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Ala, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Lys, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Arg, and amino acid 16 is Ala. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is His, and amino acid 16 is Ala. In some cases, the F42/Q126/H16 substitution variant IL-2 polypeptides have a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, such variant IL-2 polypeptides bind IL2R with a binding affinity that is at least 5%, 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence depicted in FIG. 2A for an IL2R (e.g., an IL2R comprising alpha, beta, and gamma chains comprising the amino acid sequences (mature forms) depicted in FIG. 3A-3C). In some cases, such variant IL-2 polypeptide has a length of 133 amino acids.

Fusion Polypeptides

The present disclosure provides IL-2 fusion polypeptides. A fusion polypeptide of the present disclosure comprises: a) a variant IL-2 polypeptide of the present disclosure; and b) a heterologous fusion partner. In some cases, the heterologous fusion partner is fused to the N-terminus of the variant IL-2 polypeptide. In some cases, the heterologous fusion partner is fused to the C-terminus of the variant IL-2 polypeptide. In some cases, an IL-2 fusion polypeptide of the present disclosure comprises a first heterologous fusion partner fused to the N-terminus of the variant IL-2 polypeptide, and a second heterologous fusion partner fused to the C-terminus of the variant IL-2 polypeptide.

The total length of an IL-2 fusion polypeptide of the present disclosure can range from 135 amino acids to 2000 amino acids. For example, an IL-2 fusion polypeptide of the present disclosure can range from 135 amino acids to 150 amino acids, from 150 amino acids to 175 amino acids, from 175 amino acids to 200 amino acids, from 200 amino acids to 225 amino acids, from 225 amino acids to 250 amino acids, from 250 amino acids to 275 amino acids, from 275 amino acids to 300 amino acids, from 300 amino acids to 350 amino acids, from 350 amino acids to 350 amino acids to 400 amino acids, from 400 amino acids, from 400 amino acids to 450 amino acids, from 450 amino acids to 500 amino acids, from 500 amino acids to 600 amino acids, from 600 amino acids to 700 amino acids, from 700 amino acids to 800 amino acids, from 800 amino acids to 900 amino acids, from 900 amino acids to 1000 amino acids, from 1000 amino acids to 1250 amino acids, from 1250 amino acids to 1500 amino acids, from 1500 amino acids to 1750 amino acids, or from 1750 amino acids to 2000 amino acids.

Suitable fusion partners include, but are not limited to, a transmembrane domain; an antibody Fc region; an antigen-binding region of an antibody; a cytokine (other than IL-2); an immunomodulatory domain; an intracellular signaling domain; and the like.

T-Cell Modulatory Multimeric Polypeptides

Figure 1A:
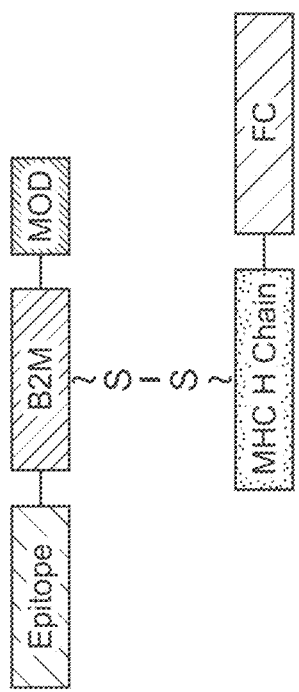
Figure 1B:
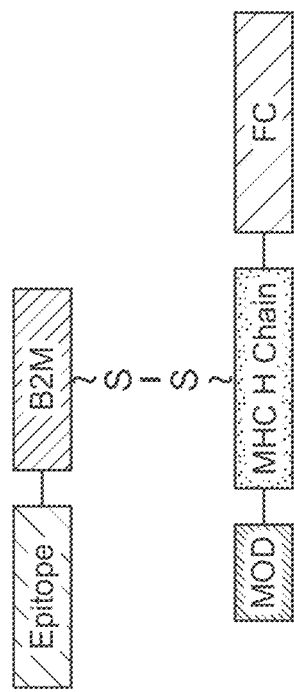

The present disclosure provides multimeric (e.g., heterodimeric, heterotrimeric) polypeptides. The multimeric polypeptides are T cell modulatory polypeptides, and are also referred to herein as "T-cell modulatory multimeric polypeptides," or "synTac" (for "immunological synapse for T cell activation"). FIG. 1A-ID provide schematic depictions of T-cell modulatory multimeric polypeptides of the present disclosure. A T-cell modulatory multimeric polypeptide of the present disclosure is also referred to as an "IL-2/synTac," a "synTac polypeptide" or a "multimeric polypeptide."

In some cases, a synTac polypeptide of the present disclosure comprises a wild-type IL-2 polypeptide. In some cases, a synTac polypeptide of the present disclosure comprises a single copy of a wild-type IL-2 polypeptide. In some cases, a synTac polypeptide of the present disclosure comprises two copies of a wild-type IL-2 polypeptide. In some cases, a synTac polypeptide of the present disclosure comprises three copies of a wild-type IL-2 polypeptide. In some cases, the wild-type IL-2 polypeptide comprises an amino acid sequence having at least 90%, at least 95%, at least 98%, or at least 99%, amino acid sequence identity to the amino acid sequence depicted in FIG. 2A.

In some cases, a synTac polypeptide of the present disclosure comprises a variant IL-2 polypeptide of the present disclosure. As noted above, a variant IL-2 polypeptide present in a multimeric polypeptide of the present disclosure exhibits reduced binding affinity to an IL-2R, compared to the binding affinity of wild-type IL-2 to the IL-2R. A multimeric polypeptide of the present disclosure that comprises a variant IL-2 polypeptide of the present disclosure also exhibits reduced binding affinity for an IL-2R, compared to a control multimeric polypeptide comprising a wild-type IL-2 for IL-2R (e.g., an IL-2R comprising alpha, beta, and gamma polypeptides comprising the amino acid sequences (mature form) depicted in FIG. 3A-3C).

In some cases, a synTac polypeptide of the present disclosure exhibits reduced binding affinity to IL-2R, compared to the binding affinity of an IL-2 polypeptide comprising the amino acid sequence depicted in FIG. 2A for IL-2R. For example, in some cases, a synTac polypeptide of the present disclosure binds IL-2R with a binding affinity that is less than the binding affinity of a control synTac polypeptide comprising an IL-2 polypeptide comprising the amino acid sequence depicted in FIG. 2A for an IL-2R comprising alpha, beta, and gamma polypeptides comprising the amino acid sequences (mature form) depicted in FIG. 3A-3C. For example, in some cases, a synTac polypeptide of the present disclosure binds IL-2R with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a control synTac polypeptide comprising an IL-2 polypeptide comprising the amino acid sequence depicted in FIG. 2A for IL-2R (e.g., an IL-2R comprising alpha, beta, and gamma polypeptides comprising the amino acid sequences (mature form) depicted in FIG. 3A-3C).

In some cases, a synTac polypeptide of the present disclosure has a binding affinity for IL-2R that is from 100 nm to about 100 µM. In some cases, a synTac polypeptide of the present disclosure has a binding affinity for IL-2R that is from about 100 nM to 500 nM. For example, in some cases, a synTac polypeptide of the present disclosure has a binding affinity for IL-2R (e.g., an IL-2R comprising alpha, beta, and gamma polypeptides comprising the amino acid sequences (mature form) depicted in FIG. 3A-3C) that is from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, or from about 450 nM to about 500 nM. In some cases, a synTac polypeptide of the present disclosure has a binding affinity for IL-2R (e.g., an IL-2R comprising alpha, beta, and gamma polypeptides comprising the amino acid sequences (mature form) depicted in FIG. 3A-3C) that is from about 500 nM to 1 µM. For example, in some cases, a synTac polypeptide of the present disclosure has a binding affinity for IL-2R (e.g., an IL-2R comprising alpha, beta, and gamma polypeptides comprising the amino acid sequences (mature form) depicted in FIG. 3A-3C) that is from about 500 nM to about 600 nM, from about 600 nM to about 700 nM, from about 700 nM to about 800 nM, from about 800 nM to about 900 nM, or from about 900 nM to about 1 µM. In some cases, a synTac polypeptide of the present disclosure has a binding affinity for IL-2R (e.g., an IL-2R comprising alpha, beta, and gamma polypeptides comprising the amino acid sequences (mature form) depicted in FIG. 3A-3C) that is from about 1 µM to 10 µM. For example, in some cases, a synTac polypeptide of the present disclosure has a binding affinity for IL-2R (e.g., an IL-2R comprising alpha, beta, and gamma polypeptides comprising the amino acid sequences (mature form) depicted in FIG. 3A-3C) that is from about 1 µM to 2 µM, from about 2 µM to about 3 µM, from about 3 µM to about 4 µM, from about 4 µM to about 5 µM, from about 5 µM to about 6 µM, from about 6 µM to about 7 µM, from about 7 µM to about 8 µM, from about 8 µM to about 9 µM, or from about 9 µM to about 10 µM. In some cases, a synTac polypeptide of the present disclosure has a binding affinity for IL-2R (e.g., an IL-2R comprising alpha, beta, and gamma polypeptides comprising the amino acid sequences (mature form) depicted in FIG. 3A-3C) that is from about 10 µM to 100 µM. For example, in some cases, a synTac polypeptide of the present disclosure has a binding affinity for IL-2R (e.g., an IL-2R comprising alpha, beta, and gamma polypeptides comprising the amino acid sequences (mature form) depicted in FIG. 3A-3C) that is from about 10 µM to about 20 µM, from about 20 µM to about 30 µM, from about 30 µM to about 40 µM, from about 40 µM to about 50 µM, from about 50 µM to about 60 µM, from about 60 µM to about 70 µM, from about 70 µM to about 80 µM, from about 80 µM to about 90 µM, or from about 90 µM to about 100 µM.

Determining Binding Affinity

Binding affinity between an immunomodulatory polypeptide and its cognate co-immunomodulatory polypeptide can be determined by bio-layer interferometry (BLI) using purified immunomodulatory polypeptide and purified cognate co-immunomodulatory polypeptide. Binding affinity between a synTac of the present disclosure and its cognate co-immunomodulatory polypeptide can also be determined by BLI using purified synTac and the cognate co-immunomodulatory polypeptide. BLI methods are well known to those skilled in the art. See, e.g., Lad et al. (2015) *J. Biomol. Screen.* 20(4):498-507; and Shah and Duncan (2014) *J. Vis. Exp.* 18:e51383. The specific and relative binding affinities described in this disclosure between an immunomodulatory polypeptide and its cognate co-immunomodulatory polypeptide, or between a synTac and its cognate co-immunomodulatory polypeptide, can be determined using the following procedures.

To determine binding affinity between a synTac of the present disclosure and its cognate co-immunomodulatory polypeptide, a BLI assay can be carried out using an Octet RED 96 (Pal FortéBio) instrument, or a similar instrument, as follows. To determining binding affinity of a T-cell modulatory multimeric polypeptide (e.g., a synTac of the present disclosure; or a control T-cell modulatory multimeric polypeptide (where a control T-cell modulatory multimeric polypeptide comprises a wild-type immunomodulatory polypeptide)), the T-cell modulatory multimeric polypeptide is immobilized onto an insoluble support (a "biosensor"). The immobilized T-cell modulatory multimeric polypeptide is the "target." Immobilization can be effected by immobilizing a capture antibody onto the insoluble support, where the capture antibody immobilizes the T-cell modulatory multimeric polypeptide. For example, immobilization can be effected by immobilizing anti-Fc (e.g., anti-human IgG Fc) antibodies onto the insoluble support, where the immobilized anti-Fc antibodies bind to and immobilize the T-cell modulatory multimeric polypeptide (where the T-cell modulatory multimeric polypeptide comprises an IgFc polypeptide). A co-immunomodulatory polypeptide is applied, at several different concentrations, to the immobilized T-cell modulatory multimeric polypeptide, and the instrument's response recorded. Assays are conducted in a liquid medium comprising 25 mM HEPES pH 6.8, 5% poly(ethylene glycol) 6000, 50 mM KCl, 0.1% bovine serum albumin, and 0.02% Tween 20 nonionic detergent. Binding of the co-immunomodulatory polypeptide to the immobilized T-cell modulatory multimeric polypeptide is conducted at 30° C. As a positive control for binding affinity, an anti-MHC Class I monoclonal antibody can be used. For example, anti-HLA Class I monoclonal antibody W6/32 (American Type Culture Collection No. HB-95; Parham et al. (1979) *J. Immunol.* 123:342), which has a $K_D$ of 7 nM, can be used. A standard curve can be generated using serial dilutions of the anti-MHC Class I monoclonal antibody. The co-immunomodulatory polypeptide, or the anti-MHC Class I mAb, is the "analyte." BLI analyzes the interference pattern of white light reflected from two surfaces: i) from the immobilized polypeptide ("target"); and ii) an internal reference layer. A change in the number of molecules ("analyte"; e.g., co-immunomodulatory polypeptide; anti-HLA antibody) bound to the biosensor tip causes a shift in the interference pattern; this shift in interference pattern can be measured in real time. The two kinetic terms that describe the affinity of the target/analyte interaction are the association constant ($k_a$) and dissociation constant ($k_d$). The ratio of these two terms ($k_d/_a$) gives rise to the affinity constant $K_D$.

As noted above, determining binding affinity between an immunomodulatory polypeptide (e.g., IL-2 or an IL-2 variant) and its cognate co-immunomodulatory polypeptide (e.g., IL-2R) also can be determined by BLI. The assay is similar to that described above for the synTac multimeric polypeptide. A BLI assay can be carried out using an Octet RED 96 (Pal FortéBio) instrument, or a similar instrument, as follows. A component immunomodulatory polypeptide of a synTac of the present disclosure (e.g., a variant IL-2 polypeptide of the present disclosure); and a control immunomodulatory polypeptide (where a control immunomodulatory polypeptide comprises a wild-type immunomodulatory polypeptide, e.g. wild-type IL-2)) are immobilized onto an insoluble support (a "biosensor"). The immunomodulatory polypeptide is the "target." Immobilization can be effected by immobilizing a capture antibody onto the insoluble support, where the capture antibody immobilizes the immunomodulatory polypeptide. For example, if the target is fused to an immuno-affinity tag (e.g. FLAG, human IgG Fc) immobilization can be effected by immobilizing with the appropriate antibody to the immuno-affinity tag (e.g. anti-human IgG Fc) onto the insoluble support, where the immobilized antibodies bind to and immobilize the immunomodulatory polypeptide (where the immunomodulatory polypeptide comprises an IgFc polypeptide). A co-immunomodulatory polypeptide (or polypeptides) is applied, at several different concentrations, to the immobilized immunomodulatory polypeptide, and the instrument's response recorded. Alternatively, a co-immunomodulatory polypeptide (or polypeptides) is immobilized to the biosensor (e.g., for the IL-2 receptor heterotrimer, as a monomeric subunit, heterodimeric subcomplex, or the complete heterotrimer) and the immunomodulatory polypeptide is applied, at several different concentrations, to the immobilized coimmunomodulatory polypeptide(s), and the instrument's response is recorded. Assays are conducted in a liquid medium comprising 25 mM HEPES pH 6.8, 5% poly(ethylene glycol) 6000, 50 mM KCl, 0.1% bovine serum albumin, and 0.02% Tween 20 nonionic detergent. Binding of the co-immunomodulatory polypeptide to the immobilized immunomodulatory polypeptide is conducted at 30° C. As a positive control for binding affinity, an anti-MHC Class I monoclonal antibody can be used. For example, anti-HLA Class I monoclonal antibody W6/32 (American Type Culture Collection No. HB-95; Parham et al. (1979) *J. Immunol.* 123:342), which has a $K_D$ of 7 nM, can be used. A standard curve can be generated using serial dilutions of the anti-MHC Class I monoclonal antibody. The co-immunomodulatory polypeptide, or the anti-MHC Class I mAb, is the "analyte." BLI analyzes the interference pattern of white light reflected from two surfaces: i) from the immobilized polypeptide ("target"); and ii) an internal reference layer. A change in the number of molecules ("analyte"; e.g., co-immunomodulatory polypeptide; anti-HLA antibody) bound to the biosensor tip causes a shift in the interference pattern; this shift in interference pattern can be measured in real time. The two kinetic terms that describe the affinity of the target/analyte interaction are the associa-tion constant ($k_a$) and dissociation constant ($k_d$). The ratio of these two terms ($k_d/_a$) gives rise to the affinity constant $K_D$. Determining the binding affinity of both a wild-type immunomodulatory polypeptide (e.g., IL-2) for its receptor (e.g., IL-2R) and a variant immunomodulatory polypeptide (e.g., an IL-2 variant as disclosed herein) for its cognate co-immunomodulatory polypeptide (e.g., its receptor) (e.g., IL-2R) thus allows one to determine the relative binding affinity of the variant co-immunomodulatory polypeptide, as compared to the wild-type co-immunomodulatory polypeptide, for the cognate co-immunomodulatory polypeptide. That is, one can determine whether the binding affinity of a variant immunomodulatory polypeptide for its receptor (its cognate co-immunomodulatory polypeptide) is reduced as compared to the binding affinity of the wild-type immunomodulatory polypeptide for the same cognate co-immunomodulatory polypeptide, and, if so, what is the percentage reduction from the binding affinity of the wild-type co-immunomodulatory polypeptide.

The BLI assay is carried out in a multi-well plate. To run the assay, the plate layout is defined, the assay steps are defined, and biosensors are assigned in Octet Data Acquisition software. The biosensor assembly is hydrated. The hydrated biosensor assembly and the assay plate are equilibrated for 10 minutes on the Octet instrument. Once the data are acquired, the acquired data are loaded into the Octet Data Analysis software. The data are processed in the Processing window by specifying method for reference subtraction, y-axis alignment, inter-step correction, and Savitzky-Golay filtering. Data are analyzed in the Analysis window by specifying steps to analyze (Association and Dissociation), selecting curve fit model (1:1), fitting method (global), and window of interest (in seconds). The quality of fit is evaluated. $K_D$ values for each data trace (analyte concentration) can be averaged if within a 3-fold range. $K_D$ error values should be within one order of magnitude of the affinity constant values; $R^2$ values should be above 0.95. See, e.g., Abdiche et al. (2008) *J. Anal. Biochem.* 377:209.

In some cases, the ratio of: i) the binding affinity of a control T-cell modulatory multimeric polypeptide (where the control comprises a wild-type immunomodulatory polypeptide, e.g., wild-type IL-2) to a cognate co-immunomodulatory polypeptide (e.g., IL-2R) to ii) the binding affinity of a T-cell modulatory multimeric polypeptide of the present disclosure comprising a variant of the wild-type immunomodulatory polypeptide (e.g., variant IL-2) to the cognate co-immunomodulatory polypeptide (e.g., IL-2R), when measured by BLI (as described above), is at least 1.5:1, at least 2:1, at least 5:1, at least 10:1, at least 15:1, at least 20:1, at least 25:1, at least 50:1, at least 100:1, at least 500:1, at least $10^2$:1, at least $5\times10^2$:1, at least $10^3$:1, at least $5\times10^3$:1, at least $10^4$:1, at least $10^5$:1, or at least $10^6$:1. In some cases, the ratio of: i) the binding affinity of a control T-cell modulatory multimeric polypeptide (where the control comprises a wild-type immunomodulatory polypeptide) to a cognate co-immunomodulatory polypeptide to ii) the binding affinity of a T-cell modulatory multimeric polypeptide of the present disclosure comprising a variant of the wild-type immunomodulatory polypeptide to the cognate co-immunomodulatory polypeptide, when measured by BLI, is in a range of from 1.5:1 to $10^6$:1, e.g., from 1.5:1 to 10:1, from 10:1 to 50:1, from 50:1 to $10^2$:1, from $10^2$:1 to $10^1$:1, from $10^3$:1 to $10^4$:1, from $10^4$:1 to $10^5$:1, or from $10^5$:1 to $10^6$:1.

In some cases, the ratio of: i) the binding affinity of a control immunomodulatory polypeptide (where the control comprises a wild-type immunomodulatory polypeptide, e.g., wild-type IL-2) to a cognate co-immunomodulatory polypeptide (e.g., IL-2R) to ii) the binding affinity of a immunomodulatory polypeptide of the present disclosure comprising a variant of the wild-type immunomodulatory polypeptide (e.g., variant IL-2) to the cognate co-immunomodulatory polypeptide (e.g., IL-2R), when measured by BLI (as described above), is at least 1.5:1, at least 2:1, at least 5:1, at least 10:1, at least 15:1, at least 20:1, at least 25:1, at least 50:1, at least 100:1, at least 500:1, at least $10^2$:1, at least $5\times10^2$:1, at least $10^3$:1, at least $5\times10^3$:1, at least $10^4$:1, at least $10^5$:1, or at least $10^6$:1. In some cases, the ratio of: i) the binding affinity of a control immunomodulatory polypeptide (where the control comprises a wild-type immunomodulatory polypeptide) to a cognate co-immunomodulatory polypeptide to ii) the binding affinity of a immunomodulatory polypeptide of the present disclosure comprising a variant of the wild-type immunomodulatory polypeptide to the cognate co-immunomodulatory polypeptide, when measured by BLI, is in a range of from 1.5:1 to $10^6$:1, e.g., from 1.5:1 to 10:1, from 10:1 to 50:1, from 50:1 to $10^2$:1, from $10^2$:1 to $10^3$:1, from $10^3$:1 to $10^4$:1, from $10^4$:1 to $10^5$:1, or from $10^5$:1 to $10^6$:1.

A variant IL-2 polypeptide present in a synTac polypeptide of the present disclosure can have a single amino acid substitution relative to a wild-type IL-2 polypeptide (e.g., a IL-2 polypeptide comprising the amino acid sequence depicted in FIG. 2A or as set forth in SEQ ID NO:1). In some cases, a variant IL-2 polypeptide present in a synTac polypeptide of the present disclosure has from 2 to 10 amino acid substitutions relative to a wild-type IL-2 polypeptide (e.g., a IL-2 polypeptide comprising the amino acid sequence depicted in FIG. 2A or as set forth in SEQ ID NO:1). In some cases, a variant IL-2 polypeptide present in a synTac polypeptide of the present disclosure has 2 amino acid substitutions relative to a wild-type IL-2 polypeptide (e.g., a IL-2 polypeptide comprising the amino acid sequence depicted in FIG. 2A or as set forth in SEQ ID NO:1). In some cases, a variant IL-2 polypeptide present in a synTac polypeptide of the present disclosure has 3 amino acid substitutions relative to a wild-type IL-2 polypeptide (e.g., a IL-2 polypeptide comprising the amino acid sequence depicted in FIG. 2A or as set forth in SEQ ID NO:1). In some cases, a variant IL-2 polypeptide present in a synTac polypeptide of the present disclosure has 4 amino acid substitutions relative to a wild-type IL-2 polypeptide (e.g., a IL-2 polypeptide comprising the amino acid sequence depicted in FIG. 2A or as set forth in SEQ ID NO:1). In some cases, a variant IL-2 polypeptide present in a synTac polypeptide of the present disclosure has 5 amino acid substitutions relative to a wild-type IL-2 polypeptide (e.g., a IL-2 polypeptide comprising the amino acid sequence depicted in FIG. 2A or as set forth in SEQ ID NO:1). In some cases, a variant IL-2 polypeptide present in a synTac polypeptide of the present disclosure has 6 amino acid substitutions relative to a wild-type IL-2 polypeptide (e.g., a IL-2 polypeptide comprising the amino acid sequence depicted in FIG. 2A or as set forth in SEQ ID NO:1). In some cases, a variant IL-2 polypeptide present in a synTac polypeptide of the present disclosure has 7 amino acid substitutions relative to a wild-type IL-2 polypeptide (e.g., a IL-2 polypeptide comprising the amino acid sequence depicted in FIG. 2A or as set forth in SEQ ID NO:1). In some cases, a variant IL-2 polypeptide present in a synTac polypeptide of the present disclosure has 8 amino acid substitutions relative to a wild-type IL-2 polypeptide (e.g., a IL-2 polypeptide comprising the amino acid sequence depicted in FIG. 2A or as set forth in SEQ ID NO:1). In some cases, a variant IL-2 polypeptide present in a synTac polypeptide of the present disclosure has 9 amino acid substitutions relative to a wild-type IL-2 polypeptide (e.g., a IL-2 polypeptide comprising the amino acid sequence depicted in FIG. 2A or as set forth in SEQ ID NO:1). In some cases, a variant IL-2 polypeptide present in a synTac polypeptide of the present disclosure has 10 amino acid substitutions relative to a wild-type IL-2 polypeptide (e.g., a IL-2 polypeptide comprising the amino acid sequence depicted in FIG. 2A or as set forth in SEQ ID NO:1).

In some cases, a multimeric polypeptide of the present disclosure comprises a first polypeptide and a second polypeptide, where the first polypeptide comprises, in order from amino terminus (N-terminus) to carboxyl terminus (C-terminus): a) an epitope (e.g., a T-cell epitope); b) a first major histocompatibility complex (MHC) polypeptide and c) an immunomodulatory polypeptide (e.g., a variant IL-2 polypeptide of the present disclosure); and where the second polypeptide comprises, in order from N-terminus to C-terminus: a) a second MHC polypeptide; and b) an immunoglobulin (Ig) Fc polypeptide. In other cases, a multimeric polypeptide of the present disclosure comprises a first polypeptide and a second polypeptide, where the first polypeptide comprises, in order from N-terminus to C-terminus: a) an epitope (e.g., a T-cell epitope); and b) a first MHC polypeptide; and where the second polypeptide comprises, in order from N-terminus to C-terminus: a) an immunomodulatory polypeptide (e.g., a variant IL-2 polypeptide of the present disclosure); b) a second MHC polypeptide; and c) an Ig Fc polypeptide. In some instances, the first and the second MHC polypeptides are Class I MHC polypeptides; e.g., in some cases, the first MHC polypeptide is an MHC Class I β2-microglobulin (B2M or β2M) polypeptide, and the second MHC polypeptide is an MHC Class I heavy chain (H chain); or the first MHC polypeptide is an MHC Class I H chain, and the second MHC polypeptide is an MHC Class I β2M polypeptide). In other cases, the first and the second MHC polypeptides are Class II MHC polypeptides; e.g., in some cases, the first MHC polypeptide is an MHC Class II α-chain polypeptide, and the second MHC polypeptide is an MHC Class II R-chain polypeptide. In other cases, the first polypeptide is an MHC Class II-chain polypeptide, and the second MHC polypeptide is an MHC Class II α-chain polypeptide. In some cases, the multimeric polypeptide includes two or more immunomodulatory polypeptides, where at least one of the immunomodulatory polypeptides is a variant IL-2 immunomodulatory polypeptide of the present disclosure. Where a multimeric polypeptide of the present disclosure includes two or more immunomodulatory polypeptides, in some cases, the two or more immunomodulatory polypeptides are present in the same polypeptide chain, and may be in tandem. Where a multimeric polypeptide of the present disclosure includes two or more immunomodulatory polypeptides, in some cases, the two or more immunomodulatory polypeptides are present in separate polypeptides. In some cases, a multimeric polypeptide of the present disclosure is a heterodimer. In some cases, a multimeric polypeptide of the present disclosure is a trimeric polypeptide.

In some cases, a multimeric polypeptide of the present disclosure comprises: a) a first polypeptide comprising, in order from N-terminus to C-terminus: i) an epitope; and ii) a first MHC polypeptide; and b) a second polypeptide comprising, in order from N-terminus to C-terminus: i) a second MHC polypeptide; and ii) an Ig Fc polypeptide; and iii) an immunomodulatory domain (e.g., a variant IL-2 polypeptide of the present disclosure). In some cases, a multimeric polypeptide of the present disclosure comprises: a) a first polypeptide comprising, in order from N-terminus to C-terminus: i) an epitope; and ii) a first MHC polypeptide; and b) a second polypeptide comprising, in order from N-terminus to C-terminus: i) a second MHC polypeptide; and ii) an immunomodulatory domain (e.g., a variant IL-2 polypeptide of the present disclosure). In some cases, a multimeric polypeptide of the present disclosure comprises: a) a first polypeptide comprising, in order from N-terminus to C-terminus: i) an epitope; and ii) a first MHC polypeptide; and b) a second polypeptide comprising, in order from N-terminus to C-terminus: i) an immunomodulatory domain (e.g., a variant IL-2 polypeptide of the present disclosure); and ii) a second MHC polypeptide. In some cases, a multimeric polypeptide of the present disclosure comprises: a) a first polypeptide comprising, in order from N-terminus to C-terminus: i) an epitope; ii) a first MHC polypeptide; and iii) an immunomodulatory domain (e.g., a variant IL-2 polypeptide of the present disclosure); and b) a second polypeptide comprising, in order from N-terminus to C-terminus: i) a second MHC polypeptide. In some cases, where a multimeric polypeptide of the present disclosure comprises a non-Ig scaffold, the non-Ig scaffold is an XTEN peptide, a transferrin polypeptide, an Fc receptor polypeptide, an elastin-like polypeptide, a silk-like polypeptide, or a silk-elastin-like polypeptide.

In some cases, a multimeric polypeptide of the present disclosure is monovalent. In some cases, a multimeric polypeptide of the present disclosure is multivalent. In some cases, a multivalent multimeric polypeptide of the present disclosure comprises an immunoglobulin Fc polypeptide on one of the first or the second polypeptide. For example, depending on the Fc polypeptide present in a multimeric polypeptide of the present disclosure, the multimeric polypeptide can be a homodimer, where two molecules of the multimeric polypeptide are present in the homodimer, where the two molecules of the multimeric polypeptide can be disulfide linked to one another, e.g., via the Fc polypeptide present in the two molecules. As another example, a multimeric polypeptide of the present disclosure can comprise three, four, or five molecules of the multimeric polypeptide, where the molecules of the multimeric polypeptide can be disulfide linked to one another, e.g., via the Fc polypeptide present in the molecules.

In some cases, a multimeric polypeptide of the present disclosure comprises: a) a first polypeptide comprising, in order from N-terminus to C-terminus: i) an epitope; ii) a β2M polypeptide; and iii) a variant IL-2 polypeptide of the present disclosure; and b) a second polypeptide comprising, in order from N-terminus to C-terminus: i) a Class I MHC heavy chain; and ii) an Fc polypeptide. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a variant IL-2 polypeptide of the present disclosure; ii) a Class I MHC heavy chain; and iii) an Fc polypeptide. In some cases, a multimeric polypeptide of the present disclosure comprises: a) a first polypeptide comprising, in order from N-terminus to C-terminus: i) an epitope; ii) a β2M polypeptide; iii) a first variant IL-2 polypeptide of the present disclosure; iv) a second variant IL-2 polypeptide of the present disclosure; and v) a third variant IL-2 polypeptide of the present disclosure; and b) a second polypeptide comprising, in order from N-terminus to C-terminus: i) a Class I MHC heavy chain; and ii) an Fc polypeptide. In some cases, the first, second, and third variant IL-2 polypeptides have the same amino acid sequence. In some cases, the first, second, and third variant IL-2 polypeptides differ from one another in amino acid sequence. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant IL-2 polypeptide of the present disclosure; ii) a second variant IL-2 polypeptide of the present disclosure; and iii) a third variant IL-2 polypeptide of the present disclosure; iv) a Class I MHC heavy chain; and v) an Fc polypeptide. In some cases, the first, second, and third variant IL-2 polypeptides have the same amino acid sequence. In some cases, the first, second, and third variant IL-2 polypeptides differ from one another in amino acid sequence.

Linkers

A multimeric polypeptide of the present disclosure can include linker peptides interposed between, e.g., an epitope and an MHC polypeptide; between an MHC polypeptide and an immunomodulatory polypeptide; between an MHC polypeptide and an Ig Fc polypeptide; between a first variant IL-2 polypeptide and a second variant IL-2 polypeptide; or a between a second variant IL-2 polypeptide and a third variant IL-2 polypeptide.

Suitable linkers (also referred to as "spacers") can be readily selected and can be of any of a number of suitable lengths, such as from 1 amino acid to 25 amino acids, from 3 amino acids to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids. A suitable linker can be 1, 2, 3, 4, 5, 6, 7, 8, 9, 10, 11, 12, 13, 14, 15, 16, 17, 18, 19, 20, 21, 22, 23, 24, or 25 amino acids in length.

Exemplary linkers include glycine polymers $(G)_n$, glycine-serine polymers (including, for example, $(GS)_n$, $(GSGGS)_n$ (SEQ ID NO:89) and $(GGGS)_n$ (SEQ ID NO:86), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see Scheraga, Rev. Computational Chem. 11173-142 (1992)). Exemplary linkers can comprise amino acid sequences including, but not limited to, GGSG (SEQ ID NO:2), GGSGG (SEQ ID NO:3), GSGSG (SEQ ID NO:4), GSGGG (SEQ ID NO:5), GGGSG (SEQ ID NO:6), GSSSG (SEQ ID NO:7), and the like. Exemplary linkers can include, e.g., Gly(Ser$_4$)n, where n is 1, 2, 3, 4, 5, 6, 7, 8, 9, or 10. In some cases, a linker comprises the amino acid sequence (GSSSS)n (SEQ ID NO:93), where n is 4. In some cases, a linker comprises the amino acid sequence (GSSSS)n (SEQ ID NO:94), where n is 5. In some cases, a linker comprises the amino acid sequence (GGGGS)n (SEQ ID NO:9), where n is 1. In some cases, a linker comprises the amino acid sequence (GGGGS)n (SEQ ID NO:92), where n is 2. In some cases, a linker comprises the amino acid sequence (GGGGS)n (SEQ ID NO:89), where n is 3. In some cases, a linker comprises the amino acid sequence (GGGGS)n (SEQ ID NO:90), where n is 4. In some cases, a linker comprises the amino acid sequence (GGGGS)n (SEQ ID NO:91), where n is 5.

In some cases, a linker polypeptide, present in a first polypeptide of a multimeric polypeptide of the present disclosure, includes a cysteine residue that can form a disulfide bond with a cysteine residue present in a second polypeptide of a multimeric polypeptide of the present disclosure. In some cases, for example, a suitable linker comprises the amino acid sequence GCGASGGGGSGGGGS (SEQ ID NO:10).

Epitopes

An epitope present in a multimeric polypeptide of the present disclosure can have a length of from about 4 amino acids to about 25 amino acids, e.g., the epitope can have a length of from 4 amino acids (aa) to 10 aa, from 10 aa to 15 aa, from 15 aa to 20 aa, or from 20 aa to 25 aa. For example, an epitope present in a multimeric polypeptide of the present disclosure can have a length of 4 amino acids (aa), 5 aa, 6 aa, 7, aa, 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, 24 aa, or 25 aa. In some cases, an epitope present in a multimeric polypeptide of the present disclosure has a length of from 5 amino acids to 10 amino acids, e.g., 5 aa, 6 aa, 7 aa, 8 aa, 9 aa, or 10 aa.

An epitope present in a multimeric polypeptide of the present disclosure is specifically bound by a T-cell, i.e., the epitope is specifically bound by an epitope-specific T cell. An epitope-specific T cell binds an epitope having a reference amino acid sequence, but does not substantially bind an epitope that differs from the reference amino acid sequence. For example, an epitope-specific T cell binds an epitope having a reference amino acid sequence, and binds an epitope that differs from the reference amino acid sequence, if at all, with an affinity that is less than $10^{-6}$ M, less than $10^{-5}$ M, or less than $10^{-4}$ M. An epitope-specific T cell can bind an epitope for which it is specific with an affinity of at least $10^{-7}$ M, at least $10^{-8}$ M, at least $10^{-9}$ M, or at least $10^{-10}$ M.

Suitable epitopes include, but are not limited to, epitopes present in a cancer-associated antigen. Cancer-associated antigens include, but are not limited to, α-folate receptor; carbonic anhydrase IX (CAIX); CD19; CD20; CD22; CD30; CD33; CD44v7/8; carcinoembryonic antigen (CEA); epithelial glycoprotein-2 (EGP-2); epithelial glycoprotein-40 (EGP-40); folate binding protein (FBP); fetal acetylcholine receptor; ganglioside antigen GD2; Her2/neu; IL-13R-a2; kappa light chain; LeY; L1 cell adhesion molecule; melanoma-associated antigen (MAGE); MAGE-A1; mesothelin; MUC1; NKG2D ligands; oncofetal antigen (h5T4); prostate stem cell antigen (PSCA); prostate-specific membrane antigen (PSMA); tumor-associate glycoprotein-72 (TAG-72); and vascular endothelial growth factor receptor-2 (VEGF-R2). See, e.g., Vigneron et al. (2013) *Cancer Immunity* 13:15; and Vigneron (2015) *BioMed Res. Int'l* Article ID 948501. In some cases, the epitope is a human papilloma virus E7 antigen epitope; see, e.g., Ramos et al. (2013) *J. Immunother.* 36:66.

In some cases, the epitope is HPV16E7/82-90 (LLMGTLGIV; SEQ ID NO:11). In some cases, the epitope is HPV16E7/86-93 (TLGIVCPI; SEQ ID NO:12). In some cases, the epitope is HPV16E7/11-20 (YMLDLQPETT; SEQ ID NO:13). In some cases, the epitope is HPV16E7/11-19 (YMLDLQPET; SEQ ID NO:87). See, e.g., Ressing et al. ((1995) *J. Immunol.* 154:5934) for additional suitable HPV epitopes.

MHC Polypeptides

As noted above, a multimeric polypeptide of the present disclosure includes MHC polypeptides. For the purposes of the instant disclosure, the term "major histocompatibility complex (MHC) polypeptides" is meant to include MHC polypeptides of various species, including human MHC (also referred to as human leukocyte antigen (HLA)) polypeptides, rodent (e.g., mouse, rat, etc.) MHC polypeptides, and MHC polypeptides of other mammalian species (e.g., lagomorphs, non-human primates, canines, felines, ungulates (e.g., equines, bovines, ovines, caprines, etc.), and the like. The term "MHC polypeptide" is meant to include Class I MHC polypeptides (e.g., β-2 microglobulin and MHC class I heavy chain) and MHC Class II polypeptides (e.g., MHC Class II a polypeptide and MHC Class II polypeptide).

As noted above, in some embodiments of a multimeric polypeptide of the present disclosure, the first and the second MHC polypeptides are Class I MHC polypeptides; e.g., in some cases, the first MHC polypeptide is an MHC Class I β2-microglobulin (β2M) polypeptide, and the second MHC polypeptide is an MHC Class I heavy chain (H chain). In other cases, the first and the second MHC polypeptides are Class II MHC polypeptides; e.g., in some cases, the first MHC polypeptide is an MHC Class II α-chain polypeptide, and the second MHC polypeptide is an MHC Class II R-chain polypeptide. In other cases, the first polypeptide is an MHC Class II β-chain polypeptide, and the second MHC polypeptide is an MHC Class II α-chain polypeptide.

In some cases, an MHC polypeptide of a multimeric polypeptide of the present disclosure is a human MHC polypeptide, where human MHC polypeptides are also referred to as "human leukocyte antigen" ("HLA") polypeptides. In some cases, an MHC polypeptide of a multimeric polypeptide of the present disclosure is a Class I HLA polypeptide, e.g., a β2-microglobulin polypeptide, or a Class I HLA heavy chain polypeptide. Class I HLA heavy chain polypeptides include HLA-A heavy chain polypeptides, HLA-B heavy chain polypeptides, HLA-C heavy chain polypeptides, HLA-E heavy chain polypeptides, HLA-F heavy chain polypeptides, and HLA-G heavy chain polypeptides. In some cases, an MHC polypeptide of a multimeric polypeptide of the present disclosure is a Class II HLA polypeptide, e.g., a Class II HLA α chain or a Class II HLA β chain. MHC Class II polypeptides include MCH Class II DP α and β polypeptides, DM α and β polypeptides, DOA α and β polypeptides, DOB a and f polypeptides, DQ α and β polypeptides, and DR α and β polypeptides.

As an example, an MHC Class I heavy chain polypeptide of a multimeric polypeptide of the present disclosure can comprise an amino acid sequence having at least 75%, at least 80%, at least 85%, at least 90%, at least 95%, at least 98%, at least 99%, or 100%, amino acid sequence identity to amino acids 25-365 of the amino acid sequence of the human HLA-A heavy chain polypeptide depicted in FIG. 5A.

As an example, an MHC Class I heavy chain polypeptide of a multimeric polypeptide of the present disclosure can comprise an amino acid sequence having at least 75%, at least 80%, at least 85%, at least 90%, at least 95%, at least 98%, at least 99%, or 100%, amino acid sequence identity to amino acids 25-365 of the amino acid sequence of the following human HLA-A heavy chain amino acid sequence:

```
                                        (SEQ ID NO: 14)
GSHSMRYFFTSVSRPGRGEPRFIAVGYVDDTQFVRFDSDAASQRMEPRAP

WIEQEGPEYWDGETRKVKAHSQTHRVDLGTLRGYYNQSEAGSHTVQRMYG

CDVGSDWRFLRGYHQYAYDGKDYIALKEDLRSWTAADMAAQTTKHKWEAA

HVAEQLRAYLEGTCVEWLRRYLENGKETLQRTDAPKTHMTHHAVSDHEAT
```

```
LRCWALSFYPAEITLTWQRDGEDQTQDTELVETRPAGDTFQKWAAVVVP

SGQEQRYTCHVQHEGLPKPLTLRWEP.
```

As another example, an MHC Class I heavy chain polypeptide of a multimeric polypeptide of the present disclosure can comprise an amino acid sequence having at least 75%, at least 80%, at least 85%, at least 90%, at least 95%, at least 98%, at least 99%, or 100%, amino acid sequence identity to amino acids 25-362 of the amino acid sequence of the human HLA-B heavy chain polypeptide depicted in FIG. 5B.

As another example, an MHC Class I heavy chain polypeptide of a multimeric polypeptide of the present disclosure can comprise an amino acid sequence having at least 75%, at least 80%, at least 85%, at least 90%, at least 95%, at least 98%, at least 99%, or 100%, amino acid sequence identity to amino acids 25-362 of the amino acid sequence of the human HLA-C heavy chain polypeptide depicted in FIG. 5C.

As another example, an MHC Class I heavy chain polypeptide of a multimeric polypeptide of the present disclosure can comprise an amino acid sequence having at least 75%, at least 80%, at least 85%, at least 90%, at least 95%, at least 98%, at least 99%, or 100%, amino acid sequence identity to the following amino acid sequence:

```
                                          (SEQ ID NO: 15)
GPHSLRYFVTAVSRPGLGEPRFIAVGYVDDTQFVRFDSDADNPRFEPRAP

WMEQEGPEYWEEQTQRAKSDEQWFRVSLRTAQRYYNQSKGGSHTFQRMFG

CDVGSDWRLLRGYQQFAYDGRDYIALNEDLKTWTAADTAALITRRKWEQA

GDAEYYRAYLEGECVEWLRRYLELGNETLLRTDSPKAHVTYHPRSQVDVT

LRCWALGFYPADITLTWQLNGEDLTQDMELVETRPAGDTFQKWAAVVVP

LGKEQNYTCHVHHKGLPEPLTLRW.
```

A β2-microglobulin (β2M) polypeptide of a multimeric polypeptide of the present disclosure can be a human β2M polypeptide, a non-human primate β2M polypeptide, a murine β2M polypeptide, and the like. In some instances, a β2M polypeptide comprises an amino acid sequence having at least 75%, at least 80%, at least 85%, at least 90%, at least 95%, at least 98%, at least 99%, or 100%, amino acid sequence identity to a β2M amino acid sequence depicted in FIG. 6. In some instances, a β2M polypeptide comprises an amino acid sequence having at least 75%, at least 80%, at least 85%, at least 90%, at least 95%, at least 98%, at least 99%, or 100%, amino acid sequence identity to amino acids 21 to 119 of a β2M amino acid sequence depicted in FIG. 6.

In some cases, an MHC polypeptide comprises a single amino acid substitution relative to a reference MHC polypeptide (where a reference MHC polypeptide can be a wild-type MHC polypeptide), where the single amino acid substitution substitutes an amino acid with a cysteine (Cys) residue. Such cysteine residues, when present in an MHC polypeptide of a first polypeptide of a multimeric polypeptide of the present disclosure, can form a disulfide bond with a cysteine residue present in a second polypeptide chain of a multimeric polypeptide of the present disclosure.

In some cases, a first MHC polypeptide in a first polypeptide of a multimeric polypeptide of the present disclosure, and/or the second MHC polypeptide in the second polypeptide of a multimeric polypeptide of the present disclosure, includes an amino acid substitution to substitute an amino acid with a cysteine, where the substituted cysteine in the first MHC polypeptide forms a disulfide bond with a cysteine in the second MHC polypeptide, where a cysteine in the first MHC polypeptide forms a disulfide bond with the substituted cysteine in the second MHC polypeptide, or where the substituted cysteine in the first MHC polypeptide forms a disulfide bond with the substituted cysteine in the second MHC polypeptide.

For example, in some cases, one of following pairs of residues in an HLA β2-microglobulin and an HLA Class I heavy chain is substituted with cysteines (where residue numbers are those of the mature polypeptide): 1) β2M residue 12, HLA Class I heavy chain residue 236; 2) β2M residue 12, HLA Class I heavy chain residue 237; 3) β2M residue 8, HLA Class I heavy chain residue 234; 4) β2M residue 10, HLA Class I heavy chain residue 235; 5) β2M residue 24, HLA Class I heavy chain residue 236; 6) β2M residue 28, HLA Class I heavy chain residue 232; 7) β2M residue 98, HLA Class I heavy chain residue 192; 8) β2M residue 99, HLA Class I heavy chain residue 234; 9) β2M residue 3, HLA Class I heavy chain residue 120; 10) β2M residue 31, HLA Class I heavy chain residue 96; 11) β2M residue 53, HLA Class I heavy chain residue 35; 12) β2M residue 60, HLA Class I heavy chain residue 96; 13) β2M residue 60, HLA Class I heavy chain residue 122; 14) β2M residue 63, HLA Class I heavy chain residue 27; 15) β2M residue Arg3, HLA Class I heavy chain residue Gly120; 16) β2M residue His31, HLA Class I heavy chain residue Gln96; 17) β2M residue Asp53, HLA Class I heavy chain residue Arg35; 18) β2M residue Trp60, HLA Class I heavy chain residue Gln96; 19) β2M residue Trp60, HLA Class I heavy chain residue Asp122; 20) β2M residue Tyr63, HLA Class I heavy chain residue Tyr27; 21) β2M residue Lys6, HLA Class I heavy chain residue Glu232; 22) β2M residue Gln8, HLA Class I heavy chain residue Arg234; 23) β2M residue Tyr10, HLA Class I heavy chain residue Pro235; 24) β2M residue Ser11, HLA Class I heavy chain residue Gln242; 25) β2M residue Asn24, HLA Class I heavy chain residue Ala236; 26) β2M residue Ser28, HLA Class I heavy chain residue Glu232; 27) β2M residue Asp98, HLA Class I heavy chain residue His192; and 28) β2M residue Met99, HLA Class I heavy chain residue Arg234. The amino acid numbering of the MHC/HLA Class I heavy chain is in reference to the mature MHC/HLA Class I heavy chain, without a signal peptide. For example, in the amino acid sequence depicted in FIG. 5A, which includes a signal peptide, Gly120 is Gly144; Gln96 is Gln120; etc. In some cases, the β2M polypeptide comprises an R12C substitution, and the HLA Class I heavy chain comprises an A236C substitution; in such cases, a disulfide bond forms between Cys-12 of the β2M polypeptide and Cys-236 of the HLA Class I heavy chain. For example, in some cases, residue 236 of the mature HLA-A amino acid sequence (i.e., residue 260 of the amino acid sequence depicted in FIG. 5A) is substituted with a Cys. In some cases, residue 236 of the mature HLA-B amino acid sequence (i.e., residue 260 of the amino acid sequence depicted in FIG. 5B) is substituted with a Cys. In some cases, residue 236 of the mature HLA-C amino acid sequence (i.e., residue 260 of the amino acid sequence depicted in FIG. 5C) is substituted with a Cys. In some cases, residue 32 (corresponding to Arg-12 of mature β2M) of an amino acid sequence depicted in FIG. 6 is substituted with a Cys.

In some cases, a β2M polypeptide comprises the amino acid sequence: IQRTPKIQVY SRHPAENGKS NFLN-CYVSGF HPSDIEVDLLKNGERIEKVE HSDLSFSKDW SFYLLYYTEF TPTEKDEYAC RVNHVTLSQP KIVKWDRDM (SEQ ID NO:16). In some cases, a β2M polypeptide comprises the amino acid sequence: IQRTPKIQVY SCHPAENGKS NFLNCYVSGF HPSDIEVDLLKNGERIEKVE HSDLSFSKDW SFYLLYYTEF TPTEKDEYAC RVNHVTLSQP KIVKWDRDM (SEQ ID NO:17).

In some cases, an HLA Class I heavy chain polypeptide comprises the amino acid sequence:

```
                                        (SEQ ID NO: 14)
GSHSMRYFFTSVSRPGRGEPRFIAVGYVDDTQFVRFDSDAASQRMEPRAP

WIEQEGPEYWDGETRKVKAHSQTHRVDLGTLRGYYNQSEAGSHTVQRMYG

CDVGSDWRFLRGYHQYAYDGKDYIALKEDLRSWTAADMAAQTTKHKWEAA

HVAEQLRAYLEGTCVEWLRRYLENGKETLQRIDAPKTHMTHHAVSDHEAT

LRCWALSFYPAEITLTWQRDGEDQTQDTELVETRP<u>A</u>GDGTFQKWAAVVVP

SGQEQRYTCHVQHEGLPKPLTLRWEP.
```

In some cases, an HLA Class I heavy chain polypeptide comprises the amino acid sequence:

```
                                        (SEQ ID NO: 18)
GSHSMRYFFTSVSRPGRGEPRFIAVGYVDDTQFVRFDSDAASQRMEPRAP

WIEQEGPEYWDGETRKVKAHSQTHRVDLGTLRGYYNQSEAGSHTVQRMYG

CDVGSDWRFLRGYHQYAYDGKDYIALKEDLRSWTAADMAAQTTKHKWEAA

HVAEQLRAYLEGTCVEWLRRYLENGKETLQRTDAPKTHMTHHAVSDHEAT

LRCWALSFYPAEITLTWQRDGEDQTQDTELVETRP<u>C</u>GDGTFQKWAAVVVP

SGQEQRYTCHVQHEGLPKPLTLRWEP.
```

In some cases, an HLA Class I heavy chain polypeptide comprises the amino acid sequence:

```
                                        (SEQ ID NO: 19)
GSHSMRYFFTSVSRPGRGEPRFIAVGYVDDTQFVREDSDAASQRMEPRAP

WIEQEGPEYWDGETRKVKAHSQTHRVDLGTLRG<u>A</u>YNQSEAGSHTVQRMYG

CDVGSDWRFLRGYHQYAYDGKDYIALKEDLRSWTAADMAAQTTKHKWEAA

HVAEQLRAYLEGTCVEWLRRYLENGKETLQRIDAPKTHMTHHAVSDHEAT

LRCWALSFYPAEITLIWQRDGEDQTQDTELVETRP<u>C</u>GDGTFQKWAAVVVP

SGQEQRYTCHVQHEGLPKPLTLRWE.
```

In some cases, the β2M polypeptide comprises the following amino acid sequence:
IQRTPKIQVY SCHPAENGKS NFLNCYVSGF HPSDIEVDLLKNGERIEKVE HSDLSFSKDW SFYLLYYTEF TPTEKDEYAC RVNHVTLSQP KIVKWDRDM (SEQ ID NO:17); and the HLA ClassI heavy chain polypeptide of a multimeric polypeptide of the present disclosure comprises the following amino acid sequence:
GSHSMRYFFTSVSRPGRGEPRFIAVGYVDDTQFVRFDSDAASQRMEPRAPWIEQEGPEYWDGETRKVKAHSQTHRVDLGTLRGYYNQSEAGSHTVQRMYGCDVGSDWRFLRGYHQYAYDGKDYIALKEDLRSWTAADMAAQTTKHKWEAAHVAEQLRAYLEGTCVEWLRRYLENGKETLQRTDAPKTHMTHHAVSDHEATLRCWALSFYPAEITLTWQRDGEDQTQDTELVETRPCGDGTFQKWAAVVVPS GQEQRYTCHVQHEGLPKPLTLRWEP (SEQ ID NO:18), where the Cys residues that are underlined and in bold form a disulfide bond with one another in the multimeric polypeptide.

In some cases, the β2M polypeptide comprises the amino acid sequence:

```
                                        (SEQ ID NO: 17)
IQRTPKIQVYS<u>C</u>HPAENGKSNFLNCYVSGFHPSDIEVDLLKNGERIEKVE

HSDLSFSKDWSFYLLYYTEFTPTEKDEYACRVNHVILSQPKIVKWDRDM.
```

Immunomodulatory Polypeptides

A multimeric polypeptide of the present disclosure comprises a variant IL-2 polypeptide of the present disclosure, as described above, that is a variant of a naturally occurring costimulatory protein, which variant exhibits a reduced affinity for its counterpart (cognate) costimulatory protein on the T cell (e.g., IL-2R) as compared to the affinity of the naturally occurring IL-2 polypeptide for the counterpart costimulatory protein (IL-2R). Thus, a multimeric polypeptide of the present disclosure comprises the variant IL-2 polypeptide present in a multimeric polypeptide of the present disclosure.

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2E, where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2E, where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2E, where amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2E, where amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2E, where amino acid 16 is Val. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2E, where amino acid 16 is Leu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2E, where amino acid 16 is Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2E, where amino acid 16 is Asn. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2E, where amino acid 16 is Asp. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2E, where amino acid 16 is Cys. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2E, where amino acid 16 is Gln. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2E, where amino acid 16 is Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2E, where amino acid 16 is Met. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2E, where amino acid 16 is Phe. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2E, where amino acid 16 is Ser. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2E, where amino acid 16 is Thr. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2E, where amino acid 16 is Trp. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2E, where amino acid 16 is Tyr. In some cases, the variant IL-2 polypeptide has a binding affinity for IL-2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide has a length of 133 amino acids.

F42 Substitution

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is Val. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is Leu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is Ile. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or the synTac comprising same, has a binding affinity for IL-2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide present in a multimeric polypeptide of the present disclosure has a length of 133 amino acids.

Y45 Substitution

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is Val. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is Leu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is Ile. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or the synTac comprising same, has a binding affinity for IL-2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide present in a multimeric polypeptide of the present disclosure has a length of 133 amino acids.

Q126 Substitution

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is Val. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is Leu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is Ile. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL-2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide present in a multimeric polypeptide of the present disclosure has a length of 133 amino acids.

F42 and H16 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is Ala and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is Ala and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is Val and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is Leu, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is Ile and amino acid 16 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, a multimeric polypeptide of the present disclosure comprises 2 copies of the IL-2 variant comprising F42A and H16A substitutions, where the multimeric polypeptide comprises HLA Class I heavy chain and β2M polypeptides, and where the 2 copies of IL-2 (F42A, H16A) are on the polypeptide chain comprising the HLA Class I heavy chain. In some cases, the variant IL-2 polypeptide, or a synTac comprising same, has a binding affinity for IL-2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, from 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide present in a multimeric polypeptide of the present disclosure has a length of 133 amino acids. In some cases, the variant IL-2 polypeptide comprises the amino acid sequence depicted in FIG. 34B (comprising H16A and F42A substitutions).

F42 and D20 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; and where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala, Gly, Val, Leu, or Ile; and where amino acid 20 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala, Gly, Val, Leu, or Ile; and where amino acid 20 is Asn, Gln, Lys, Arg, or His. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Val and amino acid 20 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Leu, and amino acid 20 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ile and amino acid 20 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Asn. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Gln. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Lys. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Arg. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is His. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL-2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide present in a multimeric polypeptide of the present disclosure has a length of 133 amino acids.

F42, D20, and E15 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; and where amino acid 15 is an amino acid other than a glutamic acid, e.g., where amino acid 15 is Gly, Ala, Val, Leu, Ile, Pro, Phe, Tyr, Trp, Ser, Thr, Cys, Met, Asn, Gln, Lys, Arg, His, or Asp. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, Gly, Val, Leu, or Ile; where amino acid 20 is Ala, Gly, Val, Leu, or Ile; and where amino acid 15 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, Gly, Val, Leu, or Ile; where amino acid 20 is Asn, Gln, Lys, Arg, or His; and where amino acid 15 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Ala, and amino acid 15 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Gly, and amino acid 15 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Val, amino acid 20 is Ala, and amino acid 15 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Leu, amino acid 20 is Ala, and amino acid 15 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ile, amino acid 20 is Ala, and amino acid 15 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Asn, and amino acid 15 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala, amino acid 20 is Gln, and amino acid 15 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Lys, and amino acid 15 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Arg, and amino acid 15 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala, amino acid 20 is His, and amino acid 15 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, the variant IL-2 polypeptide, or a synTac comprising same, has a binding affinity for IL-2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide present in a multimeric polypeptide of the present disclosure has a length of 133 amino acids.

F42, D20, and H16 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, Gly, Val, Leu, or Ile; where amino acid 20 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, Gly, Val, Leu, or Ile; where amino acid 20 is Asn, Gln, Lys, Arg, or His; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Gly, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Val, amino acid 20 is Ala, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Leu, amino acid 20 is Ala, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ile, amino acid 20 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Asn, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Gln, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Lys, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Arg, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is His, and amino acid 16 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL-2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide present in a multimeric polypeptide of the present disclosure has a length of 133 amino acids.

F42, D20, and Q126 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; and where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, Gly, Val, Leu, or Ile; where amino acid 20 is Ala, Gly, Val, Leu, or Ile; and where amino acid 126 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, Gly, Val, Leu, or Ile; where amino acid 20 is Asn, Gln, Lys, Arg, or His; and where amino acid 126 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Gly, and amino acid 126 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Val, amino acid 20 is Ala, and amino acid 126 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Leu, amino acid 20 is Ala, and amino acid 126 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ile, amino acid 20 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Asn, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Gln, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Lys, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Arg, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is His, and amino acid 126 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL-2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide present in a multimeric polypeptide of the present disclosure has a length of 133 amino acids.

F42, D20, and Y45 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; and where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, Gly, Val, Leu, or Ile; where amino acid 20 is Ala, Gly, Val, Leu, or Ile; and where amino acid 45 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, Gly, Val, Leu, or Ile; where amino acid 20 is Asn, Gln, Lys, Arg, or His; and where amino acid 45 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Ala, and amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Gly, and amino acid 45 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Val, amino acid 20 is Ala, and amino acid 45 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Leu, amino acid 20 is Ala, and amino acid 45 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ile, amino acid 20 is Ala, and amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Asn, and amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Gln, and amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Lys, and amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Arg, and amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is His, and amino acid 45 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL-2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide present in a multimeric polypeptide of the present disclosure has a length of 133 amino acids.

F42, D20, Y45, and H16 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, Gly, Val, Leu, or Ile; where amino acid 20 is Ala, Gly, Val, Leu, or Ile; where amino acid 45 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, Gly, Val, Leu, or Ile; where amino acid 20 is Asn, Gln, Lys, Arg, or His; where amino acid 45 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Ala, amino acid 45 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Gly, amino acid 45 is Gly, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Val, amino acid 20 is Ala, amino acid 45 is Gly, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Leu, amino acid 20 is Ala, amino acid 45 is Gly, and amino acid 16 is Val. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ile, amino acid 20 is Ala, amino acid 45 is Ala, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Asn, amino acid 45 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Gln, amino acid 45 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Lys, amino acid 45 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Arg, amino acid 45 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is His, amino acid 45 is Ala, and amino acid 16 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL-2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide present in a multimeric polypeptide of the present disclosure has a length of 133 amino acids.

F42, D20, Y45, and Q126 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu; and where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, Gly, Val, Leu, or Ile; where amino acid 20 is Ala, Gly, Val, Leu, or Ile; where amino acid 45 is Ala, Gly, Val, Leu, or Ile; and where amino acid 126 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, Gly, Val, Leu, or Ile; where amino acid 20 is Asn, Gln, Lys, Arg, or His; where amino acid 45 is Ala, Gly, Val, Leu, or Ile; and where amino acid 126 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Ala, amino acid 45 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Gly, amino acid 45 is Gly, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Val, amino acid 20 is Ala, amino acid 45 is Gly, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Leu, amino acid 20 is Ala, amino acid 45 is Gly, and amino acid 126 is Val. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ile, amino acid 20 is Ala, amino acid 45 is Ala, and amino acid 126 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Asn, amino acid 45 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Gln, amino acid 45 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Lys, amino acid 45 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Arg, amino acid 45 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is His, amino acid 45 is Ala, and amino acid 126 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL-2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide present in a multimeric polypeptide of the present disclosure has a length of 133 amino acids.

F42, D20, Y45, H16, and Q126 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu; where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, Gly, Val, Leu, or Ile; where amino acid 20 is Ala, Gly, Val, Leu, or Ile; where amino acid 45 is Ala, Gly, Val, Leu, or Ile; where amino acid 126 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, Gly, Val, Leu, or Ile; where amino acid 20 is Asn, Gln, Lys, Arg, or His; where amino acid 45 is Ala, Gly, Val, Leu, or Ile; where amino acid 126 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Ala, amino acid 45 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Gly, amino acid 45 is Gly, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Val, amino acid 20 is Ala, amino acid 45 is Gly, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Leu, amino acid 20 is Ala, amino acid 45 is Gly, amino acid 126 is Val, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ile, amino acid 20 is Ala, amino acid 45 is Ala, amino acid 126 is Gly, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Asn, amino acid 45 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Gln, amino acid 45 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Lys, amino acid 45 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Arg, amino acid 45 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is His, amino acid 45 is Ala, amino acid 126 is Ala, and amino acid 16 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL-2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide present in a multimeric polypeptide of the present disclosure has a length of 133 amino acids.

F42, Q126, and H16 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, Gly, Val, Leu, or Ile; where amino acid 126 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, Gly, Val, Leu, or Ile; where amino acid 126 is Asn, Gln, Lys, Arg, or His; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Gly, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Val, amino acid 126 is Ala, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Leu, amino acid 126 is Ala, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ile, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Asn, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Lys, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Arg, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is His, and amino acid 16 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising the variant IL-2 polypeptide, has a binding affinity for IL-2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide has a length of 133 amino acids.

Multiple Immunomodulatory Domains

As noted above, in some cases, a multimeric polypeptide of the present disclosure comprises two or more immunomodulatory polypeptides, where at least one of the two or more immunomodulatory polypeptide is a variant IL-2 polypeptide of the present disclosure.

In some cases, a multimeric polypeptide of the present disclosure comprises two or more copies of a variant IL-2 polypeptide of the present disclosure. In some cases, the two or more variant IL-2 polypeptides are on the same polypeptide chain of a multimeric polypeptide of the present disclosure. In some cases, the two or more variant IL-2 polypeptides are on separate polypeptide chains of a multimeric polypeptide of the present disclosure.

In some cases, a multimeric polypeptide of the present disclosure comprises a first immunomodulatory polypeptide, and at least a second immunomodulatory polypeptide, where the first immunomodulatory polypeptide is a variant IL-2 polypeptide of the present disclosure, and the second immunomodulatory polypeptide is not an IL-2 polypeptide. For example, in some cases, the second immunomodulatory polypeptide is a member of the tumor necrosis factor (TNF) superfamily; e.g., a FasL polypeptide, a 4-1BBL polypeptide, a CD40 polypeptide, an OX40L polypeptide, a CD30L polypeptide, a CD70 polypeptide, etc. In some cases, the second immunomodulatory polypeptide of a multimeric polypeptide of the present disclosure is a T-cell co-stimulatory polypeptide and is a member of the immunoglobulin (Ig) superfamily; e.g., a CD7 polypeptide, a CD86 polypeptide, an ICAM polypeptide, etc. In some cases, the second immunomodulatory polypeptide is 4-1BBL, OX40L, ICOS-L, ICAM, PD-L1, CD86, FasL, and PD-L2. Suitable immunomodulatory polypeptides of a multimeric polypeptide of the present disclosure include, e.g., CD7, CD30L, CD40, CD70, CD83, HLA-G, MICA, MICB, HVEM, lymphotoxin beta receptor, 3/TR6, ILT3, ILT4, or HVEM. In some cases, the second immunomodulatory polypeptide is a variant (e.g., a variant of naturally-occurring 4-1BBL) that exhibits an affinity (determined as described above) for its counterpart costimulatory protein found on the T cell that is reduced as compared to the affinity of the naturally occurring costimulatory protein (immunomodulatory polypeptide) for its counterpart (cognate) costimulatory protein. In some cases, a multimeric polypeptide of the present disclosure comprises a first immunomodulatory polypeptide, and at least a second immunomodulatory polypeptide, wherein neither is a variant IL-2 polypeptide. It should be understood that this disclosure relates generally to the use of immodulatory polypeptides that are variants of naturally occurring immodulatory polypeptides, which variants exhibit an affinity (determined as described above) for counterpart costimulatory proteins that is reduced as compared to the affinity of the naturally occurring costimulatory protein (immunomodulatory polypeptide) for the counterpart (cognate) costimulatory protein.

Further T cell modulatory domains (MODs) that can be included in a multimeric polypeptide of the present disclosure include naturally occurring or synthetic human gene products (protein), affinity reagents (e.g., an antibody, antibody fragment, single chain Fvs, aptamers, nanobody) targeting a human gene product, including, but not limited to all secreted proteins arising from classical and non-classical (e.g., FGF2, IL1, S100A4) secretion mechanisms, and ectodomains of all cell surface proteins anchored by naturally occurring genetically encoded protein segments (single or multiple membrane spans) or post-translational modifications such as GPI linkages). Any naturally occurring or synthetic affinity reagent (e.g., antibody, antibody fragment, single chain Fvs, aptamer, nanobody, lectin, etc) targeting a cell surface glycan or other post-translational modification (e.g., sulfation). Examples include, but are not limited to, members of the TNF/TNFR family (OX40L, ICOSL, FASL, LTA, LTB TRAIL, CD153, TNFSF9, RANKL, TWEAK, TNFSF13, TNFSF13b, TNFSF14, TNFSF15, TNFSF18, CD40LG, CD70) or affinity reagents directed at the TNF/TNFR family members; members of the Immunoglobulin superfamily (VISTA, PD1, PD-L1, PD-L2, B71, B72, CTLA4, CD28, TIM3, CD4, CD8, CD19, T cell receptor chains, ICOS, ICOS ligand, HHLA2, butyrophilins, BTLA, B7-H3, B7-H4, CD3, CD79a, CD79b, IgSF CAMS (including CD2, CD58, CD48, CD150, CD229, CD244, ICAM-1), Leukocyte immunoglobulin like receptors (LILR), killer cell immunoglobulin like receptors (KIR)), lectin superfamily members, selectins, cytokines/chemokine and cytokine/chemokine receptors, growth factors and growth factor receptors), adhesion molecules (integrins, fibronectins, cadherins), or ecto-domains of multi-span integral membrane protein, or affinity reagents directed at the Immunoglobulin superfamily and listed gene products. In addition, active homologs/orthologs of these gene products, including but not limited to, viral sequences (e.g., CMV, EBV), bacterial sequences, fungal sequences, eukaryotic pathogens (e.g., *Schistosoma, Plasmodium, Babesia, Eimeria, Theileria, Toxoplasma, Entamoeba, Leishmania,* and *Trypanosoma*), and mammalian-derived coding regions. In addition. a MOD may comprise a small molecules drug targeting a human gene product.

Scaffold Polypeptides

A T-cell modulatory multimeric polypeptide of the present disclosure comprises an Fc polypeptide, or another suitable scaffold polypeptide.

Suitable scaffold polypeptides include antibody-based scaffold polypeptides and non-antibody-based scaffolds. Non-antibody-based scaffolds include, e.g., albumin, an XTEN (extended recombinant) polypeptide, transferrin, an Fc receptor polypeptide, an elastin-like polypeptide (see, e.g., Hassouneh et al. (2012) *Methods Enzymol.* 502:215; e.g., a polypeptide comprising a pentapeptide repeat unit of (Val-Pro-Gly-X-Gly; SEQ ID NO:100), where X is any amino acid other than proline), an albumin-binding polypeptide, a silk-like polypeptide (see, e.g., Valluzzi et al. (2002) *Philos Trans R Soc Lond B Biol Sci.* 357:165), a silk-elastin-like polypeptide (SELP; see, e.g., Megeed et al. (2002) *Adv Drug Deliv Rev.* 54:1075), and the like. Suitable XTEN polypeptides include, e.g., those disclosed in WO 2009/023270, WO 2010/091122, WO 2007/103515, US 2010/0189682, and US 2009/0092582; see also Schellenberger et al. (2009) *Nat Biotechnol.* 27:1186). Suitable albumin polypeptides include, e.g., human serum albumin.

Suitable scaffold polypeptides will in some cases be a half-life extending polypeptides. Thus, in some cases, a suitable scaffold polypeptide increases the in vivo half-life (e.g., the serum half-life) of the multimeric polypeptide, compared to a control multimeric polypeptide lacking the scaffold polypeptide. For example, in some cases, a scaffold polypeptide increases the in vivo half-life (e.g., the serum half-life) of the multimeric polypeptide, compared to a control multimeric polypeptide lacking the scaffold polypeptide, by at least about 10%, at least about 15%, at least about 20%, at least about 25%, at least about 50%, at least about 2-fold, at least about 2.5-fold, at least about 5-fold, at least about 10-fold, at least about 25-fold, at least about 50-fold, at least about 100-fold, or more than 100-fold. As an example, in some cases, an Fc polypeptide increases the in vivo half-life (e.g., the serum half-life) of the multimeric polypeptide, compared to a control multimeric polypeptide lacking the Fc polypeptide, by at least about 10%, at least about 15%, at least about 20%, at least about 25%, at least about 50%, at least about 2-fold, at least about 2.5-fold, at least about 5-fold, at least about 10-fold, at least about 25-fold, at least about 50-fold, at least about 100-fold, or more than 100-fold.

Fc Polypeptides

In some cases, the first and/or the second polypeptide chain of a multimeric polypeptide of the present disclosure comprises an Fc polypeptide. The Fc polypeptide of a multimeric polypeptide of the present disclosure can be a human IgG1 Fc, a human IgG2 Fc, a human IgG3 Fc, a human IgG4 Fc, etc. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to an amino acid sequence of an Fc region depicted in FIGS. 4A-C. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 4A. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 4A; and comprises a substitution of N77; e.g., the Fc polypeptide comprises an N77A substitution. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgG2 Fc polypeptide depicted in FIG. 4A; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 99-325 of the human IgG2 Fc polypeptide depicted in FIG. 4A. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgG3 Fc polypeptide depicted in FIG. 4A; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 19-246 of the human IgG3 Fc polypeptide depicted in FIG. 4A. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgM Fc polypeptide depicted in FIG. 4B; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 1-276 to the human IgM Fc polypeptide depicted in FIG. 4B. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgA Fc polypeptide depicted in FIG. 4C; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 1-234 to the human IgA Fc polypeptide depicted in FIG. 4C.

In some cases, the Fc polypeptide present in a multimeric polypeptide of the present disclosure comprises the amino acid sequence depicted in FIG. 33A (human IgG1 Fc). In some cases, the Fc polypeptide present in a multimeric polypeptide of the present disclosure comprises the amino acid sequence depicted in FIG. 33A (human IgG1 Fc), except for a substitution of N297 with an amino acid other than asparagine. In some cases, the Fc polypeptide present in a multimeric polypeptide of the present disclosure comprises the amino acid sequence depicted in FIG. 33C (human IgG1 Fc comprising an N297A substitution). In some cases, the Fc polypeptide present in a multimeric polypeptide of the present disclosure comprises the amino acid sequence depicted in FIG. 33A (human IgG1 Fc), except for a substitution of L234 with an amino acid other than leucine. In some cases, the Fc polypeptide present in a multimeric polypeptide of the present disclosure comprises the amino acid sequence depicted in FIG. 33A (human IgG1 Fc), except for a substitution of L235 with an amino acid other than leucine. In some cases, the Fc polypeptide present in a multimeric polypeptide of the present disclosure comprises the amino acid sequence depicted in FIG. 33D (human IgG1 Fc comprising an L234A substitution and an L235A substitution). In some cases, the Fc polypeptide present in a multimeric polypeptide of the present disclosure comprises the amino acid sequence depicted in FIG. 33A (human IgG1 Fc), except for a substitution of P331 with an amino acid other than proline; in some cases, the substitution is a P331S substitution. In some cases, the Fc polypeptide present in a multimeric polypeptide of the present disclosure comprises the amino acid sequence depicted in FIG. 33A (human IgG1 Fc), except for substitutions at L234 and L235 with amino acids other than leucine. In some cases, the Fc polypeptide present in a multimeric polypeptide of the present disclosure comprises the amino acid sequence depicted in FIG. 33A (human IgG1 Fc), except for substitutions at L234 and L235 with amino acids other than leucine, and a substitution of P331 with an amino acid other than proline. In some cases, the Fc polypeptide present in a multimeric polypeptide of the present disclosure comprises the amino acid sequence depicted in FIG. 33B (human IgG1 Fc comprising L234F, L235E, and P331S substitutions).

Additional Polypeptides

A polypeptide chain of a multimeric polypeptide of the present disclosure can include one or more polypeptides in addition to those described above. Suitable additional polypeptides include epitope tags and affinity domains. The one or more additional polypeptide can be included at the N-terminus of a polypeptide chain of a multimeric polypeptide of the present disclosure, at the C-terminus of a polypeptide chain of a multimeric polypeptide of the present disclosure, or internally within a polypeptide chain of a multimeric polypeptide of the present disclosure.

Epitope Tag

Suitable epitope tags include, but are not limited to, hemagglutinin (HA; e.g., YPYDVPDYA (SEQ ID NO:20); FLAG (e.g., DYKDDDDK (SEQ ID NO:21); c-myc (e.g., EQKLISEEDL; SEQ ID NO:22), and the like.

Affinity Domain

Affinity domains include peptide sequences that can interact with a binding partner, e.g., such as one immobilized on a solid support, useful for identification or purification. DNA sequences encoding multiple consecutive single amino acids, such as histidine, when fused to the expressed protein, may be used for one-step purification of the recombinant protein by high affinity binding to a resin column, such as nickel sepharose. Exemplary affinity domains include His5 (HHHHH) (SEQ ID NO:23), HisX6 (HHHHHH) (SEQ ID NO:24), C-myc (EQKLISEEDL) (SEQ ID NO:22), Flag (DYKDDDDK) (SEQ ID NO:21), StrepTag (WSHPQFEK) (SEQ ID NO:25), hemagglutinin, e.g., HA Tag (YPYDVPDYA) (SEQ ID NO:20), glutathione-S-transferase (GST), thioredoxin, cellulose binding domain, RYIRS (SEQ ID NO:26), Phe-His-His-Thr (SEQ ID NO:88), chitin binding domain, S-peptide, T7 peptide, SH2 domain, C-end RNA tag, WEAAAREACCRECCARA (SEQ ID NO:27), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, Id, leucine zipper sequences, and maltose binding protein.

Examples of Multimeric Polypeptides of the Present Disclosure

The following are non-limiting embodiments of an IL-2/synTac multimeric polypeptide of the present disclosure.

In some cases, an IL-2/synTac multimeric polypeptide of the present disclosure comprises: a) a first polypeptide comprising, in order from N-terminus to C-terminus: i) an epitope; ii) a β2-microglobulin (β2M) polypeptide comprising the amino acid sequence depicted in FIG. 34A; and b) a second polypeptide comprising, in order from N-terminus to C-terminus: i) a variant IL-2 polypeptide of the present disclosure; ii) a major histocompatibility complex (MHC) heavy chain polypeptide comprising the amino acid sequence depicted in FIG. 34C; and iii) an IgG1 Fc polypeptide comprising one or more amino acid substitutions selected from N297A, L234A, L235A, L234F, L235E, and P331S. In some cases, the variant IL-2 polypeptide comprises an H16A and an F42A substitution. In some cases, the IgG1 Fc polypeptide comprises an N297A substitution. In some cases, the IgG1 Fc polypeptide comprises an L234A substitution and an L235A substitution. In some cases, the IgG1 Fc polypeptide comprises an L234F substitution and an L235E substitution. In some cases, the IgG1 Fc polypeptide comprises an L234F substitution, an L235E substitution, and a P331S substitution. In some cases, the second polypeptide comprises two copies of the variant IL-2 polypeptide. In some cases, the first polypeptide comprises a peptide linker between the epitope and the β2M polypeptide. In some cases, the second polypeptide comprises a peptide linker between one or more of: a) a first copy of the variant IL-2 polypeptide and a second copy of the variant IL-2 polypeptide; b) the variant IL-2 polypeptide and the MHC heavy chain polypeptide; and c) between the MHC heavy chain polypeptide and the IgG1 Fc polypeptide. In some cases, the peptide linker is selected from (GGGGS)$_3$ (SEQ ID NO:89), (GGGGS)$_4$ (SEQ ID NO:90), and AAAGG (SEQ ID NO:28). In some cases, the IgG1 Fc polypeptide comprises the amino acid sequence depicted in FIG. 33B. In some cases, the IgG1 Fc polypeptide comprises the amino acid sequence depicted in FIG. 33C. In some cases, the IgG1 Fc polypeptide comprises the amino acid sequence depicted in FIG. 33D.

In some cases, a multimeric polypeptide of the present disclosure comprises: a) a first polypeptide comprising, in order from N-terminus to C-terminus: i) an epitope; ii) a 2-microglobulin polypeptide comprising the amino acid sequence depicted in FIG. 34A; and b) a second polypeptide comprising, in order from N-terminus to C-terminus: i) a variant IL-2 polypeptide comprising the amino acid sequence depicted in FIG. 34B; ii) a major histocompatibility complex (MHC) heavy chain polypeptide comprising the amino acid sequence depicted in FIG. 34C; and iii) an IgG1 Fc polypeptide comprising one or more amino acid substitutions selected from N297A, L234A, L235A, L234F, L235E, and P331S. In some cases, the IgG1 Fc polypeptide comprises an N297A substitution. In some cases, the IgG1 Fc polypeptide comprises an L234A substitution and an L235A substitution. In some cases, the IgG1 Fc polypeptide comprises an L234F substitution and an L235E substitution. In some cases, the IgG1 Fc polypeptide comprises an L234F substitution, an L235E substitution, and a P331S substitution. In some cases, the IgG1 Fc polypeptide comprises the amino acid sequence depicted in FIG. 33B. In some cases, the IgG1 Fc polypeptide comprises the amino acid sequence depicted in FIG. 33C. In some cases, the IgG1 Fc polypeptide comprises the amino acid sequence depicted in FIG. 33D. In some cases, in the second polypeptide comprises two copies of the variant IL-2 polypeptide. In some cases, the first polypeptide comprises a peptide linker between the epitope and the β2M polypeptide. In some cases, the second polypeptide comprises a peptide linker between one or more of: a) a first copy of the variant IL-2 polypeptide and a second copy of the variant IL-2 polypeptide; b) the variant IL-2 polypeptide and the MHC heavy chain polypeptide; and c) between the MHC heavy chain polypeptide and the IgG1 Fc polypeptide. In some cases, the peptide linker is selected from (GGGGS)$_3$ (SEQ ID NO:89), (GGGGS)$_4$ (SEQ ID NO:90), and AAAGG (SEQ ID NO:28).

In some cases, multimeric polypeptide of the present disclosure comprises: a) a first polypeptide comprising, in order from N-terminus to C-terminus: i) an epitope comprising the amino acid sequence YMLDLQPETT (SEQ ID NO:13); ii) a β2-microglobulin polypeptide comprising the amino acid sequence depicted in FIG. 34A; and b) a second polypeptide comprising, in order from N-terminus to C-terminus: i) a variant IL-2 polypeptide comprising the amino acid sequence depicted in FIG. 34B; ii) a major histocompatibility complex (MHC) heavy chain polypeptide comprising the amino acid sequence depicted in FIG. 34C; and iii) an IgG1 Fc polypeptide comprising the amino acid sequence depicted in FIG. 33A, 33B, 33C, or 33D. In some cases, the IgG1 Fc polypeptide comprises the amino acid sequence depicted in FIG. 33B. In some cases, the IgG1 Fc polypeptide comprises the amino acid sequence depicted in FIG. 33C. In some cases, the IgG1 Fc polypeptide comprises the amino acid sequence depicted in FIG. 33D. In some cases, the second polypeptide comprises two copies of the variant IL-2 polypeptide. In some cases, the first polypeptide comprises a peptide linker between the epitope and the β2M polypeptide. In some cases, the second polypeptide comprises a peptide linker between one or more of: a) a first copy of the variant IL-2 polypeptide and a second copy of the variant IL-2 polypeptide; b) the variant IL-2 polypeptide and the MHC heavy chain polypeptide; and c) between the MHC heavy chain polypeptide and the IgG1 Fc polypeptide. In some cases, the peptide linker is selected from (GGGGS)$_3$ (SEQ ID NO:89), (GGGGS)$_4$ (SEQ ID NO:90), and AAAGG (SEQ ID NO:28). In some cases, the IgG1 Fc polypeptide comprises the amino acid sequence depicted in FIG. 33B. In some cases, the IgG1 Fc polypeptide comprises the amino acid sequence depicted in FIG. 33C. In some cases, the IgG1 Fc polypeptide comprises the amino acid sequence depicted in FIG. 33D.

In some cases, a multimeric polypeptide of the present disclosure comprises: a) a first polypeptide comprising the amino acid sequence depicted in FIG. 31; and b) a second polypeptide comprising the amino acid sequence depicted in FIG. 22.

In some cases, a multimeric polypeptide of the present disclosure comprises: a) a first polypeptide comprising the amino acid sequence depicted in FIG. 31; and b) a second polypeptide comprising the amino acid sequence depicted in FIG. 25.

In some cases, a multimeric polypeptide of the present disclosure comprises: a) a first polypeptide comprising the amino acid sequence depicted in FIG. 31; and ab) a second polypeptide comprising the amino acid sequence depicted in FIG. 28.

Nucleic Acids

The present disclosure provides a nucleic acid comprising a nucleotide sequence encoding a variant IL-2 polypeptide of the present disclosure. The present disclosure provides a nucleic acid comprising a nucleotide sequence encoding an IL-2 fusion polypeptide of the present disclosure.

The present disclosure provides nucleic acids comprising nucleotide sequences encoding a multimeric polypeptide of the present disclosure. In some cases, the individual polypeptide chains of a multimeric polypeptide of the present disclosure are encoded in separate nucleic acids. In some cases, all polypeptide chains of a multimeric polypeptide of the present disclosure are encoded in a single nucleic acid. In some cases, a first nucleic acid comprises a nucleotide sequence encoding a first polypeptide of a multimeric polypeptide of the present disclosure; and a second nucleic acid comprises a nucleotide sequence encoding a second polypeptide of a multimeric polypeptide of the present disclosure. In some cases, single nucleic acid comprises a nucleotide sequence encoding a first polypeptide of a multimeric polypeptide of the present disclosure and a second polypeptide of a multimeric polypeptide of the present disclosure.

Non-limiting examples of nucleic acids of the present disclosure are depicted in FIG. 23A, FIG. 26A, FIG. 29A, and FIG. 32.

Separate Nucleic Acids Encoding Individual Polypeptide Chains of a Multimeric Polypeptide The present disclosure provides nucleic acids comprising nucleotide sequences encoding a multimeric polypeptide of the present disclosure. As noted above, in some cases, the individual polypeptide chains of a multimeric polypeptide of the present disclosure are encoded in separate nucleic acids. In some cases, nucleotide sequences encoding the separate polypeptide chains of a multimeric polypeptide of the present disclosure are operably linked to transcriptional control elements, e.g., promoters, such as promoters that are functional in a eukaryotic cell, where the promoter can be a constitutive promoter or an inducible promoter.

The present disclosure provides a first nucleic acid and a second nucleic acid, where the first nucleic acid comprises a nucleotide sequence encoding a first polypeptide of a multimeric polypeptide of the present disclosure, where the first polypeptide comprises, in order from N-terminus to C-terminus: a) an epitope (e.g., a T-cell epitope); b) a first MHC polypeptide; and c) an immunomodulatory polypeptide (e.g., a variant IL-2 polypeptide of the present disclosure); and where the second nucleic acid comprises a nucleotide sequence encoding a second polypeptide of a multimeric polypeptide of the present disclosure, where the second polypeptide comprises, in order from N-terminus to C-terminus: a) a second MHC polypeptide; and b) an Ig Fc polypeptide. Suitable T-cell epitopes, MHC polypeptides, immunomodulatory polypeptides, and Ig Fc polypeptides, are described above. In some cases, the nucleotide sequences encoding the first and the second polypeptides are operably linked to transcriptional control elements. In some cases, the transcriptional control element is a promoter that is functional in a eukaryotic cell. In some cases, the nucleic acids are present in separate expression vectors.

The present disclosure provides a first nucleic acid and a second nucleic acid, where the first nucleic acid comprises a nucleotide sequence encoding a first polypeptide of a multimeric polypeptide of the present disclosure, where the first polypeptide comprises, in order from N-terminus to C-terminus: a) an epitope (e.g., a T-cell epitope); and b) a first MHC polypeptide; and where the second nucleic acid comprises a nucleotide sequence encoding a second polypeptide of a multimeric polypeptide of the present disclosure, where the second polypeptide comprises, in order from N-terminus to C-terminus: a) an immunomodulatory polypeptide (e.g., a variant IL-2 polypeptide of the present disclosure); b) a second MHC polypeptide; and c) an Ig Fc polypeptide. Suitable T-cell epitopes, MHC polypeptides, immunomodulatory polypeptides, and Ig Fc polypeptides, are described above. In some cases, the nucleotide sequences encoding the first and the second polypeptides are operably linked to transcriptional control elements. In some cases, the transcriptional control element is a promoter that is functional in a eukaryotic cell. In some cases, the nucleic acids are present in separate expression vectors.

Nucleic Acid Encoding Two or More Polypeptides Present in a Multimeric Polypeptide The present disclosure provides a nucleic acid comprising nucleotide sequences encoding at least the first polypeptide and the second polypeptide of a multimeric polypeptide of the present disclosure. In some cases, where a multimeric polypeptide of the present disclosure includes a first, second, and third polypeptide, the nucleic acid includes a nucleotide sequence encoding the first, second, and third polypeptides. In some cases, the nucleotide sequences encoding the first polypeptide and the second polypeptide of a multimeric polypeptide of the present disclosure includes a proteolytically cleavable linker interposed between the nucleotide sequence encoding the first polypeptide and the nucleotide sequence encoding the second polypeptide. In some cases, the nucleotide sequences encoding the first polypeptide and the second polypeptide of a multimeric polypeptide of the present disclosure includes an internal ribosome entry site (IRES) interposed between the nucleotide sequence encoding the first polypeptide and the nucleotide sequence encoding the second polypeptide. In some cases, the nucleotide sequences encoding the first polypeptide and the second polypeptide of a multimeric polypeptide of the present disclosure includes a ribosome skipping signal (or cis-acting hydrolase element, CHYSEL) interposed between the nucleotide sequence encoding the first polypeptide and the nucleotide sequence encoding the second polypeptide. Examples of nucleic acids are described below, where a proteolytically cleavable linker is provided between nucleotide sequences encoding the first polypeptide and the second polypeptide of a multimeric polypeptide of the present disclosure; in any of these embodiments, an IRES or a ribosome skipping signal can be used in place of the nucleotide sequence encoding the proteolytically cleavable linker.

In some cases, a first nucleic acid (e.g., a recombinant expression vector, an mRNA, a viral RNA, etc.) comprises a nucleotide sequence encoding a first polypeptide chain of a multimeric polypeptide of the present disclosure; and a second nucleic acid (e.g., a recombinant expression vector, an mRNA, a viral RNA, etc.) comprises a nucleotide sequence encoding a second polypeptide chain of a multimeric polypeptide of the present disclosure. In some cases, the nucleotide sequence encoding the first polypeptide, and the second nucleotide sequence encoding the second polypeptide, are each operably linked to transcriptional control elements, e.g., promoters, such as promoters that are functional in a eukaryotic cell, where the promoter can be a constitutive promoter or an inducible promoter.

The present disclosure provides a nucleic acid comprising a nucleotide sequence encoding a recombinant polypeptide, where the recombinant polypeptide comprises, in order from N-terminus to C-terminus: a) an epitope (e.g., a T-cell epitope); b) a first MHC polypeptide; c) an immunomodulatory polypeptide (e.g., a variant IL-2 polypeptide of the present disclosure); d) a proteolytically cleavable linker; e) a second MHC polypeptide; and f) an immunoglobulin (Ig) Fc polypeptide. The present disclosure provides a nucleic acid comprising a nucleotide sequence encoding a recombinant polypeptide, where the recombinant polypeptide comprises, in order from N-terminus to C-terminus: a) a first leader peptide; b) the epitope; c) the first MHC polypeptide; d) the immunomodulatory polypeptide (e.g., a variant IL-2 polypeptide of the present disclosure); e) the proteolytically cleavable linker; f) a second leader peptide; g) the second MHC polypeptide; and h) the Ig Fc polypeptide. The present disclosure provides a nucleic acid comprising a nucleotide sequence encoding a recombinant polypeptide, where the recombinant polypeptide comprises, in order from N-terminus to C-terminus: a) an epitope; b) a first MHC polypeptide; c) a proteolytically cleavable linker; d) an immunomodulatory polypeptide (e.g., a variant IL-2 polypeptide of the present disclosure); e) a second MHC polypeptide; and f) an Ig Fc polypeptide. In some cases, the first leader peptide and the second leader peptide is a β2-M leader peptide. In some cases, the nucleotide sequence is operably linked to a transcriptional control element. In some cases, the transcriptional control element is a promoter that is functional in a eukaryotic cell.

Suitable MHC polypeptides are described above. In some cases, the first MHC polypeptide is a β2-microglobulin polypeptide; and wherein the second MHC polypeptide is an MHC class I heavy chain polypeptide. In some cases, the β2-microglobulin polypeptide comprises an amino acid sequence having at least 85% amino acid sequence identity to one of the amino acid sequences set forth in FIG. 6. In some cases, the MHC class I heavy chain polypeptide is an HLA-A, HLA-B, HLA-C, HLA-E, HLA-F, HLA-G, HLA-K, or HLA-L heavy chain. In some cases, the MHC class I heavy chain polypeptide comprises an amino acid sequence having at least 85% amino acid sequence identity to the amino acid sequence set forth in one of FIG. 5A-5C. In some cases, the first MHC polypeptide is an MHC Class II alpha chain polypeptide; and wherein the second MHC polypeptide is an MHC class II beta chain polypeptide.

Suitable Fc polypeptides are described above. In some cases, the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide. In some cases, the Ig Fc polypeptide comprises an amino acid sequence having at least 85% amino acid sequence identity to an amino acid sequence depicted in FIGS. 4A-4C.

Suitable immunomodulatory polypeptides are described above.

Suitable proteolytically cleavable linkers are described above. In some cases, the proteolytically cleavable linker comprises an amino acid sequence selected from: a) LEVLFQGP (SEQ ID NO:29); b) ENLYTQS (SEQ ID NO:30); c) DDDDK (SEQ ID NO:31); d) LVPR (SEQ ID NO:32); and e) GSGATNFSLLKQAGDVEENPGP (SEQ ID NO:33).

In some cases, a linker between the epitope and the first MHC polypeptide comprises a first Cys residue, and the second MHC polypeptide comprises an amino acid substitution to provide a second Cys residue, such that the first and the second Cys residues provide for a disulfide linkage between the linker and the second MHC polypeptide. In some cases, first MHC polypeptide comprises an amino acid substitution to provide a first Cys residue, and the second MHC polypeptide comprises an amino acid substitution to provide a second Cys residue, such that the first Cys residue and the second Cys residue provide for a disulfide linkage between the first MHC polypeptide and the second MHC polypeptide.

Recombinant Expression Vectors

The present disclosure provides recombinant expression vectors comprising nucleic acids of the present disclosure. In some cases, the recombinant expression vector is a non-viral vector. In some embodiments, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, a non-integrating viral vector, etc.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology,* 153:516-544).

In some embodiments, a nucleotide sequence encoding a DNA-targeting RNA and/or a site-directed modifying polypeptide is operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell). In some embodiments, a nucleotide sequence encoding a DNA-targeting RNA and/or a site-directed modifying polypeptide is operably linked to multiple control elements that allow expression of the nucleotide sequence encoding a DNA-targeting RNA and/or a site-directed modifying polypeptide in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

Genetically Modified Host Cells

The present disclosure provides a genetically modified host cell, where the host cell is genetically modified with a nucleic acid of the present disclosure.

Suitable host cells include eukaryotic cells, such as yeast cells, insect cells, and mammalian cells. In some cases, the host cell is a cell of a mammalian cell line. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some cases, the host cell is a mammalian cell that has been genetically modified such that it does not synthesize endogenous MHC β2-M.

Methods of Producing a Multimeric Polypeptide

The present disclosure provides methods of producing a multimeric polypeptide of the present disclosure. The methods generally involve culturing, in a culture medium, a host cell that is genetically modified with a recombinant expression vector comprising a nucleotide sequence encoding the multimeric polypeptide; and isolating the multimeric polypeptide from the genetically modified host cell and/or the culture medium. A host cell that is genetically modified with a recombinant expression vector comprising a nucleotide sequence encoding the multimeric polypeptide is also referred to as an "expression host." As noted above, in some cases, the individual polypeptide chains of a multimeric polypeptide of the present disclosure are encoded in separate recombinant expression vectors. In some cases, all polypeptide chains of a multimeric polypeptide of the present disclosure are encoded in a single recombinant expression vector.

Isolation of the multimeric polypeptide from the expression host cell (e.g., from a lysate of the expression host cell) and/or the culture medium in which the host cell is cultured, can be carried out using standard methods of protein purification.

For example, a lysate may be prepared of the expression host and the lysate purified using high performance liquid chromatography (HPLC), exclusion chromatography, gel electrophoresis, affinity chromatography, or other purification technique. Alternatively, where the multimeric polypeptide is secreted from the expression host cell into the culture medium, the multimeric polypeptide can be purified from the culture medium using HPLC, exclusion chromatography, gel electrophoresis, affinity chromatography, or other purification technique. In some cases, the compositions which are used will comprise at least 80% by weight of the desired product, at least about 85% by weight, at least about 95% by weight, or at least about 99.5% by weight, in relation to contaminants related to the method of preparation of the product and its purification. The percentages can be based upon total protein.

In some cases, e.g., where the multimeric polypeptide comprises an affinity tag, the multimeric polypeptide can be purified using an immobilized binding partner of the affinity tag.

Compositions

The present disclosure provides compositions, including pharmaceutical compositions, comprising a variant IL-2 polypeptide of the present disclosure. The present disclosure provides compositions, including pharmaceutical compositions, comprising a multimeric polypeptide of the present disclosure. The present disclosure provides compositions, including pharmaceutical compositions, comprising a nucleic acid or a recombinant expression vector of the present disclosure.

Compositions Comprising a Multimeric Polypeptide

A composition of the present disclosure can comprise, in addition to a multimeric polypeptide of the present disclosure, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino) ethanesulfonic acid sodium salt (MES), 3-(N-Morpholino) propanesulfonic acid (MOPS), N-tris[Hydroxymethyl] methyl-3-aminopropanesulfonic acid (TAPS), etc.; a solubilizing agent; a detergent, e.g., a non-ionic detergent such as Tween-20, etc.; a protease inhibitor; glycerol; and the like.

The composition may comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", $19^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A pharmaceutical composition can comprise a multimeric polypeptide of the present disclosure, and a pharmaceutically acceptable excipient. In some cases, a subject pharmaceutical composition will be suitable for administration to a subject, e.g., will be sterile. For example, in some embodiments, a subject pharmaceutical composition will be suitable for administration to a human subject, e.g., where the composition is sterile and is free of detectable pyrogens and/or other toxins.

The protein compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like.

For example, compositions may include aqueous solution, powder form, granules, tablets, pills, suppositories, capsules, suspensions, sprays, and the like. The composition may be formulated according to the various routes of administration described below.

Where a multimeric polypeptide of the present disclosure is administered as an injectable (e.g. subcutaneously, intraperitoneally, intramuscularly, and/or intravenously) directly into a tissue, a formulation can be provided as a ready-to-use dosage form, or as non-aqueous form (e.g. a reconstitutable storage-stable powder) or aqueous form, such as liquid composed of pharmaceutically acceptable carriers and excipients. The protein-containing formulations may also be provided so as to enhance serum half-life of the subject protein following administration. For example, the protein may be provided in a liposome formulation, prepared as a colloid, or other conventional techniques for extending serum half-life. A variety of methods are available for preparing liposomes, as described in, e.g., Szoka et al. 1980 *Ann. Rev. Biophys. Bioeng.* 9:467, U.S. Pat. Nos. 4,235,871, 4,501,728 and 4,837,028. The preparations may also be provided in controlled release or slow-release forms.

Other examples of formulations suitable for parenteral administration include isotonic sterile injection solutions, anti-oxidants, bacteriostats, and solutes that render the formulation isotonic with the blood of the intended recipient, suspending agents, solubilizers, thickening agents, stabilizers, and preservatives. For example, a subject pharmaceutical composition can be present in a container, e.g., a sterile container, such as a syringe. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

The concentration of a multimeric polypeptide of the present disclosure in a formulation can vary widely (e.g., from less than about 0.1%, usually at or at least about 2% to as much as 20% to 50% or more by weight) and will usually be selected primarily based on fluid volumes, viscosities, and patient-based factors in accordance with the particular mode of administration selected and the patient's needs.

The present disclosure provides a container comprising a composition of the present disclosure, e.g., a liquid composition. The container can be, e.g., a syringe, an ampoule, and the like. In some cases, the container is sterile. In some cases, both the container and the composition are sterile.

The present disclosure provides compositions, including pharmaceutical compositions, comprising a variant IL-2 polypeptide of the present disclosure. A composition can comprise: a) a variant IL-2 polypeptide of the present disclosure; and b) an excipient, as described above for the multimeric polypeptides. In some cases, the excipient is a pharmaceutically acceptable excipient.

Compositions Comprising a Nucleic Acid or a Recombinant Expression Vector

The present disclosure provides compositions, e.g., pharmaceutical compositions, comprising a nucleic acid or a recombinant expression vector of the present disclosure. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A composition of the present disclosure can include: a) a subject nucleic acid or recombinant expression vector; and b) one or more of: a buffer, a surfactant, an antioxidant, a hydrophilic polymer, a dextrin, a chelating agent, a suspending agent, a solubilizer, a thickening agent, a stabilizer, a bacteriostatic agent, a wetting agent, and a preservative. Suitable buffers include, but are not limited to, (such as N,N-bis(2-hydroxyethyl)-2-aminoethanesulfonic acid (BES), bis(2-hydroxyethyl)amino-tris(hydroxymethyl)methane (BIS-Tris), N-(2-hydroxyethyl)piperazine-N'3-propanesulfonic acid (EPPS or HEPPS), glycylglycine, N-2-hydroxyehtylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris(hydroxymethyl)-aminomethane (Tris), etc.). Suitable salts include, e.g., NaCl, $MgCl_2$, KCl, $MgSO_4$, etc.

A pharmaceutical formulation of the present disclosure can include a nucleic acid or recombinant expression vector of the present disclosure in an amount of from about 0.001% to about 90% (w/w). In the description of formulations, below, "subject nucleic acid or recombinant expression vector" will be understood to include a nucleic acid or recombinant expression vector of the present disclosure. For example, in some embodiments, a subject formulation comprises a nucleic acid or recombinant expression vector of the present disclosure.

A subject nucleic acid or recombinant expression vector can be admixed, encapsulated, conjugated or otherwise associated with other compounds or mixtures of compounds; such compounds can include, e.g., liposomes or receptor-targeted molecules. A subject nucleic acid or recombinant expression vector can be combined in a formulation with one or more components that assist in uptake, distribution and/or absorption.

A subject nucleic acid or recombinant expression vector composition can be formulated into any of many possible dosage forms such as, but not limited to, tablets, capsules, gel capsules, liquid syrups, soft gels, suppositories, and enemas. A subject nucleic acid or recombinant expression vector composition can also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

A formulation comprising a subject nucleic acid or recombinant expression vector can be a liposomal formulation. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that can interact with negatively charged DNA molecules to form a stable complex. Liposomes that are pH sensitive or negatively charged are believed to entrap DNA rather than complex with it. Both cationic and non-cationic liposomes can be used to deliver a subject nucleic acid or recombinant expression vector.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein by reference in its entirety.

The formulations and compositions of the present disclosure may also include surfactants. The use of surfactants in drug products, formulations and in emulsions is well known in the art. Surfactants and their uses are further described in U.S. Pat. No. 6,287,860.

In one embodiment, various penetration enhancers are included, to effect the efficient delivery of nucleic acids. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein by reference in its entirety.

Compositions and formulations for oral administration include powders or granules, microparticulates, nanoparticulates, suspensions or solutions in water or non-aqueous media, capsules, gel capsules, sachets, tablets, or minitablets. Thickeners, flavoring agents, diluents, emulsifiers, dispersing aids or binders may be desirable. Suitable oral formulations include those in which a subject antisense nucleic acid is administered in conjunction with one or more penetration enhancers surfactants and chelators. Suitable surfactants include, but are not limited to, fatty acids and/or esters or salts thereof, bile acids and/or salts thereof. Suitable bile acids/salts and fatty acids and their uses are further described in U.S. Pat. No. 6,287,860. Also suitable are combinations of penetration enhancers, for example, fatty acids/salts in combination with bile acids/salts. An exemplary suitable combination is the sodium salt of lauric acid, capric acid, and UDCA. Further penetration enhancers include, but are not limited to, polyoxyethylene-9-lauryl ether, and polyoxyethylene-20-cetyl ether. Suitable penetration enhancers also include propylene glycol, dimethylsulfoxide, triethanoiamine, N,N-dimethylacetamide, N,N-dimethylformamide, 2-pyrrolidone and derivatives thereof, tetrahydrofurfuryl alcohol, and AZONE™.

Methods of Modulating T Cell Activity

The present disclosure provides a method of selectively modulating the activity of an epitope-specific T cell, the method comprising contacting the T cell with a multimeric polypeptide of the present disclosure, where contacting the T cell with a multimeric polypeptide of the present disclosure selectively modulates the activity of the epitope-specific T cell. In some cases, the contacting occurs in vitro. In some cases, the contacting occurs in vivo. In some cases, the contacting occurs ex vivo.

In some cases, e.g., where the target T cell is a CD8$^+$ T cell, the multimeric polypeptide comprises Class I MHC polypeptides (e.g., β2-microglobulin and Class I MHC heavy chain). In some cases, e.g., where the target T cell is a CD4$^+$ T cell, the multimeric polypeptide comprises Class II MHC polypeptides (e.g., Class II MHC α chain; Class II MHC β chain).

Where a multimeric polypeptide of the present disclosure includes an immunomodulatory polypeptide that is an activating polypeptide, contacting the T cell with the multimeric polypeptide activates the epitope-specific T cell. In some instances, the epitope-specific T cell is a T cell that is specific for an epitope present on a cancer cell, and contacting the epitope-specific T cell with the multimeric polypeptide increases cytotoxic activity of the T cell toward the cancer cell. In some instances, the epitope-specific T cell is a T cell that is specific for an epitope present on a cancer cell, and contacting the epitope-specific T cell with the multimeric polypeptide increases the number of the epitope-specific T cells.

In some instances, the epitope-specific T cell is a T cell that is specific for an epitope present on a virus-infected cell, and contacting the epitope-specific T cell with the multimeric polypeptide increases cytotoxic activity of the T cell toward the virus-infected cell. In some instances, the epitope-specific T cell is a T cell that is specific for an epitope present on a virus-infected cell, and contacting the epitope-specific T cell with the multimeric polypeptide increases the number of the epitope-specific T cells.

Where a multimeric polypeptide of the present disclosure includes an immunomodulatory polypeptide that is an inhibiting polypeptide, contacting the T cell with the multimeric inhibits the epitope-specific T cell. In some instances, the epitope-specific T cell is a self-reactive T cell that is specific for an epitope present in a self antigen, and the contacting reduces the number of the self-reactive T cells.

Methods of Selectively Delivering a Costimulatory Polypeptide (e.g., IL-2)

The present disclosure provides a method of delivering a costimulatory polypeptide such as IL-2, or a reduced-affinity variant of a naturally occurring costimulatory polypeptide such as an IL-2 variant disclosed herein, to a selected T cell or a selected T cell population, e.g., in a manner such that a TCR specific for a given epitope is targeted. The present disclosure provides a method of delivering a costimulatory polypeptide such as IL-2, or a reduced-affinity variant of a naturally occurring costimulatory polypeptide such as an IL-2 variant disclosed herein, selectively to a target T cell bearing a TCR specific for the epitope present in a multimeric polypeptide of the present disclosure. The method comprises contacting a population of T cells with a multimeric polypeptide of the present disclosure. The population of T cells can be a mixed population that comprises: i) the target T cell; and ii) non-target T cells that are not specific for the epitope (e.g., T cells that are specific for an epitope(s) other than the epitope to which the epitope-specific T cell binds). The epitope-specific T cell is specific for the epitope-presenting peptide present in the multimeric polypeptide, and binds to the peptide HLA complex or peptide MHC complex provided by the multimeric polypeptide. Contacting the population of T cells with the multimeric polypeptide delivers the costimulatory polypeptide (e.g., IL-2 or a reduced-affinity variant of IL-2) present in the multimeric polypeptide selectively to the T cell(s) that are specific for the epitope present in the multimeric polypeptide.

Thus, the present disclosure provides a method of delivering a costimulatory polypeptide such as IL-2, or a reduced-affinity variant of a naturally occurring costimulatory polypeptide such as an IL-2 variant disclosed herein, or a combination of both, selectively to a target T cell, the method comprising contacting a mixed population of T cells with a multimeric polypeptide of the present disclosure. The mixed population of T cells comprises the target T cell and non-target T cells. The target T cell is specific for the epitope present within the multimeric polypeptide. Contacting the mixed population of T cells with a multimeric polypeptide of the present disclosure delivers the costimulatory polypeptide(s) present within the multimeric polypeptide to the target T cell.

For example, a multimeric polypeptide of the present disclosure is contacted with a population of T cells comprising: i) a target T cell(s) that is specific for the epitope present in the multimeric polypeptide; and ii) a non-target T cell(s), e.g., a T cell(s) that is specific for a second epitope(s) that is not the epitope present in the multimeric polypeptide. Contacting the population results in selective delivery of the costimulatory polypeptide(s) (e.g., naturally-occurring costimulatory polypeptide (e.g., naturally occurring IL-2) or reduced-affinity variant of a naturally occurring costimulatory polypeptide (e.g., an IL-2 variant disclosed herein)), which is present in the multimeric polypeptide, to the target T cell. Thus, e.g., less than 50%, less than 40%, less than 30%, less than 25%, less than 20%, less than 15%, less than 10%, less than 5%, or less than 4%, 3%, 2% or 1%, of the non-target T cells bind the multimeric polypeptide and, as a result, the costimulatory polypeptide (e.g., IL-2 or IL-2 variant) is not delivered to the non-target T cells.

In some cases, the population of T cells is in vitro. In some cases, the population of T cells is in vitro, and a biological response (e.g., T cell activation and/or expansion and/or phenotypic differentiation) of the target T cell population to the multimeric polypeptide of the present disclosure is elicited in the context of an in vitro culture. For example, a mixed population of T cells can be obtained from an individual, and can be contacted with the multimeric polypeptide in vitro. Such contacting can comprise single or multiple exposures of the population of T cells to a defined dose(s) and/or exposure schedule(s). In some cases, said contacting results in selectively binding/activating and/or expanding target T cells within the population of T cells, and results in generation of a population of activated and/or expanded target T cells. As an example, a mixed population of T cells can be peripheral blood mononuclear cells (PBMC). For example, PBMC from a patient can be obtained by standard blood drawing and PBMC enrichment techniques before being exposed to 0.1-1000 nM of a multimeric polypeptide of the present disclosure under standard lymphocyte culture conditions. At time points before, during, and after exposure of the mixed T cell population at a defined dose and schedule, the abundance of target T cells in the in vitro culture can be monitored by specific peptide-MHC multimers and/or phenotypic markers and/or functional activity (e.g. cytokine ELISpot assays). In some cases, upon achieving an optimal abundance and/or phenotype of antigen specific cells in vitro, all or a portion of the population of activated and/or expanded target T cells is administered to the individual (the individual from whom the mixed population of T cells was obtained).

In some cases, the population of T cells is in vitro. For example, a mixed population of T cells is obtained from an individual, and is contacted with a multimeric polypeptide of the present disclosure in vitro. Such contacting, which can comprise single or multiple exposures of the T cells to a defined dose(s) and/or exposure schedule(s) in the context of in vitro cell culture, can be used to determine whether the mixed population of T cells includes T cells that are specific for the epitope presented by the multimeric polypeptide. The presence of T cells that are specific for the epitope of the multimeric polypeptide can be determined by assaying a sample comprising a mixed population of T cells, which population of T cells comprises T cells that are not specific for the epitope (non-target T cells) and may comprise T cells that are specific for the epitope (target T cells). Known assays can be used to detect activation and/or proliferation of the target T cells, thereby providing an ex vivo assay that can determine whether a particular multimeric polypeptide (synTac) possesses an epitope that binds to T cells present in the individual and thus whether the multimeric polypeptide has potential use as a therapeutic composition for that individual. Suitable known assays for detection of activation and/or proliferation of target T cells include, e.g., flow cytometric characterization of T cell phenotype and/or antigen specificity and/or proliferation. Such an assay to detect the presence of epitope-specific T cells, e.g., a companion diagnostic, can further include additional assays (e.g. effector cytokine ELISpot assays) and/or appropriate controls (e.g. antigen-specific and antigen-nonspecific multimeric peptide-HLA staining reagents) to determine whether the multimeric polypeptide is selectively binding/activating and/or expanding the target T cell. Thus, for example, the present disclosure provides a method of detecting, in a mixed population of T cells obtained from an individual, the presence of a target T cell that binds an epitope of interest, the method comprising: a) contacting in vitro the mixed population of T cells with a multimeric polypeptide of the present disclosure, wherein the multimeric polypeptide comprises the epitope of interest; and b) detecting activation and/or proliferation of T cells in response to said contacting, wherein activated and/or proliferated T cells indicates the presence of the target T cell. Alternatively, and/or in addition, if activation and/or expansion (proliferation) of the desired T cell population is obtained using the multimeric polypeptide, then all or a portion of the population of T cells comprising the activated/expanded T cells can be administered back to the individual as a therapy.

In some instances, the population of T cells is in vivo in an individual. In such instances, a method of the present disclosure for selectively delivering a costimulatory polypeptide (e.g., IL-2 or a reduced-affinity IL-2) to an epitope-specific T cell comprises administering the multimeric polypeptide to the individual.

The epitope-specific T cell to which a costimulatory polypeptide (e.g., IL-2 or a reduced-affinity IL-2) is being selectively delivered is also referred to herein as a "target T cell." In some cases, the target T cell is a regulatory T cell (Treg). In some cases, the Treg inhibits or suppresses activity of an autoreactive T cell.

In some cases, the target T cell is a cytotoxic T cell. For example, the target T cell can be a cytotoxic T cell specific for a cancer epitope (e.g., an epitope presented by a cancer cell).

Treatment Methods

The present disclosure provides a method of selectively modulating the activity of an epitope-specific T cell in an individual, the method comprising administering to the individual an amount of the multimeric polypeptide of the present disclosure, or one or more nucleic acids encoding the multimeric polypeptide, effective to selectively modulate the activity of an epitope-specific T cell in an individual. In some cases, a treatment method of the present disclosure comprises administering to an individual in need thereof one or more recombinant expression vectors comprising nucleotide sequences encoding a multimeric polypeptide of the present disclosure. In some cases, a treatment method of the present disclosure comprises administering to an individual in need thereof one or more mRNA molecules comprising nucleotide sequences encoding a multimeric polypeptide of the present disclosure. In some cases, a treatment method of the present disclosure comprises administering to an individual in need thereof a multimeric polypeptide of the present disclosure.

The present disclosure provides a method of selectively modulating the activity of an epitope-specific T cell in an individual, the method comprising administering to the individual an effective amount of a multimeric polypeptide of the present disclosure, or one or more nucleic acids (e.g., expression vectors; mRNA; etc.) comprising nucleotide sequences encoding the multimeric polypeptide, where the multimeric polypeptide selectively modulates the activity of the epitope-specific T cell in the individual. Selectively modulating the activity of an epitope-specific T cell can treat a disease or disorder in the individual. Thus, the present disclosure provides a treatment method comprising administering to an individual in need thereof an effective amount of a multimeric polypeptide of the present disclosure.

In some cases, the immunomodulatory polypeptide is an activating polypeptide, and the multimeric polypeptide activates the epitope-specific T cell. In some cases, the epitope is a cancer-associated epitope, and the multimeric polypeptide increases the activity of a T cell specific for the cancer-associate epitope.

The present disclosure provides a method of treating cancer in an individual, the method comprising administering to the individual an effective amount of a multimeric polypeptide of the present disclosure, or one or more nucleic acids (e.g., expression vectors; mRNA; etc.) comprising nucleotide sequences encoding the multimeric polypeptide, where the multimeric polypeptide comprises a T-cell epitope that is a cancer epitope, and where the multimeric polypeptide comprises one or more stimulatory immunomodulatory polypeptides, as described herein. In some cases, an "effective amount" of a multimeric polypeptide is an amount that, when administered in one or more doses to an individual in need thereof, reduces the number of cancer cells in the individual. For example, in some cases, an "effective amount" of a multimeric polypeptide of the present disclosure is an amount that, when administered in one or more doses to an individual in need thereof, reduces the number of cancer cells in the individual by at least 10%, at least 15%, at least 20%, at least 25%, at least 30%, at least 40%, at least 50%, at least 60%, at least 70%, at least 80%, at least 90%, or at least 95%, compared to the number of cancer cells in the individual before administration of the multimeric polypeptide, or in the absence of administration with the multimeric polypeptide. In some cases, an "effective amount" of a multimeric polypeptide of the present disclosure is an amount that, when administered in one or more doses to an individual in need thereof, reduces the number of cancer cells in the individual to undetectable levels. In some cases, an "effective amount" of a multimeric polypeptide of the present disclosure is an amount that, when administered in one or more doses to an individual in need thereof, reduces the tumor mass in the individual. For example, in some cases, an "effective amount" of a multimeric polypeptide of the present disclosure is an amount that, when administered in one or more doses to an individual in need thereof, reduces the tumor mass in the individual by at least 10%, at least 15%, at least 20%, at least 25%, at least 30%, at least 40%, at least 50%, at least 60%, at least 70%, at least 80%, at least 90%, or at least 95%, compared to the tumor mass in the individual before administration of the multimeric polypeptide, or in the absence of administration with the multimeric polypeptide. In some cases, an "effective amount" of a multimeric polypeptide of the present disclosure is an amount that, when administered in one or more doses to an individual in need thereof, increases survival time of the individual. For example, in some cases, an "effective amount" of a multimeric polypeptide of the present disclosure is an amount that, when administered in one or more doses to an individual in need thereof, increases survival time of the individual by at least 1 month, at least 2 months, at least 3 months, from 3 months to 6 months, from 6 months to 1 year, from 1 year to 2 years, from 2 years to 5 years, from 5 years to 10 years, or more than 10 years, compared to the expected survival time of the individual in the absence of administration with the multimeric polypeptide.

In some instances, the epitope-specific T cell is a T cell that is specific for an epitope present on a virus-infected cell, and contacting the epitope-specific T cell with the multimeric polypeptide increases cytotoxic activity of the T cell toward the virus-infected cell. In some instances, the epitope-specific T cell is a T cell that is specific for an epitope present on a virus-infected cell, and contacting the epitope-specific T cell with the multimeric polypeptide increases the number of the epitope-specific T cells.

Thus, the present disclosure provides a method of treating a virus infection in an individual, the method comprising administering to the individual an effective amount of a multimeric polypeptide of the present disclosure, or one or more nucleic acids comprising nucleotide sequences encoding the multimeric polypeptide, where the multimeric polypeptide comprises a T-cell epitope that is a viral epitope, and where the multimeric polypeptide comprises one or more stimulatory immunomodulatory polypeptides as described herein. In some cases, an "effective amount" of a multimeric polypeptide is an amount that, when administered in one or more doses to an individual in need thereof, reduces the number of virus-infected cells in the individual. For example, in some cases, an "effective amount" of a multimeric polypeptide of the present disclosure is an amount that, when administered in one or more doses to an individual in need thereof, reduces the number of virus-infected cells in the individual by at least 10%, at least 15%, at least 20%, at least 25%, at least 30%, at least 40%, at least 50%, at least 60%, at least 70%, at least 80%, at least 90%, or at least 95%, compared to the number of virus-infected cells in the individual before administration of the multimeric polypeptide, or in the absence of administration with the multimeric polypeptide. In some cases, an "effective amount" of a multimeric polypeptide of the present disclosure is an amount that, when administered in one or more doses to an individual in need thereof, reduces the number of virus-infected cells in the individual to undetectable levels.

Thus, the present disclosure provides a method of treating an infection in an individual, the method comprising administering to the individual an effective amount of a multimeric polypeptide of the present disclosure, or one or more nucleic acids comprising nucleotide sequences encoding the multimeric polypeptide, where the multimeric polypeptide comprises a T-cell epitope that is a pathogen-associated epitope, and where the multimeric polypeptide comprises one or more stimulatory immunomodulatory polypeptides as described herein. In some cases, an "effective amount" of a multimeric polypeptide is an amount that, when administered in one or more doses to an individual in need thereof, reduces the number of pathogens in the individual. For example, in some cases, an "effective amount" of a multimeric polypeptide of the present disclosure is an amount that, when administered in one or more doses to an individual in need thereof, reduces the number of pathogens in the individual by at least 10%, at least 15%, at least 20%, at least 25%, at least 30%, at least 40%, at least 50%, at least 60%, at least 70%, at least 80%, at least 90%, or at least 95%, compared to the number of pathogens in the individual before administration of the multimeric polypeptide, or in the absence of administration with the multimeric polypeptide. In some cases, an "effective amount" of a multimeric polypeptide of the present disclosure is an amount that, when administered in one or more doses to an individual in need thereof, reduces the number of pathogens in the individual to undetectable levels. Pathogens include viruses, bacteria, protozoans, and the like.

In some cases, the immunomodulatory polypeptide is an inhibitory polypeptide, and the multimeric polypeptide inhibits activity of the epitope-specific T cell. In some cases, the epitope is a self-epitope, and the multimeric polypeptide selectively inhibits the activity of a T cell specific for the self-epitope.

The present disclosure provides a method of treating an autoimmune disorder in an individual, the method comprising administering to the individual an effective amount of a multimeric polypeptide of the present disclosure, or one or more nucleic acids comprising nucleotide sequences encoding the multimeric polypeptide, where the multimeric polypeptide comprises a T-cell epitope that is a self epitope, and where the multimeric polypeptide comprises an inhibitory immunomodulatory polypeptide. In some cases, an "effective amount" of a multimeric polypeptide is an amount that, when administered in one or more doses to an individual in need thereof, reduces the number self-reactive T cells by at least 10%, at least 15%, at least 20%, at least 25%, at least 30%, at least 40%, at least 50%, at least 60%, at least 70%, at least 80%, at least 90%, or at least 95%, compared to number of self-reactive T cells in the individual before administration of the multimeric polypeptide, or in the absence of administration with the multimeric polypeptide. In some cases, an "effective amount" of a multimeric polypeptide is an amount that, when administered in one or more doses to an individual in need thereof, reduces production of Th2 cytokines in the individual. In some cases, an "effective amount" of a multimeric polypeptide is an amount that, when administered in one or more doses to an individual in need thereof, ameliorates one or more symptoms associated with an autoimmune disease in the individual.

As noted above, in some cases, in carrying out a subject treatment method, a multimeric polypeptide of the present disclosure is administered to an individual in need thereof, as the polypeptide per se. In other instances, in carrying out a subject treatment method, one or more nucleic acids comprising nucleotide sequences encoding a multimeric polypeptide of the present disclosure is/are administering to an individual in need thereof. Thus, in other instances, one or more nucleic acids of the present disclosure, e.g., one or more recombinant expression vectors of the present disclosure, is/are administered to an individual in need thereof.

Formulations

Suitable formulations are described above, where suitable formulations include a pharmaceutically acceptable excipient. In some cases, a suitable formulation comprises: a) a multimeric polypeptide of the present disclosure; and b) a pharmaceutically acceptable excipient. In some cases, a suitable formulation comprises: a) a nucleic acid comprising a nucleotide sequence encoding a multimeric polypeptide of the present disclosure; and b) a pharmaceutically acceptable excipient; in some instances, the nucleic acid is an mRNA. In some cases, a suitable formulation comprises: a) a first nucleic acid comprising a nucleotide sequence encoding the first polypeptide of a multimeric polypeptide of the present disclosure; b) a second nucleic acid comprising a nucleotide sequence encoding the second polypeptide of a multimeric polypeptide of the present disclosure; and c) a pharmaceutically acceptable excipient. In some cases, a suitable formulation comprises: a) a recombinant expression vector comprising a nucleotide sequence encoding a multimeric polypeptide of the present disclosure; and b) a pharmaceutically acceptable excipient. In some cases, a suitable formulation comprises: a) a first recombinant expression vector comprising a nucleotide sequence encoding the first polypeptide of a multimeric polypeptide of the present disclosure; b) a second recombinant expression vector comprising a nucleotide sequence encoding the second polypeptide of a multimeric polypeptide of the present disclosure; and c) a pharmaceutically acceptable excipient.

Suitable pharmaceutically acceptable excipients are described above.

Dosages

A suitable dosage can be determined by an attending physician or other qualified medical personnel, based on various clinical factors. As is well known in the medical arts, dosages for any one patient depend upon many factors, including the patient's size, body surface area, age, the particular polypeptide or nucleic acid to be administered, sex of the patient, time, and route of administration, general health, and other drugs being administered concurrently. A multimeric polypeptide of the present disclosure may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 µg to 10 mg per kilogram of body weight per minute. A multimeric polypeptide of the present disclosure can be administered in an amount of from about 1 mg/kg body weight to 50 mg/kg body weight, e.g., from about 1 mg/kg body weight to about 5 mg/kg body weight, from about 5 mg/kg body weight to about 10 mg/kg body weight, from about 10 mg/kg body weight to about 15 mg/kg body weight, from about 15 mg/kg body weight to about 20 mg/kg body weight, from about 20 mg/kg body weight to about 25 mg/kg body weight, from about 25 mg/kg body weight to about 30 mg/kg body weight, from about 30 mg/kg body weight to about 35 mg/kg body weight, from about 35 mg/kg body weight to about 40 mg/kg body weight, or from about 40 mg/kg body weight to about 50 mg/kg body weight.

In some cases, a suitable dose of a multimeric polypeptide of the present disclosure is from 0.01 µg to 100 g per kg of body weight, from 0.1 µg to 10 g per kg of body weight, from 1 g to 1 g per kg of body weight, from 10 µg to 100 mg per kg of body weight, from 100 µg to 10 mg per kg of body weight, or from 100 µg to 1 mg per kg of body weight. Persons of ordinary skill in the art can easily estimate repetition rates for dosing based on measured residence times and concentrations of the administered agent in bodily fluids or tissues. Following successful treatment, it may be desirable to have the patient undergo maintenance therapy to prevent the recurrence of the disease state, wherein a multimeric polypeptide of the present disclosure is administered in maintenance doses, ranging from 0.01 µg to 100 g per kg of body weight, from 0.1 µg to 10 g per kg of body weight, from 1 µg to 1 g per kg of body weight, from 10 µg to 100 mg per kg of body weight, from 100 µg to 10 mg per kg of body weight, or from 100 µg to 1 mg per kg of body weight.

Those of skill will readily appreciate that dose levels can vary as a function of the specific multimeric polypeptide, the severity of the symptoms and the susceptibility of the subject to side effects. Preferred dosages for a given compound are readily determinable by those of skill in the art by a variety of means.

In some embodiments, multiple doses of a multimeric polypeptide of the present disclosure, a nucleic acid of the present disclosure, or a recombinant expression vector of the present disclosure are administered. The frequency of administration of a multimeric polypeptide of the present disclosure, a nucleic acid of the present disclosure, or a recombinant expression vector of the present disclosure can vary depending on any of a variety of factors, e.g., severity of the symptoms, etc. For example, in some embodiments, a multimeric polypeptide of the present disclosure, a nucleic acid of the present disclosure, or a recombinant expression vector of the present disclosure, is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of a multimeric polypeptide of the present disclosure, a nucleic acid of the present disclosure, or a recombinant expression vector of the present disclosure, e.g., the period of time over which a multimeric polypeptide of the present disclosure, a nucleic acid of the present disclosure, or a recombinant expression vector of the present disclosure is administered, can vary, depending on any of a variety of factors, e.g., patient response, etc. For example, a multimeric polypeptide of the present disclosure, a nucleic acid of the present disclosure, or a recombinant expression vector of the present disclosure can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Routes of Administration

An active agent (a multimeric polypeptide of the present disclosure, a nucleic acid of the present disclosure, or a recombinant expression vector of the present disclosure) is administered to an individual using any available method and route suitable for drug delivery, including in vivo and ex vivo methods, as well as systemic and localized routes of administration.

Conventional and pharmaceutically acceptable routes of administration include intratumoral, peritumoral, intramuscular, intratracheal, intracranial, subcutaneous, intradermal, topical application, intravenous, intraarterial, rectal, nasal, oral, and other enteral and parenteral routes of administration. Routes of administration may be combined, if desired, or adjusted depending upon the multimeric polypeptide and/or the desired effect. A multimeric polypeptide of the present disclosure, or a nucleic acid or recombinant expression vector of the present disclosure, can be administered in a single dose or in multiple doses.

In some embodiments, a multimeric polypeptide of the present disclosure, a nucleic acid of the present disclosure, or a recombinant expression vector of the present disclosure is administered intravenously. In some embodiments, a multimeric polypeptide of the present disclosure, a nucleic acid of the present disclosure, or a recombinant expression vector of the present disclosure is administered intramuscularly. In some embodiments, a multimeric polypeptide of the present disclosure, a nucleic acid of the present disclosure, or a recombinant expression vector of the present disclosure is administered locally. In some embodiments, a multimeric polypeptide of the present disclosure, a nucleic acid of the present disclosure, or a recombinant expression vector of the present disclosure is administered intratumorally. In some embodiments, a multimeric polypeptide of the present disclosure, a nucleic acid of the present disclosure, or a recombinant expression vector of the present disclosure is administered peritumorally. In some embodiments, a multimeric polypeptide of the present disclosure, a nucleic acid of the present disclosure, or a recombinant expression vector of the present disclosure is administered intracranially. In some embodiments, a multimeric polypeptide of the present disclosure, a nucleic acid of the present disclosure, or a recombinant expression vector of the present disclosure is administered subcutaneously.

In some embodiments, a multimeric polypeptide of the present disclosure is administered intravenously. In some embodiments, a multimeric polypeptide of the present disclosure is administered intramuscularly. In some embodiments, a multimeric polypeptide of the present disclosure is administered locally. In some embodiments, a multimeric polypeptide of the present disclosure is administered intratumorally. In some embodiments, a multimeric polypeptide of the present disclosure is administered peritumorally. In some embodiments, a multimeric polypeptide of the present disclosure is administered intracranially. In some embodiments, a multimeric polypeptide is administered subcutaneously.

A multimeric polypeptide of the present disclosure, a nucleic acid of the present disclosure, or a recombinant expression vector of the present disclosure can be administered to a host using any available conventional methods and routes suitable for delivery of conventional drugs, including systemic or localized routes. In general, routes of administration contemplated for use in a method of the present disclosure include, but are not necessarily limited to, enteral, parenteral, and inhalational routes.

Parenteral routes of administration other than inhalation administration include, but are not necessarily limited to, topical, transdermal, subcutaneous, intramuscular, intraorbital, intracapsular, intraspinal, intrasternal, intratumoral, peritumoral, and intravenous routes, i.e., any route of administration other than through the alimentary canal. Parenteral administration can be carried to effect systemic or local delivery of a multimeric polypeptide of the present disclosure, a nucleic acid of the present disclosure, or a recombinant expression vector of the present disclosure. Where systemic delivery is desired, administration typically involves invasive or systemically absorbed topical or mucosal administration of pharmaceutical preparations.

Subjects Suitable for Treatment

Subjects suitable for treatment with a method of the present disclosure include individuals who have cancer, including individuals who have been diagnosed as having cancer, individuals who have been treated for cancer but who failed to respond to the treatment, and individuals who have been treated for cancer and who initially responded but subsequently became refractory to the treatment. Subjects suitable for treatment with a method of the present disclosure include individuals who have an infection (e.g., an infection with a pathogen such as a bacterium, a virus, a protozoan, etc.), including individuals who have been diagnosed as having an infection, and individuals who have been treated for an infection but who failed to respond to the treatment. Subjects suitable for treatment with a method of the present disclosure include individuals who have bacterial infection, including individuals who have been diagnosed as having a bacterial infection, and individuals who have been treated for a bacterial infection but who failed to respond to the treatment. Subjects suitable for treatment with a method of the present disclosure include individuals who have a viral infection, including individuals who have been diagnosed as having a viral infection, and individuals who have been treated for a viral infection but who failed to respond to the treatment. Subjects suitable for treatment with a method of the present disclosure include individuals who have an autoimmune disease, including individuals who have been diagnosed as having an autoimmune disease, and individuals who have been treated for a autoimmune disease but who failed to respond to the treatment.

In some cases, e.g., where the epitope is an HPV epitope, a subject suitable for treatment with a method of the present disclosure is an individual who has been diagnosed as having an HPV-associated cancer or an HPV-attributable cancer. HPV-associated and HPV-attributable cancers include, e.g., head and neck cancer; cervical cancer; and genitoanal cancer.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-132 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A variant IL-2 polypeptide comprising an amino acid sequence having at least 85% amino acid sequence identity to set forth in SEQ ID NO:1, wherein the variant IL-2 polypeptide has one or more amino acid substitutions relative to set forth in SEQ ID NO:1, and wherein the variant IL-2 polypeptide exhibits reduced binding affinity to an IL-2 receptor (IL-2R) comprising alpha, beta, and gamma polypeptides having amino acid sequences depicted in FIG. 3A-3C, compared to the binding affinity of the IL-2 amino acid sequence set forth in one of SEQ ID NO:1 for the IL-2R.

Aspect 2. The variant IL-2 polypeptide of aspect 1, wherein the variant comprises a substitution of one or more of E15, H16, D20, F42, Y45, and Q126.

Aspect 3. The variant IL-2 polypeptide of aspect 1 or aspect 2, wherein the variant immunomodulatory polypeptide exhibits from less than 10% to less than 50% of the binding affinity exhibited by the IL-2 amino acid sequence set forth in SEQ ID NO:1 for the IL-2R.

Aspect 4. The variant IL-2 polypeptide of any one of aspects 1-3, wherein the variant comprises substitutions of F42 with Ala, Gly, Val, Ile, or Leu.

Aspect 5. The variant IL-2 polypeptide of any one of aspects 1-3, wherein the variant comprises substitutions of F42 and D20 or substitutions of F42 and H16.

Aspect 6. The variant IL-2 polypeptide of any one of aspects 1-3, wherein the variant comprises substitutions of F42, D20, and Y45; or wherein the variant comprises substitutions of F42, H16, and Q126.

Aspect 7. A multimeric polypeptide comprising:

a) a first polypeptide comprising, in order from N-terminus to C-terminus:
 i) an epitope;
 ii) a first major histocompatibility complex (MHC) polypeptide; and
b) a second polypeptide comprising, in order from N-terminus to C-terminus:
 i) a second MHC polypeptide; and
 ii) optionally an immunoglobulin (Ig) Fc polypeptide or a non-Ig scaffold, wherein the multimeric polypeptide comprises one or more immunomodulatory domains, wherein the one or more immunomodulatory domain is:
 A) at the C-terminus of the first polypeptide;
 B) at the N-terminus of the second polypeptide;
 C) at the C-terminus of the second polypeptide; or
 D) at the C-terminus of the first polypeptide and at the N-terminus of the second polypeptide, and wherein at least one of the immunomodulatory domains is a variant of a naturally occurring costimulatory protein, and wherein the variant exhibits a reduced affinity for its counterpart costimulatory protein as compared to the affinity of the naturally occurring costimulatory protein for the counterpart costimulatory protein.

Aspect 8. A multimeric polypeptide comprising:

a) a first polypeptide comprising, in order from N-terminus to C-terminus:
 i) an epitope;
 ii) a first major histocompatibility complex (MHC) polypeptide; and
b) a second polypeptide comprising, in order from N-terminus to C-terminus:
 i) a second MHC polypeptide; and
 ii) optionally an immunoglobulin (Ig) Fc polypeptide or a non-Ig scaffold, wherein the multimeric polypeptide comprises one or more immunomodulatory domains, wherein the one or more immunomodulatory domain is:
 A) at the C-terminus of the first polypeptide;
 B) at the N-terminus of the second polypeptide;
 C) at the C-terminus of the second polypeptide; or
 D) at the C-terminus of the first polypeptide and at the N-terminus of the second polypeptide, wherein at least one of the one or more immunomodulatory domains is a variant IL-2 polypeptide of any one of aspects 1-6, and wherein the multimeric polypeptide exhibits reduced binding affinity to an IL-2 receptor (IL-2R) comprising alpha, beta, and gamma polypeptides having amino acid sequences depicted in FIG. 3A-3C, compared to the binding affinity of a control multimeric polypeptide comprising the IL-2 amino acid sequence set forth in SEQ ID NO:1 for the IL-2R polypeptide.

Aspect 9. The multimeric polypeptide of aspect 8, wherein:

a) the first polypeptide comprises, in order from N-terminus to C-terminus:
 i) the epitope;
 ii) the first MHC polypeptide; and
 iii) the variant IL-2 polypeptide; and
b) the second polypeptide comprises, in order from N-terminus to C-terminus:
 i) the second MHC polypeptide; and
 ii) the Ig Fc polypeptide.

Aspect 10. The multimeric polypeptide of aspect 8, wherein:

a) the first polypeptide comprises, in order from N-terminus to C-terminus:
 i) the epitope; and
 ii) the first MHC polypeptide; and
b) the second polypeptide comprises, in order from N-terminus to C-terminus:
 i) the variant IL-2 polypeptide;
 ii) the second MHC polypeptide; and
 iii) the Ig Fc polypeptide.

Aspect 11. The multimeric polypeptide of aspect 8, wherein:

a) the first polypeptide comprises, in order from N-terminus to C-terminus:
 i) the epitope; and
 ii) the first MHC polypeptide; and
b) the second polypeptide comprises, in order from N-terminus to C-terminus:
 i) the second MHC polypeptide; and
 ii) the variant IL-2 polypeptide.

Aspect 12. The multimeric polypeptide of aspect 8, wherein:

a) the first polypeptide comprises, in order from N-terminus to C-terminus:
 i) the epitope; and
 ii) the first MHC polypeptide; and
b) second polypeptide comprising, in order from N-terminus to C-terminus:
 i) the variant IL-2 polypeptide; and
 ii) the second MHC polypeptide.

Aspect 13. The multimeric polypeptide of aspect 8, wherein:

a) the first polypeptide comprises, in order from N-terminus to C-terminus:
 i) the epitope;
 ii) the first MHC polypeptide; and
 iii) the variant IL-2 polypeptide; and b) the second polypeptide comprises the second MHC polypeptide.

Aspect 14. The multimeric polypeptide of aspect 7 or 8, wherein the non-Ig scaffold is an XTEN polypeptide, a transferrin polypeptide, an elastin-like polypeptide, a silk-like polypeptide, or a silk-elastin-like polypeptide.

Aspect 15. The multimeric polypeptide of any one of aspects 7-14, wherein the first MHC polypeptide is a β2-microglobulin polypeptide; and wherein the second MHC polypeptide is an MHC class I heavy chain polypeptide.

Aspect 16. The multimeric polypeptide of aspect 15, wherein the β2-microglobulin polypeptide comprises an amino acid sequence having at least 85% amino acid sequence identity to one of the amino acid sequences set forth in FIG. 6.

Aspect 17. The multimeric polypeptide of aspect 15, wherein the MHC class I heavy chain polypeptide is an HLA-A, an HLA-B, or an HLA-C heavy chain.

Aspect 18. The multimeric polypeptide of aspect 15, wherein the MHC class I heavy chain polypeptide comprises an amino acid sequence having at least 85% amino acid sequence identity to the amino acid sequence set forth in one of FIG. 5A-5C.

Aspect 19. The multimeric polypeptide of any one of aspects 7-14, wherein the first MHC polypeptide is an MHC Class II alpha chain polypeptide; and wherein the second MHC polypeptide is an MHC class II beta chain polypeptide.

Aspect 20. The multimeric polypeptide of any one of aspects 7-19, wherein the epitope is a T-cell epitope.

Aspect 21. The multimeric polypeptide of any one of aspects 7-13 and 15-20, wherein multimeric polypeptide comprises an Fc polypeptide, and wherein the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide.

Aspect 22. The multimeric polypeptide of aspect 21, wherein the Ig Fc polypeptide comprises an amino acid sequence having at least 85% amino acid sequence identity to an amino acid sequence depicted in FIG. 4A-4C.

Aspect 23. The multimeric polypeptide of any one of aspects 7-22, wherein the first polypeptide and the second polypeptide are non-covalently associated.

Aspect 24. The multimeric polypeptide of any one of aspects 7-22, wherein the first polypeptide and the second polypeptide are covalently linked to one another.

Aspect 25. The multimeric polypeptide of aspect 24, wherein the covalent linkage is via a disulfide bond.

Aspect 26. The multimeric polypeptide of aspect 25, wherein the first MHC polypeptide or a linker between the epitope and the first MHC polypeptide comprises an amino acid substitution to provide a first Cys residue, and the second MHC polypeptide comprises an amino acid substitution to provide a second Cys residue, and wherein the disulfide linkage is between the first and the second Cys residues.

Aspect 27. The multimeric polypeptide of any one of aspects 7-26, comprising a linker interposed between the epitope and the first MHC polypeptide.

Aspect 28. The multimeric polypeptide of any one of aspects 7-26, comprising a linker interposed between the MHC polypeptide and the immunomodulatory polypeptide.

Aspect 29. The multimeric polypeptide of any one of aspects 7-28, comprising 2 variant IL-2 polypeptides.

Aspect 30. The multimeric polypeptide of any one of aspects 8-28, comprising 3 variant IL-2 polypeptides.

Aspect 31. The multimeric polypeptide of aspect 29 or aspect 30, wherein the 2 or 3 variant IL-2 polypeptides are in tandem, and wherein the multimeric polypeptide comprises a linker between the variant IL-2 polypeptides.

Aspect 32. The multimeric polypeptide of any one of aspects 8-31, wherein the variant IL-2 comprises a substitution of one or more of E15, H16, D20, F42, Y45, and Q126/

Aspect 33. The multimeric polypeptide of any one of aspects 8-32, wherein the variant IL-2 comprises a substitution of F42 with Ala, Gly, Val, Ile, or Leu.

Aspect 34. The multimeric polypeptide of aspect 33, wherein the variant IL-2 comprises substitutions of F42 and D20, or substitutions of F42 and H16.

Aspect 35. The multimeric polypeptide of aspect 33, wherein the variant IL-2 comprises substitutions of F42, D20, and Y45; or wherein the variant IL-2 comprising substitutions of F42, H16, and Q126.

Aspect 36. A nucleic acid comprising a nucleotide sequence encoding a recombinant polypeptide,
  i) wherein the recombinant polypeptide comprises, in order from N-terminus to C-terminus:
  a) an epitope;
  b) a first major histocompatibility complex (MHC) polypeptide;
  c) an immunomodulatory polypeptide;
  d) a proteolytically cleavable linker or a ribosome skipping signal;
  e) a second MHC polypeptide; and
  f) an immunoglobulin (Ig) Fc polypeptide;
  wherein the immunomodulatory polypeptide is a variant of a naturally occurring costimulatory protein, and wherein the variant exhibits a reduced affinity for its counterpart costimulatory protein as compared to the affinity of the naturally occurring costimulatory protein for the counterpart costimulatory protein; or
  ii) wherein the recombinant polypeptide comprises, in order from N-terminus to C-terminus:
  a) an epitope;
  b) a first MHC polypeptide;
  c) a proteolytically cleavable linker or a ribosome skipping signal;
  d) an immunomodulatory polypeptide
  e) a second MHC polypeptide; and
  f) an Ig Fc polypeptide,
  wherein the immunomodulatory polypeptide is a variant of a naturally occurring costimulatory protein, and wherein the variant exhibits a reduced affinity for its counterpart costimulatory protein as compared to the affinity of the naturally occurring costimulatory protein for the counterpart costimulatory protein.

Aspect 37. A nucleic acid comprising a nucleotide sequence encoding a recombinant polypeptide,
  i) wherein the recombinant polypeptide comprises, in order from N-terminus to C-terminus:
  a) an epitope;
  b) a first major histocompatibility complex (MHC) polypeptide;
  c) an immunomodulatory polypeptide;
  d) a proteolytically cleavable linker or a ribosome skipping signal;
  e) a second MHC polypeptide; and
  f) an immunoglobulin (Ig) Fc polypeptide;
  wherein the immunomodulatory polypeptide is a variant immunomodulatory polypeptide of any one of aspects 1-6; or ii) wherein the recombinant polypeptide comprises, in order from N-terminus to C-terminus:
   a) an epitope;
   b) a first MHC polypeptide;
   c) a proteolytically cleavable linker or a ribosome skipping signal;
   d) an immunomodulatory polypeptide
   e) a second MHC polypeptide; and
   f) an Ig Fc polypeptide,
   wherein the immunomodulatory polypeptide is a variant immunomodulatory polypeptide of any one of aspects 1-6.

Aspect 38. The nucleic acid of aspect 36 or 37, wherein the first MHC polypeptide is a β2-microglobulin polypeptide; and wherein the second MHC polypeptide is an MHC class I heavy chain polypeptide.

Aspect 39. The nucleic acid of aspect 38, wherein the β2-microglobulin polypeptide comprises an amino acid sequence having at least 85% amino acid sequence identity to one of the amino acid sequences set forth in FIG. 6.

Aspect 40. The nucleic acid of aspect 38, wherein the MHC class I heavy chain polypeptide is an HLA-A, HLA-B, or HLA-C heavy chain.

Aspect 41. The nucleic acid of aspect 40, wherein the MHC class I heavy chain polypeptide comprises an amino acid sequence having at least 85% amino acid sequence identity to the amino acid sequence set forth in any one of FIG. 5A-5C.

Aspect 42. The nucleic acid of aspect 36 or 37, wherein the first MHC polypeptide is an MHC Class II alpha chain polypeptide; and wherein the second MHC polypeptide is an MHC class II beta chain polypeptide.

Aspect 43. The nucleic acid of any one of aspects 36-42, wherein the epitope is a T-cell epitope.

Aspect 44. The nucleic acid of any one of aspects 36-43, wherein the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide.

Aspect 45. The nucleic acid of aspect 44, wherein the Ig Fc polypeptide comprises an amino acid sequence having at least 85% amino acid sequence identity to an amino acid sequence depicted in FIGS. 4A-4C.

Aspect 46. The nucleic acid of any one of aspects 37-45, wherein the variant IL-2 immunomodulatory polypeptide comprises a substitution of one or more of E15, H16, D20, F42, Y45, and Q126.

Aspect 47. The nucleic acid of any one of aspects 36-46, wherein the multimeric polypeptide comprises a second immunomodulatory polypeptide selected from a CD7, CD30L, CD40, CD70, CD83, HLA-G, MICA, MICB, HVEM, lymphotoxin beta receptor, 3/TR6, ILT3, ILT4, and HVEM.

Aspect 48. The nucleic acid of any one of aspects 36-47, wherein the proteolytically cleavable linker or ribosome skipping signal comprises an amino acid sequence selected from:

a)
                              (SEQ ID NO: 29)
LEVLFQGP;

b)
                              (SEQ ID NO: 30)
ENLYTQS;

c) a furin cleavage site;

d)
                              (SEQ ID NO: 32)
LVPR;

e)
                              (SEQ ID NO: 33)
GSGATNFSLLKQAGDVEENPGP;

f)
                              (SEQ ID NO: 34)
GSGEGRGSLLTCGDVEENPGP;

g)
                              (SEQ ID NO: 35)
GSGQCTNYALLKLAGDVESNPGP;
and h)
                              (SEQ ID NO: 36)
GSGVKQTLNFDLLKLAGDVESNPGP.

Aspect 49. The nucleic acid of aspect 36-48, wherein the recombinant polypeptide comprises, in order from N-terminus to C-terminus:
   a) a first leader peptide;
   b) the epitope;
   c) the first MHC polypeptide;
   d) the immunomodulatory polypeptide;
   e) the proteolytically cleavable linker or ribosome skipping signal;
   f) a second leader peptide;
   g) the second MHC polypeptide; and
   h) the immunoglobulin (Ig) Fc polypeptide.

Aspect 50. The nucleic acid of aspect 49, wherein the first leader peptide and the second leader peptide is a β2-M leader peptide.

Aspect 51. The nucleic acid of any one of aspects 36-50, wherein the nucleotide sequence is operably linked to a transcriptional control element.

Aspect 52. The nucleic acid of aspect 51, wherein the transcriptional control element is a promoter that is functional in a eukaryotic cell.

Aspect 53. The nucleic acid of any one of aspects 36-52, wherein the first MHC polypeptide or a linker between the epitope and the first MHC polypeptide comprises an amino acid substitution to provide a first Cys residue, and the second MHC polypeptide comprises an amino acid substitution to provide a second Cys residue, and wherein the first and the second Cys residues provide for a disulfide linkage between the first MHC polypeptide and the second MHC polypeptide.

Aspect 54. A recombinant expression vector comprising the nucleic acid of any one of aspects 36-52, and wherein the vector is optionally a viral vector or a non-viral vector.

Aspect 55. A host cell genetically modified with the recombinant expression vector of aspect 54.

Aspect 56. The host cell of aspect 55, wherein the host cell is in vitro, and wherein the host cell is optionally genetically modified such that the cell does not produce an endogenous MHC β2-microglobulin polypeptide.

Aspect 57. A composition comprising:
a) a first nucleic acid comprising a nucleotide sequence encoding a first polypeptide comprising, in order from N-terminus to C-terminus:
  i) an epitope;
  ii) a first MHC polypeptide; and
  iii) an immunomodulatory domain,
wherein the immunomodulatory polypeptide is a variant of a naturally occurring costimulatory protein, and wherein the variant exhibits a reduced affinity for its counterpart costimulatory protein as compared to the affinity of the naturally occurring costimulatory protein for the counterpart costimulatory protein; and
b) a first nucleic acid comprising a nucleotide sequence encoding a second polypeptide comprising, in order from N-terminus to C-terminus:
  i) a second MHC polypeptide; and
  ii) an Ig Fc polypeptide.

Aspect 58. A composition comprising:
a) a first nucleic acid comprising a nucleotide sequence encoding a first polypeptide comprising, in order from N-terminus to C-terminus:
  i) an epitope; and
  ii) a first MHC polypeptide; and
b) a first nucleic acid comprising a nucleotide sequence encoding a second polypeptide comprising, in order from N-terminus to C-terminus:
  i) an immunomodulatory domain, wherein the immunomodulatory domain is a variant of a naturally occurring costimulatory protein, and wherein the variant exhibits a reduced affinity for its counterpart costimulatory protein as compared to the affinity of the naturally occurring costimulatory protein for the counterpart costimulatory protein;
  ii) a second MHC polypeptide; and
  iii) an Ig Fc polypeptide.

Aspect 59. A composition comprising:
a) a first nucleic acid comprising a nucleotide sequence encoding a first polypeptide comprising, in order from N-terminus to C-terminus:
  i) an epitope;
  ii) a first MHC polypeptide; and
  iii) an immunomodulatory domain,
wherein the immunomodulatory domain is a variant IL-2 polypeptide of any one of aspects 1-6; and
b) a first nucleic acid comprising a nucleotide sequence encoding a second polypeptide comprising, in order from N-terminus to C-terminus:
  i) a second MHC polypeptide; and
  ii) an Ig Fc polypeptide.

Aspect 60. A composition comprising:
a) a first nucleic acid comprising a nucleotide sequence encoding a first polypeptide comprising, in order from N-terminus to C-terminus:
  i) an epitope; and
  ii) a first MHC polypeptide; and
b) a first nucleic acid comprising a nucleotide sequence encoding a second polypeptide comprising, in order from N-terminus to C-terminus:
  i) an immunomodulatory domain, wherein the immunomodulatory domain is a variant IL-2 polypeptide of any one of aspects 1-6;
  ii) a second MHC polypeptide; and
  iii) an Ig Fc polypeptide.

Aspect 61. The composition of any one of aspects 57-60, wherein the first and/or the second nucleic acid is present in a recombinant expression vector.

Aspect 62. A host cell genetically modified with the composition of any one of aspects 57-61.

Aspect 63. A method of producing the multimeric polypeptide of any one of aspects 7-36, the method comprising:
a) culturing the host cell of any one of aspects 55, 56, and 62 in vitro in a culture medium under conditions such that the host cell synthesizes the multimeric polypeptide; and
b) isolating the multimeric polypeptide from the host cell and/or from the culture medium.

Aspect 64. The method of aspect 63, wherein the second polypeptide comprises an affinity tag, and wherein said isolating comprises contacting the multimeric polypeptide produced by the cell with a binding partner for the affinity tag, wherein the binding partner is immobilized, thereby immobilizing the multimeric polypeptide.

Aspect 65. The method of aspect 64, comprising eluting the immobilized multimeric polypeptide.

Aspect 66. A method of selectively activating an epitope-specific T cell, the method comprising contacting the T cell with the multimeric polypeptide of any one of aspects 7-35, wherein said contacting selectively activates the epitope-specific T cell.

Aspect 67. The method of aspect 66, wherein said contacting is in vitro.

Aspect 68. The method of aspect 66, wherein said contacting is in vivo.

Aspect 69. The method of aspect 66, wherein the epitope is a cancer-associated epitope, and wherein said administering selectively increases the activity of a T cell specific for the cancer-associate epitope.

Aspect 70. A method of treating cancer in an individual, the method comprising administering to the individual an effective amount of:
a) the multimeric polypeptide of any one of aspects 7-35; or
b) one or more recombinant expression vectors comprising nucleotide sequences encoding the multimeric polypeptide of any one of aspects 7-35; or
c) one or more mRNAs comprising nucleotide sequences encoding the multimeric polypeptide of any one of aspects 7-35,
wherein the epitope is a cancer-associated epitope, and wherein said administering effective to selectively activate a cancer epitope-specific T cell in an individual.

Aspect 71. The method of aspect 70, wherein said administering is subcutaneous.

Aspect 72. The method of aspect 70, wherein said administering is intravenous.

Aspect 73. The method of aspect 70, wherein said administering is peritumoral.

Aspect 74. The method of aspect 70, wherein said administering is systemic.

Aspect 75. The method of aspect 70, wherein said administering is distal to a treatment site.

Aspect 76. The method of aspect 70, wherein said administering is local.

Aspect 77. The method of aspect 70, wherein said administering is at or near a treatment site.

Aspect 78. A composition comprising:
a) the multimeric polypeptide of any one of aspects 7-35; and
b) a pharmaceutically acceptable excipient.

Aspect 79. A composition comprising:
a) the nucleic acid of any one of aspects 36-53 or the recombinant expression vector of aspect 54; and
b) a pharmaceutically acceptable excipient.

Aspect 80. A multimeric polypeptide comprising:
a) a first polypeptide comprising, in order from N-terminus to C-terminus:
  i) an epitope;
  ii) a β2-microglobulin (β2M) polypeptide comprising the amino acid sequence depicted in FIG. 34A; and
b) a second polypeptide comprising, in order from N-terminus to C-terminus:
  i) a variant of a naturally occurring costimulatory protein, and wherein the variant exhibits a reduced affinity for its counterpart costimulatory protein as compared to the affinity of the naturally occurring costimulatory protein for the counterpart costimulatory protein, which variant optionally may be a variant IL-2 polypeptide of any one of aspects 1-6;
  ii) a major histocompatibility complex (MHC) heavy chain polypeptide comprising the amino acid sequence depicted in FIG. 34C; and
  iii) an IgG1 Fc polypeptide comprising one or more amino acid substitutions selected from N297A, L234A, L235A, L234F, L235E, and P331S (N77A, L14A, L15A, L14F, L15E, and P111S, respectively, based on the amino acid numbering depicted in FIG. 33A).

Aspect 81. The multimeric polypeptide of aspect 80, wherein the IgG1 Fc polypeptide comprises an N297A substitution (N77A based on the amino acid numbering depicted in FIG. 33A).

Aspect 82. The multimeric polypeptide of aspect 80, wherein the IgG1 Fc polypeptide comprises an L234A substitution and an L235A substitution (L14A and L15A based on the amino acid numbering depicted in FIG. 33A).

Aspect 83. The multimeric polypeptide of aspect 80, wherein the IgG1 Fc polypeptide comprises an L234F substitution and an L235E substitution (L14F and L15E based on the amino acid numbering depicted in FIG. 33A).

Aspect 84. The multimeric polypeptide of aspect 80, wherein the IgG1 Fc polypeptide comprises an L234F substitution, an L235E substitution, and a P331S (L14F, L15E, and P111S substitutions based on the amino acid numbering depicted in FIG. 33A).

Aspect 85. The multimeric polypeptide of any one of aspects 80-84, wherein the second polypeptide comprises two copies of the variant IL-2 polypeptide.

Aspect 86. The multimeric polypeptide of any one of aspects 80-85, wherein the first polypeptide comprises a peptide linker between the epitope and the β2M polypeptide.

Aspect 87. The multimeric polypeptide of any one of aspects 80-86, wherein the second polypeptide comprises a peptide linker between one or more of:
  a) a first copy of the variant IL-2 polypeptide and a second copy of the variant IL-2 polypeptide;
  b) the variant IL-2 polypeptide and the MHC heavy chain polypeptide; and
  c) between the MHC heavy chain polypeptide and the IgG1 Fc polypeptide.

Aspect 88. The multimeric polypeptide of aspect 86 or aspect 87, wherein the peptide linker is selected from (GGGGS)₃, (GGGGS)₄, and AAAGG.

Aspect 89. A multimeric polypeptide comprising:
a) a first polypeptide comprising, in order from N-terminus to C-terminus:
  i) an epitope;
  ii) a β2-microglobulin polypeptide comprising the amino acid sequence depicted in FIG. 34A; and
b) a second polypeptide comprising, in order from N-terminus to C-terminus:
  i) a variant IL-2 polypeptide comprising the amino acid sequence depicted in FIG. 34B;
  ii) a major histocompatibility complex (MHC) heavy chain polypeptide comprising the amino acid sequence depicted in FIG. 34C; and
  iii) an IgG1 Fc polypeptide comprising one or more amino acid substitutions selected from N297A, L234A, L235A, L234F, L235E, and P331S (N77A, L14A, L15A, L14F, L15E, and P111S, respectively, based on the amino acid numbering depicted in FIG. 33A).

Aspect 90. The multimeric polypeptide of aspect 89, wherein the IgG1 Fc polypeptide comprises an N297A substitution (N77A based on the amino acid numbering depicted in FIG. 33A).

Aspect 91. The multimeric polypeptide of aspect 89, wherein the IgG1 Fc polypeptide comprises an L234A substitution and an L235A substitution (L14A and L15A based on the amino acid numbering depicted in FIG. 33A).

Aspect 92. The multimeric polypeptide of aspect 89, wherein the IgG1 Fc polypeptide comprises an L234F substitution and an L235E substitution (L14F and L15E based on the amino acid numbering depicted in FIG. 33A).

Aspect 93. The multimeric polypeptide of aspect 89, wherein the IgG1 Fc polypeptide comprises an L234F substitution, an L235E substitution, and a P331S substitution (L14F, L15E, and P111S based on the amino acid numbering depicted in FIG. 33A).

Aspect 94. The multimeric polypeptide of any one of aspects 89-93, wherein the second polypeptide comprises two copies of the variant IL-2 polypeptide.

Aspect 95. The multimeric polypeptide of any one of aspects 89-94, wherein the first polypeptide comprises a peptide linker between the epitope and the β2M polypeptide.

Aspect 96. The multimeric polypeptide of any one of aspects 89-95, wherein the second polypeptide comprises a peptide linker between one or more of:
  a) a first copy of the variant IL-2 polypeptide and a second copy of the variant IL-2 polypeptide;
  b) the variant IL-2 polypeptide and the MHC heavy chain polypeptide; and
  c) the MHC heavy chain polypeptide and the IgG1 Fc polypeptide.

Aspect 97. The multimeric polypeptide of aspect 95 or aspect 96, wherein the peptide linker is selected from (GGGGS)₃, (GGGGS)₄, and AAAGG.

Aspect 98. A multimeric polypeptide comprising:
a) a first polypeptide comprising, in order from N-terminus to C-terminus:
  i) an epitope comprising the amino acid sequence YMLDLQPETT (SEQ ID NO:13);
  ii) a β2-microglobulin polypeptide comprising the amino acid sequence depicted in FIG. 34A; and
b) a second polypeptide comprising, in order from N-terminus to C-terminus:
  i) a variant IL-2 polypeptide comprising the amino acid sequence depicted in FIG. 34B;
  ii) a major histocompatibility complex (MHC) heavy chain polypeptide comprising the amino acid sequence depicted in FIG. 34C; and
  iii) an IgG1 Fc polypeptide comprising the amino acid sequence depicted in FIG. 33A, 33B, 33C, or 33D.

Aspect 99. The multimeric polypeptide of aspect 98, wherein the IgG1 Fc polypeptide comprises the amino acid sequence depicted in FIG. 33B.

Aspect 100. The multimeric polypeptide of aspect 98, wherein the IgG1 Fc polypeptide comprises the amino acid sequence depicted in FIG. 33C.

Aspect 101. The multimeric polypeptide of aspect 98, wherein the IgG1 Fc polypeptide comprises the amino acid sequence depicted in FIG. 33D.

Aspect 102. The multimeric polypeptide of any one of aspects 98-101, wherein the second polypeptide comprises two copies of the variant IL-2 polypeptide.

Aspect 103. The multimeric polypeptide of any one of aspects 98-102, wherein the first polypeptide comprises a peptide linker between the epitope and the β2M polypeptide.

Aspect 104. The multimeric polypeptide of any one of aspects 98-103, wherein the second polypeptide comprises a peptide linker between one or more of:
 a) a first copy of the variant IL-2 polypeptide and a second copy of the variant IL-2 polypeptide;
 b) the variant IL-2 polypeptide and the MHC heavy chain polypeptide; and
 c) the MHC heavy chain polypeptide and the IgG1 Fc polypeptide.

Aspect 105. The multimeric polypeptide of aspect 103 or aspect 104, wherein the peptide linker is selected from (GGGGS)$_3$, (GGGGS)$_4$, and AAAGG.

Aspect 106. A multimeric polypeptide comprising:
 a) a first polypeptide comprising the amino acid sequence depicted in FIG. 31;
 b) a second polypeptide comprising the amino acid sequence depicted in FIG. 22.

Aspect 107. A multimeric polypeptide comprising:
 a) a first polypeptide comprising the amino acid sequence depicted in FIG. 31;
 b) a second polypeptide comprising the amino acid sequence depicted in FIG. 25.

Aspect 108. A multimeric polypeptide comprising:
 a) a first polypeptide comprising the amino acid sequence depicted in FIG. 31;
 b) a second polypeptide comprising the amino acid sequence depicted in FIG. 28.

Aspect 109. A pharmaceutical composition comprising:
 a) a multimeric polypeptide according to any one of aspects 80-108; and
 b) a pharmaceutically acceptable excipient.

Aspect 110. One or more nucleic acids comprising nucleotide sequences encoding the first and/or the second polypeptide of the multimeric polypeptide according to any one of aspects 80-108.

Aspect 111. The one or more nucleic acids of aspect 110, wherein the nucleic acid(s) is/are present in recombinant expression vectors.

Aspect 112. A method of selectively activating an epitope-specific T cell, the method comprising contacting the T cell with the multimeric polypeptide of any one of aspects 80-108, wherein said contacting selectively activates the epitope-specific T cell.

Aspect 113. The method of aspect 112, wherein said contacting is in vitro.

Aspect 114. The method of aspect 112, wherein said contacting is in vivo.

Aspect 115. A method comprising administering to an individual an effective amount of:
 a) the multimeric polypeptide of any one of aspects 80-108; or
 b) one or more recombinant expression vectors comprising nucleotide sequences encoding the multimeric polypeptide of any one of aspects 80-108; or
 c) one or more mRNAs comprising nucleotide sequences encoding the multimeric polypeptide of any one of aspects 80-108, wherein said administering induces a T cell response to epitope in the individual.

Aspect 116. The method of aspect 115, wherein said administering is subcutaneous.

Aspect 117. The method of aspect 115, wherein said administering is intravenous.

Aspect 118. The method of aspect 115, wherein said administering is systemic.

Aspect 119. The method of aspect 115, wherein said administering is intramuscular.

Aspect 120. The method of aspect 115, wherein said administering is distal to a treatment site.

Aspect 121. The method of aspect 115, wherein said administering is local.

Aspect 122. The method of aspect 115, wherein said administering is at or near a treatment site.

Aspect 123. A method of delivering a costimulatory polypeptide selectively to target T cell, the method comprising contacting a mixed population of T cells with a multimeric polypeptide of any one of aspects 7-35 and 80-108, wherein the mixed population of T cells comprises the target T cell and non-target T cells, wherein the target T cell is specific for the epitope present within the multimeric polypeptide, and wherein said contacting delivers the costimulatory polypeptide present within the multimeric polypeptide to the target T cell.

Aspect 124. A method of delivering IL-2 or an IL-2 variant selectively to a target T cell, the method comprising contacting a mixed population of T cells with the multimeric polypeptide of any one of aspects 8-35 and 80-108, wherein the mixed population of T cells comprises the target T cell and non-target T cells, wherein the target T cell is specific for the epitope present within the multimeric polypeptide, and wherein said contacting delivers the IL-2 or IL-2 variant present within the multimeric polypeptide to the target T cell.

Aspect 125. The method of aspect 123 or 124, wherein the population of T cells is in vitro.

Aspect 126. The method of aspect 123 or 124, wherein the population of T cells is in vivo in an individual.

Aspect 127. The method of aspect 126, comprising administering the multimeric polypeptide to the individual.

Aspect 128. The method of any one of aspects 123-127, wherein the target T cell is a regulatory T cell.

Aspect 129. The method of any one of aspects 123-127, wherein the target T cell is a cytotoxic T cell.

Aspect 130. The method of aspect 123 or 124, wherein the mixed population of T cells is an in vitro population of mixed T cells obtained from an individual, and wherein said contacting results in activation and/or proliferation of the target T cell, generating a population of activated and/or proliferated target T cells.

Aspect 131. The method of aspect 130, further comprising administering the population of activated and/or proliferated target T cells to the individual.

Aspect 132. A method of detecting, in a mixed population of T cells obtained from an individual, the presence of a target T cell that binds an epitope of interest, the method comprising: a) contacting in vitro the mixed population of T cells with the multimeric polypeptide of any one of aspects 7-35 and 80-108, wherein the multimeric polypeptide comprises the epitope of interest; and b) detecting activation and/or proliferation of T cells in response to said contacting, wherein activated and/or proliferated T cells indicates the presence of the target T cell.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); kiloDalton(s), kDa; i.m., intramuscular(ly); i.p., intraperitoneal(ly); s.c., subcutaneous(ly); and the like.

Example 1: Production of IL-2/synTac

Figure 7A:

Production of IL-2/synTac by transiently transfected mammalian cells was analyzed. As shown in FIG. 7A, production levels (in mg/L culture medium) of two different IL-2/synTacs, 6-7 days following transient transfection of the cells, was greater than 90 mg/L.

The IL-2/synTacs produced by the mammalian cells was purified, and subjected to reducing and non-reducing polyacrylamide gel electrophoresis. The results are depicted in FIG. 7B. Sizes are given in kDa.

IL-2/synTacs were generated, in which the IL-2 polypeptide was in the "light chain" (i.e., the polypeptide comprising MHC Class I light chain; e.g., β2M) or in the "heavy chain" (i.e., the polypeptide comprising MHC Class I heavy chain). Expression levels and stability of the IL-2/synTacs were analyzed.

Figure 8A:
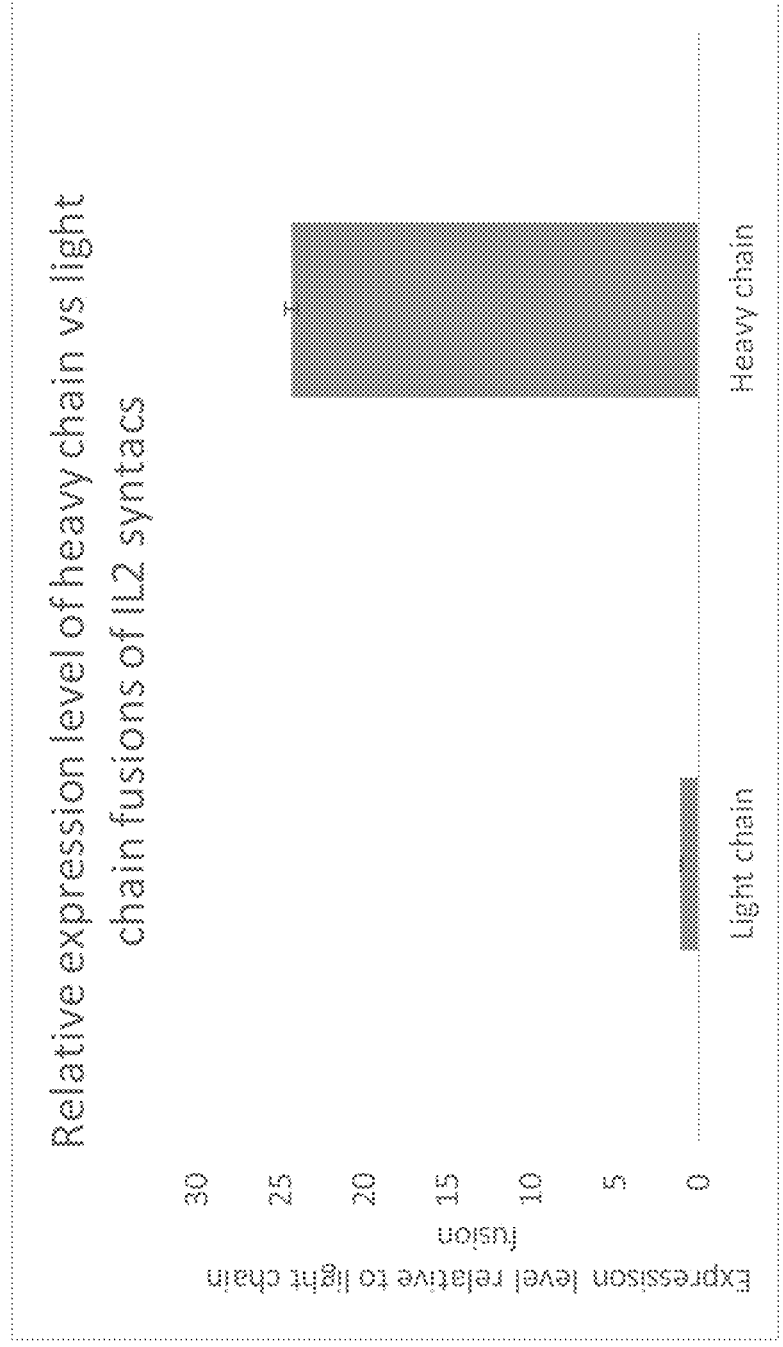
FIG. 8A-8B depict production of IL-2/synTacs of the present disclosure, in which the IL-2 polypeptide is present on the light chain (the polypeptide chain with the light chain (e.g., β2M) of an MHC Class I molecule) or on the heavy chain (the polypeptide chain with the heavy chain of an MHC Class I molecule).

The synTacs were produced in mammalian cells. As shown in FIG. 8A, the IL-2/synTac comprising IL-2 on the heavy chain was produced at levels about 25-fold higher than the level of the IL-2/synTac comprising IL-2 on the light chain.

Figure 8B:
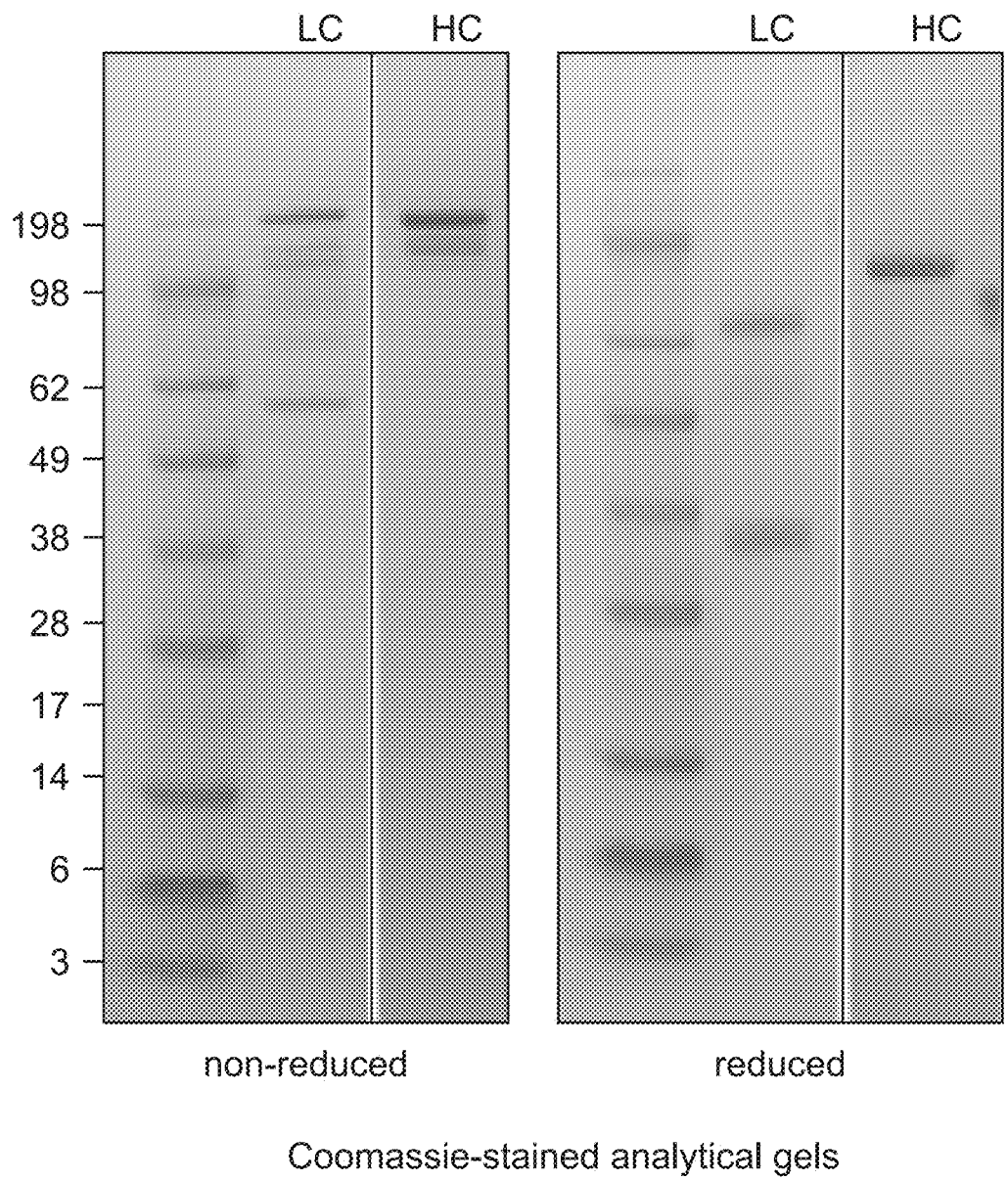

The IL-2/synTacs produced by mammalian cells were subjected to reducing and non-reducing polyacrylamide gel electrophoresis; and the gels were stained with Coomassie blue. As shown in FIG. 8B, the IL-2/synTac comprising IL-2 on the heavy chain was more stable than the IL-2/synTac comprising IL-2 on the light chain. Sizes are given in kDa.

Figure 9:
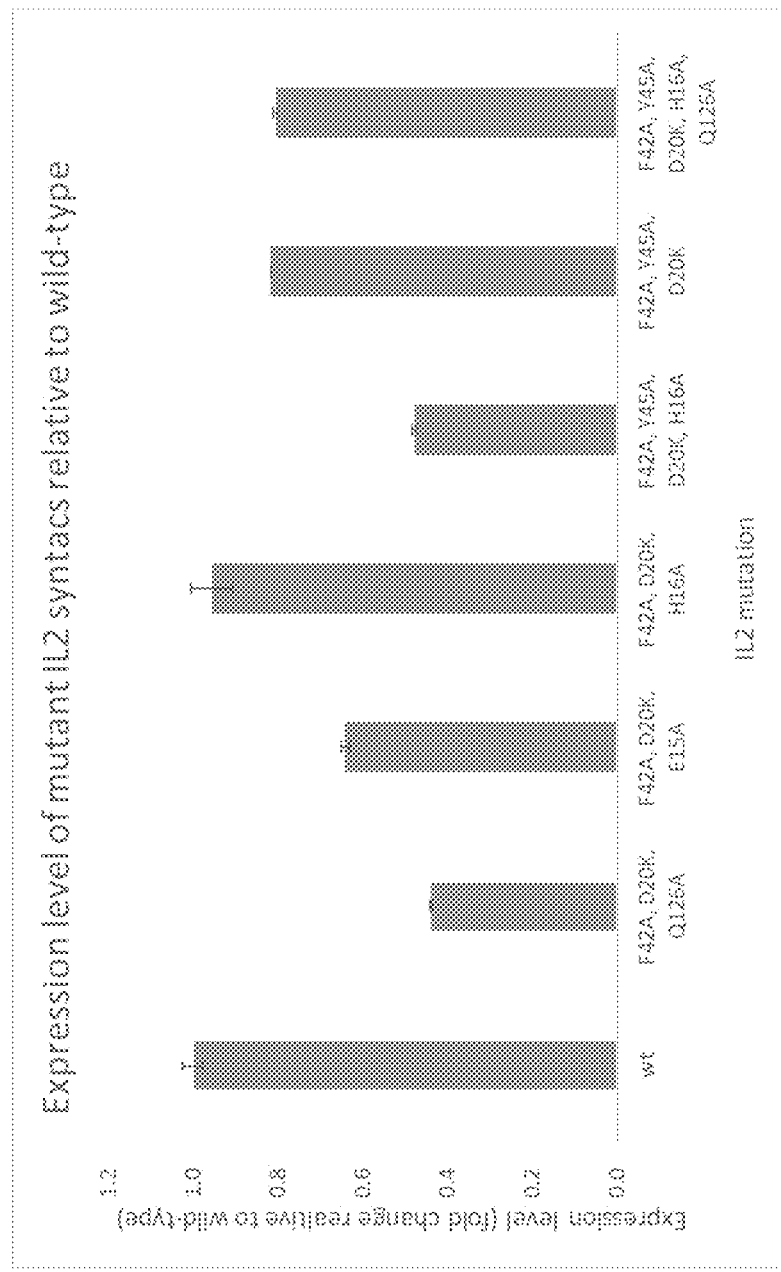
FIG. 9 depicts the expression level of IL-2/syn-Tacs, in which the IL-2 is wild-type (wt), or comprises various combinations of F42A, D20K, Q126A, E15A, Y45A, and H16A.

Expression levels of IL-2/synTacs comprising variant IL-2 were assessed. FIG. 9 depicts the expression level of IL-2/syn-Tacs, in which the IL-2 is wild-type (wt), or comprises various combinations of F42A, D20K, Q126A, E15A, Y45A, and H16A. The expression levels are expressed as percent change relative to expression levels of a synTac with wild-type IL-2.

Figure 10:
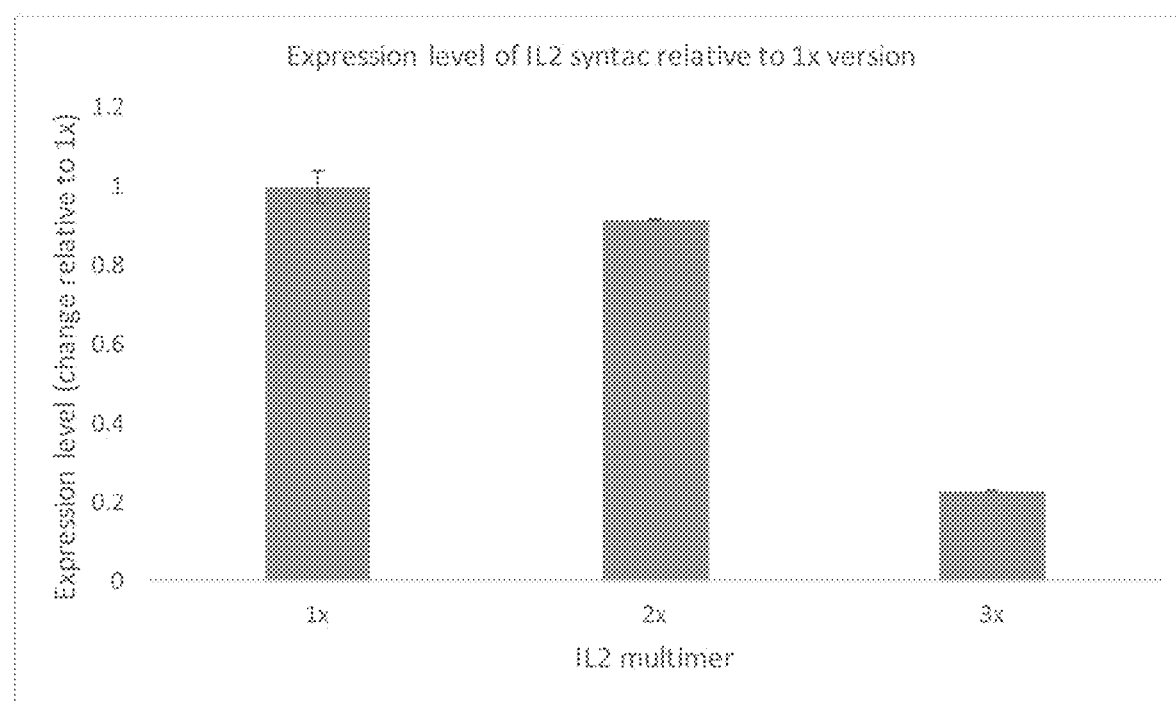
FIG. 10 depicts expression of IL-2/synTacs of the present disclosure, in which the IL-2 is present in one copy (1×), two copies (2×) or three copies (3×) in the synTac.

The effect of the copy number of IL-2 in an IL-2/synTac on expression levels was evaluated. IL-2/synTacs comprising one copy (1×), two copies (2×) or three copies (3×) in the synTac. The various IL-2/synTacs were produced in mammalian cells, and expression levels were assayed. The data are depicted in FIG. 10. IL-2/synTacs with one or two copies of IL-2 exhibit similar expression levels, while an IL-2/synTac with three copies of IL-2 exhibited lower expression levels. Expression levels are expressed as fold change relative to the expression level of the IL-2/synTac with a single copy of IL-2.

Example 2: In Vitro Activity of IL-2/synTac

To achieve maximal specificity of targeting through a T-cell receptor, the affinity of the co-stimulatory polypeptide for its ligand should be lower than the affinity of MHC for the TCR. The peptide/MHC affinity for TCR can be about 10 μM.

An IL-2/synTac was generated, comprising two copies of a variant IL-2 comprising F42A and H16A substitutions. Costimulatory signaling induced by the IL-2/synTac was tested on antigen-specific CD8+ T cells and non-specific CD8+ T cells. Antigen-specific CD8+ T cells and non-specific CD8+ T cells were contacted with various concentrations of the IL-2/synTac.

Figure 11:
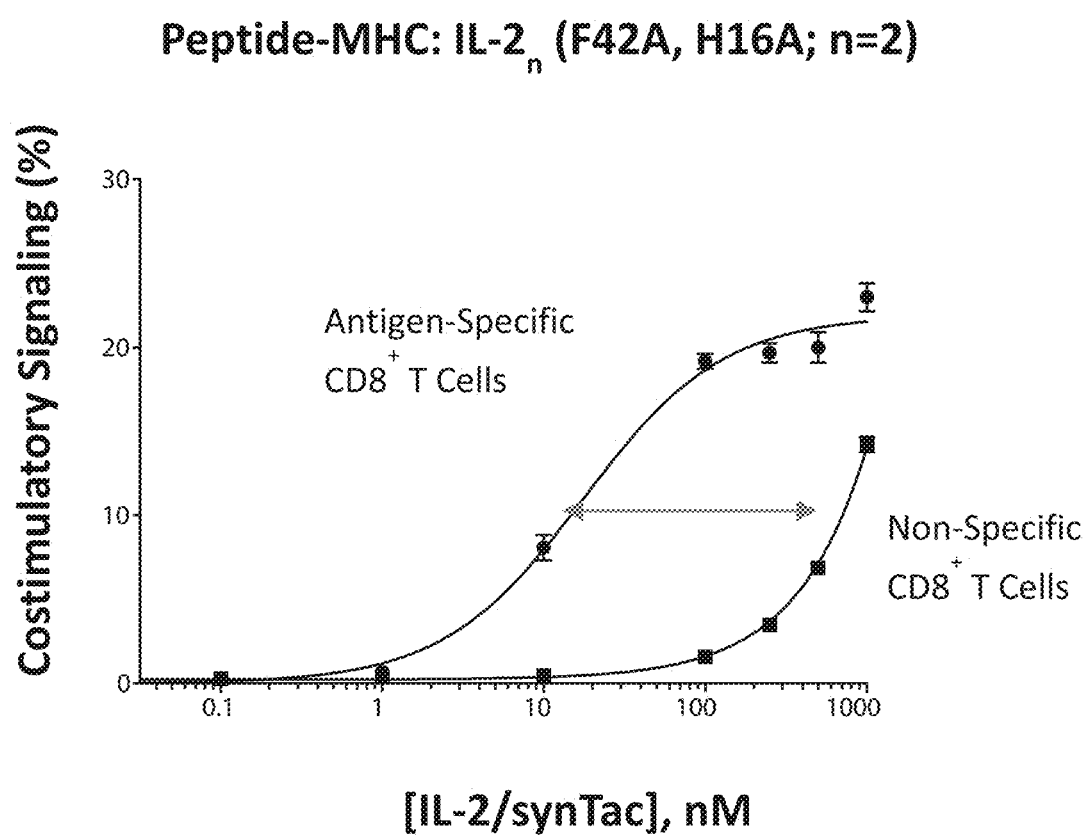
FIG. 11 depicts in vitro stimulation of antigen-specific CD8$^+$ T cells and non-specific CD8$^+$ T cells by an IL-2/synTac of the present disclosure, where the IL-2 variant comprising F42A and H16A substitutions is present in the synTac in two copies.

As shown in FIG. 11, the IL-2/synTac induced costimulatory signaling in antigen-specific CD8+ T cells at a much lower concentration than in non-specific CD8+ T cells.

Selectivity of IL-2/synTac binding was tested. CD8+ T cells were isolated from spleens of LCMV or OT1 mice. The CD8+ T cells were incubated with IL-2/synTacs at various concentrations, and allowed to bind for 20 minutes. The IL-2/synTacs comprise IgG2a Fc. Binding of IL-2/synTacs to the CD8+ T cells was detected using phycoerythrin (PE)-labeled anti-IgG2a antibody. PE fluorescence was detected using flow cytometry to determine the percent of cells bound to IL-2/synTac.

As shown in FIG. 12, IL-2/synTac binds in an antigen-specific manner to LCMV CD8+ T cells, but does not exhibit significant binding to OT1 CD8+ T cells. Thus, IL-2/synTac selectively binds to CD8+ T cells specific for the epitope present in the IL-2/synTac.

It was determined whether an IL-2/synTac selectively activates target T cells. CD8+ T cells were isolated from spleens of LCMV or OT1 mice. The IL-2/synTacs used included either the F42A single amino acid substitution, or the F42A and H16A substitutions. The CD8+ T cells were stimulated with IL-2/synTacs at various concentrations for 20 minutes. The cells were then stained with PE-labelled anti-phospho-STAT5 antibody. PE fluorescence was detected using flow cytometry to determine the percent of cells that are phospho-STAT5 positive, where phospho-STAT5 is a marker of activation.

As shown in FIG. 13, IL-2/synTac induced CD8+ stimulation (as indicated by the % phospho-STAT5-positive cells) in antigen-specific (LCMV) CD8+ T cells at much lower concentrations than in non-specific (BL6) CD8+ T cells.

The specific activity of various IL-2/synTacs was analyzed. IL-2/synTacs comprising a single copy of IL-2, two copies of IL-2, or three copies of IL-2, where the IL-2 comprised various combinations of F42A, D20K, Q126A, E15A, H16A, and Y45A substitutions, were tested at various concentrations for stimulation of CD8+ antigen-specific (LCMV) or non-specific (BL6) cells. The percent phospho-signal transducer and activator of transcription 5 (pSTAT5)-positive was determined. The data are depicted in FIG. 14A-14F.

Example 3: In Vivo Activity of IL-2/synTac

The in vivo activity of IL-2/synTac was tested. The in vivo fold change in antigen-specific CD8+ T cells was tested, following administration of phosphate buffered saline (PBS), recombinant IL-2 (rIL-2), or an IL-2/synTac of the present disclosure. The data are shown in FIG. 15, left panel. The data indicate that IL-2/synTac is 10 times more potent than rIL-2.

The in vivo specificity of IL-2/synTac was tested. Antigen-specific and non-antigen-specific responses following administration of PBS, rIL-2, or IL-2/synTac was assessed. The data are expressed as percent of lymph node cells that were antigen-specific or antigen non-specific following administration of PBS, rIL-2, or IL-2/synTac. As depicted in FIG. 15, right panel, IL-2/synTac induced an antigen-specific response (expressed as % maximum dilution of carboxyfluorescein succinimidyl ester (CFSE), an index of T cell proliferation). In contrast, the response induced by rIL-2 was not antigen-specific.

Figure 16A:
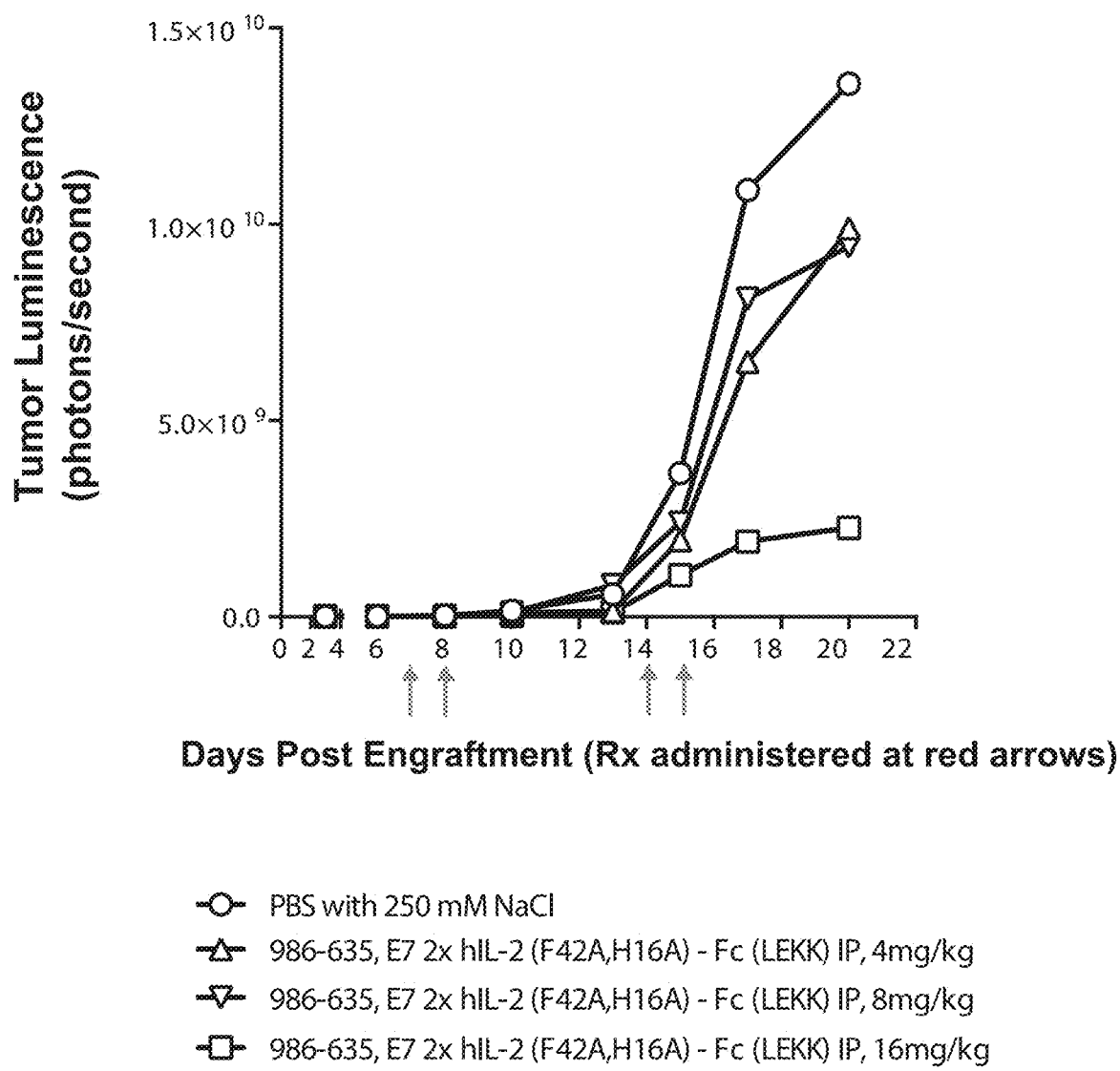
FIG. 16A-16B depict dose escalation (FIG. 16A) and route of administration (FIG. 16B) effects.

A dose response assay was conducted. IL-2/synTac (F42A, H16A) was administered intraperitoneally at concentrations of 4 mg/kg, 8 mg/kg, and 16 mg/kg. The results are shown in FIG. 16A. As shown in FIG. 16A, IL-2/synTac administered at 4 mg/kg or 8 mg/kg gave similar results; IL-2/synTac administered at 16 mg/kg induced the most potent immunostimulatory activity.

Figure 16B:
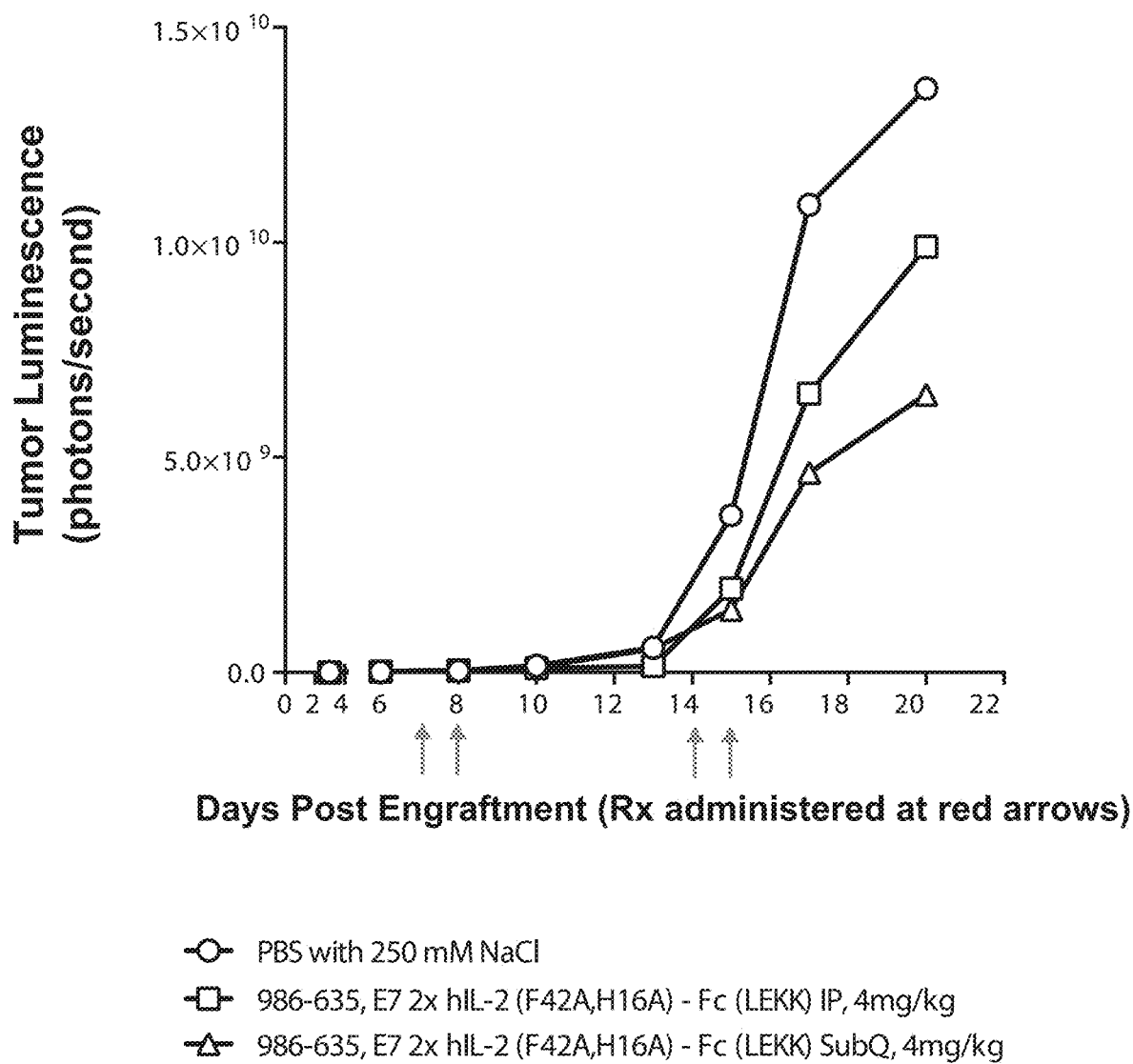

The effect of route of administration of IL-2/synTac was tested. IL-2/synTac (F42A, H16A) was administered at 4 mg/kg, either subcutaneously (SubQ) or intraperitoneally (IP). As shown in FIG. 16B, subcutaneous administration resulted in a more potent immunostimulatory activity than IP administration.

Figure 17A:
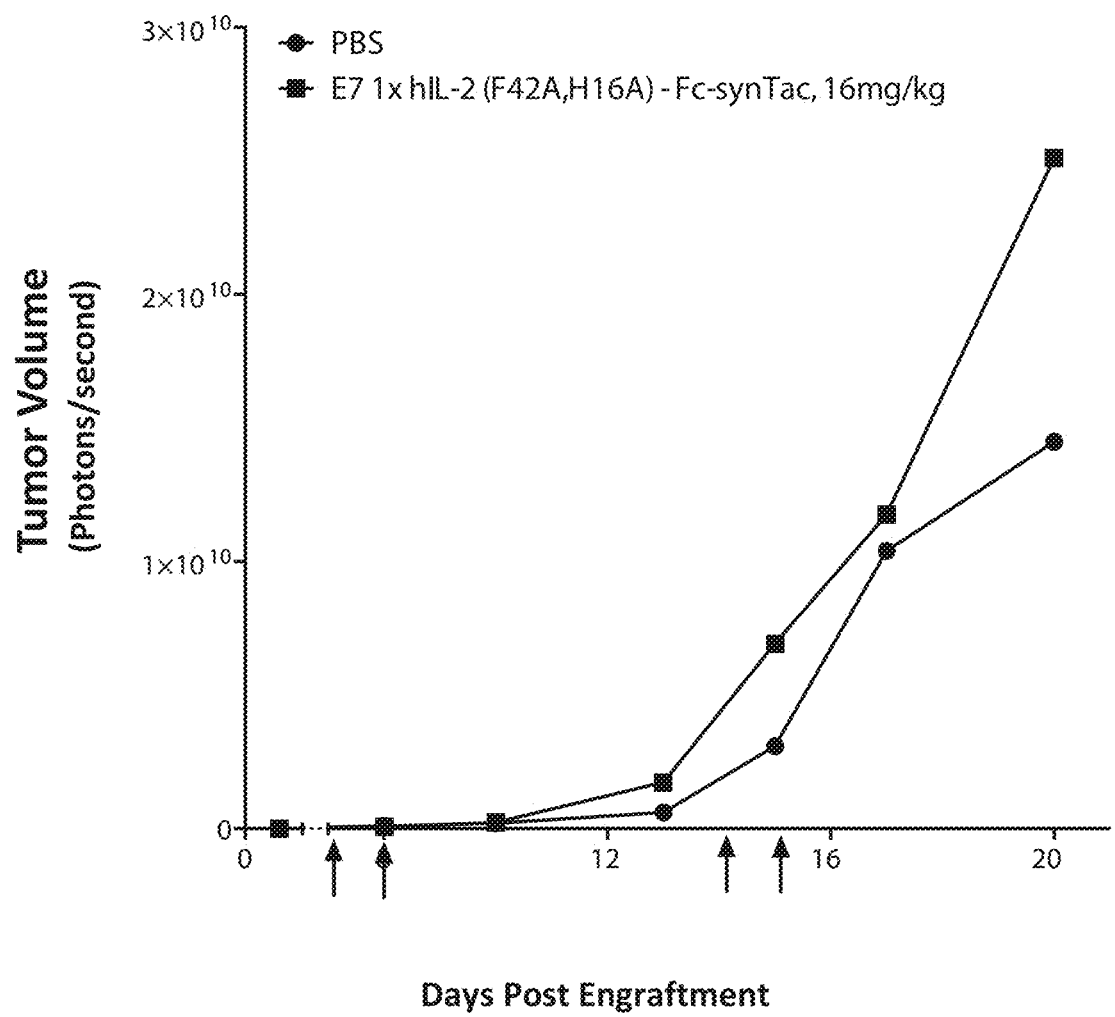
FIG. 17A-17B depict the effect of IL-2 copy number on in vivo efficacy against a tumor.
Figure 17B:
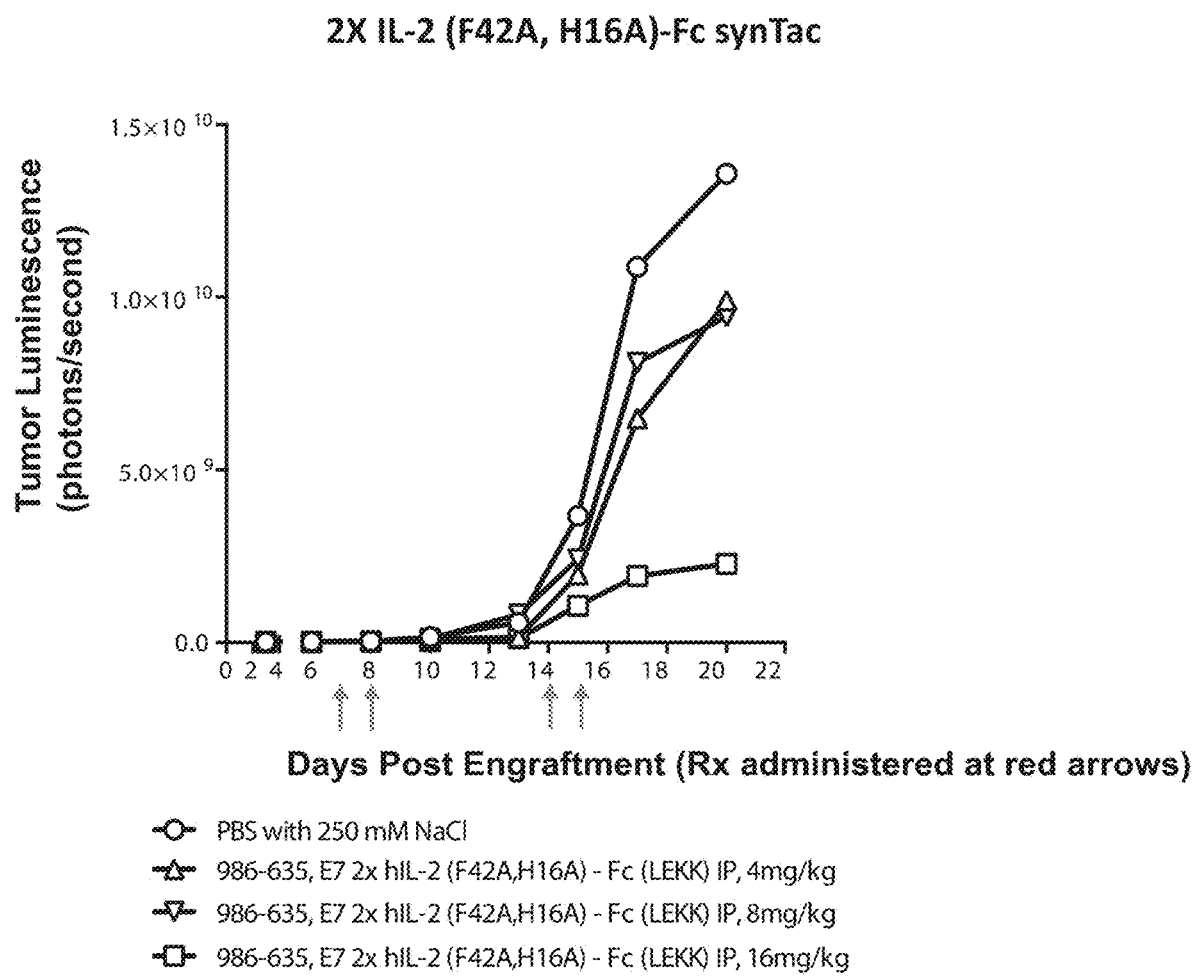

The effect of IL-2 copy number on efficacy was determined. IL-2/synTacs comprising a single copy of IL-2 (F42A, H16A) or two copies of IL-2 (F42A, H16A) were injected into mice with tumors bearing an HPV E7 epitope. The epitope included in the IL-2/synTacs was the HPV E7 epitope. As shown in FIGS. 17A and 17B, an IL-2/synTac comprising two copies of IL-2(F42A, H16A) were more effective at reducing tumor size than an IL-2/synTac comprising only a single copy of IL-2(F42A, H16A).

Example 4: PK/PD and Stability Studies of IL-2/synTac

Figure 18:
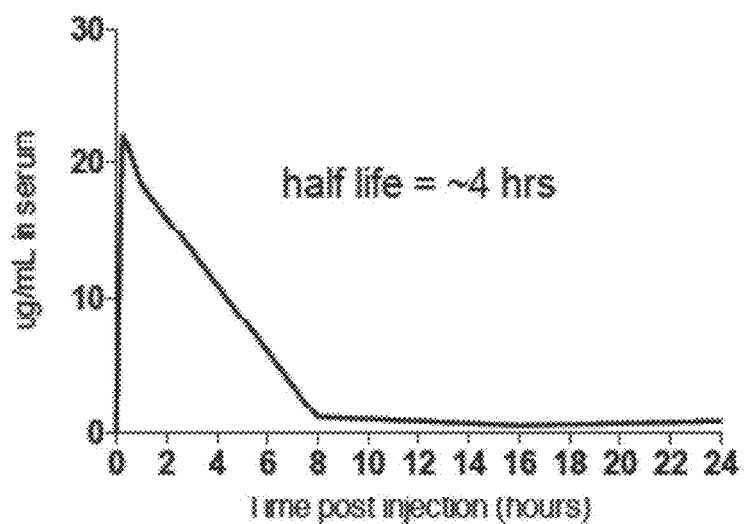
FIG. 18 depicts the serum half-life of an IL-2/synTac of the present disclosure, following intraperitoneal administration of the IL-2/synTac in an amount of 10 mg/kg.

Pharmacokinetic (PK) analysis of IL-2/synTac was carried out. IL-2/synTac (F42A, D20K, H16A) was administered IP at 10 mg/kg. At various time points post-administration, serum samples were obtained and the level of IL-2/synTac was measured in the serum samples. As shown in FIG. 18, the serum half-life of the IL-2/synTac was about 4 hours.

Figure 19:
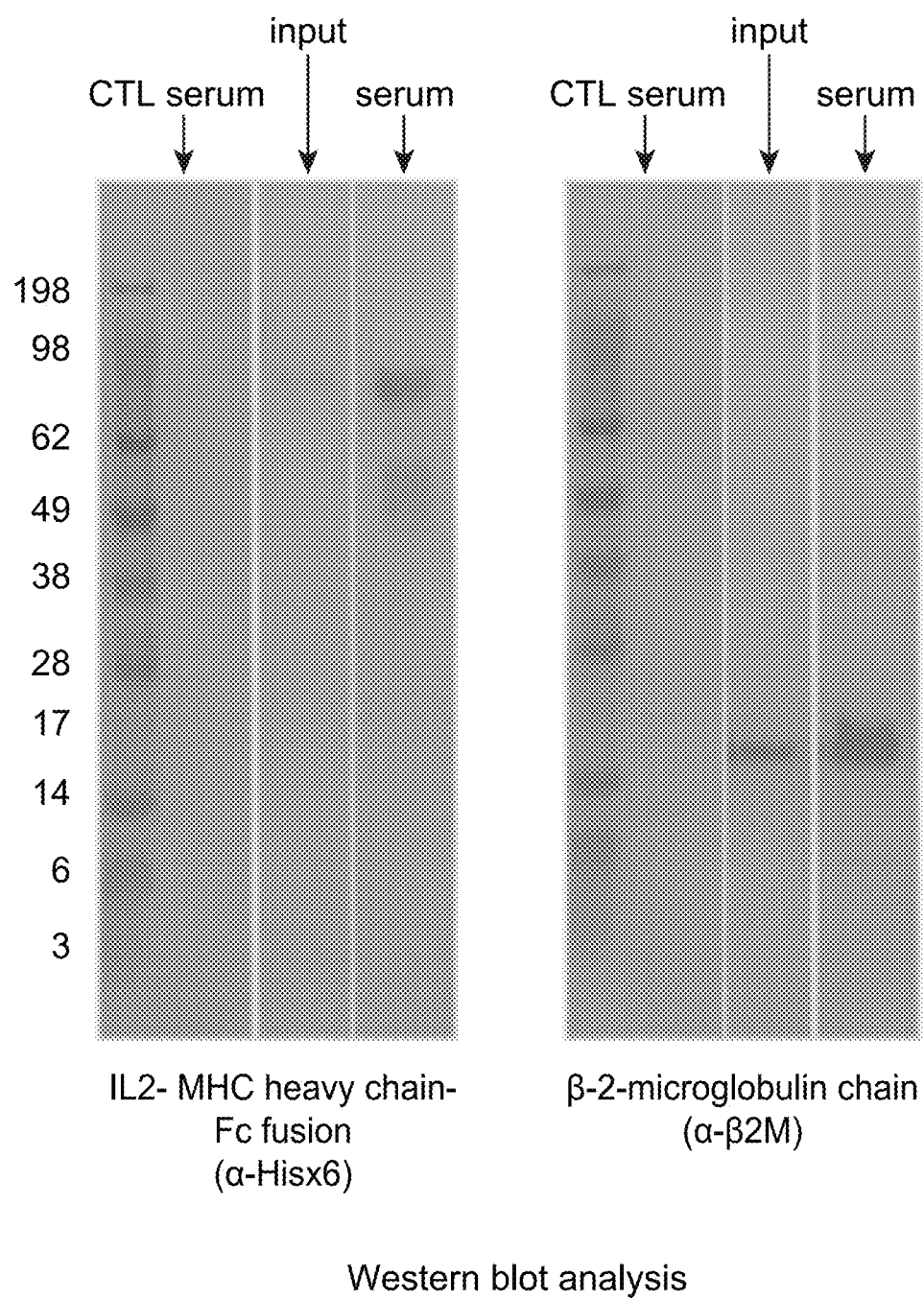
FIG. 19 depicts stability of an IL-2/synTac of the present disclosure 2 hours following intraperitoneal administration of the IL-2/synTac in an amount of 10 mg/kg.

IL-2/synTac was injected IP into a C57BL/6 mouse at 10 mg/kg, and serum was collected two hours after injections. The IL-2/synTac included a $His_6$ tag. 100 ng of the input protein, or the equivalent of 40 µl of serum, was subjected to sodium dodecyl sulfate-polyacrylamide gel electrophoresis (SDS-PAGE), and probed with an anti-$(His)_6$ antibody or an anti-β-2M antibody. The results, depicted in FIG. 19, show that IL-2/synTac remains stable and intact for at least 2 hours in vivo.

Figure 20:
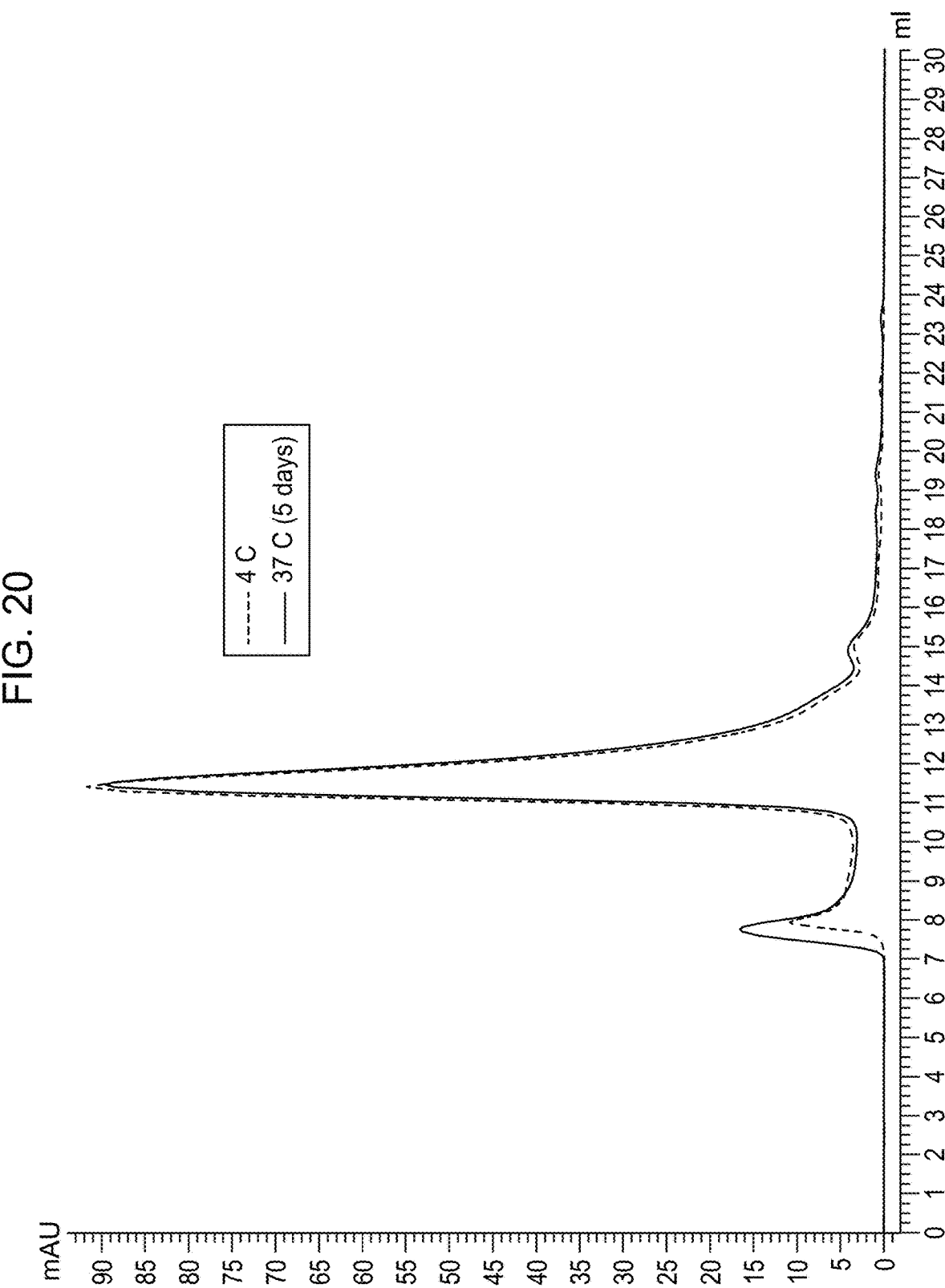
FIG. 20 depicts size exclusion chromatography data on an IL-2/synTac of the present disclosure after keeping the IL-2/synTac at 4° C. or 37° C. for 5 days.

IL-2/synTac was kept at 4° C. or 37° C. for 5 days. 0.5 mg of each sample (at 10 mg/ml) was analyzed by size exclusion chromatography. As shown in FIG. 20, IL-2/synTac is stable and intact for at least 5 days at 4° C. or 37° C.

Figure 35:
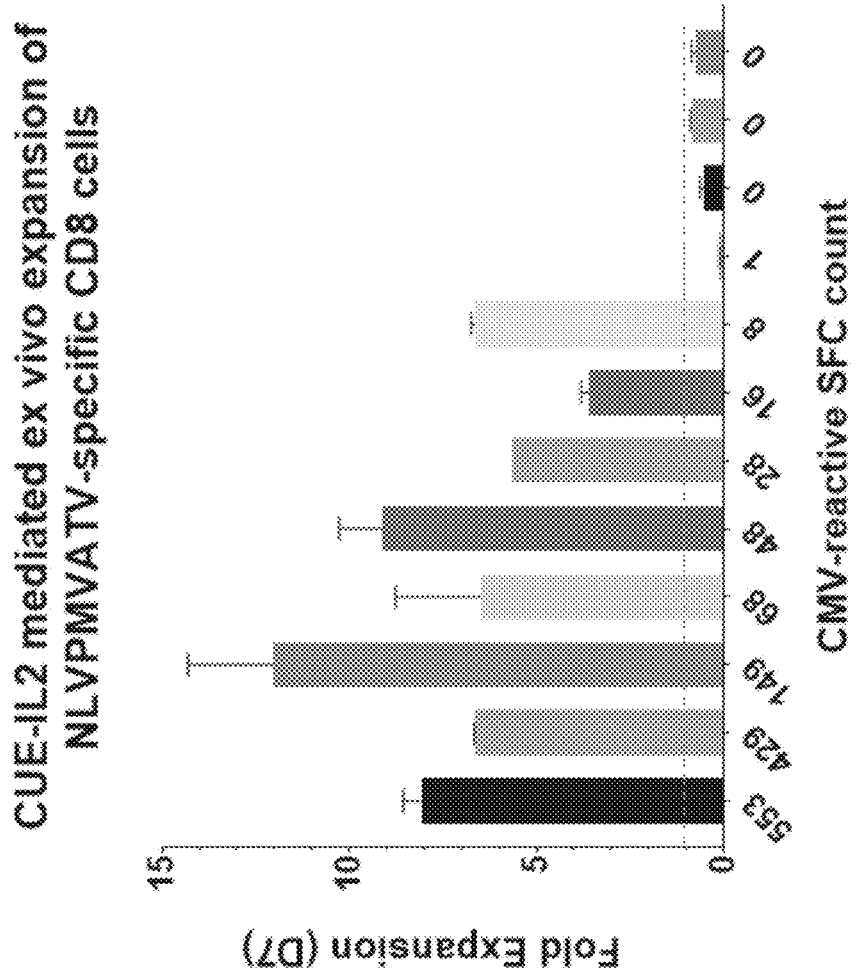
FIG. 35 depicts IL-2/synTac-mediated expansion of human CMV-specific CD8$^+$ T cells.

Example 5: IL-2/synTac-Mediated Expansion of Human CMV-Specific CD8+ T Cells Peripheral blood mononuclear cells (PBMCs) from human donors were screened for reactivity towards a cytomegalovirus (CMV)-peptide pool using an IFN-gamma enzyme-linked immunospot (ELISPOT) assay. The PBMCs were categorized by spot forming count (SFC) as high, medium, low, or no CMV-precursor groups. PBMCs from each group were stimulated with doses of IL-2/synTac ("CUE:IL-2"; a synTac comprising 2 copies of a variant IL-2 MOD comprising H16A and F42A substitutions) ranging from 30 nM to 2 nM. Fifty percent of the conditioned media was replaced with fresh media on day 5. On day 7, the samples were stained with a panel of antibodies and analyzed by flow cytometry. Pentamer staining targeting the CMV peptide NLVPMVATV (SEQ ID NO:37) was used to determine the frequency of antigen-specific CD8+ cells. The data are presented in FIG. 35. The $EC_{50}$ of IL-2/synTac was determined to be in the range of from about 1 nM to about 5 nM. FIG. 35 shows the fold expansion of antigen-specific CD8+ cells compared to untreated controls. Numerical values on the X-axis represent the SFC count of each donor PBMC. Error bars represent the mean+/−SD values from the technical replicates of each data points.

The data shown in FIG. 35 indicate that an IL-2/synTac is effective to expand the number of epitope-specific CD8+ T cells, where there is a measurable (e.g., by pentamer staining or by SFC) precursor population of such epitope-specific CD8+ T cells.

Example 6: IL-2/synTac with Amino Acid Substitutions at H16

IL-2/synTac variants were generated with substitutions at H16. Expression levels and affinity for IL-2R were determined. Affinity for IL-2 R was determined using BLI. The data are presented in FIG. 36.

Example 7: IL-2/synTac Effects on Primary Human Antigen-Specific CD8+ T Cells A variant IL-2/synTac was contacted with primary CD8+ T cells from a human subject. The variant IL-2/synTac includes: i) HPV16 E7 (11-20) (YMLDLQPETT; SEQ ID NO:13) as the epitope-presenting peptide; and ii) 2 copies of a variant IL-2 MOD comprising H16A and F42A substitutions). Binding of the variant IL-2/synTac to CD8+ T cells specific for HPV16 E7 (11-20), or to bulk CD8+ T cells was assessed. The data are shown in FIG. 37.

Figure 37:
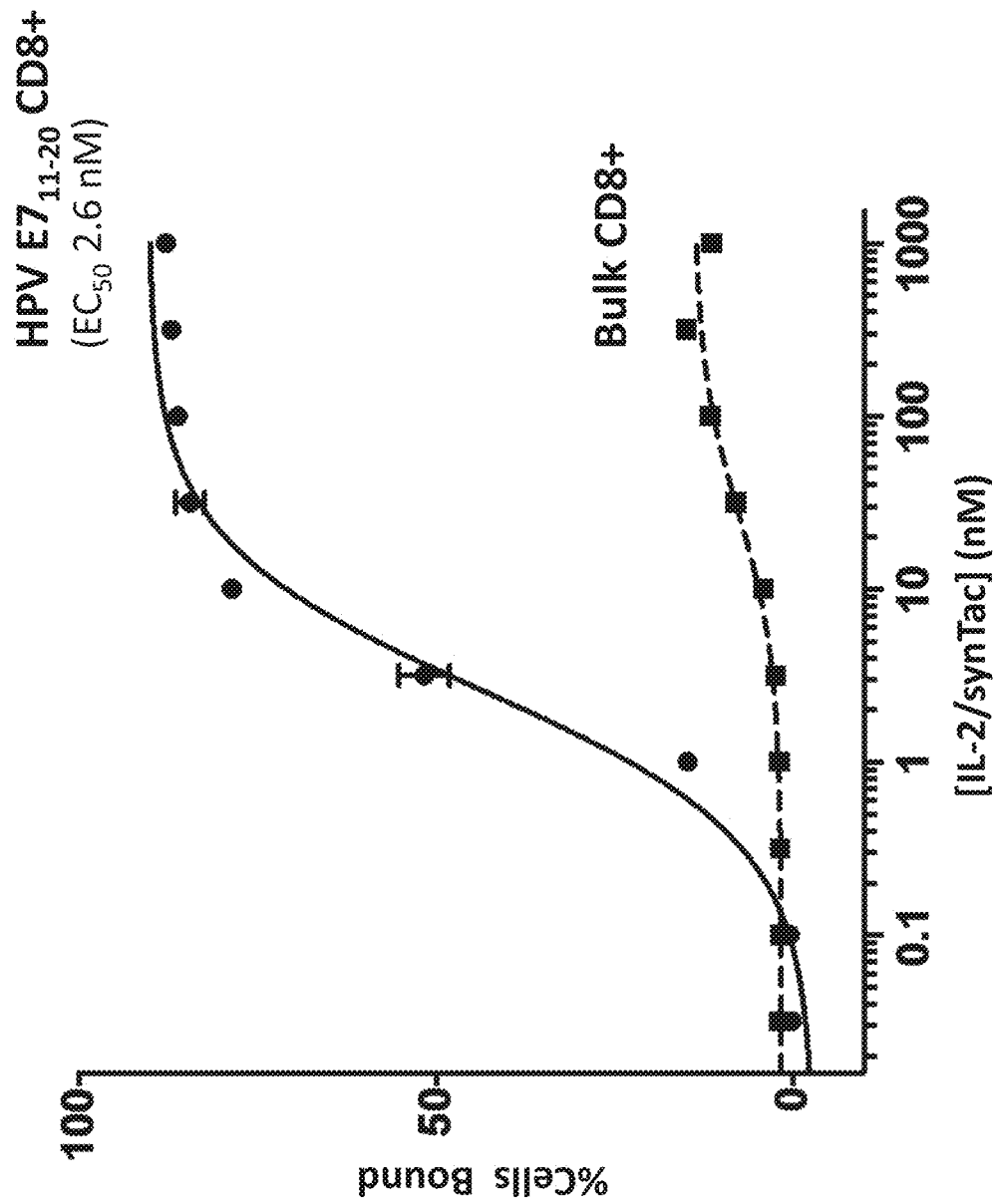
FIG. 37 depicts binding of an IL-2/synTac to primary human HPV16 E7 (11-20)-specific CD8$^+$ T cells, as detected by flow cytometry.

FIG. 37 depicts binding of a variant IL-2/synTac of the present disclosure to primary human HPV16 E7 (11-20)-specific CD8+ T cells, as detected by flow cytometry. The $EC_{50}$ for binding to CD8+ T cells specific for HPV16 E7 (11-20) was 2.6 nM. Thus, the variant IL-2/synTac exhibited high-affinity interaction with tumor antigen-specific primary human T cells. Binding was highly selective for antigen-specific T cells, compared to the binding to non-target (bulk) CD8+ T cells.

The effect of binding of the variant IL-2/synTac to primary human HPV16 E7 (11-20)-specific CD8+ T cells on phosphorylation of the T-cell receptor (TCR)-proximal marker SLP76 was assessed. The data are shown in FIG. 38.

Figure 38:
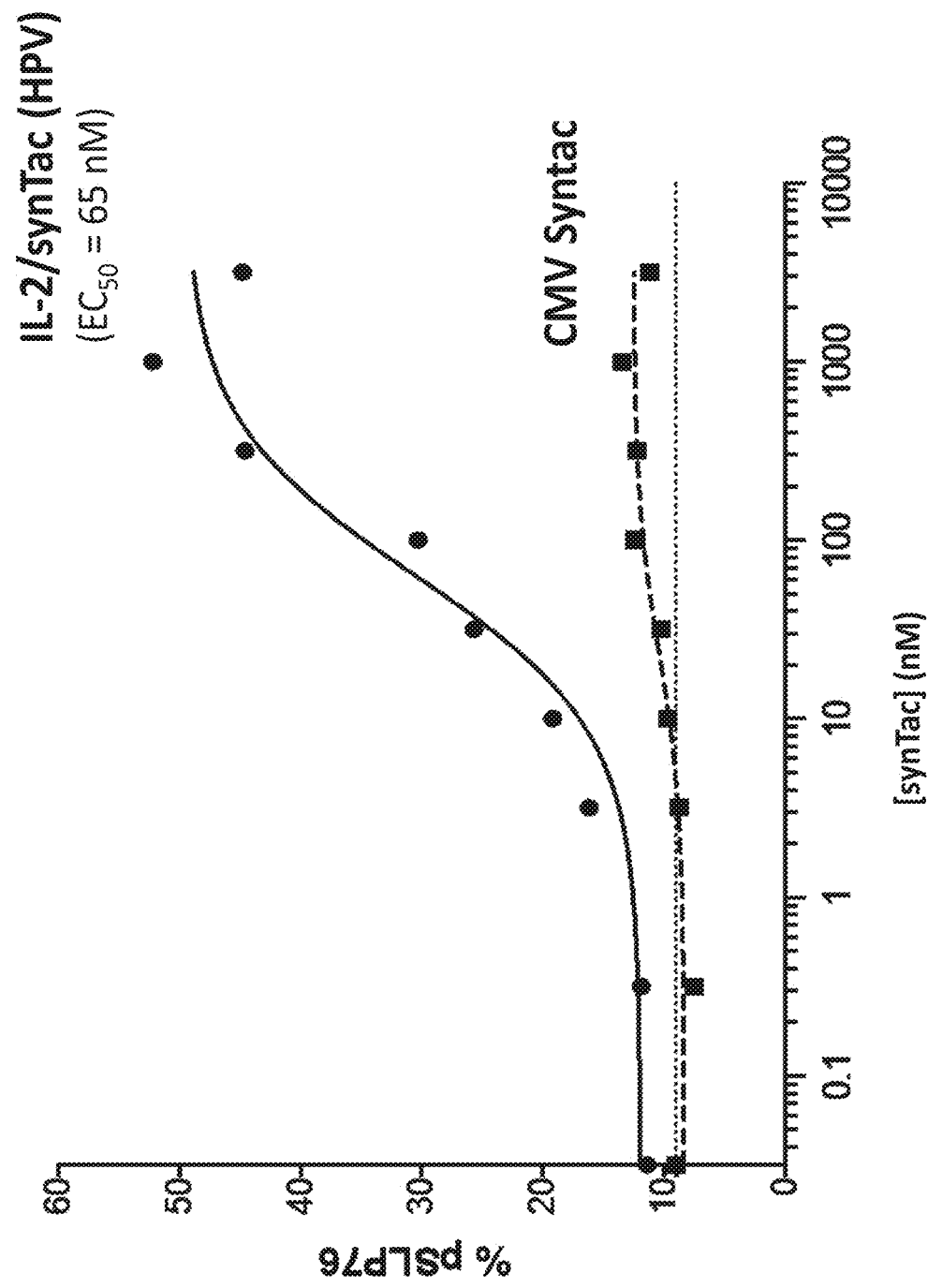
FIG. 38 depicts the effect of binding of the variant IL-2/synTac to primary human HPV16 E7 (11-20)-specific CD8$^+$ T cells on phosphorylation of SLP76.
Figure 38:
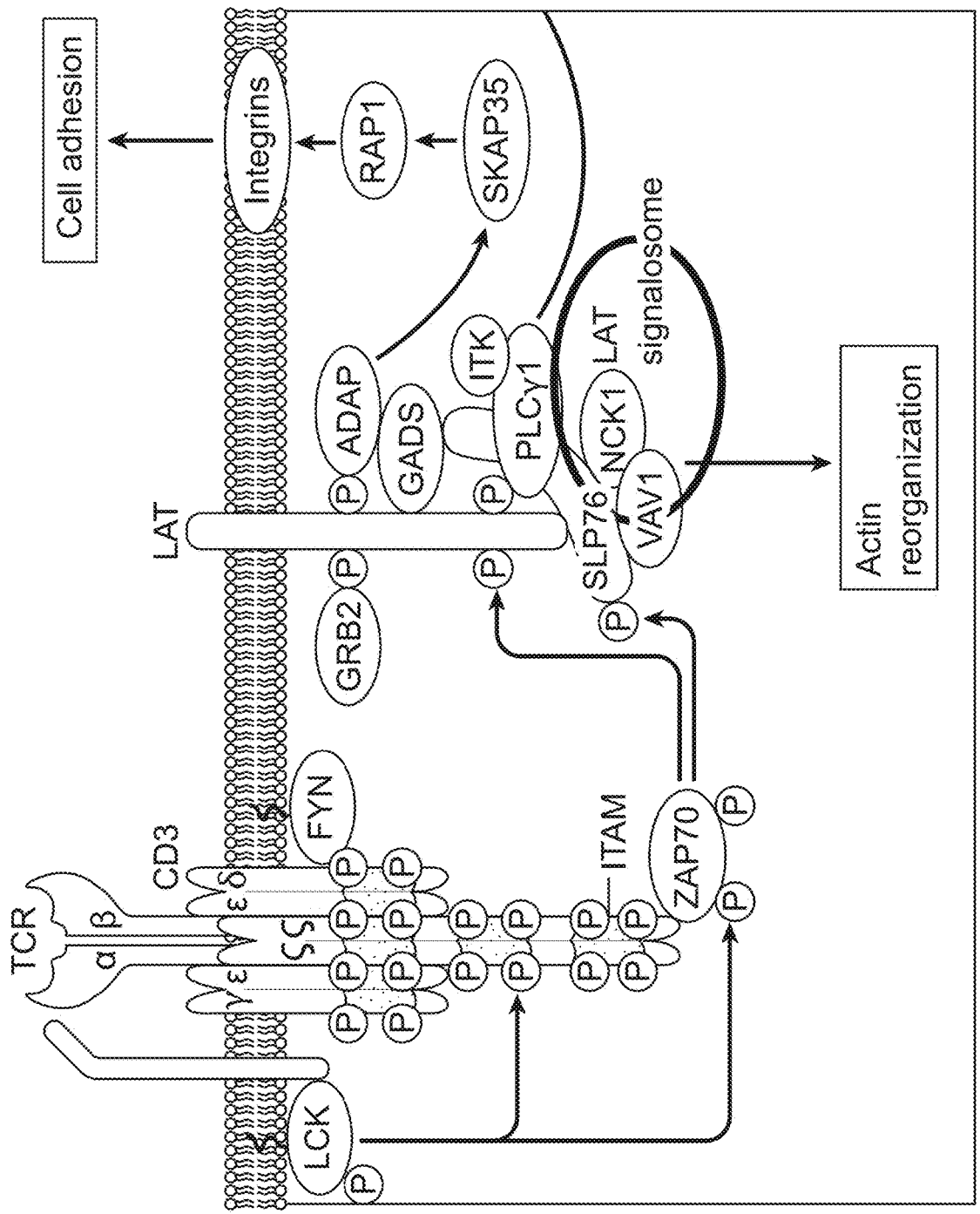

FIG. 38 depicts the effect of binding of the variant IL-2/synTac to primary human HPV16 E7 (11-20)-specific CD8+ T cells on phosphorylation of SLP76. Binding of the variant IL-2/synTac to primary human HPV16 E7 (11-20)-specific CD8+ T cells resulted in a rapid increase in phosphorylation of SLP76. The effect was potent ($EC_{50}$=65 nM). The effect was also selective, as a control IL-2/synTac that comprises a CMV peptide instead of HPV16 E7 (11-20) resulted in only low levels of SLP76 phosphorylation.

Key markers of T-cell activation and cytolytic activity were assessed. Primary human HPV16 E7 (11-20)-specific T cells were incubated for 2 days with 0 nM or 100 nM variant IL-2/synTac. The variant IL-2/synTac includes: i) HPV16 E7 (11-20) as the epitope-presenting peptide; and ii) 2 copies of a variant IL-2 MOD comprising H16A and F42A substitutions). Production of: i) CD25, a marker of CD8+ T cell activation; ii) granzyme B, a key mediator of target cell death via the granule-mediated pathway; and iii) CD107a, a marker of degranulation on CD8+ T cells, was assessed. The data are shown in FIG. 39.

Figure 39:
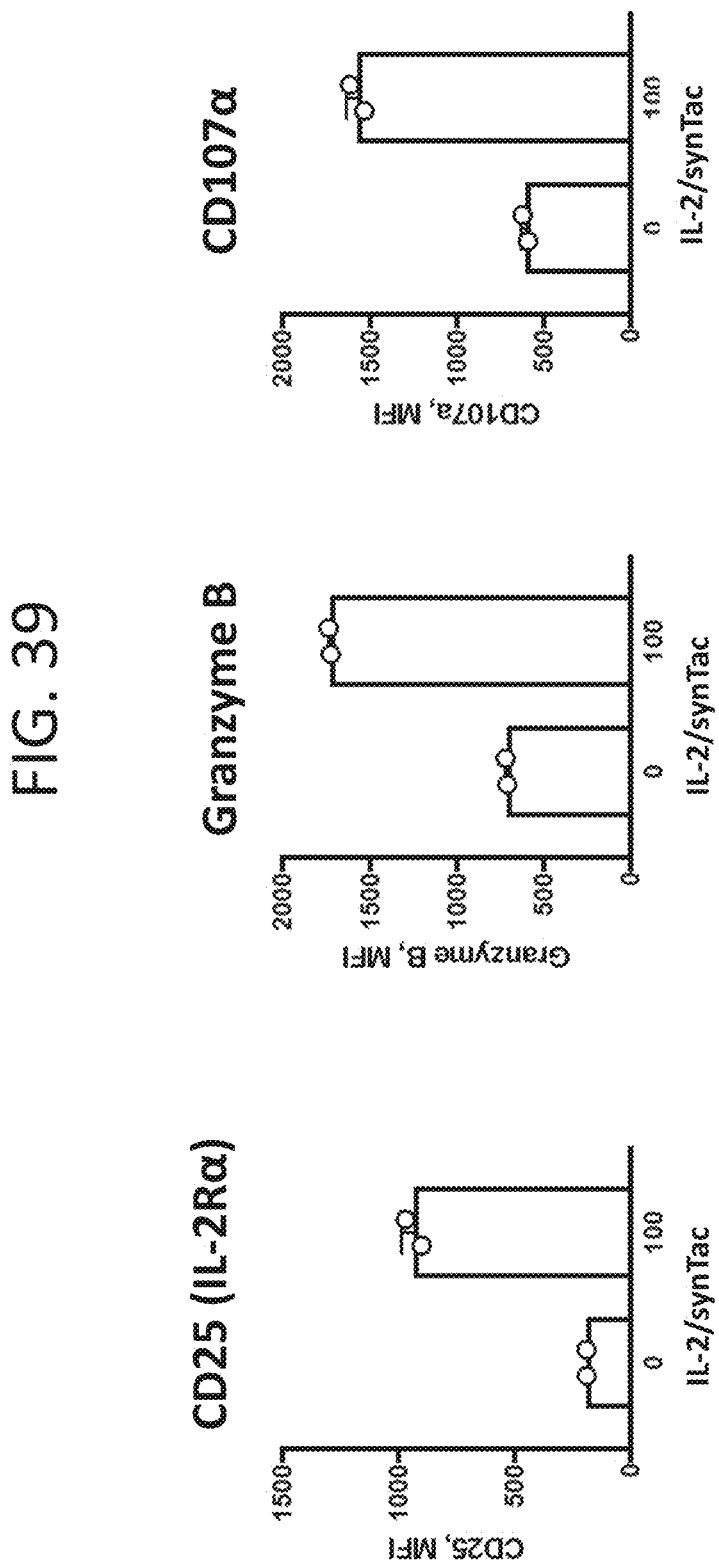
FIG. 39 depicts the effect of binding of the variant IL-2/synTac to primary human HPV16 E7 (11-20)-specific T cells on production of CD25, granzyme B, and CD107α.

FIG. 39 depicts the effect of binding of the variant IL-2/synTac to primary human HPV16 E7 (11-20)-specific T cells on production of CD25, granzyme B, and CD107a. The data show that binding of the variant IL-2/synTac to primary human HPV16 E7 (11-20)-specific T cells induces differentiation of the T cells into cytolytic effector cells, as evidenced by the increased expression of CD25, granzyme B, and CD107a.

The effect of binding of the variant IL-2/synTac to primary human HPV16 E7 (11-20)-specific CD8+ T cells on production of IFN-γ was assessed. An ELISpot assay was used to detect IFN-γ production. The data are shown in FIG. 40.

Figure 40:
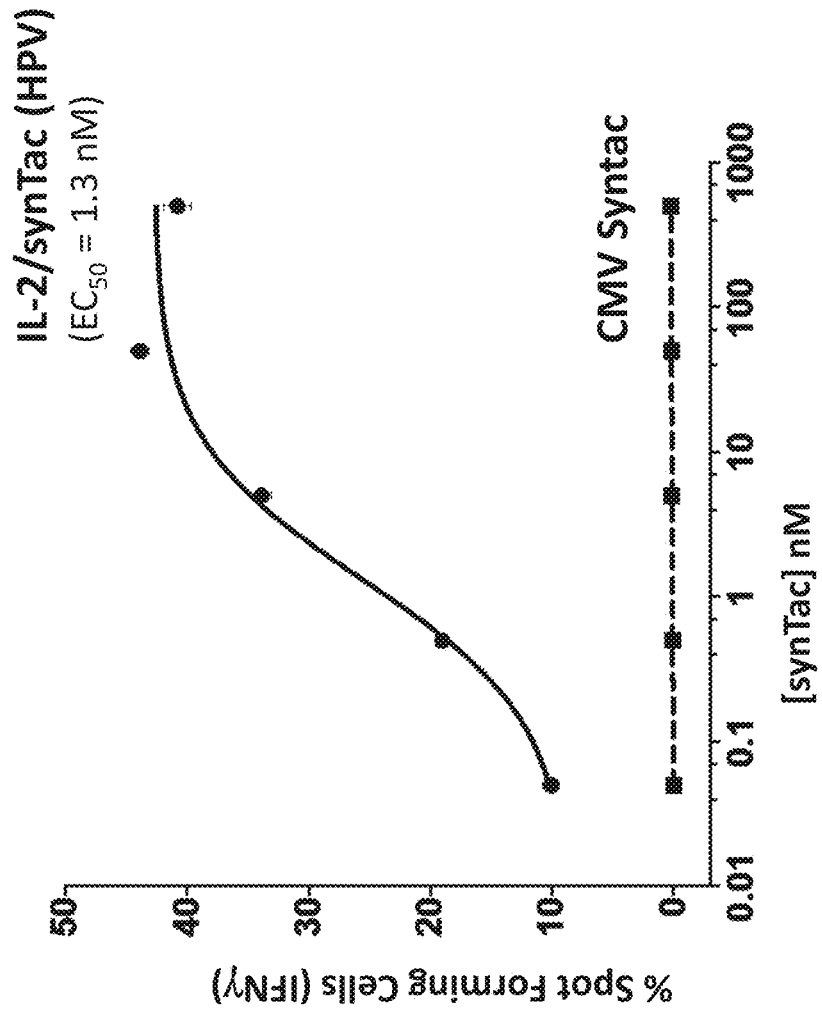
FIG. 40 depicts the effect of binding of the variant IL-2/synTac to primary human HPV16 E7 (11-20)-specific CD8$^+$ T cells on production of IFN-γ.

FIG. 40 depicts the effect of binding of the variant IL-2/synTac to primary human HPV16 E7 (11-20)-specific CD8+ T cells on production of IFN-γ. The data show that binding of the variant IL-2/synTac to primary human HPV16 E7 (11-20)-specific CD8+ T cells resulted in a dose-dependent secretion of IFN-γ. No IFN-γ production was observed with a control IL-2/synTac that comprises a CMV peptide instead of HPV16 E7 (11-20).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

```
Sequence total quantity: 100
SEQ ID NO: 1            moltype = AA   length = 133
FEATURE                 Location/Qualifiers
source                  1..133
                        mol_type = protein
                        organism = Homo sapiens
SEQUENCE: 1
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 2            moltype = AA   length = 4
FEATURE                 Location/Qualifiers
REGION                  1..4
                        note = Synthetic Polypeptide Sequence
source                  1..4
                        mol_type = protein
                        organism = synthetic construct
SEQUENCE: 2
GGSG                                                                  4

SEQ ID NO: 3            moltype = AA   length = 5
FEATURE                 Location/Qualifiers
REGION                  1..5
                        note = Synthetic Polypeptide Sequence
source                  1..5
                        mol_type = protein
                        organism = synthetic construct
SEQUENCE: 3
GGSGG                                                                 5

SEQ ID NO: 4            moltype = AA   length = 5
FEATURE                 Location/Qualifiers
REGION                  1..5
                        note = Synthetic Polypeptide Sequence
source                  1..5
                        mol_type = protein
                        organism = synthetic construct
SEQUENCE: 4
GSGSG                                                                 5

SEQ ID NO: 5            moltype = AA   length = 5
FEATURE                 Location/Qualifiers
REGION                  1..5
                        note = Synthetic Polypeptide Sequence
source                  1..5
                        mol_type = protein
                        organism = synthetic construct
SEQUENCE: 5
GSGGG                                                                 5
```

```
SEQ ID NO: 6        moltype = AA  length = 5
FEATURE             Location/Qualifiers
REGION              1..5
                    note = Synthetic Polypeptide Sequence
source              1..5
                    mol_type = protein
                    organism = synthetic construct
SEQUENCE: 6
GGGSG                                                                    5

SEQ ID NO: 7        moltype = AA  length = 5
FEATURE             Location/Qualifiers
REGION              1..5
                    note = Synthetic Polypeptide Sequence
source              1..5
                    mol_type = protein
                    organism = synthetic construct
SEQUENCE: 7
GSSSG                                                                    5

SEQ ID NO: 8        moltype = AA  length = 5
FEATURE             Location/Qualifiers
REGION              1..5
                    note = Synthetic Polypeptide Sequence
source              1..5
                    mol_type = protein
                    organism = synthetic construct
SEQUENCE: 8
GSSSS                                                                    5

SEQ ID NO: 9        moltype = AA  length = 5
FEATURE             Location/Qualifiers
REGION              1..5
                    note = Synthetic Polypeptide Sequence
source              1..5
                    mol_type = protein
                    organism = synthetic construct
SEQUENCE: 9
GGGGS                                                                    5

SEQ ID NO: 10       moltype = AA  length = 15
FEATURE             Location/Qualifiers
REGION              1..15
                    note = Synthetic Polypeptide Sequence
source              1..15
                    mol_type = protein
                    organism = synthetic construct
SEQUENCE: 10
GCGASGGGGS GGGGS                                                        15

SEQ ID NO: 11       moltype = AA  length = 9
FEATURE             Location/Qualifiers
REGION              1..9
                    note = Synthetic Polypeptide Sequence
source              1..9
                    mol_type = protein
                    organism = synthetic construct
SEQUENCE: 11
LLMGTLGIV                                                                9

SEQ ID NO: 12       moltype = AA  length = 8
FEATURE             Location/Qualifiers
REGION              1..8
                    note = Synthetic Polypeptide Sequence
source              1..8
                    mol_type = protein
                    organism = synthetic construct
SEQUENCE: 12
TLGIVCPI                                                                 8

SEQ ID NO: 13       moltype = AA  length = 10
FEATURE             Location/Qualifiers
REGION              1..10
                    note = Synthetic Polypeptide Sequence
source              1..10
                    mol_type = protein
                    organism = synthetic construct
SEQUENCE: 13
YMLDLQPETT                                                              10
```

```
SEQ ID NO: 14              moltype = AA   length = 276
FEATURE                    Location/Qualifiers
source                     1..276
                           mol_type = protein
                           organism = Homo sapiens
SEQUENCE: 14
GSHSMRYFFT SVSRPGRGEP RFIAVGYVDD TQFVRFDSDA ASQRMEPRAP WIEQEGPEYW    60
DGETRKVKAH SQTHRVDLGT LRGYYNQSEA GSHTVQRMYG CDVGSDWRFL RGYHQYAYDG   120
KDYIALKEDL RSWTAADMAA QTTKHKWEAA HVAEQLRAYL EGTCVEWLRR YLENGKETLQ   180
RTDAPKTHMT HHAVSDHEAT LRCWALSFYP AEITLTWQRD GEDQTQDTEL VETRPAGDGT   240
FQKWAAVVVP SGQEQRYTCH VQHEGLPKPL TLRWEP                             276

SEQ ID NO: 15              moltype = AA   length = 274
FEATURE                    Location/Qualifiers
source                     1..274
                           mol_type = protein
                           organism = Mus musculus
SEQUENCE: 15
GPHSLRYFVT AVSRPGLGEP RFIAVGYVDD TQFVRFDSDA DNPRFEPRAP WMEQEGPEYW    60
EEQTQRAKSD EQWFRVSLRT AQRYYNQSKG GSHTFQRMFG CDVGSDWRLL RGYQQFAYDG   120
RDYIALNEDL KTWTAADTAA LITRRKWEQA GDAEYYRAYL EGECVEWLRR YLELGNETLL   180
RTDSPKAHVT YHPRSQVDVT LRCWALGFYP ADITLTWQLN GEDLTQDMEL VETRPAGDGT   240
FQKWAAVVVP LGKEQNYTCH VHHKGLPEPL TLRW                               274

SEQ ID NO: 16              moltype = AA   length = 99
FEATURE                    Location/Qualifiers
REGION                     1..99
                           note = Synthetic Polypeptide Sequence
source                     1..99
                           mol_type = protein
                           organism = synthetic construct
SEQUENCE: 16
IQRTPKIQVY SRHPAENGKS NFLNCYVSGF HPSDIEVDLL KNGERIEKVE HSDLSFSKDW    60
SFYLLYYTEF TPTEKDEYAC RVNHVTLSQP KIVKWDRDM                          99

SEQ ID NO: 17              moltype = AA   length = 99
FEATURE                    Location/Qualifiers
REGION                     1..99
                           note = Synthetic Polypeptide Sequence
source                     1..99
                           mol_type = protein
                           organism = synthetic construct
SEQUENCE: 17
IQRTPKIQVY SCHPAENGKS NFLNCYVSGF HPSDIEVDLL KNGERIEKVE HSDLSFSKDW    60
SFYLLYYTEF TPTEKDEYAC RVNHVTLSQP KIVKWDRDM                          99

SEQ ID NO: 18              moltype = AA   length = 276
FEATURE                    Location/Qualifiers
source                     1..276
                           mol_type = protein
                           organism = Homo sapiens
SEQUENCE: 18
GSHSMRYFFT SVSRPGRGEP RFIAVGYVDD TQFVRFDSDA ASQRMEPRAP WIEQEGPEYW    60
DGETRKVKAH SQTHRVDLGT LRGYYNQSEA GSHTVQRMYG CDVGSDWRFL RGYHQYAYDG   120
KDYIALKEDL RSWTAADMAA QTTKHKWEAA HVAEQLRAYL EGTCVEWLRR YLENGKETLQ   180
RTDAPKTHMT HHAVSDHEAT LRCWALSFYP AEITLTWQRD GEDQTQDTEL VETRPCGDGT   240
FQKWAAVVVP SGQEQRYTCH VQHEGLPKPL TLRWEP                             276

SEQ ID NO: 19              moltype = AA   length = 275
FEATURE                    Location/Qualifiers
source                     1..275
                           mol_type = protein
                           organism = Homo sapiens
SEQUENCE: 19
GSHSMRYFFT SVSRPGRGEP RFIAVGYVDD TQFVRFDSDA ASQRMEPRAP WIEQEGPEYW    60
DGETRKVKAH SQTHRVDLGT LRGAYNQSEA GSHTVQRMYG CDVGSDWRFL RGYHQYAYDG   120
KDYIALKEDL RSWTAADMAA QTTKHKWEAA HVAEQLRAYL EGTCVEWLRR YLENGKETLQ   180
RTDAPKTHMT HHAVSDHEAT LRCWALSFYP AEITLTWQRD GEDQTQDTEL VETRPCGDGT   240
FQKWAAVVVP SGQEQRYTCH VQHEGLPKPL TLRWE                              275

SEQ ID NO: 20              moltype = AA   length = 9
FEATURE                    Location/Qualifiers
REGION                     1..9
                           note = Synthetic Polypeptide Sequence
source                     1..9
                           mol_type = protein
                           organism = synthetic construct
SEQUENCE: 20
```

```
YPYDVPDYA                                                                         9

SEQ ID NO: 21        moltype = AA  length = 8
FEATURE              Location/Qualifiers
REGION               1..8
                     note = Synthetic Polypeptide Sequence
source               1..8
                     mol_type = protein
                     organism = synthetic construct
SEQUENCE: 21
DYKDDDDK                                                                          8

SEQ ID NO: 22        moltype = AA  length = 10
FEATURE              Location/Qualifiers
REGION               1..10
                     note = Synthetic Polypeptide Sequence
source               1..10
                     mol_type = protein
                     organism = synthetic construct
SEQUENCE: 22
EQKLISEEDL                                                                       10

SEQ ID NO: 23        moltype = AA  length = 5
FEATURE              Location/Qualifiers
REGION               1..5
                     note = Synthetic Polypeptide Sequence
source               1..5
                     mol_type = protein
                     organism = synthetic construct
SEQUENCE: 23
HHHHH                                                                             5

SEQ ID NO: 24        moltype = AA  length = 6
FEATURE              Location/Qualifiers
REGION               1..6
                     note = Synthetic Polypeptide Sequence
source               1..6
                     mol_type = protein
                     organism = synthetic construct
SEQUENCE: 24
HHHHHH                                                                            6

SEQ ID NO: 25        moltype = AA  length = 8
FEATURE              Location/Qualifiers
REGION               1..8
                     note = Synthetic Polypeptide Sequence
source               1..8
                     mol_type = protein
                     organism = synthetic construct
SEQUENCE: 25
WSHPQFEK                                                                          8

SEQ ID NO: 26        moltype = AA  length = 5
FEATURE              Location/Qualifiers
REGION               1..5
                     note = Synthetic Polypeptide Sequence
source               1..5
                     mol_type = protein
                     organism = synthetic construct
SEQUENCE: 26
RYIRS                                                                             5

SEQ ID NO: 27        moltype = AA  length = 17
FEATURE              Location/Qualifiers
REGION               1..17
                     note = Synthetic Polypeptide Sequence
source               1..17
                     mol_type = protein
                     organism = synthetic construct
SEQUENCE: 27
WEAAAREACC RECCARA                                                               17

SEQ ID NO: 28        moltype = AA  length = 5
FEATURE              Location/Qualifiers
REGION               1..5
                     note = Synthetic Polypeptide Sequence
source               1..5
                     mol_type = protein
                     organism = synthetic construct
```

```
SEQUENCE: 28
AAAGG                                                                    5

SEQ ID NO: 29           moltype = AA  length = 8
FEATURE                 Location/Qualifiers
REGION                  1..8
                        note = Synthetic Polypeptide Sequence
source                  1..8
                        mol_type = protein
                        organism = synthetic construct
SEQUENCE: 29
LEVLFQGP                                                                 8

SEQ ID NO: 30           moltype = AA  length = 7
FEATURE                 Location/Qualifiers
REGION                  1..7
                        note = Synthetic Polypeptide Sequence
source                  1..7
                        mol_type = protein
                        organism = synthetic construct
SEQUENCE: 30
ENLYTQS                                                                  7

SEQ ID NO: 31           moltype = AA  length = 5
FEATURE                 Location/Qualifiers
REGION                  1..5
                        note = Synthetic Polypeptide Sequence
source                  1..5
                        mol_type = protein
                        organism = synthetic construct
SEQUENCE: 31
DDDDK                                                                    5

SEQ ID NO: 32           moltype = AA  length = 4
FEATURE                 Location/Qualifiers
REGION                  1..4
                        note = Synthetic Polypeptide Sequence
source                  1..4
                        mol_type = protein
                        organism = synthetic construct
SEQUENCE: 32
LVPR                                                                     4

SEQ ID NO: 33           moltype = AA  length = 22
FEATURE                 Location/Qualifiers
REGION                  1..22
                        note = Synthetic Polypeptide Sequence
source                  1..22
                        mol_type = protein
                        organism = synthetic construct
SEQUENCE: 33
GSGATNFSLL KQAGDVEENP GP                                                22

SEQ ID NO: 34           moltype = AA  length = 21
FEATURE                 Location/Qualifiers
REGION                  1..21
                        note = Synthetic Polypeptide Sequence
source                  1..21
                        mol_type = protein
                        organism = synthetic construct
SEQUENCE: 34
GSGEGRGSLL TCGDVEENPG P                                                 21

SEQ ID NO: 35           moltype = AA  length = 23
FEATURE                 Location/Qualifiers
REGION                  1..23
                        note = Synthetic Polypeptide Sequence
source                  1..23
                        mol_type = protein
                        organism = synthetic construct
SEQUENCE: 35
GSGQCTNYAL LKLAGDVESN PGP                                               23

SEQ ID NO: 36           moltype = AA  length = 25
FEATURE                 Location/Qualifiers
REGION                  1..25
                        note = Synthetic Polypeptide Sequence
source                  1..25
                        mol_type = protein
```

```
                              -continued organism = synthetic construct
SEQUENCE: 36
GSGVKQTLNF DLLKLAGDVE SNPGP                                           25

SEQ ID NO: 37              moltype = AA   length = 9
FEATURE                    Location/Qualifiers
REGION                     1..9
                           note = Synthetic Polypeptide Sequence
source                     1..9
                           mol_type = protein
                           organism = synthetic construct
SEQUENCE: 37
NLVPMVATV                                                              9

SEQ ID NO: 38              moltype = AA   length = 133
FEATURE                    Location/Qualifiers
VARIANT                    42
                           note = X is any amino acid other than a phenylalanine
source                     1..133
                           mol_type = protein
                           organism = Homo sapiens
SEQUENCE: 38
APTSSSTKKT QLQLEHLLLD LQMILNGINN YKNPKLTRML TXKFYMPKKA TELKHLQCLE      60
EELKPLEEVL NLAQSKNFHL RPRDLISNIN VIVLELKGSE TTFMCEYADE TATIVEFLNR     120
WITFCQSIIS TLT                                                       133

SEQ ID NO: 39              moltype = AA   length = 133
FEATURE                    Location/Qualifiers
VARIANT                    20
                           note = X is any amino acid other than an aspartic acid
source                     1..133
                           mol_type = protein
                           organism = Homo sapiens
SEQUENCE: 39
APTSSSTKKT QLQLEHLLLX LQMILNGINN YKNPKLTRML TFKFYMPKKA TELKHLQCLE      60
EELKPLEEVL NLAQSKNFHL RPRDLISNIN VIVLELKGSE TTFMCEYADE TATIVEFLNR     120
WITFCQSIIS TLT                                                       133

SEQ ID NO: 40              moltype = AA   length = 133
FEATURE                    Location/Qualifiers
VARIANT                    15
                           note = X is any amino acid other than a glutamic acid
source                     1..133
                           mol_type = protein
                           organism = Homo sapiens
SEQUENCE: 40
APTSSSTKKT QLQLXHLLLD LQMILNGINN YKNPKLTRML TFKFYMPKKA TELKHLQCLE      60
EELKPLEEVL NLAQSKNFHL RPRDLISNIN VIVLELKGSE TTFMCEYADE TATIVEFLNR     120
WITFCQSIIS TLT                                                       133

SEQ ID NO: 41              moltype = AA   length = 133
FEATURE                    Location/Qualifiers
VARIANT                    16
                           note = X is any amino acid other than a histidine
source                     1..133
                           mol_type = protein
                           organism = Homo sapiens
SEQUENCE: 41
APTSSSTKKT QLQLEXLLLD LQMILNGINN YKNPKLTRML TFKFYMPKKA TELKHLQCLE      60
EELKPLEEVL NLAQSKNFHL RPRDLISNIN VIVLELKGSE TTFMCEYADE TATIVEFLNR     120
WITFCQSIIS TLT                                                       133

SEQ ID NO: 42              moltype = AA   length = 133
FEATURE                    Location/Qualifiers
VARIANT                    45
                           note = X is any amino acid other than a tyrosine
source                     1..133
                           mol_type = protein
                           organism = Homo sapiens
SEQUENCE: 42
APTSSSTKKT QLQLEHLLLD LQMILNGINN YKNPKLTRML TFKFXMPKKA TELKHLQCLE      60
EELKPLEEVL NLAQSKNFHL RPRDLISNIN VIVLELKGSE TTFMCEYADE TATIVEFLNR     120
WITFCQSIIS TLT                                                       133

SEQ ID NO: 43              moltype = AA   length = 133
FEATURE                    Location/Qualifiers
VARIANT                    126
                           note = X is any amino acid other than a glutamine
source                     1..133
```

```
                              mol_type = protein
                              organism = Homo sapiens
SEQUENCE: 43
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCXSIIS TLT                                                     133

SEQ ID NO: 44             moltype = AA  length = 133
FEATURE                   Location/Qualifiers
VARIANT                   16
                          note = X is any amino acid other than a histidine
VARIANT                   42
                          note = X is any amino acid other than a phenylalanine
source                    1..133
                          mol_type = protein
                          organism = Homo sapiens
SEQUENCE: 44
APTSSSTKKT QLQLEXLLLD LQMILNGINN YKNPKLTRML TXKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 45             moltype = AA  length = 133
FEATURE                   Location/Qualifiers
VARIANT                   20
                          note = X is any amino acid other than an aspartic acid
VARIANT                   42
                          note = X is any amino acid other than an phenylalanine
source                    1..133
                          mol_type = protein
                          organism = Homo sapiens
SEQUENCE: 45
APTSSSTKKT QLQLEHLLLX LQMILNGINN YKNPKLTRML TXKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 46             moltype = AA  length = 133
FEATURE                   Location/Qualifiers
VARIANT                   15
                          note = X is any amino acid other than a glutamic acid
VARIANT                   20
                          note = X is any amino acid other than a aspartic acid
VARIANT                   42
                          note = X is any amino acid other than a phenylalanine
source                    1..133
                          mol_type = protein
                          organism = Homo sapiens
SEQUENCE: 46
APTSSSTKKT QLQLXHLLLX LQMILNGINN YKNPKLTRML TXKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 47             moltype = AA  length = 133
FEATURE                   Location/Qualifiers
VARIANT                   16
                          note = X is any amino acid other than a histidine
VARIANT                   20
                          note = X is any amino acid other than an aspartic acid
SITE                      42
                          note = X is any amino acid other than a phenylalanine
                          note = MISC_FEATURE - Xaa is an amino acid other than a
                           phenylalanine
source                    1..133
                          mol_type = protein
                          organism = Homo sapiens
SEQUENCE: 47
APTSSSTKKT QLQLEXLLLX LQMILNGINN YKNPKLTRML TXKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 48             moltype = AA  length = 133
FEATURE                   Location/Qualifiers
VARIANT                   20
                          note = X is any amino acid other than an aspartic acid
VARIANT                   42
                          note = X is any amino acid other than a phenylalanine
VARIANT                   126
                          note = X is any amino acid other than a glutamine
source                    1..133
                          mol_type = protein
```

```
                            organism = Homo sapiens
SEQUENCE: 48
APTSSSTKKT QLQLEHLLLX LQMILNGINN YKNPKLTRML TXKFYMPKKA TELKHLQCLE   60
EELKPLEEVL NLAQSKNFHL RPRDLISNIN VIVLELKGSE TTFMCEYADE TATIVEFLNR  120
WITFCXSIIS TLT                                                    133

SEQ ID NO: 49               moltype = AA  length = 133
FEATURE                     Location/Qualifiers
VARIANT                     20
                            note = X is any amino acid other than an aspartic acid
VARIANT                     42
                            note = X is any amino acid other than a phenylalanine
VARIANT                     45
                            note = X is any amino acid other than a tyrosine
source                      1..133
                            mol_type = protein
                            organism = Homo sapiens
SEQUENCE: 49
APTSSSTKKT QLQLEHLLLX LQMILNGINN YKNPKLTRML TXKFXMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133

SEQ ID NO: 50               moltype = AA  length = 133
FEATURE                     Location/Qualifiers
VARIANT                     16
                            note = X is any amino acid other than a histidine
VARIANT                     20
                            note = X is any amino acid other than an aspartic acid
VARIANT                     42
                            note = X is any amino acid other than a phenylalanine
VARIANT                     45
                            note = X is any amino acid other than a tyrosine
source                      1..133
                            mol_type = protein
                            organism = Homo sapiens
SEQUENCE: 50
APTSSSTKKT QLQLEXLLLX LQMILNGINN YKNPKLTRML TXKFXMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133

SEQ ID NO: 51               moltype = AA  length = 133
FEATURE                     Location/Qualifiers
VARIANT                     20
                            note = X is any amino acid other than an aspartic acid
VARIANT                     42
                            note = X is any amino acid other than a phenylalanine
VARIANT                     45
                            note = X is any amino acid other than a tyrosine
VARIANT                     126
                            note = X is any amino acid other than a glutamine
source                      1..133
                            mol_type = protein
                            organism = Homo sapiens
SEQUENCE: 51
APTSSSTKKT QLQLEHLLLX LQMILNGINN YKNPKLTRML TXKFXMPKKA TELKHLQCLE   60
EELKPLEEVL NLAQSKNFHL RPRDLISNIN VIVLELKGSE TTFMCEYADE TATIVEFLNR  120
WITFCXSIIS TLT                                                    133

SEQ ID NO: 52               moltype = AA  length = 133
FEATURE                     Location/Qualifiers
VARIANT                     16
                            note = X is any amino acid other than a histidine
VARIANT                     20
                            note = X is any amino acid other than an aspartic acid
VARIANT                     42
                            note = X is any amino acid other than a phenylalanine
VARIANT                     45
                            note = X is any amino acid other than a tyrosine
VARIANT                     126
                            note = X is any amino acid other than a glutamine
source                      1..133
                            mol_type = protein
                            organism = Homo sapiens
SEQUENCE: 52
APTSSSTKKT QLQLEXLLLX LQMILNGINN YKNPKLTRML TXKFXMPKKA TELKHLQCLE   60
EELKPLEEVL NLAQSKNFHL RPRDLISNIN VIVLELKGSE TTFMCEYADE TATIVEFLNR  120
WITFCXSIIS TLT                                                    133

SEQ ID NO: 53               moltype = AA  length = 133
```

```
FEATURE                 Location/Qualifiers
VARIANT                 16
                        note = X is any amino acid other than a histidine
VARIANT                 42
                        note = X is any amino acid other than a phenylalanine
VARIANT                 126
                        note = X is any amino acid other than a glutamine
source                  1..133
                        mol_type = protein
                        organism = Homo sapiens
SEQUENCE: 53
APTSSSTKKT QLQLEXLLLD LQMILNGINN YKNPKLTRML TXKFYMPKKA TELKHLQCLE   60
EELKPLEEVL NLAQSKNFHL RPRDLISNIN VIVLELKGSE TTFMCEYADE TATIVEFLNR  120
WITFCXSIIS TLT                                                    133

SEQ ID NO: 54           moltype = AA  length = 272
FEATURE                 Location/Qualifiers
source                  1..272
                        mol_type = protein
                        organism = Homo sapiens
SEQUENCE: 54
MDSYLLMWGL LTFIMVPGCQ AELCDDDPPE IPHATFKAMA YKEGTMLNCE CKRGFRRIKS   60
GSLYMLCTGN SSHSSWDNQC QCTSSATRNT TKQVTPQPEE QKERKTTEMQ SPMQPVDQAS  120
LPGHCREPPP WENEATERIY HFVVGQMVYY QCVQGYRALH RGPAESVCKM THGKTRWTQP  180
QLICTGEMET SQFPGEEKPQ ASPEGRPESE TSCLVTTTDF QIQTEMAATM ETSIFTTEYQ  240
VAVAGCVFLL ISVLLLSGLT WQRRQRKSRR TI                               272

SEQ ID NO: 55           moltype = AA  length = 491
FEATURE                 Location/Qualifiers
source                  1..491
                        mol_type = protein
                        organism = Homo sapiens
SEQUENCE: 55
MAAPALSWRL PLLILLLPLA TSWASAAVNG TSQFTCFYNS RANISCVWSQ DGALQDTSCQ   60
VHAWPDRRRW NQTCELLPVS QASWACNLIL GAPDSQKLTT VDIVTLRVLC REGVRWRVMA  120
APLLTLKQKQ EWICLETLTP DTQYEFQVRV KPLQGEFTTW SPWSQPLAFR TKPAALGKDT  180
IPWLGHLLVG LSGAFGFIIL VYLLINCRNT GPWLKKVLKC NTPDPSKFFS QLSSEHGGDV  240
QKWLSSPFPS SSFSPGGLAP EISPLEVLER DKVTQLLLQQ DKVPEPASLS NSHSLTSCFT  300
NQGYFFFHLP DALEIEACQV YFTYDPYSEE DPDEGVAGAP TGSSPQPLQP LSGEDDAYCT  360
FPSRDDLLLF SPSLLGGPSP PSTAPGGSGA GEERMPPSLQ ERVPRDWDPQ PLGPPTPGVP  420
DLVDFQPPPE LVLREAGEEV PDAGPREGVS FPWSRPPGQG EFRALNARLP LNTDAYLSLQ  480
ELQGQDPTHL V                                                      491

SEQ ID NO: 56           moltype = AA  length = 369
FEATURE                 Location/Qualifiers
source                  1..369
                        mol_type = protein
                        organism = Homo sapiens
SEQUENCE: 56
MLKPSLPFTS LLFLQLPLLG VGLNTTILTP NGNEDTTADF FLTTMPTDSL SVSTLPLPEV   60
QCFVFNVEYM NCTWNSSSEP QPTNLTLHYW YKNSDNDKVQ KCSHYLFSEE ITSGCQLQKK  120
EIHLYQTFVV QLQDPREPRR QATQMLKLQN LVIPWAPENL TLHKLSESQL ELNWNNRFLN  180
HCLEHLVQYR TDWDHSWTEQ SVDYRHKFSL PSVDGQKRYT FRVRSRFNPL CGSAQHWSEW  240
SHPIHWGSNT SKENPLFLAL EAVVISVGSM GLIISLLCVY FWLERTMPRI PTLKNLEDLV  300
TEYHGNFSAW SGVSKGLAES LQPDYSERLC LVSEIPPKGG ALGEGPGASP CNQHSPYWAP  360
PCYTLKPET                                                         369

SEQ ID NO: 57           moltype = AA  length = 227
FEATURE                 Location/Qualifiers
source                  1..227
                        mol_type = protein
                        organism = Homo sapiens
SEQUENCE: 57
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK              227

SEQ ID NO: 58           moltype = AA  length = 325
FEATURE                 Location/Qualifiers
source                  1..325
                        mol_type = protein
                        organism = Homo sapiens
SEQUENCE: 58
STKGPSVFPL APCSRSTSES TAALGCLVKD YFPEPVTVSW NSGALTSGVH TFPAVLQSSG   60
LYSLSSVVTV PSSNFGTQTY TCNVDHKPSN TKVDKTVERK CCVECPPCPA PPVAGPSVFL  120
FPPKPKDTLM ISRTPEVTCV VVDVSHEDPE VQFNWYVDGV EVHNAKTKPR EEQFNSTFRV  180
VSVLTVVHQD WLNGKEYKCK VSNKGLPAPI EKTISKTKGQ PREPQVYTLP PSREEMTKNQ  240
VSLTCLVKGF YPSDIAVEWE SNGQPENNYK TTPPMLDSDG SFFLYSKLTV DKSRWQQGNV  300
```

```
FSCSVMHEAL HNHYTQKSLS LSPGK                                                     325

SEQ ID NO: 59              moltype = AA   length = 246
FEATURE                    Location/Qualifiers
source                     1..246
                           mol_type = protein
                           organism = Homo sapiens
SEQUENCE: 59
HKPSNTKVDK RVELKTPLGD TTHTCPPCPA PELLGGPSVF LFPPKPKDTL MISRTPEVTC   60
VVVDVSHEDP EVKFNWYVDG VEVHNAKTKP REEQYNSTYR VVSVLTVLHQ DWLNGKEYKC  120
KVSNKALPAP IEKTISKAKG QPREPQVYTL PPSRDELTKN QVSLTCLVKG FYPSDIAVEW  180
ESNGQPENNY KTTPPVLDSD GSFFLYSKLT VDKSRWQQGN VFSCSVMHEA LHNHYTQKSL  240
SLSPGK                                                             246

SEQ ID NO: 60              moltype = AA   length = 383
FEATURE                    Location/Qualifiers
source                     1..383
                           mol_type = protein
                           organism = Homo sapiens
SEQUENCE: 60
PTKAPDVFPI ISGCRHPKDN SPVVLACLIT GYHPTSVTVT WYMGTQSQPQ RTFPEIQRRD   60
SYYMTSSQLS TPLQQWRQGE YKCVVQHTAS KSKKEIFRWP ESPKAQASSV PTAQPQAEGS  120
LAKATTAPAT TRNTGRGGEE KKKEKEKEEQ EERETKTPEC PSHTQPLGVY LLTPAVQDLW  180
LRDKATFTCF VVGSDLKDAH LTWEVAGKVP TGGVEEGLLE RHSNGSQSQH SRLTLPRSLW  240
NAGTSVTCTL NHPSLPPQRL MALREPAAQA PVKLSLNLLA SSDPPEAASW LLCEVSGFSP  300
PNILLMWLED QREVNTSGFA PARPPPQPRS TTFWAWSVLR VPAPPSPQPA TYTCVVSHED  360
SRTLLNASRS LEVSYVTDHG PMK                                          383

SEQ ID NO: 61              moltype = AA   length = 276
FEATURE                    Location/Qualifiers
source                     1..276
                           mol_type = protein
                           organism = Homo sapiens
SEQUENCE: 61
VTSTLTIKZS DWLGESMFTC RVDHRGLTFQ QNASSMCVPD QDTAIRVFAI PPSFASIFLT   60
KSTKLTCLVT DLTTYBSVTI SWTREENGAV KTHTNISESH PNATFSAVGE ASICEDBDWS  120
GERFTCTVTH TDLPSPLKQT ISRPKGVALH RPBVYLLPPA RZZLNLRESA TITCLVTGFS  180
PADVFVEWMQ RGEPLSPQKY VTSAPMPEPQ APGRYFAHSI LTVSEEEWNT GGTYTCVVAH  240
EALPNRVTER TVDKSTGKPT LYNVSLVMSD TAGTCY                            276

SEQ ID NO: 62              moltype = AA   length = 353
FEATURE                    Location/Qualifiers
source                     1..353
                           mol_type = protein
                           organism = Homo sapiens
SEQUENCE: 62
ASPTSPKVFP LSLCSTQPDG NVVIACLVQG FFPQEPLSVT WSESGQGVTA RNFPPSQDAS   60
GDLYTTSSQL TLPATQCLAG KSVTCHVKHY TNPSQDVTVP CPVPSTPPTP SPSTPPTPSP  120
SCCHPRLSLH RPALEDLLLG SEANLTCTLT GLRDASGVTF TWTPSSGKSA VQGPPERDLC  180
GCYSVSSVLP GCAEPWNHGK TFTCTAAYPE SKTPLTATLS KSGNTFRPEV HLLPPPSEEL  240
ALNELVTLTC LARGFSPKDV LVRWLQGSQE LPREKYLTWA SRQEPSQGTT TFAVTSILRV  300
AAEDWKKGDT FSCMVGHEAL PLAFTQKTID RLAGKPTHVN VSVVMAEVDG TCY         353

SEQ ID NO: 63              moltype = AA   length = 222
FEATURE                    Location/Qualifiers
source                     1..222
                           mol_type = protein
                           organism = Homo sapiens
SEQUENCE: 63
ADPCDSNPRG VSAYLSRPSP FDLFIRKSPT ITCLVVDLAP SKGTVNLTWS RASGKPVNHS   60
TRKEEKQRNG TLTVTSTLPV GTRDWIEGET YQCRVTHPHL PRALMRSTTK TSGPRAAPEV  120
YAFATPEWPG SRDKRTLACL IQNFMPEDIS VQWLHNEVQL PDARHSTTQP RKTKGSGFFV  180
FSRLEVTRAE WEQKDEFICR AVHEAASPSQ TVQRAVSVNP GK                     222

SEQ ID NO: 64              moltype = AA   length = 327
FEATURE                    Location/Qualifiers
source                     1..327
                           mol_type = protein
                           organism = Homo sapiens
SEQUENCE: 64
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 65              moltype = AA   length = 365
FEATURE                    Location/Qualifiers
```

```
source                          1..365
                                mol_type = protein
                                organism = Homo sapiens
SEQUENCE: 65
MAVMAPRTLL LLLSGALALT QTWAGSHSMR YFFTSVSRPG RGEPRFIAVG YVDDTQFVRF    60
DSDAASQKME PRAPWIEQEG PEYWDQETRN MKAHSQTDRA NLGTLRGYYN QSEDGSHTIQ   120
IMYGCDVGPD GRFLRGYRQD AYDGKDYIAL NEDLRSWTAA DMAAQITKRK WEAVHAAEQR   180
RVYLEGRCVD GLRRYLENGK ETLQRTDPPK THMTHHPISD HEATLRCWAL GFYPAEITLT   240
WQRDGEDQTQ DTELVETRPA GDGTFQKWAA VVVPSGEEQR YTCHVQHEGL PKPLTLRWEL   300
SSQPTIPIVG IIAGLVLLGA VITGAVVAAV MWRRKSSDRK GGSYTQAASS DSAQGSDVSL   360
TACKV                                                              365

SEQ ID NO: 66                   moltype = AA    length = 362
FEATURE                         Location/Qualifiers
source                          1..362
                                mol_type = protein
                                organism = Homo sapiens
SEQUENCE: 66
MLVMAPRTVL LLLSAALALT ETWAGSHSMR YFYTSVSRPG RGEPRFISVG YVDDTQFVRF    60
DSDAASPREE PRAPWIEQEG PEYWDRNTQI YKAQAQTDRE SLRNLRGYYN QSEAGSHTLQ   120
SMYGCDVGPD GRLLRGHDQY AYDGKDYIAL NEDLRSWTAA DTAAQITQRK WEAAREAEQR   180
RAYLEGECVE WLRRYLENGK DKLERADPPK THVTHHPKEH HEATLRCWAL GFYPAEITLT   240
WQRDGEDQTQ DTELVETRPA GDRTFQKWAA VVVPSGEEQR YTCHVQHEGL PKPLTLRWEP   300
SSQSTVPIVG IVAGLAVLAV VVIGAVVAAV MCRRKSSGGK GGSYSQAACS DSAQGSDVSL   360
TA                                                                 362

SEQ ID NO: 67                   moltype = AA    length = 366
FEATURE                         Location/Qualifiers
source                          1..366
                                mol_type = protein
                                organism = Homo sapiens
SEQUENCE: 67
MRVMAPRALL LLLSGGLALT ETWACSHSMR YFDTAVSRPG RGEPRFISVG YVDDTQFVRF    60
DSDAASPRGE PRAPWVEQEG PEYWDRETQN YKRQAQADRV SLRNLRGYYN QSEDGSHTLQ   120
RMYGCDLGPD GRLLRGYDQS AYDGKDYIAL NEDLRSWTAA DTAAQITQRK LEAARAAEQL   180
RAYLEGTCVE WLRRYLENGK ETLQRAEPPK THVTHHPLSD HEATLRCWAL GFYPAEITLT   240
WQRDGEDQTQ DTELVETRPA GDGTFQKWAA VVVPSGQEQR YTCHMQHEGL QEPLTLSWEP   300
SSQPTIPIMG IVAGLAVLVV LAVLGAVVTA MMCRRKSSGG KGGSCSQAAC SNSAQGSDES   360
LITCKA                                                             366

SEQ ID NO: 68                   moltype = AA    length = 833
FEATURE                         Location/Qualifiers
source                          1..833
                                mol_type = protein
                                organism = Homo sapiens
SEQUENCE: 68
MYRMQLLSCI ALSLALVTNS APTSSSTKKT QLQLEALLLD LQMILNGINN YKNPKLTRML    60
TAKFYMPKKA TELKHLQCLE EELKPLEEVL NLAQSKNFHL RPRDLISNIN VIVLELKGSE   120
TTFMCEYADE TATIVEFLNR WITFCQSIIS TLTGGGGSGG GGSGGGGSGG GGSAPTSSST   180
KKTQLQLEAL LLDLQMILNG INNYKNPKLT RMLTAKFYMP KKATELKHLQ CLEEELKPLE   240
EVLNLAQSKN FHLRPRDLIS NINVIVLELK GSETTFMCEY ADETATIVEF LNRWITFCQS   300
IISTLTGGGG SGGGGSGGGG SGGGGSGSHS MRYFFTSVSR PGRGEPRFIA VGYVDDTQFV   360
RFDSDAASQR MEPRAPWIEQ EGPEYWDGET RKVKAHSQTH RVDLGTLRGA YNQSEAGSHT   420
VQRMYGCDVG SDWRFLRGYH QYAYDGKDYI ALKEDLRSWT AADMAAQTTK HKWEAAHVAE   480
QLRAYLEGTC VEWLRRYLEN GKETLQRTDA PKTHMTHHAV SDHEATLRCW ALSFYPAEIT   540
LTWQRDGEDQ TQDTELVETR PCGDGTFQKW AAVVVPSGQE QRYTCHVQHE GLPKPLTLRW   600
EAAAGGDKTH TCPPCPAPEL LGGPSVFLFP PKPKDTLMIS RTPEVTCVVV DVSHEDPEVK   660
FNWYVDGVEV HNAKTKPREE QYASTYRVVS VLTVLHQDWL NGKEYKCKVS NKALPAPIEK   720
TISKAKGQPR EPQVYTLPPS REEMTKNQVS LTCLVKGFYP SDIAVEWESN GQPENNYKTT   780
PPVLDSDGSF FLYSKLTVDK SRWQQGNVFS CSVMHEALHN HYTQKSLSLS PGK          833

SEQ ID NO: 69                   moltype = AA    length = 813
FEATURE                         Location/Qualifiers
source                          1..813
                                mol_type = protein
                                organism = Homo sapiens
SEQUENCE: 69
APTSSSTKKT QLQLEALLLD LQMILNGINN YKNPKLTRML TAKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTGGGGSGG GGSGGGGSGG GGSAPTSSST KKTQLQLEAL LLDLQMILNG   180
INNYKNPKLT RMLTAKFYMP KKATELKHLQ CLEEELKPLE EVLNLAQSKN FHLRPRDLIS   240
NINVIVLELK GSETTFMCEY ADETATIVEF LNRWITFCQS IISTLTGGGG SGGGGSGGGG   300
SGGGGSGSHS MRYFFTSVSR PGRGEPRFIA VGYVDDTQFV RFDSDAASQR MEPRAPWIEQ   360
EGPEYWDGET RKVKAHSQTH RVDLGTLRGA YNQSEAGSHT VQRMYGCDVG SDWRFLRGYH   420
QYAYDGKDYI ALKEDLRSWT AADMAAQTTK HKWEAAHVAE QLRAYLEGTC VEWLRRYLEN   480
GKETLQRTDA PKTHMTHHAV SDHEATLRCW ALSFYPAEIT LTWQRDGEDQ TQDTELVETR   540
PCGDGTFQKW AAVVVPSGQE QRYTCHVQHE GLPKPLTLRW EAAAGGDKTH TCPPCPAPEL   600
LGGPSVFLFP PKPKDTLMIS RTPEVTCVVV DVSHEDPEVK FNWYVDGVEV HNAKTKPREE   660
QYASTYRVVS VLTVLHQDWL NGKEYKCKVS NKALPAPIEK TISKAKGQPR EPQVYTLPPS   720
```

```
REEMTKNQVS LTCLVKGFYP SDIAVEWESN GQPENNYKTT PPVLDSDGSF FLYSKLTVDK    780
SRWQQGNVFS CSVMHEALHN HYTQKSLSLS PGK                                813

SEQ ID NO: 70           moltype = DNA  length = 2505
FEATURE                 Location/Qualifiers
source                  1..2505
                        mol_type = genomic DNA
                        organism = Homo sapiens
SEQUENCE: 70
atgtacagga tgcaactcct gtcttgcatt gcactaagtc ttgcacttgt cacaaacagt    60
gcacctactt caagttctac aaagaaaaca cagctacaac tggaggcatt actgctggat   120
ttacagatga ttttgaatgg aattaataat tacaagaatc ccaaactcac caggatgctc   180
acagcaaagt tttacatgcc caagaaggcc acagaactga acatcttca gtgtctagaa    240
gaagaactca aacctctgga ggaagtgcta aatttagctc aaagcaaaaa ctttcactta   300
agacccaggg acttaatcag caatatcaac gtaatagttc tggaactaaa gggatctgaa   360
acaacattca tgtgtgaata tgctgatgag acagcaacca ttgtagaatt ctgaacaga   420
tggattacct tttgtcaaag catcatctca acactgactg gaggcggagg atctggtggt   480
ggaggttctg gtggtggggg atctggaggc ggaggatctg cacctacttc aagttctaca   540
aagaaaacac agctacaact ggaggcatta ctgctggatt tacagatgat tttgaatgga   600
attaataatt acaagaatcc caaactcacc aggatgctca cagcaaagtt ttacatgccc   660
aagaaggcca cagaactgaa acatcttcag tgtctagaag aagaactcaa acctctggag   720
gaagtgctaa atttagctca aagcaaaaac tttcacttaa gacccaggga cttaatcagc   780
aatatcaacg taatagttct ggaactaaag gatctgaaa caacattcat gtgtgaatat   840
gctgatgaga cagcaaccat tgtagaattt ctgaacagat ggattacctt ttgtcaaagc   900
atcatctcaa cactgactgg aggcggagga tctggtggtg gaggttctgg tggtggggga   960
tctggaggcg gaggatctgg ctctcactcc atgaggtatt tcttcacatc cgtctcccgg  1020
cccgccgcg gggagccccg cttcatcgca gtgggctacg tggacgacac gcagttcgtg  1080
cggttcgaca gcgacgccgc gagccagagg atggagccgc gggcgccgtg gatagagcag  1140
gagggtccga gtattggga cggggagaca cggaaagtga aggcccactc acagactcac  1200
cgagtcgacc tgggaccct gcgcggccgc tacaaccaca gcgaggccgg ttctcacacc  1260
gtccagagga tgtatggctg cgacgtgggg tcggactggc gcttcctccg cgggtaccac  1320
cagtacgcct acgacggcaa ggattacatc gccctgaaag aggacctgcg ctcttggacc  1380
gcggcggaca tggcagctca gaccaccaag cacaagtggg aggcggccca tgtggcggag  1440
cagttgagag cctacctgga gggacgtgc gtggagtggc tccgcagata cctgagaac   1500
gggaaggaga cgctgcagcg cacggacgcc cccaaaacgc atatgactca ccacgctgtc  1560
tctgaccatg aagccaccct gaggtgctgg gccctgagct tctacccgc ggagatcaca  1620
ctgacctggc agcgggatgg ggaggaccag acccaggaca cggagctcgt ggagaccagg  1680
ccttgcgggg atggaacctt ccagaagtgg cggctgtgg tggtgcctc tggacaggag  1740
cagagataca cctgccatgt gcagcatgag ggtttgccca gccccctcac cctgagatgg  1800
gaggcagctg cgggtggcga caaaactcac acatgcccac cgtgcccagc acctgaactc  1860
ctgggggac cgtcagtctt cctcttcccc ccaaaaccca aggacaccct catgatctcc  1920
cggacccctg aggtcacatg cgtggtggtg acgtgagcc acgaagaccc tgaggtcaag  1980
ttcaactggt acgtggacgg cgtggaggtg cataatgcca agacaaagcc gcgggaggag  2040
cagtacgcaa gcacgtaccg tgtggtcagc gtcctcaccg tcctgcacca ggactggctg  2100
aatggcaagg agtacaagtg caaggtctcc aacaaagccc tcccagcccc catcgagaaa  2160
accatctcca aagccaaagg gcagcccga gaaccacagg tgtacaccct gcccccatcc  2220
cgggaggaga tgaccaagaa ccaggtcagc ctgacctgcc tggtcaaagg cttctatccc  2280
agcgacatcg ccgtggagtg ggagagcaat gggcagccgg agaacaacta caagaccacg  2340
cctcccgtgc tggactccga cggctccttc ttcctctaca gcaagctcac cgtggacaag  2400
agcagatggc agcaggggaa cgtcttctca tgctccgtga tgcacgaggc tctgcacaac  2460
cactacacgc agaagtccct ctccctgtct ccgggtaaat agtga                  2505

SEQ ID NO: 71           moltype = AA  length = 833
FEATURE                 Location/Qualifiers
source                  1..833
                        mol_type = protein
                        organism = Homo sapiens
SEQUENCE: 71
MYRMQLLSCI ALSLALVTNS APTSSSTKKT QLQLEALLLD LQMILNGINN YKNPKLTRML    60
TAKFYMPKKA TELKHLQCLE EELKPLEEVL NLAQSKNFHL RPRDLISNIN VIVLELKGSE   120
TTFMCEYADE TATIVEFLNR WITFCQSIIS TLTGGGSGG GGSGGGGSGG GGSAPTSSST   180
KKTQLQLEAL LLDLQMILNG INNYKNPKLT RMLTAKFYMP KKATELKHLQ CLEEELKPLE   240
EVLNLAQSKN FHLRPRDLIS NINVIVLELK GSETTFMCEY ADETATIVEF LNRWITFCQS   300
IISTLTGGGG SGGGGSGGGG SGGGGSGSHS MRYFFTSVSR PGRGEPRFIA VGYVDDTQFV   360
RFDSDAASQR MEPRAPWIEQ EGPEYWDGET RKVKAHSQTH RVDLGTLRGA YNQSEAGSHT   420
VQRMYGCDVG SDWRFLRGYH QYAYDGKDYI ALKEDLRSWT AADMAAQTTK HKWEAAHVAE   480
QLRAYLEGTC VEWLRRYLEN GKETLQRTDA PKTHMTHHAV SDHEATLRCW ALSFYPAEIT   540
LTWQRDGEDQ TQDTELVETR PCGDGTFQKW AAVVVPSGQE QRYTCHVQHE GLPKPLTLRW   600
EAAAGGDKTH TCPPCPAPEA AGGPSVFLFP PKPKDTLMIS RTPEVTCVVV DVSHEDPEVK   660
FNWYVDGVEV HNAKTKPREE QYNSTYRVVS VLTVLHQDWL NGKEYKCKVS NKALPAPIEK   720
TISKAKGQPR EPQVYTLPPS REEMTKNQVS LTCLVKGFYP SDIAVEWESN GQPENNYKTT   780
PPVLDSDGSF FLYSKLTVDK SRWQQGNVFS CSVMHEALHN HYTQKSLSLS PGK          833

SEQ ID NO: 72           moltype = AA  length = 813
FEATURE                 Location/Qualifiers
source                  1..813
                        mol_type = protein
                        organism = Homo sapiens
SEQUENCE: 72
```

```
APTSSSTKKT QLQLEALLLD LQMILNGINN YKNPKLTRML TAKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTGGGGSGG GGSGGGGSGG GGSAPTSSST KKTQLQLEAL LLDLQMILNG  180
INNYKNPKLT RMLTAKFYMP KKATELKHLQ CLEEELKPLE EVLNLAQSKN FHLRPRDLIS  240
NINIVLELK  GSETTFMCEY ADETATIVEF LNRWITFCQS IISTLTGGGG SGGGGSGGGG  300
SGGGGSGSHS MRYFFTSVSR PGRGEPRFIA VGYVDDTQFV RFDSDAASQR MEPRAPWIEQ  360
EGPEYWDGET RKVKAHSQTH RVDLGTLRGA YNQSEAGSHT VQRMYGCDVG SDWRFLRGYH  420
QYAYDGKDYI ALKEDLRSWT AADMAAQTTK HKWEAAHVAE QLRAYLEGTC VEWLRRYLEN  480
GKETLQRTDA PKTHMTHHAV SDHEATLRCW ALSFYPAEIT LTWQRDGEDQ TQDTELVETR  540
PCGDGTFQKW AAVVVPSGQE QRYTCHVQHE GLPKPLTRW  EAAAGGDKTH TCPPCPAPEA  600
AGGPSVFLFP PKPKDTLMIS RTPEVTCVVV DVSHEDPEVK FNWYVDGVEV HNAKTKPREE  660
QYNSTYRVVS VLTVLHQDWL NGKEYKCKVS NKALPAPIEK TISKAKGQPR EPQVYTLPPS  720
REEMTKNQVS LTCLVKGFYP SDIAVEWESN GQPENNYKTT PPVLDSDGSF FLYSKLTVDK  780
SRWQQGNVFS CSVMHEALHN HYTQKSLSLS PGK                               813

SEQ ID NO: 73          moltype = DNA  length = 2505
FEATURE                Location/Qualifiers
source                 1..2505
                       mol_type = genomic DNA
                       organism = Homo sapiens
SEQUENCE: 73
atgtacagga tgcaactcct gtcttgcatt gcactaagtc ttgcacttgt cacaaacagt   60
gcacctactt caagttctac aaagaaaaca cagctacaac tggaggcatt actgctggat  120
ttacagatga ttttgaatgg aattaataat tacaagaatc ccaaactcac caggatgctc  180
acagcaaagt tttacatgcc caagaaggcc acagaactga acatcttca gtgtctagaa   240
gaagaactca aacctctgga ggaagtgcta aatttagctc aaagcaaaaa ctttcactta  300
agacccaggg acttaatcag caatatcaac gtaatagttc tggaactaaa gggatctgaa  360
acaacattca tgtgtgaata tgctgatgag acagcaacca ttgtagaatt tctgaacaga  420
tggattacct tttgtcaaag catcatctca acactgactg gaggcggagg atctggtggt  480
ggaggttctg gtggtggggg atctggaggc ggaggttctg cacctacttc aagttctaca  540
aagaaaacac agctacaact ggaggcatta ctgctggatt tacagatgat tttgaatgga  600
attaataatt acaagaatcc caaactcacc aggatgctca cagcaaagtt ttacatgccc  660
aagaaggcca cagaactgaa acatcttcag tgtctagaag aagaactcaa acctctggag  720
gaagtgctaa atttagctca aagcaaaaac tttcacttaa gacccaggga cttaatcagc  780
aatatcaacg taatagttct ggaactaaag ggatctgaaa caacattcat gtgtgaatat  840
gctgatgaga cagcaaccat tgtagaattt ctgaacagat ggattacctt ttgtcaaagc  900
atcatctcaa cactgactgg aggcggagga tctggtggtg gaggttctgg tggtgggga   960
tctggaggcg gaggatctgg ctctcactcc atgaggtatt tcttcacatc cgtgtcccgg 1020
cccggccgcg gggagccccg cttcatcgca gtgggctacg tggacgacac gcagttcgtg 1080
cggttcgaca gcgacgccgc gagccagagg atggagcgc  gggcgccgtg gatagagcag 1140
gagggtccgg agtattggga cggggagaca cggaaagtga aggcccactc acagactcac 1200
cgagtggacc tgggaccct  gcgcggcgcc tacaaccaga cgcaggccgg ttctcacacc 1260
gtccagagga tgtatggctg cgacgtgggg tcggactggc gcttcctccg cgggtaccac 1320
cagtacgcct acgacggcaa ggattacatc gccctgaaag aggacctgcg ctcttggacc 1380
gcggcggaca tggcagctca gaccaccaag cacaagtggg aggcggccca tgtggcggag 1440
cagttgagag cctacctgga gggcacgtgc gtggagtggc tccgcagata cctggagaac 1500
gggaaggaca cgctgcagcg cacggacgcc cccaaaacgc atatgactca ccacgctgtc 1560
tctgaccatg aagccaccct gaggtgctgg gccctgagct ctacccctgc ggagatcaca 1620
ctgacctggc agcgggatgg ggaggaccag acccaggaca cggagctcgt ggagaccagg 1680
ccttgcgggg atgaaccttc cagaagtggg cggctgtgg  tggtgccttc tggacaggag 1740
cagagataca cctgccatgt gcagcatgag gtttgccca agccccctcg cctgagatgg 1800
gaggcagctg cgggtggcga caaaactcac acatgcccac cgtgcccagc acctgaagcc 1860
gccggggac  cgtcagtctt cctcttcccc ccaaaaccca aggacccct  catgatctcc 1920
cggacccctg aggtcacatg cgtggtggtg gacgtgagcc acgaagaccc tgaggtcaag 1980
ttcaactggt acgtggacgg cgtggaggtg cataatgcca agacaaagcc gcgggaggag 2040
cagtacaaca gcacgtaccg tgtggtcagc gtcctcaccg tcctgcacca ggactggctg 2100
aatggcaagg agtacaagtg caaggtctcc aacaaagccc tcccagcccc catcgagaaa 2160
accatctcca aagccaaagg gcagcccga  gaaccacagg tgtacaccct gcccccatcc 2220
cgggaggaga tgaccaagaa ccaggtcagc ctgacctgcc tggtcaaagg cttctatccc 2280
agcgacatcg ccgtggagtg ggagagcaat gggcagccgg agaacaacta caagaccacg 2340
cctcccgtgc tggactccga cggctccttc ttcctctaca gcaagctcac cgtggacaag 2400
agcagatggc agcagggaa  cgtcttctca tgctccgtga tgcacgaggc tctgcacaac 2460
cactacacgc agaagtccct ctccctgtct ccgggtaaat agtga                 2505

SEQ ID NO: 74          moltype = AA  length = 833
FEATURE                Location/Qualifiers
source                 1..833
                       mol_type = protein
                       organism = Homo sapiens
SEQUENCE: 74
MYRMQLLSCI ALSLALVTNS APTSSSTKKT QLQLEALLLD LQMILNGINN YKNPKLTRML   60
TAKFYMPKKA TELKHLQCLE EELKPLEEVL NLAQSKNFHL RPRDLISNIN VIVLELKGSE  120
TTFMCEYADE TATIVEFLNR WITFCQSIIS TLTGGGGSGG GGSGGGGSGG GGSAPTSSST  180
KKTQLQLEAL LLDLQMILNG INNYKNPKLT RMLTAKFYMP KKATELKHLQ CLEEELKPLE  240
EVLNLAQSKN FHLRPRDLIS NINIVLELK  GSETTFMCEY ADETATIVEF LNRWITFCQS  300
IISTLTGGGG SGGGGSGGGG SGGGGSGSHS MRYFFTSVSR PGRGEPRFIA VGYVDDTQFV  360
RFDSDAASQR MEPRAPWIEQ EGPEYWDGET RKVKAHSQTH RVDLGTLRGA YNQSEAGSHT  420
VQRMYGCDVG SDWRFLRGYH QYAYDGKDYI ALKEDLRSWT AADMAAQTTK HKWEAAHVAE  480
QLRAYLEGTC VEWLRRYLEN GKETLQRTDA PKTHMTHHAV SDHEATLRCW ALSFYPAEIT  540
```

```
LTWQRDGEDQ TQDTELVETR PCGDGTFQKW AAVVVPSGQE QRYTCHVQHE GLPKPLTLRW    600
EAAAGGDKTH TCPPCPAPEF EGGPSVFLFP PKPKDTLMIS RTPEVTCVVV DVSHEDPEVK    660
FNWYVDGVEV HNAKTKPREE QYNSTYRVVS VLTVLHQDWL NGKEYKCKVS NKALPASIEK    720
TISKAKGQPR EPQVYTLPPS REEMTKNQVS LTCLVKGFYP SDIAVEWESN GQPENNYKTT    780
PPVLDSDGSF FLYSKLTVDK SRWQQGNVFS CSVMHEALHN HYTQKSLSLS PGK            833

SEQ ID NO: 75           moltype = AA   length = 813
FEATURE                 Location/Qualifiers
source                  1..813
                        mol_type = protein
                        organism = Homo sapiens
SEQUENCE: 75
APTSSSTKKT QLQLEALLLD LQMILNGINN YKNPKLTRML TAKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTGGGGSGG GGSGGGGSGG GGSAPTSSST KKTQLQLEAL LLDLQMILNG    180
INNYKNPKLT RMLTAKFYMP KKATELKHLQ CLEEELKPLE EVLNLAQSKN FHLRPRDLIS    240
NINVIVLELK GSETTFMCEY ADETATIVEF LNRWITFCQS IISTLTGGGG SGGGGSGGGG    300
SGGGGSGSHS MRYFFTSVSR PGRGEPRFIA VGYVDDTQFV RFDSDAASQR MEPRAPWIEQ    360
EGPEYWDGET RKVKAHSQTH RVDLGTLRGA YNQSEAGSHT VQRMYGCDVG SDWRFLRGYH    420
QYAYDGKDYI ALKEDLRSWT AADMAAQTTK HKWEAAHVAE QLRAYLEGTC VEWLRRYLEN    480
GKETLQRTDA PKTHMTHHAV SDHEATLRCW ALSFYPAEIT LTWQRDGEDQ TQDTELVETR    540
PCGDGTFQKW AAVVVPSGQE QRYTCVQHE GLPKPLTLRW EAAAGGDKTH TCPPCPAPEF    600
EGGPSVFLFP PKPKDTLMIS RTPEVTCVVV DVSHEDPEVK FNWYVDGVEV HNAKTKPREE    660
QYNSTYRVVS VLTVLHQDWL NGKEYKCKVS NKALPASIEK TISKAKGQPR EPQVYTLPPS    720
REEMTKNQVS LTCLVKGFYP SDIAVEWESN GQPENNYKTT PPVLDSDGSF FLYSKLTVDK    780
SRWQQGNVFS CSVMHEALHN HYTQKSLSLS PGK                                  813

SEQ ID NO: 76           moltype = DNA   length = 2505
FEATURE                 Location/Qualifiers
source                  1..2505
                        mol_type = genomic DNA
                        organism = Homo sapiens
SEQUENCE: 76
atgtacagga tgcaactcct gtcttgcatt gcactaagtc ttgcacttgt cacaaacagt     60
gcacctactt caagttctac aaagaaaaca cagctcaaac tggaggcatt actgctggat    120
ttacagatga ttttgaatgg aattaataat tacaagaatc caaactcac caggatgctc    180
acagcaaagt tttacatgcc aagaaggcca cagaactgaa acatcttca gtgtctagaa    240
gaagaactca aacctctgga ggaagtgcta aatttagctc aaagcaaaaa ctttcactta    300
agacccaggg acttaatcag caatatcaac gtaatagttc tggaactaaa gggatctgaa    360
acaacattca tgtgtgaata tgctgatgag acagcaacca tttgtagaat tctgaacaga    420
tggattacct tttgtcaaag catcatctca cactgactg gaggcggagg atctggtggt    480
ggaggttctg tggtggggg atctggaggc ggaggatctg cacctacttc aagttctaca    540
aagaaaacac agctacaact ggaggcatta ctgctggatt tacagatgat tttgaatgga    600
attaataatt acaagaatcc aaactcacc aggatgctca cagcaaagtt ttacatgcc    660
aagaaggcca cagaactgaa acatcttcag tgtctagaag aagaactcaa acctctggag    720
gaagtgctaa atttagctca aagcaaaaac tttcacttaa gacccaggga cttaatcagc    780
aatatcaacg taatagttct ggaactaaag ggatctgaaa caacattcat gtgtgaatat    840
gctgatgaga cagcaaccat tgtagaatt ctgaacagat ggattacctt tgtcaaagc    900
atcatctcaa cactgactgg aggcggagga tctggtggtg gaggttctgg tggtggggga    960
tctggaggcg gaggatctgg ctctcactcc atgaggtatt tcttcacatc cgtgtcccgg   1020
cccggccgcg gggagccccg cttcatcgca gtgggctacg tggacgacac gcagttcgtg   1080
cggttcgaca gcgacgccgc gagccagagg atggagccgc gggcgccgtg gatagagcag   1140
gagggtccgg agtattggga cggggagaca cggaaagtga aggcccactc acagactcac   1200
cgagtggacc tggggaccct gcgcggcgcc tacaaccaga gcgaggccgg ttctcacacc   1260
gtccagagga tgtatggctg cgacgtgggg tcggactggc gcttcctccg cgggtaccac   1320
cagtacgcct acgacggcaa ggattacatc gccctgaaag aggacctgcg ctccttgacc   1380
gcggcggaca tggcagctca gaccaccaag cacaagtggg aggcggccca tgtggcggag   1440
cagttgagag cctacctgga gggcacgtgc gtggagtggc tccgcagata cctggagaac   1500
gggaaggaga cgctgcagcg cacggacgcc cccaaaacgc atatgactca ccacgctgtc   1560
tctgaccatg aagccaccct gaggtgctgc gccctgagct tctaccctgc ggagatcaca   1620
ctgacctggc agcgggatgg ggaggaccag acccaggaca cggagctcgt ggagaccagg   1680
ccttgcgggg atggaacctt ccagaagtgg gcggctgtgg tggtgccttc tggacaggag   1740
cagagataca cctgccatgt gcagcatgag ggtttgccca gcccctcac cctgagatgg   1800
gaggcagctg cggggtggcga caaaactcac acatgcccac cgtgcccagc acctgaattc   1860
gaggggggac cgtcagtctt cctcttcccc ccaaaaccca aggacaccct catgatctcc   1920
cggacccctg aggtcacatg cgtggtggtg gacgtgagcc acgaagaccc tgaggtcaag   1980
ttcaactggt acgtggacgg cgtggaggtg cataatgcca agacaaagcc gcgggaggag   2040
cagtacaaca gcacgtaccg tgtggtcagc gtcctcaccg tcctgcacca ggactggctg   2100
aatggcaagg agtacaagtg caaggtctcc aacaaagcc tcccagccag catcgagaaa   2160
accatctcca aagccaaagg gcagccccga gaaccacagg tgtacaccct gcccccatcc   2220
cgggaggaga tgaccaagaa ccaggtcagc ctgacctgcc tggtcaaagg cttctatccc   2280
agcgacatcg ccgtggagtg ggagagcaat gggcagccgg agaacaacta caagaccacg   2340
cctcccgtgc tggactccga cggctccttc ttcctctaca gcaagctcac cgtggacaag   2400
agcagatgg agcaggggaa cgtcttctca tgctccgtga tgcacgaggc tctgcacaac   2460
cactacacgc agaagtccct ctccctgtct ccgggtaaat agtga                    2505

SEQ ID NO: 77           moltype = AA   length = 144
FEATURE                 Location/Qualifiers
REGION                  1..144
```

```
                        note = Synthetic Polypeptide Sequence
source                  1..144
                        mol_type = protein
                        organism = synthetic construct
SEQUENCE: 77
MSRSVALAVL ALLSLSGLEA YMLDLQPETT GGGGSGGGGS GGGGSIQRTP KIQVYSCHPA    60
ENGKSNFLNC YVSGFHPSDI EVDLLKNGER IEKVEHSDLS FSKDWSFYLL YYTEFTPTEK   120
DEYACRVNHV TLSQPKIVKW DRDM                                          144

SEQ ID NO: 78           moltype = AA  length = 248
FEATURE                 Location/Qualifiers
REGION                  1..248
                        note = Synthetic Polypeptide Sequence
source                  1..248
                        mol_type = protein
                        organism = synthetic construct
SEQUENCE: 78
YMLDLQPETT GGGGSGGGGS GGGGSIQYML DLQPETTGGG GSGGGGSGGG GSIQRTPKIQ    60
VYSCHPAENG KSNFLNCYVS GFHPSDIEVD LLKNGERIEK VEHSDLSFSK DWSFYLLYYT   120
EFTPTEKDEY ACRVNHVTLS QPKIVKWDRD MRTPKIQVYS CHPAENGKSN FLNCYVSGFH   180
PSDIEVDLLK NGERIEKVEH SDLSFSKDWS FYLLYYTEFT PTEKDEYACR VNHVTLSQPK   240
IVKWDRDM                                                            248

SEQ ID NO: 79           moltype = DNA  length = 438
FEATURE                 Location/Qualifiers
misc_feature            1..438
                        note = Synthetic Polynucleotide Sequence
source                  1..438
                        mol_type = other DNA
                        organism = synthetic construct
SEQUENCE: 79
atgtctcgct ccgtggcctt agctgtgctc gcgctactct ctctttctgg cctggaggcc    60
tacatgctcg atttgcagcc cgaaacgacg ggtggaggtg gttctggagg aggcggttcg   120
ggcggaggtg gtagtatcca gcgtactcca aagattcagg tttactcatg ccatccagca   180
gagaatggaa agtcaaattt cctgaattgc tatgtgtctg ggtttcatcc atccgacatt   240
gaagttgact tactgaagaa tggagagaga attgaaaaag tggagcattc agacttgtct   300
ttcagcaagg actggtcttt ctatctcttg tattatactg aattcacccc cactgaaaaa   360
gatgagtatg cctgccgtgt gaaccacgtg actttgtcac agcccaagat agttaagtgg   420
gatcgagaca tgtagtga                                                 438

SEQ ID NO: 80           moltype = AA  length = 227
FEATURE                 Location/Qualifiers
source                  1..227
                        mol_type = protein
                        organism = Homo sapiens
SEQUENCE: 80
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 81           moltype = AA  length = 227
FEATURE                 Location/Qualifiers
source                  1..227
                        mol_type = protein
                        organism = Homo sapiens
SEQUENCE: 81
DKTHTCPPCP APEFEGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA SIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 82           moltype = AA  length = 227
FEATURE                 Location/Qualifiers
source                  1..227
                        mol_type = protein
                        organism = Homo sapiens
SEQUENCE: 82
DKTHTCPPCP APELLGGPSV FLFPPKPKDT LMISRTPEVT CVVVDVSHED PEVKFNWYVD    60
GVEVHNAKTK PREEQYASTY RVVSVLTVLH QDWLNGKEYK CKVSNKALPA PIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 83           moltype = AA  length = 227
FEATURE                 Location/Qualifiers
source                  1..227
                        mol_type = protein
                        organism = Homo sapiens
SEQUENCE: 83
```

```
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK               227

SEQ ID NO: 84           moltype = AA   length = 133
FEATURE                 Location/Qualifiers
source                  1..133
                        mol_type = protein
                        organism = Homo sapiens
SEQUENCE: 84
APTSSSTKKT QLQLEALLLD LQMILNGINN YKNPKLTRML TAKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133

SEQ ID NO: 85           moltype = AA   length = 5
FEATURE                 Location/Qualifiers
REGION                  1..5
                        note = Synthetic Sequence
source                  1..5
                        mol_type = protein
                        organism = synthetic construct
SEQUENCE: 85
GSGGS                                                               5

SEQ ID NO: 86           moltype = AA   length = 4
FEATURE                 Location/Qualifiers
REGION                  1..4
                        note = Synthetic Sequence
source                  1..4
                        mol_type = protein
                        organism = synthetic construct
SEQUENCE: 86
GGGS                                                                4

SEQ ID NO: 87           moltype = AA   length = 9
FEATURE                 Location/Qualifiers
REGION                  1..9
                        note = Synthetic Peptide
source                  1..9
                        mol_type = protein
                        organism = synthetic construct
SEQUENCE: 87
YMLDLQPET                                                           9

SEQ ID NO: 88           moltype = AA   length = 4
FEATURE                 Location/Qualifiers
REGION                  1..4
                        note = Synthetic Sequence
source                  1..4
                        mol_type = protein
                        organism = synthetic construct
SEQUENCE: 88
FHHT                                                                4

SEQ ID NO: 89           moltype = AA   length = 15
FEATURE                 Location/Qualifiers
REGION                  1..15
                        note = Synthetic Sequence
source                  1..15
                        mol_type = protein
                        organism = synthetic construct
SEQUENCE: 89
GGGGSGGGGS GGGGS                                                   15

SEQ ID NO: 90           moltype = AA   length = 20
FEATURE                 Location/Qualifiers
REGION                  1..20
                        note = Synthetic Sequence
source                  1..20
                        mol_type = protein
                        organism = synthetic construct
SEQUENCE: 90
GGGGSGGGGS GGGGSGGGGS                                              20

SEQ ID NO: 91           moltype = AA   length = 25
FEATURE                 Location/Qualifiers
REGION                  1..25
                        note = Synthetic Sequence
```

```
source                    1..25
                          mol_type = protein
                          organism = synthetic construct
SEQUENCE: 91
GGGGSGGGGS GGGGSGGGGS GGGGS                                       25

SEQ ID NO: 92             moltype = AA  length = 10
FEATURE                   Location/Qualifiers
REGION                    1..10
                          note = Synthetic Sequence
source                    1..10
                          mol_type = protein
                          organism = synthetic construct
SEQUENCE: 92
GGGGSGGGGS                                                        10

SEQ ID NO: 93             moltype = AA  length = 20
FEATURE                   Location/Qualifiers
REGION                    1..20
                          note = Synthetic Sequence
source                    1..20
                          mol_type = protein
                          organism = synthetic construct
SEQUENCE: 93
GSSSSGSSSS GSSSSGSSSS                                             20

SEQ ID NO: 94             moltype = AA  length = 25
FEATURE                   Location/Qualifiers
REGION                    1..25
                          note = Synthetic Sequence
source                    1..25
                          mol_type = protein
                          organism = synthetic construct
SEQUENCE: 94
GSSSSGSSSS GSSSSGSSSS GSSSS                                       25

SEQ ID NO: 95             moltype = AA  length = 119
FEATURE                   Location/Qualifiers
source                    1..119
                          mol_type = protein
                          organism = Homo sapiens
SEQUENCE: 95
MSRSVALAVL ALLLSLSGLEA IQRTPKIQVY SRHPAENGKS NFLNCYVSGF HPSDIEVDLL  60
KNGERIEKVE HSDLSFSKDW SFYLLYYTEF TPTEKDEYAC RVNHVTLSQP KIVKWDRDM   119

SEQ ID NO: 96             moltype = AA  length = 119
FEATURE                   Location/Qualifiers
source                    1..119
                          mol_type = protein
                          organism = Pan troglodytes
SEQUENCE: 96
MSRSVALAVL ALLLSLSGLEA IQRTPKIQVY SRHPAENGKS NFLNCYVSGF HPSDIEVDLL  60
KNGERIEKVE HSDLSFSKDW SFYLLYYTEF TPTEKDEYAC RVNHVTLSQP KIVKWDRDM   119

SEQ ID NO: 97             moltype = AA  length = 119
FEATURE                   Location/Qualifiers
source                    1..119
                          mol_type = protein
                          organism = Macaca mulatta
SEQUENCE: 97
MSRSVALAVL ALLLSLSGLEA IQRTPKIQVY SRHPPENGKP NFLNCYVSGF HPSDIEVDLL  60
KNGEKMGKVE HSDLSFSKDW SFYLLYYTEF TPNEKDEYAC RVNHVTLSGP RTVKWDRDM   119

SEQ ID NO: 98             moltype = AA  length = 118
FEATURE                   Location/Qualifiers
source                    1..118
                          mol_type = protein
                          organism = Bos taurus
SEQUENCE: 98
MARFVALVLL GLLSLSGLDA IQRPPKIQVY SRHPPEDGKP NYLNCYVGF HPPQIEIDLL   60
KNGEKIKSEQ SDLSFSKDWS FYLLSHAEFT PNSKDQYSCR VKHVTLEQPR IVKWDRDL    118

SEQ ID NO: 99             moltype = AA  length = 119
FEATURE                   Location/Qualifiers
source                    1..119
                          mol_type = protein
                          organism = Mus musculus
SEQUENCE: 99
MARSVTLVFL VLVSLTGLYA IQKTPQIQVY SRHPPENGKP NILNCYVTQF HPPHIEIQML  60
```

```
KNGKKIPKVE MSDMSFSKDW SFYILAHTEF TPTETDTYAC RVKHASMAEP KTVYWDRDM    119

SEQ ID NO: 100          moltype = AA  length = 5
FEATURE                 Location/Qualifiers
REGION                  1..5
                        note = Synthetic Sequence
VARIANT                 4
                        note = X is any amino acid other than Proline
source                  1..5
                        mol_type = protein
                        organism = synthetic construct
SEQUENCE: 100
VPGXG                                                                5
```

What is claimed is:

1. A fusion polypeptide comprising:
a) one or more variant IL-2 polypeptides, wherein each of the one or more variant IL-2 polypeptides comprises up to four amino acid substitutions relative to the amino acid sequence set forth in SEQ ID NO:1, wherein amino acid 42 is an amino acid other than a phenylalanine, wherein amino acid 16 is an amino acid other than a histidine, and wherein each of the one or more variant IL2 polypeptides exhibit reduced binding affinity to an IL-2 receptor (IL2R) comprising alpha, beta, and gamma polypeptides having amino acid sequences set forth in SEQ ID NOs: 18-20, compared to the binding affinity of the IL-2 amino acid sequence set forth in SEQ ID NO: 1 for the IL2R; and
b) a heterologous fusion partner comprising an antibody Fc region, wherein the antibody Fc region comprises an amino acid sequence having at least 95% sequence identity to the amino acid sequence set forth in SEQ ID NO:57, wherein the percent sequence identity is determinable by a sequence alignment performed using BLAST,
wherein the fusion polypeptide does not comprise a major histocompatibility complex (MHC) polypeptide.

2. The fusion polypeptide of claim 1, wherein the antibody Fc region comprises one or more substitutions selected from an L14A substitution, an L15A substitution, an N77A substitution, a P111S substitution based on the amino acid numbering of SEQ ID NO:57.

3. The fusion polypeptide of claim 1, wherein the fusion polypeptide comprises from 400 to 600 amino acids.

4. The fusion polypeptide of claim 1, wherein the fusion polypeptide comprises from 500 to 700 amino acids.

5. The fusion polypeptide of claim 1, wherein the heterologous fusion partner comprises an antibody Fc region and an antigen-binding region of an antibody.

6. The fusion polypeptide of claim 5, wherein the fusion polypeptide comprises from 400 to 700 amino acids.

7. The fusion polypeptide of claim 5, wherein the fusion polypeptide comprises from 700 to 900 amino acids.

8. The fusion polypeptide of claim 1, wherein amino acid 16 of each of the one or more variant IL-2 polypeptides is Ala, Thr, Asp, or Glu; and wherein amino acid 42 of each of the one or more variant IL-2 polypeptides is Ala or Thr.

9. The fusion polypeptide of claim 6, wherein amino acid 16 of each of the one or more variant IL-2 polypeptides is Ala, Thr, Asp, or Glu; and wherein amino acid 42 of each of the one or more variant IL-2 polypeptides is Ala or Thr.

10. The fusion polypeptide of claim 7, wherein amino acid 16 of each of the one or more variant IL-2 polypeptides is Ala, Thr, Asp, or Glu; and wherein amino acid 42 of each of the one or more variant IL-2 polypeptides is Ala or Thr.

11. A fusion polypeptide comprising:
a) one or more variant IL-2 polypeptides, wherein each of the one or more variant IL-2 polypeptides comprises up to three amino acid substitutions relative to the amino acid sequence set forth in SEQ ID NO:1, wherein amino acid 42 is an amino acid other than a phenylalanine, wherein amino acid 16 is an amino acid other than a histidine, and wherein each of the one or more variant IL2 polypeptides exhibit reduced binding affinity to an IL-2 receptor (IL2R) comprising alpha, beta, and gamma polypeptides having amino acid sequences set forth in SEQ ID NOs: 18-20, compared to the binding affinity of the IL-2 amino acid sequence set forth in SEQ ID NO: 1 for the IL2R; and
b) a heterologous fusion partner comprising an antibody Fc region, wherein the antibody Fc region comprises an amino acid sequence having at least 95% sequence identity to the amino acid sequence set forth in SEQ ID NO: 57, wherein the percent sequence identity is determinable by a sequence alignment performed using BLAST,
wherein the fusion polypeptide does not comprise a major histocompatibility complex (MHC) polypeptide.

12. The fusion polypeptide of claim 11, wherein the antibody Fc region comprises one or more substitutions selected from an L14A substitution, an L15A substitution, an N77A substitution, a P111S substitution based on the amino acid numbering of SEQ ID NO:57.

13. The fusion polypeptide of claim 11, wherein the fusion polypeptide comprises from 400 to 600 amino acids.

14. The fusion polypeptide of claim 11, wherein the fusion polypeptide comprises from 500 to 700 amino acids.

15. The fusion polypeptide of claim 11, wherein the heterologous fusion partner comprises an antibody Fc region and an antigen-binding region of an antibody.

16. The fusion polypeptide of claim 15, wherein the fusion polypeptide comprises from 400 to 700 amino acids.

17. The fusion polypeptide of claim 15, wherein the fusion polypeptide comprises from 700 to 900 amino acids.

18. The fusion polypeptide of claim 11, wherein amino acid 16 of each of the one or more variant IL-2 polypeptides is Ala, Thr, Asp, or Glu; and wherein amino acid 42 of each of the one or more variant IL-2 polypeptides is Ala or Thr.

19. The fusion polypeptide of claim 16, wherein amino acid 16 of each of the one or more variant IL-2 polypeptides is Ala, Thr, Asp, or Glu; and wherein amino acid 42 of each of the one or more variant IL-2 polypeptides is Ala or Thr.

20. The fusion polypeptide of claim 17, wherein amino acid 16 of each of the one or more variant IL-2 polypeptides is Ala, Thr, Asp, or Glu; and wherein amino acid 42 of each of the one or more variant IL-2 polypeptides is Ala or Thr.

21. A fusion polypeptide comprising:
a) one or more variant IL-2 polypeptides, wherein each of the one or more variant IL-2 polypeptides comprises two amino acid substitutions relative to the amino acid sequence set forth in SEQ ID NO:1, wherein amino acid 42 is an amino acid other than a phenylalanine, wherein amino acid 16 is an amino acid other than a histidine, and wherein each of the one or more variant IL2 polypeptides exhibit reduced binding affinity to an IL-2 receptor (IL2R) comprising alpha, beta, and gamma polypeptides having amino acid sequences set forth in SEQ ID NOs: 18-20, compared to the binding affinity of the IL-2 amino acid sequence set forth in SEQ ID NO: 1 for the IL2R; and
b) a heterologous fusion partner comprising an antibody Fc region, wherein the antibody Fc region comprises an amino acid sequence having at least 95% sequence identity to the amino acid sequence set forth in SEQ ID NO: 57, wherein the percent sequence identity is determinable by a sequence alignment performed using BLAST,
wherein the fusion polypeptide does not comprise a major histocompatibility complex (MHC) polypeptide.

22. The fusion polypeptide of claim 21, wherein the antibody Fc region comprises one or more substitutions selected from an L14A substitution, an L15A substitution, an N77A substitution, a P111S substitution based on the amino acid numbering of SEQ ID NO:57.

23. The fusion polypeptide of claim 21, wherein the fusion polypeptide comprises from 400 to 600 amino acids.

24. The fusion polypeptide of claim 21, wherein the fusion polypeptide comprises from 500 to 700 amino acids.

25. The fusion polypeptide of claim 21, wherein the heterologous fusion partner comprises an antibody Fc region and an antigen-binding region of an antibody.

26. The fusion polypeptide of claim 25, wherein the fusion polypeptide comprises from 400 to 700 amino acids.

27. The fusion polypeptide of claim 25, wherein the fusion polypeptide comprises from 700 to 900 amino acids.

28. The fusion polypeptide of claim 21, wherein amino acid 16 of each of the one or more variant IL-2 polypeptides is Ala, Thr, Asp, or Glu; and wherein amino acid 42 of each of the one or more variant IL-2 polypeptides is Ala or Thr.

29. The fusion polypeptide of claim 26, wherein amino acid 16 of each of the one or more variant IL-2 polypeptides is Ala, Thr, Asp, or Glu; and wherein amino acid 42 of each of the one or more variant IL-2 polypeptides is Ala or Thr.

30. The fusion polypeptide of claim 27, wherein amino acid 16 of each of the one or more variant IL-2 polypeptides is Ala, Thr, Asp, or Glu; and wherein amino acid 42 of each of the one or more variant IL-2 polypeptides is Ala or Thr.

* * * * *